(12) United States Patent
Shankar et al.

(10) Patent No.: US 9,512,447 B2
(45) Date of Patent: Dec. 6, 2016

(54) MODIFIED NATIVE BETA-KETOACYL-ACP SYNTHASES AND ENGINEERED MICROORGANISMS

(71) Applicant: Codexis, Inc., Redwood City, CA (US)

(72) Inventors: Smita Shankar, Millbrae, CA (US); Louis Clark, San Francisco, CA (US); Robert Osborne, Oakland, CA (US); Jonathan Vroom, South San Francisco, CA (US); Fernando Valle, Burlingame, CA (US); Catherine M. Cho, Los Angeles, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 14/650,953

(22) PCT Filed: Dec. 4, 2013

(86) PCT No.: PCT/US2013/072973
§ 371 (c)(1),
(2) Date: Jun. 10, 2015

(87) PCT Pub. No.: WO2014/093070
PCT Pub. Date: Jun. 19, 2014

(65) Prior Publication Data
US 2016/0010115 A1    Jan. 14, 2016

Related U.S. Application Data

(60) Provisional application No. 61/737,232, filed on Dec. 14, 2012.

(51) Int. Cl.
| | |
|---|---|
| *C12P 7/04* | (2006.01) |
| *C12N 9/10* | (2006.01) |
| *A61K 8/34* | (2006.01) |
| *A61Q 19/00* | (2006.01) |
| *C07C 31/125* | (2006.01) |
| *C07C 33/025* | (2006.01) |
| *C11D 3/20* | (2006.01) |

(52) U.S. Cl.
CPC ............... *C12P 7/04* (2013.01); *A61K 8/342* (2013.01); *A61Q 19/00* (2013.01); *C07C 31/125* (2013.01); *C07C 33/025* (2013.01); *C11D 3/2013* (2013.01); *C12N 9/1029* (2013.01); *C12Y 203/01041* (2013.01); *A61K 2800/10* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,356,196 A | 10/1982 | Hultquist | |
| 4,461,648 A | 7/1984 | Foody | |
| 4,556,430 A | 12/1985 | Converse et al. | |
| 4,600,590 A | 7/1986 | Dale | |
| 5,037,663 A | 8/1991 | Dale | |
| 5,171,592 A | 12/1992 | Holtzapple et al. | |
| 5,344,771 A | 9/1994 | Davies et al. | |
| 5,455,167 A | 10/1995 | Voelker et al. | |
| 5,512,482 A | 4/1996 | Voelker et al. | |
| 5,667,997 A | 9/1997 | Voelker et al. | |
| 5,723,761 A | 3/1998 | Voelker et al. | |
| 5,910,631 A | 6/1999 | Topfer et al. | |
| 5,939,544 A | 8/1999 | Karstens et al. | |
| 5,955,329 A | 9/1999 | Yuan et al. | |
| 6,106,888 A | 8/2000 | Dale et al. | |
| 6,117,679 A | 9/2000 | Stemmer | |
| 6,143,538 A | 11/2000 | Somerville et al. | |
| 6,150,512 A | 11/2000 | Yuan | |
| 6,176,176 B1 | 1/2001 | Dale et al. | |
| 6,376,246 B1 | 4/2002 | Crameri et al. | |
| 6,429,175 B1 | 8/2002 | Stuart, Jr. et al. | |
| 6,586,182 B1 | 7/2003 | Patten et al. | |
| 7,332,311 B2 | 2/2008 | Lardizabal et al. | |
| 7,465,791 B1 | 12/2008 | Hallberg et al. | |
| 7,754,457 B2 | 7/2010 | Foody et al. | |
| 7,783,428 B2 | 8/2010 | Gustafsson et al. | |
| 8,110,670 B2 | 2/2012 | Hu et al. | |
| 8,216,815 B2 | 7/2012 | McDaniel et al. | |
| 8,574,878 B2 | 11/2013 | Behrouzian et al. | |
| 2006/0195947 A1 | 8/2006 | Davis et al. | |
| 2007/0031953 A1 | 2/2007 | Dunson, Jr. et al. | |
| 2008/0104724 A1 | 5/2008 | Sticklen et al. | |
| 2008/0220990 A1 | 9/2008 | Fox | |
| 2009/0075249 A1* | 3/2009 | Dehesh ............... | C12N 9/1029 435/4 |
| 2009/0312196 A1 | 12/2009 | Colbeck et al. | |
| 2010/0203614 A1 | 8/2010 | Wahlen et al. | |
| 2011/0000125 A1 | 1/2011 | McDaniel et al. | |
| 2012/0115195 A1 | 5/2012 | Keasling et al. | |
| 2012/0142979 A1 | 6/2012 | Keasling et al. | |
| 2012/0184006 A1 | 7/2012 | Willis et al. | |

FOREIGN PATENT DOCUMENTS

| | | |
|---|---|---|
| EP | 2395074 A1 | 12/2011 |
| WO | 2007/136762 A2 | 11/2007 |
| WO | 2008/119082 A2 | 10/2008 |
| WO | 2009/045651 A2 | 4/2009 |
| WO | 2010/075483 A2 | 7/2010 |
| WO | 2010/144103 A1 | 12/2010 |
| WO | 2011/008535 A1 | 1/2011 |
| WO | 2011/019858 A1 | 2/2011 |
| WO | 2012/006114 A2 | 1/2012 |

OTHER PUBLICATIONS

Altschul, S., et al., "Basic local alignment search tool," J. Mol. Biol., 215: 403-410 (1990).

(Continued)

*Primary Examiner* — Nashaat Nashed
(74) *Attorney, Agent, or Firm* — Codexis, Inc.

(57) ABSTRACT

Genetically engineered cells and microorganisms are provided that produce fatty alcohols and fatty acids. In particular, engineered microbial cells comprise a modified native gene having β-ketoacyl-acp synthase activity.

31 Claims, 1 Drawing Sheet

(56) References Cited

OTHER PUBLICATIONS

Altschul, S.F., et al., "Gapped BLAST and PSI-BLAST: a new generation of protein database search programs," Nucleic Acids Res., 25(17):3389-3402 (1997).
Archer, C.T., et al., "The genome sequence of E. coli W (ATCC 9637): comparative genome analysis and an improved genome-scale reconstruction of E. coli," BMC Genomics, 12:9 [2011].
Baba, T., et al., "Construction of Escherichia coli K-12 in-frame,single-gene knockout mutants: the Keio collection," Mol Syst Biol, 2:1-11 [2006].
Black, P.N. et al., "Cloning, sequencing, and expression of the fadD gene of Escherichia coli encoding acyl coenzyme A synthetase," J. Biol. Chem., 267:25513-25520 [1992].
Brosius, J., et al., "Spacing of the -10 and -35 Regions in the tac Promoter," J. Biol. Chem., 260(6): 3539-3541 [1985].
Cantu, D.C., et al., "Thioesterases: a new perspective based on their primary and tertiary structures," Protein Science, 19(7):1281-1295 (2010).
Cantu, D.C., et al., "ThYme: a database for thioester-active enzymes," Nucleic Acid Research, 39:D342-D346 (2011).
Carter, P., "Site-directed mutagenesis," Biochem. J., 237:1-7 [1986].
Chen, Y., et al., "Structural classification and properties ofketoacyl synthases," Prot. Sci., 20(10): 1659-1667 [2011].
Datsenko, K.A., et al., "One-step inactivation of chromosomal genes in Escherichia coli K-12 using PCR products," PNAS, 97(12): 6640-6645 [2000].
Datta, S., et al., "A set of recombineering plasmids for gram-negative bacteria," Gene, 379: 109-115 (2006).
De Boer, H.A., et al., "The tac promoter: a functional hybrid derived from the trp and lac promoters," Proc. Natl Acad. Sci. USA, 80: 21-25 (1983).
De Lay, N.R., et al., "Gene-Specific Random Mutagenesis of Escherichia coli In Vivo: Isolation of Temperature-Sensitive Mutations in the Acyl Carrier Protein of Fatty Acid Synthesis" J. Bacteriol., 188:287-296 [2006].
Doan, T.T.P., et al., "Functional expression of five Arabidopsis fatty acyl-CoA reductase genes in Escherichia coli," J. Plant Physiol., 166: 787-796 [2009].
Dower, W.J., et al., "High efficiency transformation of E. coli by high voltage electroporation," Nucleic Acids Research, 16(13): 6127-6145 [1988].
Eblen, D.R., et al., "Studies to Select Appropriate Nonpathogenic Surrogate Escherichia coli Strains for Potential Use in Place of Escherichia coli O157:H7 and Salmonella in Pilot Plant Studies," J. of Food Protection, 68(2):282-291 [2005].
Edwards, P., et al., "Cloning of the fabF gene in an expression vector and in vitro characterization of recombinant fabF and fabB encoded enzymes from Escherichia coli," FEBS Let. 402: 62-66 [1997].
Hamiton, C.M., et al., "New method for generating deletions and gene replacements in Escherichia coli," J. Bacteriol., 171:4617-4622 [1989].
Hayashi, K., et al., "Highly accurate genome sequences of Escherichia coli K-12 strains MG1655 and W3110," Mol. Syst. Biol., 2(2006.0007):1-5 [2006].
Henikoff, S., et al., "Amino acid substitution matrices from protein blocks," Proc. Natl. Acad. Sci. USA, 89:10915-10919 [1992].
Hofvander, P., et al., "A prokaryotic acyl CoA reductase performing reduction of fatty acyl-CoA to fatty alcohol," FEBS Letters, 585: 3538-3543 (2011).
Ishige, T., et al., "Long-Chain Aldehyde Dehydrogenase That Participates in n-Alkane Utilization and Wax Ester Synthesis in Acinetobacter sp. Strain M-1," Appl. Environ. Microbiol., 66:3481-3486 (2000).
Jones, A., et al., "Palmitoyl-Acyl Carrier Protein (ACP) Thioesterase and the Evolutidnary-Origin of Plant ACyl-ACP Thioesterases," The Plant Cell, 7:359-371 (1995).
Kalscheuer, R., et al., "Neutral Lipid Biosynthesis in Engineered Escherichia coli: Jojoba Oil-Like Wax Esters and Fatty Acid Butyl Esters," Appl. Environ. Microbiol., 72:1373-79 [2006].
Kim, Y.G., et al., "Gene Replacement in Gram-Negative Bacteria: the pMAKSAC Vectors," BioTechniques, 28:198-204 [2000].
Lathe, R., et al., "Plasmid and bacteriophage vectors for excision of intact inserts," Gene, 57:193-201 [1987].
Lerner, C.G., et al., "Low copy number plasmids for regulated low-level expression of cloned genes in Escherichia cofi with blue/white insert screening capability," Nucleic Acids Research, 18(15):4631 [1990].
Li, J J. et al. "Reductions" in Modern Organic Synthesis in the Laboratory, Oxford University Press, Inc., p. 81-83 [2007].
Ling, M.M., et al., "Approaches to DNA Mutagenesis: An Overview," Anal. Biochem., 254(2):157-78 [1997].
Link, A.J., et al., "Methods for generating precise deletions and insertions in the genome of wild-type Escherichia coli: application to open reading frame characterization," J. Bact., 179: 6228-6237 [1997].
Metz, J.G., et al., "Purification of a Jojoba Embryo Fatty Acyl-Coenzyme A Reductase and Expression of Its cDNA in High Erucic Acid Rapeseed," Plant Physiol., 122:635-644 [2000].
Minshull, J., et al., "Protein evolution by molecular breeding," Curr. Op. Chem. Biol., 3:284-290 [1999].
Morgan-Kiss, R.M., et al., "The Lactococcus lactis FabF fatty acid synthetic enzyme can functionally replace both the FabB and FabF proteins of Escherichia coli and the FabH protein of Lactococcus lactis," Arch. Microbiol., 190:427-459 [2008].
Moto, K., et al., "Pheromone gland-specific fatty-acyl reductase of the silkmoth, Bombyx mori," PNAS, 100(16):9156-9161 [2003].
Needleman, S., et al., "A general method applicable to the search for similarities in the amino acid sequence of two proteins," J. Mol. Biol. 48:443-453 (1970).
Nevoigt, E., et al., "Engineering of Promoter Replacement Cassettes for Fine-Tuning of Gene Expression in Saccharomyces cerevisiae," Appl. Environ. Microbiol., 72:5266-5273 (2006).
Notredame, C., et al., "T-COFFEE: A novel method for multiple sequence alignments," JMB, 302:205-217, [2000].
Orosz, A., et al., "Analysis of the complex transcription termination region of the Escherichia coli rrnB gene," Eur. J. Biochem., 201: 653-659 [1991].
Pearson, W.R., "Improved tools for biological sequence comparison," Proc. Nat'l. Acad. Sci. USA, 85:2444-2448 (1988).
Reiser, S., et al., "Isolation of mutants of Acinetobacter calcoaceticus deficient in wax ester synthesis and complementation of one mutation with a gene encoding a fatty acyl coenzyme A reductase," J. Bacteriol., 179:2969-2975 (1997).
Rowland, O., et al., "Plant fatty acyl reductases: enzymes generating fatty alcohols for protective layers with potential for industrial applications," Plant Sci., 193-194:28-38 [2012].
Sadler, J.R., et al., "A perfectly symmetric lac operator binds the lac repressor very tightly," PNAS, 80: 6785-6789 [1983].
Smith, T., et al., "Comparison of Biosequences," Adv. Appl. Math, 2:482-489 (1981).
Smith, M., "In Vitro Mutagenesis," Ann. Rev. Genet., 19:423-462 [1985].
Terpe, K., "Overview of bacterial expression systems for heterologousprotein production: from molecular and biochemicalfundamentals to commercial systems," Appl. Microbiol. Biotechnol., 72:211-222 [2006].
Tsujita, T., et al., "Fatty Acid Alcohol Ester-Synthesizing Activity of Lipoprotein Lipase" J. Biochem. 126:1074-1079 [1999].
Villa-Komaroff, L., et al., "A bacterial clone synthesizing proinsulin," Proc. Natl Acad. Sci. USA, 75:3727-3731 (1978).
Voelker, T.A., et al., "Alteration of the specificity and regulation of fatty acid synthesis of Escherichia coli by expression of a plant medium-chain acyl-acyl carrier protein thioesterase," J. Bacteriol., 176:7320-7327[1994].
Warrens, A.N., et al., "Splicing by overlap extension by PCR using asymmetric amplification: an improved technique for the generation of hybrid proteins of immunological interest," Gene, 186(1):29-35 [1997].
Weil, J., et al. "Pretreatment of Yellow Poplar Sawdust by Pressure Cooking in Water," Appl. Biochem. Biotechnol., 68(1-2): 21-40 [1997].

(56) References Cited

OTHER PUBLICATIONS

GenBank Accession No. AAC72881 dated Nov. 11, 1998.
GenBank Accession No. AAA34215 dated Apr. 27, 1993.
GenBank Accession No. AAB71731 dated Oct. 2, 1997.
GenBank Accession No. AAC49151.1 dated Jan. 30, 1996.
GenBank Accession No. AAC49179.1 dated Mar. 6, 1996.
Genbank Accession No. AAC49269 dated Apr. 30, 1996.
GenBank Accession No. AAMD01000005.1 dated Sep. 28, 2006.
GenBank Accession No. AAQX01001105.1 dated Sep. 1, 2006.
GenBank Accession No. AB236930 dated Nov. 3, 2005.
GenBank Accession No. ABII01000018.1 dated Nov. 30, 2007.
GenBank Accession No. BAC79425.1 dated Jan. 25, 2012.
GenBank Accession No. CA022305.1 dated Oct. 8, 2007.
GenBank Accession No. DQ446732.1 dated Apr. 16, 2006.
GenBank Accession No. EDD40059.1 dated Apr. 6, 2007.
GenBank Accession No. EGM60922.1 dated Jun. 10, 2011.
GenBank Accession No. EU817405.1 dated Mar. 4, 2009.
GenBank Accession No. NM_115529.1 dated Jan. 22, 2014.
NCBI Accession No. NP_215722 dated Dec. 22, 2014.
NCBI Accession No. NP_216703 dated Dec. 22, 2014.
NCBI Accession No. NP_243969 dated Dec. 16, 2014.
NCBI Accession No. NP_251989 dated Jun. 5, 2015.
NCBI Accession No. NP_251990 dated Jun. 5, 2015.
NCBI Accession No. NP_388908 dated Mar. 25, 2015.
NCBI Accession No. NP_438551 dated Dec. 16, 2014.
NCBI Accession No. NP_460316 dated Dec. 22, 2014.
NCBI Accession No. YP_045024 dated Dec. 16, 2014.
NCBI Accession No. YP_177983 dated Dec. 22, 2014.
NCBI Accession No. YP_290214 dated Dec. 16, 2014.
NCBI Accession No. YP_350081 dated Dec. 16, 2014.
NCBI Accession No. YP_436183 dated Dec. 16, 2014.
NCBI Accession No. YP_958864 dated Dec. 18, 2014.
NCBI Accession No. ZP_01305629 dated Nov. 26, 2012.
NCBI Accession No. ZP_01892995 dated Nov. 9, 2010.
NCBI Accession No. ZP_07590374 dated Nov. 10, 2010.
UniProtKB Accession No. Q39473 dated Nov. 1, 1996.
UniProtKB Accession No. Q39513 dated Nov. 1, 1996.
UniProtKB Accession No. Q41635 dated Nov. 1, 1996.

* cited by examiner

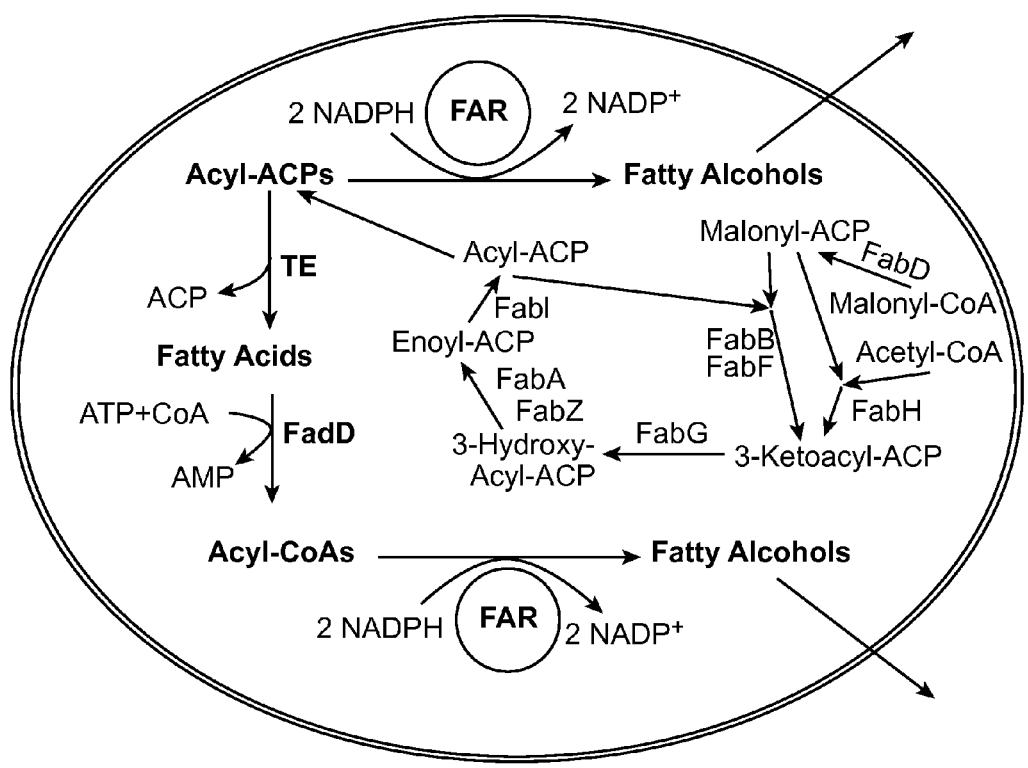

SEQUENCE LISTING

<160> NUMBER OF SEQ ID NOS: 58

<210> SEQ ID NO 1
<211> LENGTH: 1221
<212> TYPE: DNA
<213> ORGANISM: Escherichia coli

<400> SEQUENCE: 1

```
atgaaacgtg cagtgattac tggcctgggc attgtttcca gcatcggtaa taaccagcag      60
gaagtcctgg catctctgcg tgaaggacgt tcaggatca ctttctctca ggagctgaag     120
```

```
gattccggca tgcgtagcca cgtctggggc aacgtaaaac tggataccac tggcctcatt    180
gaccgcaaag ttgtgcgctt tatgagcgac gcatccattt atgcattcct ttctatggag    240
caggcaatcg ctgatgcggg cctctctccg aagcttacc agaataaccc gcgcgttggc     300
ctgattgcag gttccggcgg cggctccccg cgtttccagg tgttcggcgc tgacgcaatg    360
cgcggcccgc gcggcctgaa agcggttggc ccgtatgtgg tcaccaaagc gatggcatcc    420
ggcgtttctg cctgcctcgc caccccgttt aaaattcatg cgttaacta ctccatcagc     480 tccgcgtgtg cgacttccgc acactgtatc ggtaacgcag tagagcagat ccaactgggc    540
aaacaggaca tcgtgtttgc tggcggcggc gaagagctgt gctgggaaat ggcttgcgaa    600
ttcgacgcaa tgggtgcgct gtctactaaa tacaacgaca ccccggaaaa agcctcccgt    660
acttacgacg ctcaccgtga cggtttcgtt atcgctggcg gcggcggtat ggtagtggtt    720
gaagagctgg aacacgcgct ggcgcgtggt gctcacatct atgctgaaat cgttggctac    780
ggcgcaacct ctgatggtgc agacatggtt gctccgtctg gcgaaggcgc agtacgctgc    840
atgaagatgg cgatgcatgg cgttgatacc ccaatcgatt acctgaactc ccacggtact    900
tcgactccgg ttggcgacgt gaaagagctg gcagctatcc gtgaagtgtt cggcgataag    960
agcccggcga tttctgcaac caaagccatg accggtcact ctctgggcgc tgctggcgta   1020
caggaagcta tctactctct gctgatgctg aacacggct ttatcgcccc gagcatcaac    1080
attgaagagc tggacgagca ggctgcgggt ctgaacatcg tgaccgaaac gaccgatcgc   1140
gaactgacca ccgttatgtc taacagcttc ggcttcggcg gcaccaacgc cacgctggta   1200
atgcgcaagc tgaaagatta a                                              1221

<210> SEQ ID NO 2
<211> LENGTH: 406
<212> TYPE: PRT
<213> ORGANISM: Escherichia coli

<400> SEQUENCE: 2

Met Lys Arg Ala Val Ile Thr Gly Leu Gly Ile Val Ser Ser Ile Gly
1               5                   10                  15

Asn Asn Gln Gln Glu Val Leu Ala Ser Leu Arg Glu Gly Arg Ser Gly
            20                  25                  30

Ile Thr Phe Ser Gln Glu Leu Lys Asp Ser Gly Met Arg Ser His Val
        35                  40                  45

Trp Gly Asn Val Lys Leu Asp Thr Thr Gly Leu Ile Asp Arg Lys Val
    50                  55                  60

Val Arg Phe Met Ser Asp Ala Ser Ile Tyr Ala Phe Leu Ser Met Glu
65                  70                  75                  80

Gln Ala Ile Ala Asp Ala Gly Leu Ser Pro Glu Ala Tyr Gln Asn Asn
                85                  90                  95

Pro Arg Val Gly Leu Ile Ala Gly Ser Gly Gly Gly Ser Pro Arg Phe
            100                 105                 110

Gln Val Phe Gly Ala Asp Ala Met Arg Gly Pro Arg Gly Leu Lys Ala
        115                 120                 125

Val Gly Pro Tyr Val Val Thr Lys Ala Met Ala Ser Gly Val Ser Ala
    130                 135                 140

Cys Leu Ala Thr Pro Phe Lys Ile His Gly Val Asn Tyr Ser Ile Ser
145                 150                 155                 160

Ser Ala Cys Ala Thr Ser Ala His Cys Ile Gly Asn Ala Val Glu Gln
                165                 170                 175
```

```
Ile Gln Leu Gly Lys Gln Asp Ile Val Phe Ala Gly Gly Gly Glu
            180                 185                 190
Leu Cys Trp Glu Met Ala Cys Glu Phe Asp Ala Met Gly Ala Leu Ser
        195                 200                 205
Thr Lys Tyr Asn Asp Thr Pro Glu Lys Ala Ser Arg Thr Tyr Asp Ala
    210                 215                 220
His Arg Asp Gly Phe Val Ile Ala Gly Gly Gly Met Val Val Val
225                 230                 235                 240
Glu Glu Leu Glu His Ala Leu Ala Arg Gly Ala His Ile Tyr Ala Glu
                245                 250                 255
Ile Val Gly Tyr Gly Ala Thr Ser Asp Gly Ala Asp Met Val Ala Pro
            260                 265                 270
Ser Gly Glu Gly Ala Val Arg Cys Met Lys Met Ala Met His Gly Val
        275                 280                 285
Asp Thr Pro Ile Asp Tyr Leu Asn Ser His Gly Thr Ser Thr Pro Val
    290                 295                 300
Gly Asp Val Lys Glu Leu Ala Ala Ile Arg Glu Val Phe Gly Asp Lys
305                 310                 315                 320
Ser Pro Ala Ile Ser Ala Thr Lys Ala Met Thr Gly His Ser Leu Gly
                325                 330                 335
Ala Ala Gly Val Gln Glu Ala Ile Tyr Ser Leu Leu Met Leu Glu His
            340                 345                 350
Gly Phe Ile Ala Pro Ser Ile Asn Ile Glu Glu Leu Asp Glu Gln Ala
        355                 360                 365
Ala Gly Leu Asn Ile Val Thr Glu Thr Thr Asp Arg Glu Leu Thr Thr
    370                 375                 380
Val Met Ser Asn Ser Phe Gly Phe Gly Gly Thr Asn Ala Thr Leu Val
385                 390                 395                 400
Met Arg Lys Leu Lys Asp
                405

<210> SEQ ID NO 3
<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 3
atggctactc aacaacaaca gaacggtgca tctgcatccg gcgtcttgga caacttcgt      60 ggaaagcacg ttcttatcac aggtactacc ggatttttgg gcaaagtggt tctggaaaag    120
ttgattcgta ctgttccgga tattggaggt attcatctgc tgattcgtgg caataaacgt    180
catccagccg ctcgtgaacg tttcctgaac gaaattgcgt cctcctccgt cttcgaacgt    240
ttgcgtcacg atgataatga agccttcgag accttcttgg aagaacgtgt tcactgtatt    300
accggtgagg ttactgaatc ccgttttggt ttgacacctg aacgttttcg tgctttggcc    360
ggtcaggttg acgcttttat taacagcgct gcaagcgtga actttcgtga ggaattggat    420
aaagccctga aaatcaacac cttgtgtctt gaaaatgttg ctgctcttgc agaattgaac    480
tccgctatgg cggtcattca ggtttccact tgttacgtta acggtaaaaa ctccggtcaa    540
attaccgaat ccgtcattaa acctgctggc gaatccattc cccgttccac tgacggttac    600
tacgagatcg aagaattggt ccatctgttg caagacaaga tttccgatgt taaagctcgt    660
tactccggca agttctggga gaaaaaattg gttgatttgg gtattcgtga ggccaataat    720
```

```
tacggatggt ccgacaccta cacattcacc aaatggttgg gtgaacaact gctgatgaag    780
gccttgtctg gtcgttcttt gactattgtg cgtccctcta ttattgagtc cgctttggaa    840
gaaccttccc ctggttggat cgaaggcgtt aaagttgccg atgccattat cttggcttat    900
gcccgtgaaa aagttagcct gttccctgga aaacgttccg gcattattga tgttattcct    960
gtcgatttgg ttgcgaactc catcatcttg tctctggctg aggcgttgtc tggttctggt   1020
caacgtcgta tttatcaatg ttgcagcggt ggttctaatc caatctccct gggtaagttc   1080
attgattatt tgatggccga ggctaagacc aactatgctg cctacgatca actgttttat   1140
cgtcgtccta ctaaaccttt cgtcgccgtg aaccgtaaat tgtttgacgt tgttgttggt   1200
ggtatgcgtg ttcctctttc tattgccggt aaagctatgc gtttggctgg tcaaaatcgt   1260
gagttgaaag tgcttaagaa ccttgatacg acccgttccc ttgcaaccat ttttggcttc   1320
tatactgctc ccgactatat cttccgtaac gatagcttga tggccctggc ttctcgtatg   1380
ggtgaattgg atcgtgttct tttcccagtt gatgctcgtc aaattgattg gcagttgtac   1440
ttgtgtaaaa ttcatttggg tggtctgaac cgttacgctt tgaaggaacg taaactgtat   1500
tctttgcgtg ctgctgatac tcgtaaaaaa gctgcctaa                          1539
```

<210> SEQ ID NO 4
<211> LENGTH: 512
<212> TYPE: PRT
<213> ORGANISM: Marinobacter algicola

<400> SEQUENCE: 4

```
Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
        115                 120                 125

Ser Ala Ala Ser Val Asn Phe Arg Glu Glu Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
```

```
                    225                 230                 235                 240

Tyr Gly Trp Ser Asp Thr Tyr Thr Phe Thr Lys Trp Leu Gly Glu Gln
                        245                 250                 255

Leu Leu Met Lys Ala Leu Ser Gly Arg Ser Leu Thr Ile Val Arg Pro
                        260                 265                 270

Ser Ile Ile Glu Ser Ala Leu Glu Glu Pro Ser Pro Gly Trp Ile Glu
                        275                 280                 285

Gly Val Lys Val Ala Asp Ala Ile Ile Leu Ala Tyr Ala Arg Glu Lys
                        290                 295                 300

Val Ser Leu Phe Pro Gly Lys Arg Ser Gly Ile Ile Asp Val Ile Pro
        305                 310                 315                 320

Val Asp Leu Val Ala Asn Ser Ile Ile Leu Ser Leu Ala Glu Ala Leu
                        325                 330                 335

Ser Gly Ser Gly Gln Arg Arg Ile Tyr Gln Cys Cys Ser Gly Gly Ser
                        340                 345                 350

Asn Pro Ile Ser Leu Gly Lys Phe Ile Asp Tyr Leu Met Ala Glu Ala
                        355                 360                 365

Lys Thr Asn Tyr Ala Ala Tyr Asp Gln Leu Phe Tyr Arg Arg Pro Thr
                        370                 375                 380

Lys Pro Phe Val Ala Val Asn Arg Lys Leu Phe Asp Val Val Val Gly
        385                 390                 395                 400

Gly Met Arg Val Pro Leu Ser Ile Ala Gly Lys Ala Met Arg Leu Ala
                        405                 410                 415

Gly Gln Asn Arg Glu Leu Lys Val Leu Lys Asn Leu Asp Thr Thr Arg
                        420                 425                 430

Ser Leu Ala Thr Ile Phe Gly Phe Tyr Thr Ala Pro Asp Tyr Ile Phe
                        435                 440                 445

Arg Asn Asp Ser Leu Met Ala Leu Ala Ser Arg Met Gly Glu Leu Asp
                        450                 455                 460

Arg Val Leu Phe Pro Val Asp Ala Arg Gln Ile Asp Trp Gln Leu Tyr
        465                 470                 475                 480

Leu Cys Lys Ile His Leu Gly Gly Leu Asn Arg Tyr Ala Leu Lys Glu
                        485                 490                 495

Arg Lys Leu Tyr Ser Leu Arg Ala Ala Asp Thr Arg Lys Lys Ala Ala
                        500                 505                 510

<210> SEQ ID NO 5
<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 5
atggcgactc aacaacagaa caacggtgca tctgcatccg gcgtcttgga aattcttcgt      60
ggaaagcacg ttcttatcac aggtactacc ggattttttgg gcaaagtggt tctggaaaag    120
ttgattcgta ctgttccgga tattggaggt attcatctgc tgattcgtgg caataaacgt    180
catccagccg ctcgcgaacg tttcctgaac gaaattgcgt cctcctccgt cttcgaacgt    240
ttgcgtcacg atgataatga agccttcgag accttcttgg aagaacgtgt tcactgtatt    300
accggtgaga ttactgaatc ccgttttggt ttgacacctg agcgttttcg tgctttggcc    360
ggtcaggttg acgcttttat tcatagcgct gcaagcgtga acttcgtga gcaattggat    420 aaagccctga aaatcaacac cttgtgtctt gaaaatgttg ctgcacttgc agaattgaac    480
```

-continued

```
tccgctatgg cggtcattca ggtttccact tgttacgtta acggtaaaac ctccggtcaa    540
attaccgaat ccgtcattaa atcggctggc gaatccattc cccgttccac tgacggttac    600
tacgagatcg aagaattggt ccatctgttg aagacaaga tttccgatgt aaagctcgt     660 tactccggcc gtgttatggg gaaaaaattg gttgatttgg gtattcgtga ggccaataat    720
tacggatggt ccgacaccta cacattcacc aaatggttgg gtgaacaact gctgatgaag    780
gccttgtctg gtcgttcttt gactattgtg cgtccctcta ttattgagtc cgctttggaa    840
gaaccttccc ctggttggat cgaaggcgtt aaagttgccg atgccattat cttggcttat    900
gcccgtgaaa aagttagcct gttccctgga aaacgttccg gcattattga ttttattcct    960
gtcgatttgg ttgcgaactc catcatcttg tctctggctg aggcgttgtc tggttctggt   1020
caacgtcgta tttatcaatg ttgcagcggt ggttctaatc caatctccct gggtaagttc   1080
tttgattatt tgaacgccga ggctaagacc aactatgctg cctacgatca actgttttat   1140
cgtcgtccta ctaaaccttt cgtcgccgtg aaccgtaaat tgtttgacgt tgttgttggt   1200
gtcatgcgtg ttgtcctttc tattgcccgc aaagctatgc gtttggctgg tgtaaatcgt   1260
gagttgaaag tgcttaagaa ccttgatacg acccgtaaac ttgcaaccat ttttggcttc   1320
tatactgctc ccgactatat cttccgtaac gatagcttga tggccctggc tcagcgtatg   1380
ggtgaattgg atcgtgttct tttcccagtt gatgctcgtc aaattgattg gcagttgtac   1440
ttgtgtaaaa ttcatttgcg tggtctgaac cgttacgctt tgaagggccg taaactgtat   1500
tcttcgcgtg ctgctgatac tgacgatgaa accgcctaa                          1539
```

```
<210> SEQ ID NO 6
<211> LENGTH: 512
<212> TYPE: PRT
<213> ORGANISM: Artificial Sequence
<220> FEATURE:
<223> OTHER INFORMATION: Synthetic polypeptide

<400> SEQUENCE: 6

Met Ala Thr Gln Gln Gln Asn Asn Gly Ala Ser Ala Ser Gly Val Leu
1               5                   10                  15

Glu Ile Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Arg
                85                  90                  95

Val His Cys Ile Thr Gly Glu Ile Thr Glu Ser Arg Phe Gly Leu Thr
            100                 105                 110

Pro Glu Arg Phe Arg Ala Leu Ala Gly Gln Val Asp Ala Phe Ile His
        115                 120                 125

Ser Ala Ala Ser Val Asn Phe Arg Glu Gln Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175
```

```
Thr Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Arg
    210                 215                 220

Val Met Gly Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Phe Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Phe Asp Tyr Leu Asn Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Gly
385                 390                 395                 400

Val Met Arg Val Val Leu Ser Ile Ala Arg Lys Ala Met Arg Leu Ala
                405                 410                 415

Gly Val Asn Arg Glu Leu Lys Val Leu Lys Asn Leu Asp Thr Thr Arg
            420                 425                 430

Lys Leu Ala Thr Ile Phe Gly Phe Tyr Thr Ala Pro Asp Tyr Ile Phe
        435                 440                 445

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Arg Gly Leu Asn Arg Tyr Ala Leu Lys Gly
                485                 490                 495

Arg Lys Leu Tyr Ser Ser Arg Ala Ala Asp Thr Asp Asp Glu Thr Ala
            500                 505                 510

<210> SEQ ID NO 7
<211> LENGTH: 906
<212> TYPE: DNA
<213> ORGANISM: Artificial Sequence
<220> FEATURE:
<223> OTHER INFORMATION: Synthetic polynucleotide

<400> SEQUENCE: 7
atgaccttag agtggaaacc aaaaccgaaa ttacctcagc ttcttgacga ccacttcggc      60
ctgcatggtt tagtattccg cagaacgttt gccataagaa gctacgaagt aggaccagat     120
cgttctacct ctatacttgc tgtgatgaat catatgcagg aagccacgtt aaatcacgca     180
```

```
aagagcgtcg ggatccttgg ggacggattc ggcaccacat tggaaatgag taagcgggac    240
ctgatgtggg ttgttcgtcg tacccacgta gcggtcgaac ggtatccaac atggggcgat    300
actgttgaag tggagtgctg gattggcgct tccggaaaca acggaatgcg cagagatttt    360
ctggtgcggg actgtaaaac tggggaaatc ttaacgcgct gtacctccct gtccgttctg    420
atgaacacgc gtacccggag attaagtacg attccggacg aagtccgtgg tgaaatcggt    480
cccgctttta ttgacaacgt ggcggtaaaa gacgacgaga tcaaaaagtt gcagaaattg    540
aacgattcca cagcagatta catacagggc ggtcttacgc cccgttggaa cgacttggat    600
gtgaatcagc acgtaaataa ccttaaatat gtggcgtggg tgttcgagac cgttcccgac    660 tctattttg aaagtcacca catttccagc tttacgctgg agtacagacg cgagtgtacg     720
cgcgattccg ttttacgttc cctcaccacg gtgtctggcg gatcttccga agctgggtta    780
gtgtgtgatc acttgctgca acttgaaggc ggaagtgaag ttcttcgggc ccgcacggaa    840
tggcgtccca aactgaccga ttccttccgc ggaatatcag taattccggc cgagccgcgg    900
gtataa                                                              906
```

<210> SEQ ID NO 8
<211> LENGTH: 301
<212> TYPE: PRT
<213> ORGANISM: Artificial Sequence
<220> FEATURE:
<223> OTHER INFORMATION: Synthetic polypeptide

<400> SEQUENCE: 8

```
Met Thr Leu Glu Trp Lys Pro Lys Pro Lys Leu Pro Gln Leu Leu Asp
1               5                   10                  15

Asp His Phe Gly Leu His Gly Leu Val Phe Arg Arg Thr Phe Ala Ile
                20                  25                  30

Arg Ser Tyr Glu Val Gly Pro Asp Arg Ser Thr Ser Ile Leu Ala Val
            35                  40                  45

Met Asn His Met Gln Glu Ala Thr Leu Asn His Ala Lys Ser Val Gly
        50                  55                  60

Ile Leu Gly Asp Gly Phe Gly Thr Thr Leu Glu Met Ser Lys Arg Asp
65                  70                  75                  80

Leu Met Trp Val Val Arg Arg Thr His Val Ala Val Glu Arg Tyr Pro
                85                  90                  95

Thr Trp Gly Asp Thr Val Glu Val Glu Cys Trp Ile Gly Ala Ser Gly
            100                 105                 110

Asn Asn Gly Met Arg Arg Asp Phe Leu Val Arg Asp Cys Lys Thr Gly
        115                 120                 125

Glu Ile Leu Thr Arg Cys Thr Ser Leu Ser Val Leu Met Asn Thr Arg
    130                 135                 140

Thr Arg Arg Leu Ser Thr Ile Pro Asp Glu Val Arg Gly Glu Ile Gly
145                 150                 155                 160

Pro Ala Phe Ile Asp Asn Val Ala Val Lys Asp Glu Ile Lys Lys
                165                 170                 175

Leu Gln Lys Leu Asn Asp Ser Thr Ala Asp Tyr Ile Gln Gly Gly Leu
            180                 185                 190

Thr Pro Arg Trp Asn Asp Leu Asp Val Asn Gln His Val Asn Asn Leu
        195                 200                 205

Lys Tyr Val Ala Trp Val Phe Glu Thr Val Pro Asp Ser Ile Phe Glu
    210                 215                 220

Ser His His Ile Ser Ser Phe Thr Leu Glu Tyr Arg Arg Glu Cys Thr
```

```
                    225                 230                 235                 240

Arg Asp Ser Val Leu Arg Ser Leu Thr Thr Val Ser Gly Gly Ser Ser
                245                 250                 255

Glu Ala Gly Leu Val Cys Asp His Leu Leu Gln Leu Glu Gly Gly Ser
            260                 265                 270

Glu Val Leu Arg Ala Arg Thr Glu Trp Arg Pro Lys Leu Thr Asp Ser
        275                 280                 285

Phe Arg Gly Ile Ser Val Ile Pro Ala Glu Pro Arg Val
    290                 295                 300

<210> SEQ ID NO 9
<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 9
atggcgactc aacaacagca gaacggtgca tctgcatccg gcgtcttgga caacttcgt         60 ggaaagcacg ttcttatcac aggtactacc ggattttttgg gcaaagtggt tctggaaaag    120
ttgattcgta ctgttccgga tattggaggt attcatctgc tgattcgtgg caataaacgt     180
catccagccg ctcgtgaacg tttcctgaac gaaattgcgt cctcctccgt cttcgaacgt    240
ttgcgtcacg atgataatga agccttcgag accttcttgg aagaacgtgt tcactgtatt    300
accggtgagg ttactgaatc ccgttttggt ttgacacctg agcgttttcg tgctttggcc    360
ggtcaggttg acgcttttat taacagcgct gcaagcgtga ttttcgtga gcaattggat    420 aaagccctga aaatcaacac cttgtgtctt gaaaatgttg ctgctcttgc agaattgaac    480
tccgctatgg cggtcattca ggtttccact tgttacgtta acggtaaaaa ctccggtcaa    540
attaccgaat ccgtcattaa atcggctggc gaatccattc ccgttccac tgacggttac    600 tacgagatcg aagaattggt ccatctgttg caagacaaga tttccgatgt aaagctcgt     660 tactccggca agttctggaa gaaaaaattg gttgatttgg gtattcgtga ggccaataat    720
tacggatggc ccgacaccta cacattcacc aaatggttgg gtgaacaact gctgatgaag    780
gccttgtctg gtcgttcttt gactattgtg cgtccctcta ttattgagtc cgcttttggaa    840 gaaccttccc ctggttggat cgaaggcgtt aaagttgccg atgccattat cttggcttat    900
gcccgtgaaa aagttagcct gttccctgga aaacgttccg gcattattga tgttattcct    960 gtcgattttgg ttgcgaactc catcatcttg tctctggctg aggcgttgtc tggttctggt    1020
caacgtcgta tttatcaatg ttgcagcggt ggttctaatc caatctccct gggtaagttc    1080
attgattatt tgatggccga ggctaagacc aactatgctg cctacgatca actgttttat    1140
cgtcgtccta ctaaacctt cgtcgccgtg aaccgtaaat gtttgacgt tgttgttggt    1200 ggtatgcgtg ttgtccttttc tattgccggt aaagctatgc gtttggctgg tgtaaatcgt    1260
gagttgaaag tgcttaagaa cccttgatacg acccgtaaac ttgcaaccat ttttggcttc    1320
tatactgctc ccgactatat cttccgtaac gatagcttga tggccctggc tcagcgtatg    1380
ggtgaattgg atcgtgttct tttcccagtt gatgctcgtc aaattgattg gcagttgtac    1440
ttgtgtaaaa ttcatttggg tggtctgaac cgttacgctt gaaggaacg taaactgtat    1500 tcttcgcgtg ctgctgatac tgacgataaa accgcctaa                             1539

<210> SEQ ID NO 10
<211> LENGTH: 512
```

```
<212> TYPE: PRT
<213> ORGANISM: Artificial Sequence
<220> FEATURE:
<223> OTHER INFORMATION: Synthetic polypeptide

<400> SEQUENCE: 10

Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
                35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
            115                 120                 125

Ser Ala Ala Ser Val Ser Phe Arg Glu Gln Leu Asp Lys Ala Leu Lys
130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380
```

```
Lys Pro Phe Val Ala Val Asn Arg Lys Leu Phe Asp Val Val Gly
385                 390                 395                 400

Gly Met Arg Val Val Leu Ser Ile Ala Gly Lys Ala Met Arg Leu Ala
            405                 410                 415

Gly Val Asn Arg Glu Leu Lys Val Leu Lys Asn Leu Asp Thr Thr Arg
            420                 425                 430

Lys Leu Ala Thr Ile Phe Gly Phe Tyr Thr Ala Pro Asp Tyr Ile Phe
            435                 440                 445

Arg Asn Asp Ser Leu Met Ala Leu Ala Gln Arg Met Gly Glu Leu Asp
450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
            485                 490                 495

Arg Lys Leu Tyr Ser Ser Arg Ala Ala Asp Thr Asp Lys Thr Ala
            500                 505                 510
```

<210> SEQ ID NO 11
<211> LENGTH: 5905
<212> TYPE: DNA
<213> ORGANISM: Artificial Sequence
<220> FEATURE:
<223> OTHER INFORMATION: Synthetic polynucleotide

<400> SEQUENCE: 11

```
ggcatccgct tacagacaag ctgtgaccgt ctccgggagc tgcatgtgtc agaggttttc      60
accgtcatca ccgaaacgcg cgaggcagca gatcaattcg cgcgcgaagg cgaagcggca     120
tgcatttacg ttgacaccat cgaatggtgc aaaacctttc gcggtatggc atgatagcgc     180
ccggaagaga gtcaattcag ggtggtgaat gtgaaaccag taacgttata cgatgtcgca     240
gagtatgccg gtgtctctta tcagaccgtt tccgcgtgg tgaaccaggc cagccacgtt      300
tctgcgaaaa cgcgggaaaa agtggaagcg gcgatggcgg agctgaatta cattcccaac     360
cgcgtggcac aacaactggc gggcaaacag tcgttgctga ttggcgttgc cacctccagt     420
ctggccctgc acgcgccgtc gcaaattgtc gcggcgatta atctcgcgc cgatcaactg      480
ggtgccagcg tggtggtgtc gatggtagaa cgaagcggcg tcgaagcctg taaagcggcg     540
gtgcacaatc ttctcgcgca acgcgtcagt gggctgatca ttaactatcc gctggatgac     600
caggatgcca ttgctgtgga agctgcctgc actaatgttc cggcgttatt tcttgatgtc     660
tctgaccaga cacccatcaa cagtattatt ttctcccatg aagacggtac gcgactgggc     720
gtggagcatc tggtcgcatt gggtcaccag caaatcgcgc tgttagcggg cccattaagt     780
tctgtctcgg cgcgtctgcg tctggctggc tggcataaat atctcactcg caatcaaatt     840
cagccgatag cggaacggga aggcgactgg agtgccatgt ccggttttca acaaaccatg     900
caaatgctga atgagggcat cgttcccact gcgatgctgg ttgccaacga tcagatggcg     960
ctgggcgcaa tgcgcgccat taccgagtcc gggctgcgcg ttggtgcgga tatctcggta    1020
gtgggatacg acgataccga agacagctca tgttatatcc cgccgttaac caccatcaaa    1080
caggattttc gcctgctggg gcaaaccagc gtggaccgct tgctgcaact ctctcagggc    1140
caggcggtga agggcaatca gctgttgccc gtctcactgg tgaaaagaaa accacccctg    1200
gcgcccaata cgcaaaccgc ctctccccgc gcgttggccg attattaat gcagctggca    1260
cgacaggttt cccgactgga aagcgggcag tgagcgcaac gcaattaatg taagttagcg    1320
cgaattgatc tggtttgaca gcttatcatc gactgcacgg tgcaccaatg cttctggcgt    1380
```

```
caggcagcca tcggaagctg tggtatggct gtgcaggtcg taaatcactg cataattcgt   1440
gtcgctcaag gcgcactccc gttctggata atgtttttg cgccgacatc ataacggttc    1500
tggcaaatat tctgaaatga gctgttgaca attaatcatc cggctcgtat aatgtgtgga   1560
attgtgagcg gataacaatt tcacacagga aacagcgccg ctgagaaaaa gcgaagcggc   1620
actgctcttt aacaatttat cagacaatct gtgtgggcac tcgaccggaa ttatcgatta   1680
actttattat taaaaattaa agaggtatat attaatgtat cgattaaata aggaggaata   1740
aaccatggat ccgagctcga gatctgcagc tggtaccata tgggaattcg aagctttcta   1800
gaacaaaaac tcatctcaga gaggatctg aatagcgccg tcgaccatca tcatcatcat    1860
cattgagttt aaacggtctc cagcttggct gttttggcgg atgagagaag attttcagcc   1920
tgatacagat taaatcagaa cgcagaagcg gtctgataaa acagaatttg cctggcggca   1980
gtagcgcggt ggtcccacct gaccccatgc cgaactcaga agtgaaacgc cgtagcgccg   2040
atggtagtgt ggggtctccc catgcgagag tagggaactg ccaggcatca aataaaacga   2100
aaggctcagt cgaaagactg ggcctttcgt tttatctgtt gtttgtcggt gaacgctctc   2160
ctgaggcgcc tgatgcggta ttttctcctt acgcatctgt gcggtatttc acaccgcata   2220
tggtgcactc tcagtacaat ctgctctgat gccgcatagt taagccagcc ccgacacccg   2280
ccaacacccg ctgacgagct tagtaaagcc ctcgctagat tttaatgcgg atgttgcgat   2340
tacttcgcca actattgcga taacaagaaa aagccagcct tcatgatat atctcccaat    2400 ttgtgtaggg cttattatgc acgcttaaaa ataataaaag cagacttgac ctgatagttt   2460
ggctgtgagc aattatgtgc ttagtgcatc taacgcttga gttaagccgc gccgcgaagc   2520
ggcgtcggct tgaacgaatt gttagacatt atttgccgac taccttgtg atctcgcctt    2580 tcacgtagtg gacaaattct tccaactgat ctgcgcgcga ggccaagcga tcttcttctt   2640
gtccaagata agcctgtcta gcttcaagta tgacgggctg atactgggcc ggcaggcgct   2700
ccattgccca gtcggcagcg acatccttcg gcgcgatttt gccggttact gcgctgtacc   2760
aaatgcggga caacgtaagc actacatttc gctcatcgcc agcccagtcg gcggcgagt    2820 tccatagcgt taaggtttca tttagcgcct caaatagatc ctgttcagga accggatcaa   2880
agagttcctc cgccgctgga cctaccaagg caacgctatg ttctcttgct tttgtcagca   2940
agatagccag atcaatgtcg atcgtggctg gctcgaagat acctgcaaga atgtcattgc   3000
gctgccattc tccaaattgc agttcgcgct tagctggata acgccacgga atgatgtcgt   3060
cgtgcacaac aatggtgact tctacagcgc ggagaatctc gctctctcca ggggaagccg   3120
aagtttccaa aaggtcgttg atcaaagctc gccgcgttgt ttcatcaagc cttacggtca   3180
ccgtaaccag caaatcaata tcactgtgtg gcttcaggcc gccatccact gcggagccgt   3240
acaaatgtac ggccagcaac gtcggttcga gatggcgctc gatgacgcca actacctctg   3300
atagttgagt cgatacttcg gcgatcaccg cttccctcat gatgtttaac tttgttttag   3360
ggcgactgcc ctgctgcgta acatcgttgc tgctccataa catcaaacat cgacccacgg   3420
cgtaacgcgc ttgctgcttg gatgcccgag gcatagactg tacccaaaaa aacagtcat    3480 aacaagccat gaaaaccgcc actgcgccgt taccaccgct gcgttcggtc aaggttctgg   3540
accagttgcg tgagcgcata cgctacttgc attacagctt acgaaccgaa caggcttatg   3600
tccactgggt tcgtgcctc atccgtttcc acggtgtgcg tcaccggca accttgggca     3660 gcagcgaagt cgaggcattt ctgtcctggc tggcgaacga gcgcaaggtt tcggtctcca   3720
```

```
cgcatcgtca ggcattggcg gccttgctgt tcttctacgg caaggtgctg tgcacggatc    3780
tgccctggct tcaggagatc ggaagacctc ggccgtcgcg gcgcttgccg gtggtgctga    3840
ccccggatga agtggttcgc atcctcggtt ttctggaagg cgagcatcgt tgttcgccc     3900 agcttctgta tggaacgggc atgcggatca gtgagggttt gcaactgcgg gtcaaggatc    3960
tggatttcga tcacggcacg atcatcgtgc gggagggcaa gggctccaag gatcgggcct    4020
tgatgttacc cgagagcttg gcacccagcc tgcgcgagca ggggaattaa ttcccacggg    4080
ttttgctgcc cgcaaacggg ctgttctggt gttgctagtt tgttatcaga atcgcagatc    4140
cggcttcagc cggtttgccg gctgaaagcg ctatttcttc cagaattgcc atgattttt     4200 ccccacggga ggcgtcactg gctcccgtgt tgtcggcagc tttgattcga taagcagcat    4260
cgcctgtttc aggctgtcta tgtgtgactg ttgagctgta acaagttgtc tcaggtgttc    4320
aatttcatgt tctagttgct ttgttttact ggtttcacct gttctattag gtgttacatg    4380
ctgttcatct gttacattgt cgatctgttc atggtgaaca gctttgaatg caccaaaaac    4440
tcgtaaaagc tctgatgtat ctatcttttt tacaccgttt tcatctgtgc atatggacag    4500
ttttcccttt gatatgtaac ggtgaacagt tgttctactt tgtttgtta gtcttgatgc     4560 ttcactgata gatacaagag ccataagaac ctcagatcct tccgtattta gccagtatgt    4620
tctctagtgt ggttcgttgt ttttgcgtga gccatgagaa cgaaccattg agatcatact    4680
tactttgcat gtcactcaaa aatttttgcct caaaactggt gagctgaatt tttgcagtta    4740
aagcatcgtg tagtgttttt cttagtccgt tatgtaggta ggaatctgat gtaatggttg    4800
ttggtatttt gtcaccattc attttatct ggttgttctc aagttcggtt acagagatcca    4860 tttgtctatc tagttcaact tggaaaatca acgtatcagt cgggcggcct cgcttatcaa    4920
ccaccaattt catattgctg taagtgttta aatcttact tattggtttc aaaacccatt     4980
ggttaagcct tttaaactca tggtagttat tttcaagcat taacatgaac ttaaattcat    5040
caaggctaat ctctatattt gccttgtgag ttttctttg tgttagttct tttaataacc     5100
actcataaat cctcatagag tatttgtttt caaaagactt aacatgttcc agattatatt    5160
ttatgaattt tttaactgg aaaagataag gcaatatctc ttcactaaaa actaattcta     5220 attttttcgct tgagaacttg gcatagtttg tccactggaa aatctcaaag cctttaacca    5280
aaggattcct gatttccaca gttctcgtca tcagctctct ggttgcttta gctaatacac    5340
cataagcatt ttccctactg atgttcatca tctgagcgta ttggttataa gtgaacgata    5400
ccgtccgttc tttccttgta gggttttcaa tcgtggggtt gagtagtgcc acacagcata    5460
aaattagctt ggtttcatgc tccgttaagt catagcgact aatcgctagt tcatttgctt    5520
tgaaaacaac taattcagac atacatctca attggtctag gtgattttaa tcactatacc    5580
aattgagatg ggctagtcaa tgataattac tagtcctttt cctttgagtt gtgggtatct    5640
gtaaattctg ctagaccttt gctggaaaac ttgtaaattc tgctagaccc tctgtaaatt    5700
ccgctagacc tttgtgtgtt ttttttgttt atattcaagt ggttataatt tatagaataa    5760
agaaagaata aaaaaagata aaagaatag atcccagccc tgtgtataac tcactacttt    5820
agtcagttcc gcagtattac aaaaggatgt cgcaaacgct gtttgctcct ctacaaaaca    5880
gaccttaaaa ccctaaaggc ttaag                                          5905
```

<210> SEQ ID NO 12
<211> LENGTH: 64
<212> TYPE: DNA
<213> ORGANISM: Artificial Sequence

```
<220> FEATURE:
<223> OTHER INFORMATION: Synthetic polynucleotide

<400> SEQUENCE: 12
ggcaaggtgt tctggtcggc gcatagctga gataaatgct tcaataatat tgaaaaagga      60
agag                                                                   64

<210> SEQ ID NO 13
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 13
aggcaaagaa aacccggcgc tgaggccggg ttaccaatgc ttaatcagtg aggca           55

<210> SEQ ID NO 14
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 14
gaccttaaaa ccctaaaggc ttaagggcat cdcgcttaca gaca                      44

<210> SEQ ID NO 15
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 15
ggagaaaata ccgcatcagg cgcctcagga gagcgttcac cgac                      44

<210> SEQ ID NO 16
<211> LENGTH: 682
<212> TYPE: DNA
<213> ORGANISM: Artificial Sequence
<220> FEATURE:
<223> OTHER INFORMATION: Synthetic polynucleotide

<400> SEQUENCE: 16
gatatctcgg tagtgggata cgacgatacc gaagacagct catgttatat cccgccgtta     60
accaccatca acaggatttt tcgcctgctg gggcaaacca gcgtggaccg cttgctgcaa    120
ctctctcagg gccaggcggt gaagggcaat cagctgttgc ccgtctcact ggtgaaaaga    180 aaaccaccc tggcgcccaa tacgcaaacc gcctctcccc gcgcgttggc cgattcatta    240
atgcagctgg cacgacaggt ttcccgactg gaaagcgggc agtaataatt taaattggtt    300
tgacagctta tcatcgactg cacggtgcac caatgcttct ggcgtcaggc agccatcgga    360
agctgtggta tggctgtgca ggtcgtaaat cactgcataa ttcgtgtcgc tcaaggcgca    420
ctcccgttct ggataatgtt ttttgcgccg acataattgt gagcgctcac aatttctgaa    480
atgagctgtt gacaattaat catccggctc gtataatgtg tggaattgtg agcggataac    540
aatttcacac aggaaacagc gccgctgaga aaagcgaag cggcactgct ctttaacaat    600
ttatcagaca atctgtgtgg gcactcgacc ggaattatcg attaacttta ttattaaaaa    660
ttaaaggagg aataaaccat gg                                             682
```

<210> SEQ ID NO 17
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 17
taaaccatgg cgactcaaca acagaaca                                28

<210> SEQ ID NO 18
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 18
ctatgtcgac ttaggcggtt tcatcgtcag tatc                         34

<210> SEQ ID NO 19
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 19
gtcggtgaac gctctcctga ggattccggg gatccgtcga cc                42

<210> SEQ ID NO 20
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 20
aacctcaggc gaaaaaaccc cgccgaagcg gggttttttg cgtgtaggct ggagctgctt    60

<210> SEQ ID NO 21
<211> LENGTH: 160
<212> TYPE: DNA
<213> ORGANISM: Artificial Sequence
<220> FEATURE:
<223> OTHER INFORMATION: Synthetic polynucleotide

<400> SEQUENCE: 21
cgtcaaaatc tcgggaaaca ggtgtaccct cagcattaaa ttcgaggttg gcaggttgta    60
tggagtagtg tttcacgtaa gttactcgtc ttacaggcgg tggctcgatc ttagcgatgt   120
gtgtaaggct gcgcaaattt attccgggga tccgtcgacc                        160

<210> SEQ ID NO 22
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 22
gtacacttgt acgccgaaca agtccgatca gccatttaat agagccgcat caggcgcctc    60

<210> SEQ ID NO 23
<211> LENGTH: 53

```
<212> TYPE: DNA
<213> ORGANISM: Artificial Sequence
<220> FEATURE:
<223> OTHER INFORMATION: Synthetic polynucleotide

<400> SEQUENCE: 23
tggttccctt tttcacatca ttgacaatcg ccgattccgg ggatccgtcg acc         53

<210> SEQ ID NO 24
<211> LENGTH: 160
<212> TYPE: DNA
<213> ORGANISM: Artificial Sequence
<220> FEATURE:
<223> OTHER INFORMATION: Synthetic polynucleotide

<400> SEQUENCE: 24
attactccag aatgcagcgc aaggcgagga gtatccccgt ctcatctctc tggtttcagg   60
gttacggtgc gttggcagga tttaacgcgt acgtcttttc agaaggaaat cgacaaagcg  120
ggaagtttgc ctggaactgg tgtaggctgg agctgcttcg                        160

<210> SEQ ID NO 25
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 25
ggctgatcgg acttgttcgg cgtacaag                                      28

<210> SEQ ID NO 26
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 26
cggcgattgt caatgatgtg aaaaagg                                       27

<210> SEQ ID NO 27
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 27
cgtcaaaatc tcgggaaaca ggtg                                          24

<210> SEQ ID NO 28
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 28
attactccag aatgcagcgc aagg                                          24

<210> SEQ ID NO 29
<211> LENGTH: 505
<212> TYPE: PRT
<213> ORGANISM: Hahella chejuensis
```

-continued

<400> SEQUENCE: 29

```
Met Lys Gln Ser Leu Thr Leu Thr Ala Phe Ala Asn Lys Asn Val Leu
1               5                   10                  15

Ile Thr Gly Thr Thr Gly Phe Val Gly Lys Val Val Leu Glu Lys Leu
            20                  25                  30

Leu Arg Ser Val Pro Thr Ile Gly Lys Ile Tyr Leu Leu Ile Arg Gly
        35                  40                  45

Asn Ser Lys Asn Pro Thr Ala Arg Lys Arg Phe Gln Asn Glu Ile Ala
    50                  55                  60

Thr Ser Ser Ile Phe Asp Thr Leu Lys Ala Ser Gln Gly Ser Arg Phe
65                  70                  75                  80

Glu Glu Leu Cys Glu Thr Arg Ile His Cys Val Thr Gly Glu Val Thr
                85                  90                  95

Glu Pro Leu Phe Gly Leu Ser Glu Lys Asp Phe Thr Asp Leu Ala Ala
            100                 105                 110

Asp Ile Asp Val Ile Asn Ser Ala Ala Ser Val Asn Phe Arg Glu
        115                 120                 125

Ala Leu Asp Gln Ala Leu Thr Ile Asn Thr Leu Cys Leu Lys Asn Ile
    130                 135                 140

Ile Glu Leu Ser Arg Arg Ala Ala Asp Cys Pro Val Val Gln Val Ser
145                 150                 155                 160

Thr Cys Tyr Val Asn Gly Phe Asn Gln Gly Val Met Glu Glu Ile
                165                 170                 175

Val Ser Pro Ala Gly Glu Arg Ile Glu Arg Ser Glu Arg Gly Tyr Tyr
            180                 185                 190

Glu Val Glu Pro Leu Ile Ala Arg Leu Leu Gln Asp Val Glu Gln Val
        195                 200                 205

Ser Ala Ala Ala Asp Asp His Ser Arg Glu Lys Asp Leu Ile Asp
    210                 215                 220

Leu Gly Ile Lys Glu Ala Asn Lys Tyr Gly Trp Asn Asp Thr Tyr Thr
225                 230                 235                 240

Phe Thr Lys Trp Met Gly Glu Gln Leu Leu Met Lys Glu Leu Tyr Gly
                245                 250                 255

Lys Thr Leu Thr Ile Leu Arg Pro Ser Ile Val Glu Ser Thr Leu Leu
            260                 265                 270

Gly Pro Ala Pro Gly Trp Ile Glu Gly Val Lys Val Ala Asp Ala Ile
        275                 280                 285

Ile Leu Ala Tyr Ala Arg Glu Lys Val Ser Leu Phe Pro Gly Lys Lys
    290                 295                 300

Asn Ala Val Ile Asp Ile Pro Ala Asp Leu Val Ala Asn Ser Ile
305                 310                 315                 320

Ile Leu Ser Ala Thr Glu Ala Leu Leu Asp Ser Gly Ala His Arg Ile
                325                 330                 335

Tyr Gln Cys Cys Ser Ser Glu Val Asn Pro Ile Arg Ile Arg Glu Val
            340                 345                 350

Ile Gly His Val Gln Gln Glu Ala Glu His Asn Tyr Gln Thr His Asp
        355                 360                 365

Lys Leu Phe Tyr Arg Lys Pro Lys Lys Pro Phe Val Met Ile Pro Gly
    370                 375                 380

Ala Val Phe His Ala Leu Met Ala Ile Ser Phe His Met Leu Lys Trp
385                 390                 395                 400

Ser Ser Arg Leu Gln Ser Leu Phe Gly Arg Lys Ala Ser Gly Arg Lys
                405                 410                 415
```

Leu Ser Asn Met Glu Thr Thr Met Lys Leu Ser Lys Val Phe Ser Phe
            420                 425                 430

Tyr Thr Ser Pro Ser Tyr Thr Phe Ser Asn Arg Arg Leu Gln Glu Leu
            435                 440                 445

Ser Thr Arg Leu Gly Glu Tyr Asp Gln Ser Glu Phe Pro Val Asn Ala
450                 455                 460

Gly Met Tyr Asp Trp Ala His Tyr Leu Arg Glu Val His Val Ala Gly
465                 470                 475                 480

Leu Asn Lys Tyr Ala Leu Arg Pro Lys Val Val Lys Met Asn Pro Pro
                485                 490                 495

Ala Ala Lys Pro Arg Ser Arg Ala Ala
            500                 505

<210> SEQ ID NO 30
<211> LENGTH: 769
<212> TYPE: PRT
<213> ORGANISM: Marine actinobacterium PHSC20C1

<400> SEQUENCE: 30

Met Thr Thr Ile Arg Ala Leu Thr Thr Glu His Val Phe Leu Thr Gly
1               5                   10                  15

Ala Thr Gly Phe Val Gly Gln Ala Ile Leu Glu Arg Leu Leu Ser Ser
            20                  25                  30

His Pro Glu Thr Arg Ile Ser Ile Leu Val Arg Gly Lys Gly Ala Thr
        35                  40                  45

Thr Gly Glu Gly Arg Leu Thr Asn Leu Met Arg Lys Pro Val Phe Ala
50                  55                  60

Gln Trp Met Glu Ser Leu Gly Lys Glu Gln Ala Leu Ala Glu Val Ala
65                  70                  75                  80

Arg Arg Val Thr Val Ile Glu Gly Ser Leu Thr Asp Val Gly Thr Leu
                85                  90                  95

Pro Asp Asp Ile Asp Ile Val Ile His Gly Ala Ser Thr Val Ser Phe
            100                 105                 110

Asp Pro Pro Ile Asp Glu Ala Phe Asp Thr Asn Val Gly Gly Ala Thr
        115                 120                 125

Gly Ile Tyr Thr Ala Leu Leu Ala Ser Lys Ser Arg Pro His Val Val
130                 135                 140

His Ile Ser Thr Ala Tyr Val Gly Gly Ile Arg Lys Gly Ile Val Pro
145                 150                 155                 160

Glu Ala Ser Leu Val His Asn Val Asp Trp Arg Ala Glu Tyr Glu Ala
                165                 170                 175

Ala Arg Thr Ala Arg Thr Arg Val Glu Phe Glu Ser Arg Gln Pro Glu
            180                 185                 190

Ala Leu Arg Ala Gln Leu Thr Ala Ala Lys Ala Arg His Gly Lys Ala
        195                 200                 205

Gly Pro Gln Ala Val Ala Gln Phe Thr Glu Ala Ala Arg Ala Glu Trp
210                 215                 220

Val His Asp Arg Leu Val Asp Tyr Gly Arg Met Arg Ala Glu Ser Leu
225                 230                 235                 240

Gly Trp Thr Asp Val Tyr Thr Leu Thr Lys Ala Phe Ala Glu Arg Val
                245                 250                 255

Ala Glu Glu Met Trp Ala Gln Ala Gly His Arg Leu Ser Val Val Arg
            260                 265                 270

Pro Ser Ile Ile Glu Ser Ala Leu His His Pro Phe Pro Gly Trp Ile

```
              275                 280                 285
Asp Gly Phe Lys Val Ala Asp Pro Leu Ile Leu Ala Tyr Gly Arg Gly
    290                 295                 300

Gln Leu Pro Asp Phe Pro Gly Leu Pro Asp Ser Ile Leu Asp Val Ile
305                 310                 315                 320

Pro Val Asp Phe Val Val Asn Ala Thr Leu Ala Ala Ala Ala Ala Lys
                325                 330                 335

Ala Asp Pro Lys Ala Pro Arg Tyr Tyr His Val Ser Ser Gly Ala Ser
            340                 345                 350

Asn Pro Leu Pro Phe His Arg Met Tyr Glu Asn Val Asn Ala Tyr Phe
        355                 360                 365

Thr Ala Asn Pro Leu Pro Ala Glu Asp Gly Glu Ile Ser Val Pro Leu
    370                 375                 380

Trp Arg Phe Pro Gly Gly Gln Arg Val Glu Arg Ala Leu Val Lys Arg
385                 390                 395                 400

Glu Arg Gln Ala Ala Arg Ala Glu Arg Val Ile Thr Arg Met Pro Thr
                405                 410                 415

Thr Pro Arg Thr Arg Arg Trp Leu Asp Glu Val Lys Ser Gly Gln His
            420                 425                 430

Gln Leu Glu Val Leu Arg Ala Phe Thr Asn Leu Tyr Arg Ala Tyr Val
        435                 440                 445

Gln Thr Glu Ile Ile Phe Asp Asp Ala Asn Thr Arg Glu Leu Leu Ala
    450                 455                 460

Ser Leu Pro Lys Lys Thr Ala His Ser Ala Arg Phe Asp Val Thr Glu
465                 470                 475                 480

Ile Asp Trp Glu Asn Tyr Phe Gln Gln Val His Phe Pro Ala Ile Thr
                485                 490                 495

Thr Leu Thr Arg Ala Phe Ala Asn Arg Pro Ala Ala Lys Thr Arg Thr
            500                 505                 510

Ala Lys Lys Leu Pro Glu Arg Thr Asp Val Val Ala Val Phe Asp Leu
        515                 520                 525

Glu Gly Thr Val Val Asp Ser Asn Leu Val Lys Gln Tyr Leu Leu Leu
    530                 535                 540

Trp Gly Gly Thr Val Pro Arg Ala Lys Val Leu His Asp Leu Ala Asn
545                 550                 555                 560

Phe Thr Phe Ser Leu Arg Lys Tyr Met Arg Ala Glu Arg Arg Asp Arg
                565                 570                 575

Gly Glu Phe Ile Arg Thr Phe Met Arg Arg Tyr Glu Gly Phe Lys Ile
            580                 585                 590

Ala Glu Ile Glu Arg Met Val Arg Gly Ser Phe Gly Arg Ala Met Met
        595                 600                 605

Arg Arg Val Met Pro Asp Ala Leu Arg Val Gln Glu His Arg Asp
    610                 615                 620

Ala Gly His Arg Thr Ile Leu Val Thr Gly Thr Ile Asp Leu Met Val
625                 630                 635                 640

Thr Pro Phe Leu Pro Tyr Phe Asp Glu Val Val Ala Gly Arg Met His
                645                 650                 655

Glu Arg Asp Gly Ile Leu Thr Gly Phe Leu Ala Asp Pro Pro Leu Val
            660                 665                 670

Asp Glu Ala Arg Ala Ala Trp Leu Arg His Tyr Ala Asp Gln Asn Gly
        675                 680                 685

Phe Asn Leu Thr Gln Ser Tyr Gly Tyr Gly Asp Ser His Ala Asp Leu
    690                 695                 700
```

Met Trp Leu Gln Leu Val Gly Asn Pro Ser Ala Val Asn Pro Asp Val
705                 710                 715                 720

Asn Leu Tyr Lys His Ala Gln Glu Lys Arg Trp Asn Val Leu Asp Trp
                725                 730                 735

Lys Arg Arg Ser Pro Asn Ser Arg Ile Pro Arg Pro Arg Asp Ala Ala
            740                 745                 750

Ala Ala Thr Gln Glu Gly Asp Gly His Ser Ser Thr Pro Ser Ser Gln
        755                 760                 765

Ser

<210> SEQ ID NO 31
<211> LENGTH: 542
<212> TYPE: PRT
<213> ORGANISM: Unknown
<220> FEATURE:
<223> OTHER INFORMATION: Synthetic polypeptide encoded by DNA from NCBI
      locus EP750655 from marine metagenome collection

<400> SEQUENCE: 31

Met Ile Arg Glu Asn Leu Ser Gly Lys Arg Ile Ala Ile Thr Gly Ser
1               5                   10                  15

Thr Gly Phe Leu Gly Thr Ala Leu Val Glu Arg Phe Leu Arg Ser Val
            20                  25                  30

Pro Asp Cys Glu Leu Val Leu Leu Val Arg Pro Gly Arg Arg Gly Ala
        35                  40                  45

Glu His Arg Val Lys Arg Asp Ile Leu Lys Asn Asp Ala Phe Asp Arg
    50                  55                  60

Leu Arg Asp Ala Phe Lys Glu Asp Pro Ile Ala Ala Gly Gly Leu Asp
65                  70                  75                  80

Gly Glu Thr Phe Asp Glu Met Cys Asp Arg Arg Val Phe Ala Val Lys
                85                  90                  95

Gly Asp Val Gly Gln Asp Gly Leu Gly Leu Asp Asp Ala Gly Leu Thr
            100                 105                 110

Leu Phe Ser Thr Val Asp Ile Ala Val His Ser Ala Ala Thr Val Ser
        115                 120                 125

Phe Asp Ser Ala Leu Asp Asp Ala Val Gln Val Asn Leu Leu Gly Pro
    130                 135                 140

Gly Arg Val Ala Ala Leu Arg Val Ala Ala Glu Ala Arg Thr Glu
145                 150                 155                 160

Pro Thr Pro Gly Gly Leu Ala Pro Gly Glu Lys Ala Tyr Leu Val Ala
                165                 170                 175

Val Ser Thr Cys Tyr Val Ala Gly Ser Arg Arg Gly Asn Ala Pro Glu
            180                 185                 190

Gln Met Val Gln Asp Ser Pro Phe Phe Val Asp Val Asp Trp Arg Ala
        195                 200                 205

Glu Ala His Asn Ala Phe Gln Ala Arg Lys Asp Ala Glu Gln Ala Ser
    210                 215                 220

Arg Thr Pro Gln Arg Leu Lys Ala Leu Glu Ala Asp Ala Ile Lys Thr
225                 230                 235                 240

Leu Gly Ala Ala Gly Thr Pro Ala Ile Ala Glu Arg Val Glu Ser Leu
                245                 250                 255

Arg Gln Lys Trp Val Gly Glu Lys Met Thr Glu Thr Gly Arg Val Arg
            260                 265                 270

Ala Ala Ser Leu Gly Phe Pro Asp Ala Tyr Ala Phe Thr Lys Ala Leu
        275                 280                 285

Gly Glu Arg Ser Leu Val Glu Thr Arg Asp Gly Val Pro Val Ala Ile
            290                 295                 300

Val Arg Pro Ser Ile Ile Glu Ser Ala Leu Ala Glu Pro Val Pro Gly
305                 310                 315                 320

Trp Ile Arg Gly Phe Arg Met Ala Glu Pro Val Ile Ala Ala Tyr Ala
            325                 330                 335

Arg Gly Leu Leu Lys Glu Phe Pro Gly Val Pro Glu Gly Val Ile Asp
            340                 345                 350

Val Ile Pro Val Asp Leu Val Val Ala Ser Ile Leu Ala Thr Ala Ala
            355                 360                 365

Arg Gly Pro His Ile Ser Glu Gln Ser Gly Glu His Glu Pro Asp Ile
            370                 375                 380

Ile Gln Ile Ala Ser Gly Ser Ala Asn Pro Phe Lys Tyr Gly Gln Met
385                 390                 395                 400

Val Asp Leu Val Gln Ala Tyr Phe Thr Lys Asn Pro Val Tyr Asp Glu
            405                 410                 415

Lys Asn Gln Pro Ile Ser Val Pro Asp Trp Thr Phe Pro Gly Arg Gly
            420                 425                 430

Arg Val Thr Arg Gln Leu Asn Arg Ala Lys Phe Ala Leu Thr Thr Gly
            435                 440                 445

Glu Arg Ile Leu Asp Ala Leu Pro Leu Arg Gly Lys Gln Ala Glu Ile
450                 455                 460

Gly Ala Asp Leu Glu Gln Gln Lys Glu Gln Leu Asp Arg Ala Gly Gly
465                 470                 475                 480

Tyr Val Glu Leu Tyr Gly Ala Tyr Thr Glu Cys Glu Ala Thr Tyr Gln
            485                 490                 495

Leu Asp Arg Met Tyr Ala Leu Trp Asn Ser Leu Asp Gly Ala Asp Gln
            500                 505                 510

Arg Asp Phe Asn Met Asp Pro Leu Ser Ile Asp Trp Pro His Tyr Ala
            515                 520                 525

His Asp Ile Gln Leu Pro Ser Thr Val Lys Met Ala Arg Leu
            530                 535                 540

<210> SEQ ID NO 32
<211> LENGTH: 523
<212> TYPE: PRT
<213> ORGANISM: Unknown
<220> FEATURE:
<223> OTHER INFORMATION: Synthetic polypeptide encoded by DNA from
      marine sample JCVI_SCAF_1101670217388

<400> SEQUENCE: 32

Met Ile Lys Gln Asn Leu Ser Gly Lys Arg Ile Ala Ile Thr Gly Ala
1               5                   10                  15

Thr Gly Phe Leu Gly Thr Ala Leu Val Glu Arg Leu Leu Ser Ser Ile
            20                  25                  30

Pro Asp Cys Glu Leu Leu Leu Val Arg Pro Gly Arg Arg Gly Ala
            35                  40                  45

Glu Lys Arg Ala Glu Arg Glu Ile Leu Arg Asn Asp Ala Phe Asn Asn
50                  55                  60

Leu Arg Glu Lys Leu Gly Thr Asp Gly Phe Asp Lys Leu Cys Lys Lys
65                  70                  75                  80

Arg Val Lys Ala Ile Ser Gly Asp Val Gly Ile Asp Gly Leu Gly Leu
            85                  90                  95

Asp Glu Asn Gly Leu Thr Glu Leu Ala Lys Cys Asp Leu Phe Ile His

```
                100                 105                 110
        Ser Ala Ala Val Val Ser Phe Asp Ser Pro Leu Asp Gln Ala Val Glu
                    115                 120                 125

Val Asn Leu Leu Gly Pro Val Arg Ile Ala Gln Thr Leu Asn Glu Leu
                130                 135                 140

Ala Val Ser Pro His Leu Val Ser Ile Ser Thr Cys Tyr Val Ala Gly
        145                 150                 155                 160

Ser Arg Arg Gly Ala Ala Pro Glu Glu Pro Val Asp Ala Ser Pro Phe
                        165                 170                 175

Phe Val Asp Val Asp Trp Arg Ile Glu Val Asp Ala Ala Arg Arg Ile
                    180                 185                 190

Arg Gln Glu Thr Glu Thr Ala Ser Arg Thr Pro Glu Arg Leu Glu Glu
                195                 200                 205

Phe Arg Lys Glu Ala Arg Glu Glu Ile Gly Ala Ala Gly Ile Pro Ala
            210                 215                 220

Leu Ala Ser Lys Thr Glu Gln Leu Arg Ser Arg Trp Val Asp Asp Arg
        225                 230                 235                 240

Met Ala Glu Ala Gly Arg Ser Arg Ala His Ser Leu Gly Phe Pro Asp
                        245                 250                 255

Ala Tyr Ala Tyr Thr Lys Ala Leu Gly Glu Ile Ala Leu Arg Glu Thr
                    260                 265                 270

Ala His Thr Ile Pro Val Ser Ile Val Arg Pro Ser Ile Ile Glu Ser
                275                 280                 285

Ala Leu Ala Glu Pro Phe Pro Gly Trp Ile Arg Gly Phe Arg Met Ala
            290                 295                 300

Glu Pro Val Ile Ile Ser Tyr Ala Arg Gly Leu Leu Lys Asp Phe Pro
        305                 310                 315                 320

Gly Ile Pro Glu Gly Thr Ile Asp Val Ile Pro Val Asp Leu Val Ala
                        325                 330                 335

Asn Ser Ile Ile Leu Ser Leu Ala Glu Ala Leu Ser Gly Ser Gly Gln
                    340                 345                 350

Arg Arg Ile Tyr Gln Cys Cys Ser Gly Gly Ser Asn Pro Ile Ser Leu
                355                 360                 365

Gly Lys Phe Ile Asp Tyr Leu Met Ala Glu Ala Lys Thr Asn Tyr Ala
            370                 375                 380

Ala Tyr Asp Gln Leu Phe Tyr Arg Arg Pro Thr Lys Pro Phe Val Ala
        385                 390                 395                 400

Val Asn Arg Lys Leu Phe Asp Val Val Gly Gly Met Arg Val Pro
                        405                 410                 415

Leu Ser Ile Ala Gly Lys Ala Met Arg Leu Ala Gly Gln Asn Arg Glu
                    420                 425                 430

Leu Lys Val Leu Lys Asn Leu Asp Thr Thr Arg Ser Leu Ala Thr Ile
                435                 440                 445

Phe Gly Phe Tyr Thr Ala Pro Asp Tyr Ile Phe Arg Asn Asp Ser Leu
            450                 455                 460

Met Ala Leu Ala Ser Arg Met Gly Glu Leu Asp Arg Val Leu Phe Pro
        465                 470                 475                 480

Val Asp Ala Arg Gln Ile Asp Trp Gln Leu Tyr Leu Cys Lys Ile His
                        485                 490                 495

Leu Gly Gly Leu Asn Arg Tyr Ala Leu Lys Glu Arg Lys Leu Tyr Ser
                    500                 505                 510

Leu Arg Ala Ala Asp Thr Arg Lys Lys Ala Ala
                515                 520
```

<210> SEQ ID NO 33
<211> LENGTH: 515
<212> TYPE: PRT
<213> ORGANISM: Unknown
<220> FEATURE:
<223> OTHER INFORMATION: Synthetic polypeptide encoded by DNA from
marine sample JCVI_SCAF_1097205236585

<400> SEQUENCE: 33

Met Ile Lys Glu Ser Leu Arg Gly Lys Lys Ile Ala Ile Thr Gly Ser
1               5                   10                  15

Thr Gly Phe Leu Gly Thr Ala Leu Val Glu Leu Leu Arg Glu Ile
            20                  25                  30

Asp Asp Val Gln Leu Arg Leu Leu Ile Arg Pro Ser Gly Lys Arg Ser
                35                  40                  45

Ala Ser Lys Arg Leu Glu Arg Asp Ile Leu Arg Asn Asp Ala Phe Asp
        50                  55                  60

Gln Leu Arg Glu Lys Leu Gly Thr Glu Gly Phe Asn Glu Leu Ala Ser
65                  70                  75                  80

Asn Ala Val Glu Ala Leu Ser Ala Asp Ile Ser Leu Asp Asn Leu Gly
                85                  90                  95

Leu Asp Asp Thr Gly Leu Arg Glu Leu Ser Glu Cys Asp Ile Val Ile
            100                 105                 110

His Ser Ala Ala Ala Val Ser Phe Asp Glu Pro Leu Asp Arg Ala Ala
        115                 120                 125

Glu Val Asn Leu Met Gly Pro Val Arg Leu Val Glu Thr Leu Gln Asn
130                 135                 140

Leu Asp Ala Glu Pro His Leu Val Met Val Ser Thr Cys Tyr Val Ala
145                 150                 155                 160

Gly Asn Arg Lys Gly Thr Ala Pro Glu Lys Pro Leu Ser Gln Ser Pro
                165                 170                 175

Phe Tyr Val Pro Leu Asn Trp Arg Glu Glu Thr Glu Ala Ala Arg Arg
            180                 185                 190

Thr Arg Ser Tyr Thr Glu Asp Asp Ser Arg Arg Ser Glu Asn Leu Glu
        195                 200                 205

Lys Phe Arg Gly Glu Ala Lys Ser Glu Leu Gly Ala Pro Gly Ile Ser
    210                 215                 220

Val Ile Ala Thr Lys Thr Glu Gln Ile Arg Glu Arg Trp Val Lys Glu
225                 230                 235                 240

Lys Met Val Glu Ala Gly Arg Glu Arg Ala Thr Ser Leu Gly Phe Pro
                245                 250                 255

Asp Ala Tyr Ala Phe Thr Lys Ala Met Ala Glu Gln Ala Val Gln Glu
            260                 265                 270

Ile Arg Gly Asn Ile Pro Leu Ser Ile Val Arg Pro Ser Ile Ile Glu
        275                 280                 285

Ser Ser Trp Gly Asn Pro Lys Ser Gly Trp Ile Arg Gly Phe Arg Met
    290                 295                 300

Ala Glu Pro Ile Ile Leu Asn Phe Gly Arg Gly Thr Leu Lys Glu Phe
305                 310                 315                 320

Pro Gly Ile Pro Glu Gly Ile Ile Asp Val Ile Pro Val Asp Leu Val
                325                 330                 335

Ala Ser Ala Ile Val Ala Val Ala Gln Glu Lys Pro Ser Asp Pro
            340                 345                 350

Phe Val Val Gln Val Ala Ser Gly Ala Cys Asn Pro Ile Lys Ile Gly

```
                355                 360                 365
Ile Leu Ala Asp Tyr Val His Glu Phe Phe Gly Asn Phe Pro Ile Leu
    370                 375                 380

Asp Asp Lys Asn Gln Pro Ile Thr Pro Ser Lys Trp Glu Phe Pro Gly
385                 390                 395                 400

Arg Gly Arg Val Val Thr Gln Leu Thr Arg Ala Lys Arg Ile Leu Gln
                405                 410                 415

Ala Ala Glu Asn Gly Leu His Lys Leu Pro Ile Arg Gly Asn Gln Ala
            420                 425                 430

Met Ile Val Ala Asp Leu Glu Glu Lys Arg Asn Glu Leu Asp Lys Ala
        435                 440                 445

Met Glu Tyr Ile Thr Leu Tyr Gly Lys Tyr Val Glu Cys Glu Ala Ile
    450                 455                 460

Tyr Asp Val Ala Asn Leu Leu His Leu Trp Asp Ser Ile Asp Asp Gly
465                 470                 475                 480

Asp Arg Ser Ser Phe Leu Phe Asp Pro Arg Ile Ile Asp Trp Arg Lys
                485                 490                 495

Tyr Val Tyr Asp Ile His Leu Pro Thr Val Ile Thr Gln Gly Arg Val
            500                 505                 510

Lys Thr Thr
       515

<210> SEQ ID NO 34
<211> LENGTH: 372
<212> TYPE: PRT
<213> ORGANISM: Unknown
<220> FEATURE:
<223> OTHER INFORMATION: Synthetic polypeptide encoded by DNA from
      marine sample JCVI_SCAF_1101670289386

<400> SEQUENCE: 34

Met Ser Asn Thr Thr Val Ile Phe Leu Thr Gly Val Thr Gly Tyr Leu
1               5                   10                  15

Gly Ser Arg Leu Leu Val Gln Leu Ser Asn Leu Pro Val Lys Ile Tyr
            20                  25                  30

Cys Leu Val Arg Pro Ala Arg Ser Glu Asn Gly Ala Gln Gly Arg Leu
        35                  40                  45

Leu Lys Ile Leu Glu Asp Asn Asn Ile Thr Pro Glu Glu Gly Lys Tyr
    50                  55                  60

Ile Ala Val Glu Gly Asp Ile Arg Lys Asp Lys Leu Gly Ile Ser Asp
65                  70                  75                  80

Glu Lys Tyr Leu Ser Leu Ser Arg Glu Val Glu Val Val Phe His Ser
                85                  90                  95

Ala Ala Ser Val Asn Phe Leu Ser Thr Lys Glu Ala Leu Lys Ser Ile
            100                 105                 110

Asn Val Val Gly Ala Ile Asn Val Met Asn Phe Ala Gln Arg Cys Tyr
        115                 120                 125

Ala Asn Asn Gln Ser Phe Asp Lys Phe Cys Leu Val Ser Thr Ala Tyr
    130                 135                 140

Val Ala Gly Lys Thr Ser Gly Val Ala Glu Glu Ile Pro Val Thr Lys
145                 150                 155                 160

Ala Arg Val Phe Asn Asn Asn Tyr Glu Glu Ser Lys Trp Leu Ala Glu
                165                 170                 175

Gln Arg Val Val Glu Glu Val Asp Asp Leu Pro Tyr Val Val Ile Arg
            180                 185                 190
```

```
Pro Ser Ile Ile Ile Gly Ser Ala Ile Asp Gly Arg Ala Glu Ser Gln
            195                 200                 205

Asn Val Ile Tyr Gly Pro Phe Arg Ile Met Ile Gln Tyr Asp Asn Lys
210                 215                 220

Lys Pro Gln Trp Leu Pro Gly Tyr Lys Ser Thr Arg Leu Asp Phe Val
225                 230                 235                 240

Pro Val Asp Tyr Val Ala Glu Cys Cys Arg His Ile Ile Phe Glu Lys
                245                 250                 255

Asp Pro Lys Pro Ile Tyr His Leu Thr Ser Gly Pro Asp Asn Gln Ala
            260                 265                 270

Gly Met Asn Asn Met Phe Lys Ser Val Ser Asp Val Phe Ser Val Thr
        275                 280                 285

Val Lys Leu Tyr Pro Tyr Trp Leu Phe Asp Met Phe Ile Lys Pro Phe
290                 295                 300

Leu Lys Leu Arg Lys Asn Lys Asp Asp Leu Lys Phe Leu Arg Ile Ala
305                 310                 315                 320

Asp Ala Tyr Gly Asn Tyr Met Leu Tyr Lys Thr Gln Phe Asp Asp Arg
                325                 330                 335

Asn Thr Ala Glu Leu Arg Tyr Lys Asn Gly Ile Val Arg Pro Ser Trp
            340                 345                 350

Asn Asp Val Phe Thr Lys Ser Ile Arg Tyr Ala Lys Asp Thr Asn Phe
        355                 360                 365

Ala Arg Asp Val
    370

<210> SEQ ID NO 35
<211> LENGTH: 490
<212> TYPE: PRT
<213> ORGANISM: Vitis vinifera

<400> SEQUENCE: 35

Met Glu Leu Gly Ser Ile Val Glu Phe Leu Glu Asn Lys Ser Ile Leu
1               5                   10                  15

Val Thr Gly Ala Thr Gly Phe Leu Ala Lys Ile Phe Val Glu Arg Ile
            20                  25                  30

Leu Arg Thr Gln Pro Asn Val Lys Lys Leu Phe Leu Leu Arg Ala
        35                  40                  45

Gly Asp Thr Lys Ser Ala Thr Gln Arg Leu His Asn Glu Val Ile Gly
    50                  55                  60

Lys Glu Leu Phe Trp Val Leu Arg Glu Lys Trp Ala Ser Asp Phe Asn
65                  70                  75                  80

Ser Phe Val Ser Lys Lys Leu Thr Pro Val Pro Gly Asp Ile Ser Cys
                85                  90                  95

Asp Asp Leu Gly Val Thr Asp Ser Asn Leu Arg Glu Glu Met Trp Arg
            100                 105                 110

Glu Val Asp Ile Val Val Asn Leu Ala Ala Thr Thr Asn Phe Asp Glu
        115                 120                 125

Arg Tyr Asp Val Ala Leu Gly Ile Asn Ala Leu Gly Ala Arg His Val
    130                 135                 140

Leu Asp Phe Ala Lys Lys Cys Val Lys Ile Lys Met Leu Leu His Val
145                 150                 155                 160

Ser Thr Ala Tyr Val Ala Gly Glu Gln Ser Gly Leu Ile Leu Glu Gln
                165                 170                 175

Pro Phe Gln Met Gly Glu Thr Leu Asn Gly Thr Phe Gly Leu Asp Ile
            180                 185                 190
```

```
Glu Glu Glu Lys Lys Leu Met Glu Glu Arg Leu Asp Glu Leu Gln Ser
            195                 200                 205

Glu Gly Ala Thr Arg Glu Ala Val Thr Leu Ala Met Lys Asp Phe Gly
        210                 215                 220

Ile Gln Arg Ala Lys Met His Gly Trp Pro Asn Thr Tyr Val Phe Thr
225                 230                 235                 240

Lys Ala Met Gly Glu Met Leu Leu Gly His Leu Lys Glu Asn Leu Pro
                245                 250                 255

Leu Ala Ile Leu Arg Pro Thr Ile Val Ser Thr Tyr Lys Glu Pro
                260                 265                 270

Phe Pro Gly Trp Val Glu Gly Ile Arg Thr Ile Asp Ser Phe Ala Val
            275                 280                 285

Gly Tyr Gly Lys Gly Arg Leu Thr Phe Phe Leu Gly Asp Ile Glu Ala
        290                 295                 300

Ile Val Asp Val Ile Pro Ala Asp Met Val Val Asn Ser Met Ile Val
305                 310                 315                 320

Ala Met Ala Ala His Ala Asn Gln Pro Cys Glu Val Ile Tyr Gln Val
                325                 330                 335

Gly Ser Ser Val Lys Asn Pro Val Arg Tyr Ser Asn Leu Gln Asp Phe
            340                 345                 350

Gly Leu Arg Tyr Phe Thr Lys Asn Pro Trp Ile Asn Lys Asp Gly Lys
        355                 360                 365

Ala Val Lys Val Gly Lys Val Thr Val Leu Ser Thr Met Asp Ser Phe
370                 375                 380

His Arg Tyr Met Ala Leu Arg Tyr Leu Leu Leu Lys Gly Leu Gln
385                 390                 395                 400

Phe Val Asn Thr Ala Phe Cys Gln Tyr Phe Arg Gly Thr Tyr Thr Asp
                405                 410                 415

Leu Asn Arg Arg Ile Lys Phe Leu Leu Arg Leu Ile Glu Leu Tyr Lys
            420                 425                 430

Pro Tyr Leu Phe Phe Lys Gly Val Phe Asp Asp Met Asn Thr Glu Lys
        435                 440                 445

Leu Arg Met Ala Val Thr Ala Ser Gly Ala Glu Ala Asp Leu Phe Tyr
450                 455                 460

Phe Asp Pro Lys Cys Ile Asp Trp Glu Asp Tyr Phe Met Asn Ile His
465                 470                 475                 480

Ile Pro Gly Ala Val Lys Tyr Val Phe Lys
                485                 490

<210> SEQ ID NO 36
<211> LENGTH: 991
<212> TYPE: PRT
<213> ORGANISM: Vitis vinifera

<400> SEQUENCE: 36

Met Ala Val Ser Thr Thr Thr Thr Pro Asn Thr Ser Ile Thr Asn Gly
1               5                   10                  15

Leu Gly Ile Leu Gln Phe Leu Ala Gly Lys Thr Tyr Phe Ile Thr Gly
            20                  25                  30

Ala Thr Gly Leu Leu Ala Lys Val Val Glu Lys Ile Leu Arg Arg
        35                  40                  45

Ala Pro Asp Val Gly Lys Ile Phe Ile Leu Ile Lys Ala Lys Asn Lys
    50                  55                  60

Glu Ala Ala Val Asp Arg Leu Lys Thr Glu Ile Ile Asn Ser Glu Leu
```

-continued

```
              65                  70                  75                  80
         Phe Glu Cys Leu Lys Gln Arg His Gly Lys Tyr Tyr Gln Asp Phe Met
                          85                  90                  95

Leu Ser Lys Leu Ala Pro Val Val Gly Asn Leu Cys Glu Ser Asp Leu
                         100                 105                 110

Gly Ile Asp Ala Asn Leu Ile Ser Glu Ile Ala Glu Val Asp Val
                         115                 120                 125

Ile Ile Asn Ser Ala Ala Asn Thr Asn Phe Glu Glu Arg Tyr Asp Val
                         130                 135                 140

Ser Leu His Ala Asn Thr Ile Gly Pro Cys Arg Leu Met Asp Phe Ala
         145                 150                 155                 160

Lys Lys Tyr Cys Lys Asn Leu Arg Val Phe Leu His Val Ser Thr Ala
                         165                 170                 175

Tyr Val Asn Gly Glu Arg Glu Gly Met Ile Thr Glu Lys Pro Phe Tyr
                         180                 185                 190

Met Gly Glu Ser Ile Ala Arg Glu Lys Val Ala Ser Glu Phe Leu Pro
                         195                 200                 205

Leu Ser Tyr Pro Ala Leu Asp Val Asp Glu Ile Lys Ile Ala Leu
                         210                 215                 220

Asp Ser Lys Val Ala Phe Glu Gly Asn Leu Glu Asp Gln Lys Met Lys
         225                 230                 235                 240

Glu Leu Gly Leu Glu Arg Ala Arg Ile His Gly Trp His Asn Pro Tyr
                         245                 250                 255

Glu Phe Thr Lys Ala Met Gly Glu Met Met Ile Asn Ser Met Arg Gly
                         260                 265                 270

Asp Ile Pro Leu Val Ile Ile Arg Pro Thr Ala Ile Glu Ser Thr Leu
                         275                 280                 285

Glu Asp Pro Phe Pro Gly Trp Ile Gln Gly Asn Arg Tyr Leu Ile Ser
                         290                 295                 300

Leu Pro Phe Ser Cys Pro Cys Thr Lys Ser His Ile Phe Ser Tyr Asn
         305                 310                 315                 320

Gln Met Leu Asp Pro Met Ile Leu Ser Tyr Gly Lys Gly Asn Leu Pro
                         325                 330                 335

Ser Phe Leu Val Asn Pro Glu Val Val Ile Asp Met Ile Pro Val Asp
                         340                 345                 350

Met Val Val Asn Ala Ile Ile Ala Ala Met Ala Lys His Gly Ile Ala
                         355                 360                 365

Gly Lys Pro Gly Ile Lys Val Tyr His Val Gly Ser Ser Ala Val Asn
                         370                 375                 380

Leu Leu Pro Leu Gly Asp Leu Phe Lys Tyr Ser Tyr Glu His Phe Ile
         385                 390                 395                 400

Cys Ser Pro Ile Asn Met Asp Thr Glu Gly Lys Thr Thr Asp Met Lys
                         405                 410                 415

Glu Met Lys Phe Phe Ser Ser Met Asp Asp Phe Ser Ser His Met Gln
                         420                 425                 430

Thr Glu Ile Val Gln Gln Arg Leu Ala Ile Ser Gly Asn Asn Ala
                         435                 440                 445

Ser Gln Arg Leu Glu Arg Lys Cys Lys Met Ile Val Glu His Ala Ile
                         450                 455                 460

Asn Leu Ala Arg Val Tyr Gln Pro His Met Phe Phe Arg Gly Ser Ser
         465                 470                 475                 480

Phe Gln Glu Lys Thr Tyr Phe Ile Thr Gly Gly Thr Gly Phe Leu Ala
                         485                 490                 495
```

```
Lys Ala Val Val Glu Lys Ile Leu Arg Thr Ala Pro Asp Val Gly Lys
            500                 505                 510
Ile Phe Val Leu Ile Lys Ala Lys Asn Lys Glu Ala Ala Met Asp Arg
            515                 520                 525
Leu Lys Thr Glu Ile Ile Asp Ser Glu Leu Phe Glu Cys Leu Lys Gln
            530                 535                 540
Arg His Gly Lys Tyr Tyr Gln Asp Phe Ile Leu Ser Lys Leu Ala Pro
545                 550                 555                 560
Val Val Gly Asn Leu Cys Glu Ser Asp Leu Gly Ile Asp Ala Asn Ser
            565                 570                 575
Ile Ser Glu Ile Ala Glu Glu Val Asp Val Ile Asn Ser Ala Ala
            580                 585                 590
Asn Thr Asn Phe Glu Glu Arg Tyr Asp Val Ser Leu Ser Thr Asn Val
            595                 600                 605
Leu Gly Pro Arg Arg Leu Met Asp Phe Thr Asn Lys Tyr Cys Lys Asn
            610                 615                 620
Leu Arg Val Phe Leu His Val Ser Thr Ala Tyr Val Ser Gly Glu Arg
625                 630                 635                 640
Glu Gly Met Ile Met Glu Lys Pro Phe His Met Gly Glu Arg Ile Ala
            645                 650                 655
Arg Glu Lys Ala Ala Ser Glu Phe Pro Pro Leu Ala Tyr Pro Val Leu
            660                 665                 670
Asp Val Asp Gly Glu Ile Glu Ile Ala Leu Asp Ser Lys Val Ala Phe
            675                 680                 685
Glu Gly Asn Leu Glu Asp Glu Lys Met Lys Ala Leu Gly Leu Glu Arg
            690                 695                 700
Ala Arg Ile His Gly Trp His Asn Pro Tyr Glu Phe Thr Lys Ala Met
705                 710                 715                 720
Gly Glu Met Leu Ile Asn Ser Met Arg Gly Asp Ile Pro Leu Val Ile
            725                 730                 735
Ile Arg Pro Thr Ala Ile Gly Ser Thr Leu Asp Asp Pro Phe Pro Gly
            740                 745                 750
Trp Ile Gln Gly Asn Arg Tyr Leu Ile Ser Leu Pro Phe Ser Cys Pro
            755                 760                 765
Cys Thr Lys Ser His Phe Phe Ser Asn Asn Gln Met Ala Asp Pro Leu
            770                 775                 780
Ile Leu Ser Tyr Gly Arg Val Asn Leu Pro Ser Phe Leu Val Asn Pro
785                 790                 795                 800
Glu Ala Val Ile Asp Met Ile Pro Val Val Met Val Val Asn Ala Ile
            805                 810                 815
Ile Ala Ala Met Ala Lys His Gly Ile Ala Gly Lys Pro Gly Ile Lys
            820                 825                 830
Val Tyr His Val Gly Ser Ser Ala Val Asn Pro Leu Pro Leu Gly Asp
            835                 840                 845
Leu Phe Lys His Ser Tyr Glu His Phe Ile Cys Ser Pro Ile Asn Met
            850                 855                 860
Asp Thr Glu Gly Lys Thr Val Asp Met Lys Glu Met Lys Ile Phe Ser
865                 870                 875                 880
Pro Met Asp Asp Phe Ser Ser His Met Gln Thr Glu Ile Val Gln Gln
            885                 890                 895
Arg Arg Leu Thr Ile Ser Gly Asn Lys Ala Ser Gln Arg Leu Glu Arg
            900                 905                 910
```

```
Lys Cys Lys Met Ile Val Glu His Ala Ile Asn Leu Ala Arg Val Tyr
            915                 920                 925

Gln Pro Tyr Met Phe Phe Arg Gly Arg Phe Asp Asn Ser Asn Thr His
        930                 935                 940

Asn Leu Met Glu Gly Met Ser Glu Glu Glu Met Lys Arg Phe Arg Leu
945                 950                 955                 960

Asp Val Glu Asn Val Asp Trp Glu Asp Tyr Ile Thr Asn Ile His Ile
                965                 970                 975

Ser Gly Leu Lys Lys His Val Met Lys Gly Arg Gly Met Pro Lys
                980                 985                 990

<210> SEQ ID NO 37
<211> LENGTH: 548
<212> TYPE: PRT
<213> ORGANISM: Stigmatella aurantiaca

<400> SEQUENCE: 37

Met Ser Gln Leu Pro Glu Leu Asn Val Ser Gln Ala Phe Thr Gly Lys
1               5                   10                  15

Arg Leu Leu Phe Ala Gly Ser Thr Gly Phe Val Gly Lys Val Thr Leu
            20                  25                  30

Ser Met Leu Leu Thr His Tyr Gly Gln Ala Leu Asp Lys Val Tyr Val
        35                  40                  45

Leu Val Arg Lys Gly Ser Ala Ser Ala Glu Arg Arg Phe Asp
    50                  55                  60

Lys Val Ala Ile Ser Glu Pro Phe Gln Pro Leu Arg Asp Ala Leu Gly
65                  70                  75                  80

Glu Glu Ala Ala Leu Glu Phe Ile Arg Gln Lys Cys His Val Leu Asp
                85                  90                  95

Gly Asp Ile Thr Asp Pro Leu Met Gly Leu Thr Glu Ala Gln Ala Asp
            100                 105                 110

Glu Leu Thr Gly Lys Val Ala Ala Ile Val Asn Cys Ala Gly Leu Val
        115                 120                 125

Ser Phe Asn Pro Ser Leu Glu Val Gly Leu Asn Val Asn Thr His Gly
    130                 135                 140

Val Lys Tyr Ser Val Asp Leu Ala Leu Lys Trp Ser Ala Pro Leu Ile
145                 150                 155                 160

His Met Ser Thr Ala Phe Val Ala Gly Asn Arg Ser Gly Leu Val Phe
                165                 170                 175

Glu Asp Glu Glu Val Ala Gly Tyr Phe Pro Lys Lys Asp Glu Leu Asp
            180                 185                 190

Gly Arg Asp Phe Ser Leu Glu Gln Glu Leu Lys Asp Ala Glu Arg Ile
        195                 200                 205

Val Ala Arg Leu Arg Glu Gln Ala Asp Asp Lys Ala Leu Thr Ser Leu
    210                 215                 220

Phe Arg Lys Lys Ala Leu Asp Arg Leu Ala Glu Glu Gly Arg Asp Ser
225                 230                 235                 240

Arg Asp Glu Lys Thr Leu Arg Leu Ala Val Gly Arg Glu Arg Lys Leu
                245                 250                 255

Trp Leu Thr Thr Glu Leu Val Arg Ala Gly Met Glu Arg Ala Gln His
            260                 265                 270

Trp Gly Trp Pro Asn Thr Tyr Thr Tyr Thr Lys Ser Leu Gly Glu Gln
        275                 280                 285

Val Met Ala Ala Thr Pro Gly Leu Arg Tyr Ser Ile Val Arg Pro Ser
    290                 295                 300
```

Ile Val Glu Thr Ser Arg His Phe Pro Phe Pro Gly Trp Asn Glu Gly
305                 310                 315                 320

Phe Thr Thr Ser Ala Pro Leu Ala Phe Ala Gly Ile Lys Gly Gln Arg
            325                 330                 335

Gly Ile Pro Ala Gly Phe Lys Thr Ile Leu Asp Ile Ile Pro Val Asp
        340                 345                 350

Gln Val Ala Gly Ala Thr Leu Gly Ile Thr Ala His Ser Leu Thr Val
    355                 360                 365

His Glu Arg Arg Val Tyr His Leu Ala Ser Gly Asp Glu Asn Pro Phe
370                 375                 380

Tyr Ala Ser Arg Ser Val Glu Leu Val Gly Leu Tyr Arg Arg Arg Tyr
385                 390                 395                 400

Tyr Arg Asn Lys Glu Gly Gly Asn Ala Leu Leu Asn Glu Val Arg Ala
                405                 410                 415

Arg Ile Glu Pro Gln Pro Ile Thr Arg Gln Arg Phe Glu Ser Leu Ser
            420                 425                 430

Ala Pro Ala Phe Met Lys Gly Ala Arg Leu Leu Lys Gln Val Ile Glu
        435                 440                 445

Glu Val Arg Pro Ala Trp Gly Ala Pro Thr Val Gln Ala Leu Leu Asp
    450                 455                 460

Arg Ala Lys Val Lys Leu Asp Asp Val Glu Glu Gln Ala Ser Ser Leu
465                 470                 475                 480

Ser Gln Leu Ile Glu Leu Phe Leu Pro Phe Leu Trp Glu Asn Arg Tyr
                485                 490                 495

Val Phe Arg Cys Asp Asn Thr Arg Ser Val Tyr Ala Arg Met Leu Pro
            500                 505                 510

Ser Asp Arg Ala Lys Ile Pro Trp Asp Pro Glu Asn Ile Asn Trp Arg
        515                 520                 525

Glu Tyr Trp Met Glu Thr His Leu Pro Gly Leu Glu Lys Phe Val Phe
    530                 535                 540

Pro Gly Leu Glu
545

<210> SEQ ID NO 38
<211> LENGTH: 233508
<212> TYPE: DNA
<213> ORGANISM: Phytophthora ramorum

<400> SEQUENCE: 38
accccccccc cccccgtct cttcgtgact gttcaacgtc tgcttcgctt attcttccag    60
gttgcttcaa atctgcaat gagatccggc atttgtgaaa gattctccac tggttcccat   120
gttggcttct cttcacccat ccactccaca aggaattgtg tacgttgttc ccggtgacgc   180
tttcctcgaa gacgcttggc tatctggccg acactgccgt ctgccagaat cacattacct   240
ggtcgggata gtcgagtcga atccttgtac ggcttcaatg atccagcatt gaaaacagag   300
tggagcttgt ttctggtctg gatgttgagc tcgtaagcgt ggttgtgtac cttccgcttg   360
atcgtgttcg ggccaatcca cttcggtcca aacttcggta ggcctgagtg ctttgcgtcg   420
atgtgcttcg tgctaagtac actcggtacc caatatcgaa aacttgttcc ttacggtccc   480
aattgtaaat atcgcgcatt ccctcttggg ctttggctag tgcatcacta cagcgtagta   540
gaattgctgc ttgacgttca tggaagtcag cgccctggcg actcttgggt atacgtgcaa   600
gggtttccgc cgttagttga atcgggttca attggatata acccagatcc gcttcgaacg   660

-continued

```
gcgcaagttt cgtgctgaag attaccgtcg agttaatggt aaactcggtg ttggccaagt      720
gaacgtccca atcatcctcc agtgggccaa caaagcagcg gaggtactcc tccagcgtac      780
gcttcattcg gtctgtttgg ccatcacgtt gtgctcggtg tgccacggtc atgctcggtt      840
tcgtcccgat agacttgaag acgtgttgcc agaagttgga cacaaacttc ctatcgcgat      900
cggacacaat gttggatggc atgccgtgta gcttccagat gtcgttgatg aagagtcgga      960
caacaccttc agctgtcacc gtcttactcg tgggcacgaa gtgacaacgg ttggtcaacc     1020
gatcgacgac gacccagatg gagtcgacgt cgcgcttcgt tcgtggtagg tccgtgataa     1080
aatccataga gatggatcgc cacctctcgt ccgggatgac cagcggctcg agcagttctg     1140
gaggcttcgt caatcgtggc ttgttccgca cacggatcgc aatccgtgat ggatcgcttg     1200
atggacttga gcatattgga ccagtgccaa cggcgtgcca gtgtcaagta cgttcgttcg     1260
gcgccaggat gtccgccgta gttggtgtca tggcactcgc taatgatcgt ctgccacaac     1320
tttaaatcgt tgggcacgac aatgcgaggt acgctaccag caggtgtctg gtaccacagc     1380
aaccacttca cctcgttata gcaccgtggt gctgggtata gcggggctac acagttggtt     1440
cacctcctac cttagtgcaa cacgcactaa tggatacatt caggttgacc gcaccacaag     1500
gtggtctata ttcatagcaa aggcatatga ctggtagaaa ccaacatctt tctaccaatg     1560
agagtcattc attagatagg gattctgcca gccatccaat gacagaacct ctcattagaa     1620
aaatcagttt aggaggaaac cccatttaca atcaatacag ttctcatttg gcaccaaagc     1680
tatcgttcgg tcccattatc aaagtttaag tatacttgtg gatacaagta tactgaactt     1740
aagttaaata cacctacgct tcctcctaca cgtgcgcaca cgtgtaagca aaagtagtgg     1800
gtttaaggag acccattaca ctgagataca cgcttgggta ttacactagc tgtacgtcgc     1860
tcgatcgccg taaagattgc ttggatctca tggtcctgct tgtacgcatt catgatgctg     1920
ttgattaact cagagttggt agtcatctca ctgatcgcta agctaagtga tgcctcatca     1980
aagcttgtca cgctcaagtc gtgtaaaatc ttcgtttcgg gttctacgac tcaaagtgtc     2040
cacgataccg ttcttcgcac catacatata tgataaagcc agctggtact ccgcaaggat     2100
gtcgtaccag cgagctagcc gtcggttggc catctgctgc gtgaacaggc tttcaaggct     2160
tttatgatcg gtctcgagaa tcggaggtat gcccaagcag tagattctgg atgcggctag     2220
agtgtgaacg atcacaaggt gttcctgctg ctggggttggg tagttcagct ccgctggctt     2280
cattttcctg ttggtgtacg caatgggtcg ctcaacacca tcgataactt ggaacaggac     2340 tcccctacg gcaaacttgc tagcgcccgt acccagatac atgggtaagc tgaggttcgg     2400
cagatgtagt tctggtggtt tgcacagccg tctcttcagt tccttgaagt tcttaaactg     2460
ataatcattg aggtagatct tggcgttgcg cttggttctc ttcttgagaa gattgaacac     2520
gcttgcggtt aattctccat aatttgggca gaaacgctgg acggaaccag tcagaccaag     2580
gaagctgtga agttcctcta gagttctcgg gaccggacag tccttgatag tctgaactgc     2640
ccggatacat tcgcacacta gttcgtccga cgaaatctcc gagacatgga atctcgttcg     2700
cacagaagac acacgtgaag agtttcacat atagtttgtt atcacgcaag atgtgcaacg     2760
tcttccgtag tgtttccaag tgattttcaa tcttgtacgg cttcgtaaaa atgtagatgt     2820
cttcgtagaa ggacttcgtg tccccaagat cgcggaacaa tttcgacgtc aaccgatgca     2880
tcgtagctgg tgcgttgcaa actcccatcg gtagcacaag atattcccac agttcgtttg     2940
gtgcttggga ggtggtaaac ttgatgtctt cttcacgcag acgaacatgg tagtacgctg     3000
acatcaaatc cattgtggaa aaccagtacg ctcccgccat tgagtctaag atgtcttcct     3060
```

```
tctgtgtcat tggaacgctc tgccgaaccg tgttggtgtt caggtatcga aatcgtgtac    3120
gattcgccag ccaactggtt tccggacgca gaatgttgga gcagcatgtg ggctgatctc    3180
ggtcagacga tctacttctt caccatatct tcgacccaac gtacgatttc gcgttgctgt    3240
tccggtgact gttgccactg gtgtcggtac atcatgaggc tcggatcctt cacatcaatt    3300
cgatgctcta tctcgcgctt ctcgggtaac ccttcgggta gctcaggacg aaacacagta    3360
tccttgtaac ccttgagtaa ctcgaatgct gggttggtct ggaagctgtc ccagtcggtt    3420
tccagatact gttgtgcctt cgcacttccg acaatatcgg gtttatctcg ccgttgcttg    3480
atcatctcgt tcgacagaac cagcacgtag tctggctcgt caatcgtttt ggtcttcaat    3540
ctcaggaact ccgcagcttc tttcgcgtga tgtacttcgt ctgcacaccc atttcatcga    3600
caacccccat cttgaacatc ttctccacga cgctgtcttt gccccggtca ctagtatctc    3660
atacttctct agtgcctacg attgaagatg acctcttacc atctccatct accgctgatt    3720
cacaaaccaa cgactctttc ggttgtccgt agataacgcg tagctttcgc tctgctcttc    3780
agttcgaatt ggattaactg cagacctcac atccgtttcc agcgcggcgc ctccacagga    3840
atcaggtctt tcaacgatag gccttttcgcc ccgacatatc tcggaagctc ggaggcaatc    3900
accggtccgc cttcctcgat tgatccacag gtctcatctg ctcgtttcca gcgcaaagtc    3960
cttgttcgca ttccttccac tagtcgaccc cccagccaat atgcgggtgc ttgtctaccc    4020
acggcctgga cacgtagatc gtggtagcgc cacagtccag caaaattcgc gatatcatgc    4080
tcttgtccgc cacatcgatc tctccttcga cggtggacag cgggcgtggc ttgtaaacta    4140
gagggttttc gcacagatca ttgagactaa tattctgaaa ctttaacgtt tttgctacac    4200
catcgaccac gtcacggtcc tccttcactg acgccgttgt tcgttttcct gcttggctta    4260
ttccttcttc cacgagaatc aatcggcctt gatgtgacca ggcttcttgg agaagtagca    4320
ggtgcgtcct tcggcacgct ttgtattcga gcttgacttg aagcgacctt ttccacagaa    4380
acatttcctt ttgacgagtt cccgtttccg tgggtcgatt cccatgaaag attcagcttg    4440
tcaggacgaa ctgggtgttc gcgtgcttcc tctacgaagt gggccacttc gtacttgacg    4500
gccaaattca tggcttcgct cagcgtcttt gggttctcga gtttgacata gctctgagtc    4560
cgcggcttga gaccgttgcg tagttaagca cttggtcgag catgctcatg cctccaacac    4620
gaaatatcag tactgagtat ttgttattgt ccgtctcgat gtctgccgtc ggcttgagac    4680
gctggtgcgt ttcgcgtagg acggcctggt aattcaatgt atcgaagtgt tggactgaaa    4740
atcccccacg tgtgctcctc gactctcgtc gtcgaagacc aatgcaggaa ccaccccgaa    4800
gccggcttct ccatagccga cctggcgatc cctggtagga gcagcccttg cgtcttcgat    4860
cgggatgccg ttgatacggc aggcgttttg ctctggaaca accattcgca cacgtcttct    4920
cctctcttgc cggtgaactt ggatagattg atgggcacac gcgtgcctcc agccatggct    4980
tgattcagcc gatgtatatc ggcgcttagt tgggcgttcg tcggcatggt ctacttatgg    5040
gcaggttgct gggaccaaca agtgctatca atttatctta agcaaatagt tttgaggggg    5100
gaaggcgtgc taaaagagaa gtgcccccccc ccgcagttcg ggcagatgga agcttaaaat    5160
acagcgtcca cagctgccgt acgtctgact acttgtattc acgtaagttc actataccat    5220
actaaacctc aatgtcagca ctactgtttc taattggcca acacagaccg tctggcggcg    5280
ggcggagggg ctgccagatt ttaaatttgg tcgagggtcc ggcgctgcgc agtacttgca    5340
tattaagtgc tggcagcact tggctacgac actttcaaga acactgagga ggaggaaatc    5400
```

```
aacaaccacg agatcgttaa gacgctgtag cacttgcatg aaaacgatgt ggtgtcggta    5460
gatgagttcg ttaatcctca cgatgaaaca ccattgtgga ggagcccccg acgatagcgt    5520
aaatgaacca gaacatgttg cggatgggag tgaggctggt tcaattccac tagaagagaa    5580
tgatgcggaa cgggatactg aggaggccgt taccatcaag gaacatctga tgtggattgg    5640
tactgtaagc tgctcgttcg tgcgaatgct accgggcgtc gatgatcgag atgcagcgta    5700
cattccgcta attgttgaat agtataatgg gtagttggga tgaaagtcgt ctcacacaac    5760
tctacagttg ggggagcctc tggatgagac ggtagagcca tcccagttgc taataatact    5820
cccccacagt gctggtagga cctatgtgct aggagaagcg agttttattg aaaatacact    5880
cggcataatc gttcagggag tgccaactct cccagagtgt cttctagcga gccttctac     5940
aaataggaag cacgaccaca aagcagcaga agtcttagct agacttcgtt ggacgtcctg    6000
tgctattgtg attttcaat agttaagctc aaccggactg cttgtcgatt tcgtattcct    6060
tcgaccgctg agcggtgaga gggaatactt acttgagttt gtaaaatgac gatcgttttc    6120
atattcttgt tgagcgagta ttccaggcct gagggtcacc accagggggt ttgaccatgc    6180
tgggacgaaa tgttgtatag taaaatgctg gatgagactg gcttgctatc gctcgtatac    6240
caaaagtgca ttgacctcga tcgagtagct tcacccaccg tcgattcact cctgttatgc    6300
tgaaagcgct tctgcatcca gcatttacct cagtggggtg agatggtctt gctccagcct    6360
aatgcgatgg gaggagcctg gtgtgccaag atggcacgtg aggctgagtg cagcgcacgc    6420
atgtgttcca agcaccgcat gccgagaagc agagcgccgc cgccacagct cttgaaagcg    6480
gccggtgttt tgccgagcca agcgttgaag ttgcacgtca ttcaactgta ctggctcgtc    6540
ttcccattcg tcgactaacc gaagccaaca tgtaaatgac cggaagtcag cgtctgcacc    6600
aagcagcaat agccgccacat gaagcaacaa tcacagcgtc agcatgtatc acaaaggtaa    6660
acgccgccgc cgccgcgtaa aagaggttgg gcgctcaatt ctgctactag ctgctcatac    6720
gaaacagcag cagagactca aatagtacta gaggagagtt gcactgtggt ccaccagcgg    6780
ggtatggaga caccacaca gcaccagttc acaacgccgt gaagaagcgc ggcgtgcatc    6840
ctgcctccaa agcgccgagc acggcggcgg cctcgagcat ctggatggcg tccaacctgc    6900
cacgaatggc gcggcatgtt gtcctgtgtg gttcagagcg agactggcca cctggcaagc    6960
gcccaacgcg tgtcaatctt cgctggtaat cgacccagcc accacgacgc cagcagtagc    7020
gatgagggcg agcgcgccat gtggcagcgc gacgaaagtc tgacggcaag ttgactcgac    7080
gacagggcgg caggcgtgcg gcagtacagt accgtgcacg agactctctt ggttattacc    7140
gcggtgtcgt gtcacgctgc ccgatcgccg atcggggcga ggataccgca agcagcagcg    7200
ctaaaaggtc cgcctccgtt taggtggagc ggtagaggtc gcctgcagtc tggctgcgga    7260
gacctatacc atttcgcccg gcgttgcgcc gggaaagcct gaggaagtcg cctttggcc    7320
aattatagct cagcgtcgct tcgcgctctc gacgatacga ccgatagtcc gagaccggct    7380
ccttttcctg ctgctgcgat gccgaacaag tggcgcgtga gtagcgctcc ctcttcattc    7440
ccaaacggaa ggctaaccga ccggaaacaa ccaatttcct cggtatctgc gcggcggcaa    7500
gaggcagcaa gcgagtgaac gagcgaggga tcccccagcg acgacagcga acagtgaaca    7560
gacgcgtgcg tgacggacgg acgcgtacga ggcgaaaagc gatcgaaaca ggaaactaca    7620
ggcagctcat gtggacgaaa ctcgccgtgg cgagcgcgct gctgctgata cagggggactg    7680
cggcgcaggg tacgtccagc tcgatgtaga gaggcgtaga tggctttctg acttgcgctg    7740
ggtgttgtgc attcgtgtag actgcgcgta cactgtcagt gtgctggatg tggcgggcgt    7800
```

```
gcagtgcgtg acctcgacgc cctgctcggg gacgtactac gcgtcgggtc tgtcccaggg    7860
ggtgggcgcc tgccccaccg gcacggcctg cgcgctgctg ccgctgacgc ccatcatggg    7920
ctgcgccgcg tctggccgca cggacctcac ttacgtgaac gcggacggca cgctgaccaa    7980
ggatggcaag tcggtgacgc tctcgggcgc gtcgtctacg tcctcggaca cgaccacgac    8040
ggcccctacc acgagcagca cgagctctac gaccagctca agcacgagtt caacgaccag    8100
ctcgtcgacc agctcatcga cgagcagtgg caacggaagc aacgcgggct ccggctccgg    8160
atcagccacc agcagcacca atggtaatgc cttttctgcc accagtacca attctgtaga    8220
tattaatcct ggctctgtca ttgtagggag ctcagacgcc agcagcaaag cgactgccga    8280
caacagcacc agcaactcgg cgtccatttc cgcctcgtcg gcggcctcca acgccaacag    8340
ctcgacgtcc aactcgtgga attccgagtc gggatccggc agctacacca tctcacccgg    8400
cagcagctca gcaaatcaac aggctgagtt caaccccggg tccatcctga gcgacggctc    8460
caactcatcc acgtcttcgt cgggcgacgg cctcggtctt ggctctatca tcgccatcgt    8520
cgtgggctgc ttagcggttg tagctatcgc ggccggcgcg cggctgctga agaagggcaa    8580
ggagaccgat ggcgagctgg agacgcctgc gggagcgctc gaggactata caacgcgagg    8640
tggcggcagc ggtatgactc ccaaggagaa cgtgttgctg ctctaagtta tggccagcgg    8700
cagatgatgt ttttgagagg aatacagtga ctgtgcaaac tttgtgaaca cgagaaagcg    8760
cgttcattgc gtgaacctgg tgaatacaag tacatggcgc ggtgcattca agaaggaagc    8820
agagcgaggg aagtggtggc gttgggtgtt cggtgttgtc gtggatagat gcatggagct    8880
gtgggcgttg gaaggtgggg agagttggta gcacgtgtga atagtagctc tctgctcttc    8940
cactcagatc tctacgatca cttatatacg tcgtcgacg cgcaacgtcg tctagtttac    9000
tgcgcagctc ggacccagcg aaaggctgtc cttgcatcgt ctttcatctc ttccgttgct    9060 aaatttttgct catttatccc gagcctgtcc gtgacttctg tagaaactac gagacagaca    9120
catgaacaaa atacatgaac tcttgcgtgt tggacagatg gatggatgga tgccttgcga    9180
gcctcatccg tcagtttggt gcgctgacga tgtcagcgac ccccacgcga aaccgcgtgc    9240
gctagtgatg ccgcgttctt gtcgaaggat catttgttat tactctcaat gaaacctccg    9300
atgttgctac gtgccgctta ggtggccttg gtcttggtcg ccgcctcgga cgccgccttg    9360
gcctccttga gcgtgaagag cttggcgtcc gggtccacga cgccgtagtt ggcgtacagt    9420
cggccgacgc gccagaaggc cttgaggatc ggctcgtcgc tcttgcgcac gagctcgggg    9480
aaggcctggt ggaatgccgc cgtagcgcgg ttgagcttgt agtgcgggat gatggggaag    9540
aggtggtgga tctggtgcgt gccgatgttg tggctcaggt tgtcgatgaa cgcgccgtag    9600
gaccggtcca cggacgacag gttgcccttg acgtaggtcc agtcggagtc tccgtaccat    9660
ggggtctcct cgtcattgtg atgcaggaag gtggtgatca caagcatgct gccgaacacg    9720 aagacgggc cgtagtagta gagcgccatg gtcttgagac cgaactggaa gctcagatac    9780
acggacagcg ccaacacggc gaagtgcgcg gagagcgaga tgacgacggc ggccacctgg    9840
cgcacaaaca gcggctcgaa tgggttgaag tggttgacct tgcggggcgg gaagccctcg    9900
accaggtagg cgaaccacgc ggcgccgagc gccagcacga ggttgcgcga cagcgggtgg    9960
tcgtcggcct tgcgctgcgg gtagaagatc tcgtcgcggt caatgttgcc cgtgttcttg   10020
tggtggtggc ggtgcgtgag cttccacgac tcgaagggcg tgaggatgag cgagtggatg   10080
aaggtgccca ccacgaagtt gagcaggtgg taacgcgaga aggcgccgtg gccggcgtca   10140
```

```
tggcccaccg tgaagaagcc ccagaacacg atgccctgca gcagcacgta accgcagcag   10200
agcgcagcgt ccagcgccca caagctctcg accacgggca gcgcgcgcgc gtagttgagg   10260
ccgaacgcca gcgccacggc gatggccacg atgcgcaccg tgtagtagag cgacagcggc   10320
accgaggcct caaagcactc gctgggcagc gaccgcttga tctccgtcag ggtcgggaac   10380
tggtacggct gcttagtcgc catggtggtg gagacgtcgg tgtctgatgc gccgcacgtc   10440
ctggaatgag ctctgcggac gtgtggctgc gaaaccaccg tggagtcata gatacccttc   10500
gccatagttc gggcaagtcg aagttggatg gtgaacaagg caccgccggg attcacgatg   10560
acatcacgcg cgtaccgtct aggacgcaca cgccattcag caaagccgtc ccgcacgcgt   10620
cccgcattat cggcgctgct caacgcaatg tgtattttat tgttttatca tgcaagtagt   10680
gtaccgacgt gcagactttg gtggggttga aaacttggtt ttagcggaag ggcagcacca   10740
cctcatgctg caggatgtct tcggcgagag gccgctgcaa cgcgtctggg tgcagcatgc   10800
tggcgatcag gtgctgcagc gagttggagt attgtctgca gtgaacaagt gagcaagctt   10860
gtcagcaaaa gaaacgaggc cgcggggtgg caacagagta tcacgttcgt accggaacat   10920
cacgaggtct ccgtcgcgga tcttctgcca ttcttcgccg ccactcgcca gcgtcgttcc   10980
aagcgcgagc tcatagattg tggccccccag cgcgaagatg tcgccggcgc gcaagttatt   11040
ccggttgcct tctagcaatt cgctgcaacg aacaaggaag tgacacgtta gttaaacagc   11100
cccttgcctc ggcaagtagc tagggtagaa agcacgtacc gactaagata ccgattgtcg   11160
ccctctgtga tctccatgct gccgtcaagg tgagcgacgg ttcccaggtc acccaactgc   11220
acgcatcaaa tgtgagctcc aaaacctaga catttcggca gcattcgaga gcagcttacc   11280
ttgtaaacct cttccgggcc gaccagcaca ttttgtagct tgacgtccat atggaccatt   11340
ttcttgctgt gcatgtcgta aagagcctac ataaatcaaa gacattgtta gttccggtca   11400
aagaacagga atctagaaga caaaaagatc tacctgagca atatggcaca gcagcttgca   11460
cagcgtctct tccgggatct tgtgcggtgc gtacttattg gcaaagccag ccaacgagca   11520
cccctccagg ttttcaagct ggatgtagag caaatcgtct tctatccagg cgtcgaaata   11580
gcggacaacg tggttgctgc tactcagcgc tgccagcgcc tgcacttctc gaagagctcg   11640
ctcgctgtgg tgcaagcaca acaacaaacg taagtgccta tttacgcaaa gcaccagcaa   11700
acaatgcata gctctgcgta cgtgtctgcc ttcccgcgaa aatggcgctt gctcttttttc   11760 accgcgtaca cccagccatc aatcttttttc atgcacttgt acactttcga gaacgagccc   11820
gagccgatta actgccaagc agaacaccac atctcagtac tgtgcactga tggcaaacgg   11880
caatagatag acagcatacc ccaagctcgg agaaatccga cagatacttg gaaacgggcg   11940
atccactctg tcctcccacc cacgcagacg ggaacgaccg tcgtttgcgc ctggaaatct   12000
ttttcttccc cgagtcggtc tccggcgcga acgggttcac ataactctcg tcggacaaga   12060
acgacaccgc tcgctctctg caaaaaaacc aacaaccaca tgaaaaaata gagcacacac   12120
tagtgagcag cacgaagaca cgctctcacc actacaatca ctcacccgtt gggtcgtggt   12180
ctcttggcat tattcaccac cacgttcacc ctcttcttca gcggcgaccc cgtgtccatt   12240
gatgattggc tcgagaaaga cggaggcccc ttcctcgcgt gccgaacgtc catgtgggtc   12300
atatcctgcg tgaggttctg tacttgttcc tcctgtacca catccgctcc gctattgagt   12360
ctcggtctct tcttcaatgg ggagggagtc gtcgggttgg acagcgggat gacgggctgg   12420
tctctgggcg taaggaagtc catgtcgtcc tggctgaact ggtgcatctg gggcgtgtag   12480
cagccctgac tcgtgggcgg caagccgaag cgcacgggcg tgtgcgtggg ctcccagtcg   12540
```

```
ggctcgctgc gctggctaga gaagtcgctc ttcttaggcc tgtcgctgct ctgggaggcc   12600
gcgagtatgg gttcctcgct gctctcgtcg tccatgatgt cgtagtcgat gcgtttctgc   12660
acgggctcgt cgtcgtgctc gtccatggcg gcgctgctga agctattgcc cttggcggag   12720
gcttcgagag accgtcgcgc cttgcgcagt ttgcctccgc gctggcgact ggactgggag   12780
aaaaagtcgt ggatcgagcg ctgctttttg gctccgctgc tgccgctgga agggcccgaa   12840
gtctgcgacg agccgctgcc gcgcgcctta cttcgcaacg catttagcag cataacggca   12900
gaggtggaca attcaacaat gacccggatc gacgtttccc gccttttcgt atgctgtctg   12960
agaggtgcta ggttatgata taagataggt agtggtgaaa gagaaaaact atgagcttca   13020
acgtggaatg gctacacttt cttcttgttg agcaagttga gcccttggaa ggtcttcacc   13080
aagcgacttt gtttcttggt gcgttcctgc tcttctagtc gttgccgctc ggcttcgagc   13140
tccgctgctt cttgagctgt ttgggcgcgc tgggcggctt cttgctcttg ccgacctcgc   13200
tcctgctgct cggcttccaa tgtgccctca tccagagcga cctgaacgag ttcctagaaa   13260
ggagagactc ggttagtgca gggagttgcg ttgggattgt tgcaacacat accttgagcc   13320
ccatgcgatc accgacgagc cggagtggaa gcgctttctg ctcaccgctg gcaatcgcgc   13380
gccgactgta cttggcggaa gcgtagaatt cgcagatctc acaatcgtga aaaacgcgac   13440
agagacgaca ggcgtcatcg agtgtttctg cagtaccacg accaaacttg cggaacgatc   13500
gctcgtacgc gtcatattgg cgcagaatgg aggcgtggtc ggcatctgct tggatcgcac   13560
ggaggtagta atcgtcaagg acgctgtatt tagcggcagc agtatcgaga atgttatac   13620 actgttcaag tcgtttggca atgctatgtt gacgtaccct tgggtaggaa tgggaggcat   13680
gaccactagc gtggcgtccg cgctgcactg gaccgtaccg acacgaccta catacttgaa   13740
tgccgagtag acgccaaaca cctcgacctc tgcgaaatgg aggaaattcc tgttttgtaa   13800
ttgaactcgg acgaactgac ccacagtgtt agctgtaggg agcacccact ccgtcattcg   13860
tttgttggct cggaagagct cgaacgcgct cgactgaact ttagcggccc gcaagctaca   13920
tcgacgcaag gattaccaga gatggtttcg taagcacttt tgtacgtggt aatgtgaaat   13980
tactctcgag ctcacccttc tttgccttcc acgtctttaa acgcaaattc actcacgaag   14040
atccagcacg ggaaaagacg accgctgtac tcactcctgc tttttgatgg gttcaacggc   14100
tcgtccgttc gattccacaa ctgaaagagt acaggttagt ttcgcgcaag aaatgtatcc   14160
aattggcctg ctgcataccc gaattttttc tatgacggca ggctggccaa gatccacctc   14220
ccaccacggc ttgtcttcat gctacaaagc aattatgccc aaaaccagtg agtatggtaa   14280
tagcgagaga gtaaaaaccc tcagccttac atgagtgtgg atgcaagtcg ttaaagcacc   14340
cccagtttcc ccgttgacag ccaggtgcgg tccttgttcg ttgtagacgg taatctgacg   14400
acatggcttg tgaaatgcaa ggttgtaagg ttcaacgtgc aggcacttga gtagctctgg   14460
tttttccaga aacgcgcgct gtgctcaaga cacacaaacc gatcggggtt agtatgttaa   14520
catccttact actatcaaca aatatgtata cgtacgctgg catcgtgacc tgtacatcca   14580
tgattattgc gaccccaggt gtaaagttct ccgtatgagg atacagcggc tgtatggctt   14640
cctccacacg ccacctgacg aattccaacc tcatcaagct ctggaatacg ctcccacgac   14700
aaaacgtacc ggctaagtgc agtagcaccc ccacagatat acacctgacc accacgtagc   14760
ttcttgcttc ctctattgta ttctgacgtg acctcggtgc aaattgcgga gtgtgctgtt   14820
ccgcatgaga cctgccatac cgacactttc ttgttcacaa gatctcttac cagcgttgga   14880
```

```
acaacgatcg tatcgaccac gtgaggccca agcccaaggc ggccaccatt tgcggatccc   14940
cacatgaaca attcccctgc cgttgagact gctccgctgt gcgaggctcc gcaggacacg   15000
gatcgtattc ttcgtttacc agggaatttg accagcagtg gcgtcaaaga gtactgcttg   15060
tactcgtcct caacaattcc gacacccagt tttccattgc atgccgaccc ccaagtgtat   15120
agcgatccgt ccgagtcaat tgctgcactg tgcgaaaagg agcaagatac ctgacgcagg   15180
ctcacatcct aaaagcacgt ggaagatgca ttagtttaca gattgtcagc gtacagacat   15240
acgttcgcac attgaaagct tcgacgcgct gggggtggtt tgtgtcaaaa cagatagctc   15300
ctcgctcgtt cggctgaaga cccaggcgtc cacttgcacc aattccacat gtgtaaaggg   15360
atctaaaaac gcaggagagt gtgggttgcc aatgccaaca aattcaagaa tccgtccgta   15420
cccatcttgc ataagcaatg ccacgtggga acccctgca gaaatatttg ctacggcctg    15480
caaaatcaaa tcagcacccg tcttcacttt ttatagtata tacttaccac agctcctctg   15540
ggtgagtgaa gcggtggtcc tcttcgggta ccaacaaaat acaaagatca gatcgaggca   15600
cttgcacact accggtacgt tatttcctg tcttaccttg aagtaactcc gctcatatca    15660
atccgggaat tttcacctcg agctgtaaac tcagggattg tatcttccaa ctgaacaacc   15720
ctccgagcag ccctggactc gtatgctcga tcctacacca aggttgtcca caaggactta   15780
gccgaagggg cctagtaaaa tgatccgtcg ctttactcac cgcgcggtca acttttttcga  15840 tgattttggc ttttgcatcc tcttcacgtt ggcatgtcg gttgtcgcgc gatattttga    15900
catctgccca ctgcaaggaa acaagttaag tttactccat cagaaaacgc tccattgatg   15960
attaagatga ggcatcacat actccttgta gtagtttctc tttttcctag cacagaaaca   16020
caaaagggcc atgagttatg acagctaagc caactctgga caggcaaaaa tgtaccactt   16080
ggaggaaatt aatctgtttg tcttgagtgc gcttttttgtc tgcactgtat tcctgttcat   16140
gcacatgtac gttttgtgat tgcgagggtt gtagagaatc acattttat ctttgtacct    16200 tgatcatatt ttccgattct ttgaatgcgg tgtgaccctc ttcacctttt acctcgactt   16260
caagctcgaa gcattccccc agcgtgagtg acaaatccat tttggtcaga tgatcgagct   16320
taagcccacg cagttggcca gacgtaacca gctgctcata ttcaatcttg ggtaggagca   16380
cttgctccat gaacagcagc cgcgtcgcat tactgggagg tggttcccaa acgtcgtaat   16440
acgtgacaac tcgtttcaac cttcaaagaa gcaagttatc gaattgaaat cacgccagtc   16500
cgtttatatg ggtatccacc tacctttcat agtgttgatt ctcttcgttt tgtcgagctt   16560
catgctccag ctgttcttct tctctcgctt ccacaccagg atcatgtagc ccttctagct   16620
gtagtcaaag gcatcagaca agttttgact attgctgtat tgctgaaggc catacctgtg   16680
cgggggtaca catcttctga aacgctgacc gaggggtact cttcgactgt acgccattat   16740
ccgattgttt ctcttttctt ttcttcgtgt tggtaccttc gagatcatca tctgagtcgc   16800
tgtcaaatcc agttaggcgc cgagctgata cctcccacgt attatttctc cctccccagc   16860
tataaacact ccccgaactt gtcacggcaa aagcgacact atcgctgatt gcaccatgca   16920
cgacacttct accccacaaa ggccccgtat tgtcatcaa agatgttgat cgaaatctta    16980
agctccgaac aaattcccgg ttttcaaaga agagcttggc aagttcttcc tcgccttgat   17040
tgctctcgtc acgggtgaac tcttcaattt cggatgtttc tgtaggtgcg tttgagtcaa   17100
catgttgatc tccctcgtta cgttcattcg gcacctctct ctcacgagac attgctcgga   17160
tatgcatttt cgtctgggaa attgtctgtt tgttcaattt cggtggactc tggaacttcc   17220
agcgtttatt ttctaatctt cgacgaacgt atttggatgc cgaaacactg agctcgttac   17280
```

```
ctgctcgagg cggaagagca ttctttggct ttggcaggac ttcacttatt tccggcattg    17340
ggtccactgc tttcttttgt ttgtttacct ttgctgctgc gcgtgacttg ttttcctggg    17400
cttgatcagt tggatttacc cgataagacc aaatctcgct cacagcctta aaccctggga    17460
acagatcttc gtctctagtg acaggatttc ctgcaaactg atcgtacttc ccacttccca    17520
taacgtacac ctgccccgct gcatcaagcg cggctgctag ctcgtcttca gctcgaataa    17580
gtgctttgcg actcgacatt tctcgaaact ctttgtctcg ctggcggtcc agaaatcttt    17640
tcgctgcctc cagcgcaaca gcctcgcgag cctcctcttc gtctaaaatc gtctctagca    17700
tttgctgcat cttccatagc cgtatatgct tcggtacttc tatcccacgg ttcgtaagct    17760
cttcacgtac atctacgaga cgaacccaca tcgagcgaaa ctccttgtaa tcaatgtatc    17820
cgctcttgtc cttgtcatat ttcttgaaaa tcttctcctg cttttcatcg ctcacgtcca    17880
tgccaaagta ctccagcaca tcctatttac acatccctca tcagtcaaaa ccatgagtag    17940
ggtttcgccc cacatcactt tgaccaagct cgtaccgcaa actctaatgc atcaatctga    18000
cccgtcccgt cctcatcaaa caactcgaaa gcgtccctag acccagcaa agccgacgga    18060 gagaaccccca gggtgttacc tgacacagga tctacagcaa acatggccat cttgaactcg    18120
gcgaggtcaa tttcgcctcc gccgtcagta tcacatctac gaaaaatccg cagggctttt    18180
gcccccgaga tggaaatacc cagatccggt agctacacag cagcaagcac aaaaaagtca    18240
acaataacac attttcaat ggtacatttt gaatcctccg taccattgcc agaaactcgg    18300
atgcagatat gtttcccgac ccatccgtgt cgtatttctt gaacagctcc tctggcgata    18360
actacgtggc acgcggcagt tagcacctat ttccctcctc tacctgactt gaatgagtca    18420
ccctcacctt cgagttcagc actgcaactt tcctcttctc agcctcggct gcttccgcct    18480 cgttcaaaact ctcgtccccc ccgtccttcg cgtatcgctc gatggtcgcc tcgtcgtcgc    18540
tctcgtcgct gtcggctccg aacaagtcca agtcccccatt cttgcccttc gcagacgaag    18600
ctgccgtaga aggagacggt gcagccagag atcctcctcc tccttccgct acgcggctgc    18660
tagtgcgctg ccgctccttg cgtccgaaga gccccatagc acgagccacg ttgaagtggc    18720
gattcaaaac agccaatcat cgttaagtga tgtggttcac ttaacctggg tacactttg    18780 aatccattct gtacccactg ttgaagaccc acatgcatca gtctcacttc cgcaattgcg    18840
atcgcgagca caagtggagc aggagtgatg gtctcgtcgg actgggaggc gcaactgacc    18900
agagaaggcg cctcgggtag tacagagagc caactggtgt tccaagagga gttcgcgctg    18960
gcggagagcg tggcggccaa ggcgcagctg gtgcatcgga gctttgtgcc tggctcgcca    19020
gactttttgt actacggggc gctatgtgag ctgctggagg tgcagaggct agtggagaag    19080
gaggagcacg ggaaggcctg gcagagactg actgaggtga agacccagct agggatggca    19140
gagagacagc ttcagaccaa gagctgcagt aaacgcgcac agaggatcct tagtcgccaa    19200
ctgctgctgg agctcgacct gcagactaag ctcagcaagc cggaagagga gattgcggtg    19260
agtggggtga agtggaggat acataaaggg aaactaattt ggttttgtg ttgtgtagg    19320 tgacaacaca gcgtatctcg acgtcgctgc aggtgagctt ctcggacccg gaacctgctg    19380
gtatatcaac agaggccagg aaggagacgt atccgacagt gttgaggtgg gtgaggtgct    19440
atgtggggag gttctgtgtg tgaatgcgga gatctcatcg tgtacttgac tgcgatttgt    19500
atatattata gtaatgagtt gctggacctt gatgtatgga ttcaaacgaa gctggattcc    19560
ctgtcgtttc gcactgcaaa agatacggcg ttaatggaga tattgcatga cctcgatgtc    19620
```

```
ttcgggcgcg aaaagacttt ccaaaaaata tgtgcttggg aaggatctga ttatgatcgc   19680
tgggtgatgc tcgacgtgtt cttggacacc tacgcgtttg aatacgcgga cattccgggg   19740
tacgttgctt ctgtacagga aaccatactc atgagttgac cattttccta gcaactgact   19800
tttattaaaa cattccttga tctagatatg tggatgtgat cgtcaaggat gttgagcgta   19860
agaaggatac gtacaagggc tacagcttta acttccgttc agcgcatcgc aacttgtcct   19920
ttttgcaact attggaatgt gcaaagcgat cgccagagat atttcgtagc aacagcgagt   19980
ttgcagttcg cgggatgcaa ctacttcagg ctgctgcaga ggtggacagt gctcacagct   20040
tggacctccg aagtgaagct cggaacgaga aagagctgca gcatatcgag acctatctag   20100
agttttgcg tgattttacg ccgactgcag tatatggact tcggatgaaa actctgtacc   20160
ggaagctgga acttttgaat atggcgagct ggggaagctc tggagccttg gtgggactat   20220
tgaacgcatt ggtggagtac ctgaagatcg ctggtggtca cattgtaggt cttaataacg   20280
ttagcgggta tggtttcgcg agcgtttctc agatgagcca cgatgagatc ctccaaaaga   20340
gtttgagaac actatggtca tcccaattgg atgatgaagt cgttctcaat acgatacgtc   20400
ctcgcttgaa taacgacttc gtggaaattc agtatgcgtt ggtcatgatc aaattgggga   20460
agggcgaatt ctcccattgg acagcaaagc tcccggatga gggtcaagcg ctatcgagcc   20520
aaacgagctc gtcggaggtg attttctgtg agtcaaaccc aacttatttt ttacccgagg   20580
acccactgcg ggtttacgtg caggctcgca atgttaagtc actgaccgcc catctgtatg   20640
agatcaaaac catggagtac tattcacgat gcgccgtga atcaagggt gatatatgtc   20700
tcgatggatt gctaccgacg gaagagcagg ttatcgattt aagccatctc actgcttggc   20760
aagaagtccg tgttccaatc gaatttcttg ctaaaagaaa tccccagcgt ggtgttttg   20820
tggtagaagt gttcgaaaaa ggggttacgt gcagggctat cttgcgtaaa ggttttctcc   20880
gccacgtgga gcgaatcacg acgcaagggc acgagttcgc cgtgctcgat gaacgtggaa   20940
atcttctccg tgatgctcgt gcgcttgtga tcaatgtgaa gtctggcaac agtaggtccc   21000
aggtcggtcg cgagtatgca gcggacgagg aaggggcat atctattcca tttcggcaca   21060
gcgacgtgca ttcgagagat aagttcgcca tcgtattctg ccacgggtca tttgggaatt   21120
ttcatggatc attcagctat ttaccagaat catttgccgt ggacgttgac atacacatcg   21180
attccgagca gttggttcct ggctctgttg cccagcttgc tactcgccca cgtctgctgg   21240
ttgctggtat tgcgaccggc gaatcacttg agctgcttgt tgatgtgaag ttgacgattg   21300
agttcgatct tgtcaacacg agcaatgttg gctccagctc tcacaaggaa gtcctgtcat   21360
tttcgtccat gcagtcgatc gtgaatcacc ctccttgctt tgagattccg atggatgcca   21420
gaggcttcaa tgtcatggtt agtgcttgtg tttctccacc caacgtgaca ggctccgtta   21480
aatcgactga actgccaaaa gtgagcgacg caaaacgatt taacgttcag cgagtgaaca   21540
actttgacag cacatacacc gctcatttgg ttcgaaggtc gcttgagtcg ggaaccccgt   21600
acagttcaag cgagttccgg gtattagtgc tcggtcataa tggagaaccg gttccgagtg   21660
tgcgtgcgtt gttcacttgt aagcacgtgc actccaaaaa cgatatcaag gtgacacttc   21720
aatcagatgc cacaggtgag atcaaactgg gccaacttca agatgttgtg cgccttacgg   21780
ttcaatttga agctggtggt aaccatactg attcatatag tgggagttgc ccaacttgcg   21840
ttcatatcga cctcaaattg tgaattgctc ggtggatgaa atcgtggaga ttcctatccc   21900
gttcgcgtat tcgggtaaag tggagacttg ggtcaaggat aaactgatat cagtttgtga   21960
aatcgttgat acagtactac aaaatgcact acattgctcg gaagtgacgg tggtaaagag   22020
```

```
taatctgaat tgccctgtcg gcattgctgt tcaaataaga cgagctggta catacgtcgt    22080
ctacctccgg tcgttgaatc tcaagtatcc catcaccgtg tgcgagaaga aatccatgca    22140
cacatcgcta ccgcttggtt tgatcgtgca gccgacgcaa atccttctcg ctacccaaac    22200
tctgcccttta gtgatttgtt ctcaacagct aaaggtggaa gataaacaga agacagtact   22260
ggagattcaa ttgcggaacg cttccaggaa ttcaacgcaa gtattggtgt ttttgaagca    22320
cttttttggac actcgaacca gcaaaataag cgaggtattt gttggagatg gtctgaagcc   22380
tgcttcgagt tctggaaccc gatcaccaag actgtcattt ccctccaccc cactcgaaaa    22440
cgacttttttg aaaatgcgca agatcagcga tgaatatgct tacatacttc agcgacgcgc   22500
gctggtgtcc gctaatcaaa actctctgag ttttttgggg acctcatcga taccaaaacc    22560
atcgctactt caaaatcccc acgttcaaag tgaaacagat atggaggtgg taaatgttga    22620
ggctggtgag aaagtaactg gattcaagtc tgtggccgca aatgatatcc aatcgggagg    22680
aacttctcgg aaaaatatgt tgcagaagaa gatacatcga ggatacggag gatctacagc    22740
aggtcgtggt ggtgggatgg taccaagtat ttcgttcctt gggcagcaat cgcaactcgt    22800
agcttcgtgt attgtagatg agaatgatct tgtccgcatc gagctaagcg gtctcccttt    22860
cttttccgac ggaatgagat cttttgaagt ttgcacggtt gcatttgact gctcaagtgg    22920
atacatgtgc acgcaggagg tgccaatgag tcttcctgct gtggaagata aagtggtgat    22980
accgaagcgc gacatccgtc tatcagttga ggaggctctt tcgccatccg accatttttca   23040
tcaggttgac agccacaagt gcgtgcatag tggcgaaatg aaaaacctac gcgttcatt     23100
ttccagcaag tatgcgttgt atgaaagtct tgaaagcgct atgaacttgt ggccaacgct    23160
tgcctctgag ggtaatgtcg aagagctagc gagcaaactg aaagaatggt ggggtctgag    23220
caccttggag aaggaacatt tctactattc aaatgcgtgt gatgatcttc acttttttcct   23280
ttcgcgcaaa gacccagcct tcttcaagca gtatgctgag ccgttaattg ctgcgaagat    23340
ttgcaagtcc ttggtggact atcacgtgct tgatgatgaa gctagtttgc ggagcttcta    23400
tcttggccct gctgtatttc agcacttaaa ttgcatcgag aagttactgg tggcggaaag    23460
gatgacgaat atggaggaga aaacgcgcat ctgccgtgct gtcatcagcg agatcgaatc    23520
tatctatccc tcgggctgct cgagtgtact ggcgcgcgtg tttaacactg tgttgtccct    23580
aggtcaagtt gagccgtctg ccgtcccagc tccaccacct tacgcagcat tcggtgcacg    23640
tccagcgatg tctgggtacc aaggtggagc acaaatgctt cagcacgcct acgctcctgc    23700
tagtgaagtc tgttatagcc ccacatcacc aatgggtgcg ccatgtggat cagcaatcga    23760
tctttcttcc agtgcgctac gttttgggga ggcttgtggt gctacatgta tagaaactac    23820
cgagattgct tctttcctgg aatctgatga tgactttggt gtaagaagcc tgggcagcga    23880
gagtgacgag agcgagaata cagatgatga cgatgacgac cctcaagaag aaagcaaaag    23940
gaaaaggaag cctaagcaag aggctcagta tatcccacct ggcaaggttc gcaaagtgca    24000
agaaaagcgc tatttctctg gccaacgtcc acctctgaca ggatgcaaca tgttctggaa    24060
agagtacgca gagcacatgt tgcgccgcct agaagatggt ggtcggagac gctttgtgtc    24120
atcatatttc ccggaggcac tagcctccat ctctgaaggg ctattcgcgc tagcagtgct    24180
ggacctcgac aaggacgcaa cacccagtca agtgcaactg acctcctcaa tttcgccagc    24240
tagtgaagct gtcctctatc atcgcagcat tggccctgct gagagctcgc ccacagccaa    24300
cacaatgttg attttgaagc aacgcattcg agacgaaaat ggggactgca gcacagagct    24360
```

```
actggtcaac aaggtttaca ccacgagcgt cactttgagc aacattggct cggaccacct   24420
taccaatgtc aatttattgc tgcaaatacc tcaaggtgct cttccaatgg ggccgagtgg   24480
gttttacacg ataaacgaga tcggaagcgt ggcgcctaac catacaaatg agttcgtgtt   24540
ttcgtactac ttcccagaag aagggctatt ctcacaatat cctgcgcgtg cgtcaattga   24600
aggtgttgtg gttgcttggg caaaacttga agagaacacg acgacctgca aggtggctcg   24660
cagtgcgacg tgtgtgaatc tagcttcttg ggcagatgtc agtgctcggg gctcgctgga   24720
agagatcgta cagttcatgg agtctgcaaa acctggtgtg aagactgact tccagaagtt   24780
gttctggcgg tgccatgatg agttattttt ccgccggctg gtgaattatc ttagaaataa   24840
gatgctcttt gtgtcgggga tttggaaata cgggcttctt catcgtgatc aacaaacaat   24900
gaaggagttc ttcgcaagct cgaatgattt gtcgcagtcg gtggggagtg gcttctgctc   24960
ctcgtatgtg gacgagacac gattgtatcg tagcgagcgg tttggatcga tgtttgatca   25020
gttcgatcac tgtgagtttg gacctttcct tacaaggcgc acgcatccgg tagcgggcag   25080
agtggataca caaatttcgt gggggtctgg cgagacaggt caaacgtcag gcaagcgtat   25140
actgaatgct gaggctcgaa atactatggg ggaactttgt cagcgtctgg gaacgcacac   25200
acggatgaat gcgcagcact tgctggtgat ggcgtactat atgattctgt ttgatcgtat   25260
cgaggatgca gtcaagactt ttgctcggtt ggaaaatctt gacacgccaa ggaagttgga   25320
gcttgagaat acggttcagt atgcatacct ctctgctttc ctcgactttt ccgtagcaa    25380 cggcgagcat ggccgagcat ttggcgtcgc tcgtcgtatt atttcgcgtt atgctgcgca   25440
tccacaacct cgctggcaac gtcggttcca caaaatggag gagtttctgg aagagtttga   25500
cgccttcgag gcacaaagct taggccgcct tgaggacatg gaagtggtcg atactcctat   25560
ggagactgaa cgagagagcc ccttcaatca agatacagcc catggaaacc aagttaagct   25620
agaagcaagt gtggacaatg gcctggttac actgttgtca cggtctctag gagcgtgtga   25680
gctcgcgttc tatccgattg atgtggagct tatgttttcg accgagcctt tcaacacatt   25740
ttctgactcc gcagcatctg catcaagtct tctcttggtc gagcctcggc gacaattgtc   25800
tgtcgatctt ggtactctac caaacgatgt aaacctgtca aagacatcgg tgccaattcc   25860
tcaagagctt cgtgctacgc aaatgatgat tagaatccaa gaagtttcgt cgtcgcgcac   25920
tgtcagtagt gtggctccgc ctatcgacat gattcagcca tacttcaatt cgagtttaac   25980
tgtcgagatc atgactcagt gtggtgtact ccaagttttc cacgacggat tgccagttcg   26040
ctcctgttac gtgaaagcgt acgccaagct atcgtctgga agctcaaccc accacaccaa   26100
gactgagttt tcaaggacg gctacaccga cttgctcggc aaaattcgact atgtgggcat   26160 caacggagac ctcatttcga atgtcgagaa attctctatc ctgatctctc acgacaagtt   26220
tggtgcaagc gtggaacaag ctgacccacc tgtacttgcg gctaccgttg gcgatttcac   26280
cagccagccg gagcgcaagc tgcttctcta ctagggcgct cgaactgctg agcacggtga   26340
agcagaaaaa aaagtacttt gacgcaggga gtgcagttga atcgatattc attttcctgt   26400
ctgactttgt tgatcacgtt ttcgcagccg actaacatct tcatagcaca gactcaagca   26460
tatgggcttc tcacctcca gacagcagag gagtctcaat agtagctaca gccgcacgtc   26520
ttccacttcc tgccgcacag gaaacaaaac tcatggccgt tcaagcacgc catgcggttg   26580
caccccatcg acttctgcac ccccactcca caaccaggac actgcaccc ctggtgtagc   26640 tgcaccacac gcgtgtattc acgatccgac tgaaggtcca gcgcgcgcca aggtttgtcc   26700
tggagaaagc gttcataagt tacgaattcg gcaacattca acgcctcgcg cacgtagtcg   26760
```

```
gagggggaact ctctcttgca gcagtgtgcc ggtaccatgg agcgatcgcg gacacccata    26820
cgacaacgag tcgcaacaca cttggtgcag tacagatgac cacacgacaa aatgcgacgg    26880
ataccctcgt cttccagggg caacagacag catgcgcagc ttggaggtgg tttggactcg    26940
ccatccacca agccggagac gtctaccaca gccaacgtct cgtccgcact gtccgcttcc    27000
tgatcagcct ccgcgggatg gagtaacttg tgttcctcct tggcgtagaa gctaagagca    27060
accgcttcat caagtacaat ttgctctgca cgacggatct cttcgctgta cacctccaac    27120
gcgtacgctt ccgccagttg ggcttcaaca gcagcttcct cgcgaccggc aacttcatcg    27180
acaaagtcat ttgtgtcgga gtttaggtag accacgtgtt cgaagtgacc atcagcagca    27240
ggctcttcca gctccctcaa cgtcggaaga acttccatgg cgtcacttaa gagcccaagt    27300
cgcttatgct ccaacaggga aattggaaag tgacatcacc accaacacga gtttccacta    27360
caacaacaat aagaagaact tcttcgccag ttagagtcac cccttcccag cctgccgttg    27420
agtcttgacg atggcgtgca gacagcaaca tatcaatcaa ttacatcaag aagagagaga    27480
actgctagtt ctcgaaatgc atgattagta gattagttag ttaccaattc aacactatcc    27540
aaatctgcag attgcacgtg cacattgact ggagtcagtc ttactgatag atctttccgc    27600
aagtacactg cacgtgcaga cagttccaac agaaaacgtg gccgagggtg cactgcatag    27660
cattgcaccc cgagatctta acaactccga tcccgcacac aggacactgc tttcccttaa    27720
cttgacgcac caccttgcgc tagtcctggt cggactgaag cgttgatgaa cgtgggtcac    27780
gctcggcaag aaagcgctcg tattgagcga actggccctt ggccagtacc agtttgacgt    27840
agtccatagg gaactctttc gagcagcaac gaatcggaac ttgttcacga ttcgcaagac    27900
tcgtcttcgc catcttcgtc aagcaggatc ggcagtagcc gtggccacac gggcccacca    27960
gccacttggc acgtggtgac acagtcgaca agcaggaact acatttacgc gcgctcagct    28020
gcttctggtt gtttatcttc tccacctttt tggtaggtcg gagctgcttc acggatgaag    28080
cacgcgcttt cccttttgcg ggcgctgcgg ccagcacggt ctcgggatct gccttgcgct    28140 tggttcccg tgtgtttgca gtggtggtgg tggtcgttgc gccggtgtat ttaagcatga    28200
gcttggcata tcttgtgagc tcgccgcgtg gaataacgcg attcaccaga tgcagtggca    28260
gcacttgatc acaacagcta actggtgccc cactattggg agcatttaga tagctgcgga    28320
cgccagtttc aacgcaatgg tgacaaagcg cgtgaccaca gtgcgcttta atttgtgaag    28380
tggacatccc gatgccacac atatggcacg gttgactgga taacgccacc gattgttttc    28440
cgggcgctgg aggcacggtg ttcccactct gcttcgagtt ctgcacctga acacgtcgaa    28500
ccttagagcc gcgagtgaag tatctgcgct gaggcggttg gggtggtgag ttatcagctc    28560
ggtcatcaag aaatgaagat agcgcagccg acgctgtcgt ggtgacgttg tcctgcacca    28620
acttcgccgg ttgtttcatc tcggtgtcat cactcacgac aggagggggcg ggaagaggta    28680 gcgcaggtgt actcttaacg ttcattcggg tagcaggcgg cttaccactc ccagcttcgt    28740
cgcgaggttg tttcatcagg aatgagtagt aaatatcttc ttggcacgcg agtaccatac    28800
gaatgaagtc gtgcggaacc acttttggc agcactgcaa gggcgcgatc ctgcgtgaca    28860
atgcctcccg agcttgccgt cccagacatg ctcggcataa aacgtctcca cacaacagcg    28920
ggaacagttg ctgcgtcgac tccacccccg accacgagaa ctctcctgca cacccagaac    28980
attgagcaga gggcgccatc tcaacgtgct cttcggatct tttgccagaa tgcaaagtgt    29040
gagtgtttga tcaaaccgcg taggatctgg gacgcggcac tcgctttctc tttggccaaa    29100
```

```
agcgttggat tccataggac gggccaagtc gagacgcatc aacgccatac agtcgtgcaa    29160
ttacaggaaa tacaacgttg aatgcaacag ctcctattaa ccgacaccaa gccgaagatc    29220
actcgccaag aattgctcgc agttcatcct ctgggatcag cgggcagttg caggagcccc    29280
agcgctgcag gcaggtgtag caaaactgat gcccattagg gcatgacatg tgcacgcaac    29340
cgaaggcacg ctgcacgccg ataccacaac ccgggcactg cttcgctccg aaggctttga    29400
cggttgccga gtactcggca tcagacacga ggtccgatat tttccagtct ttctccatca    29460
cgatcttctg gtactttgcg taatcctcag gtccagtcaa cgcttcacgc acgtagtcat    29520
caggcagttc tttcttgcag caccgcagtg gcgccagtgc gcggtcaccc agcgctagac    29580
ggcacatgcg cagaagacac ggcgggcaat agtagtggcc gcaaggcgca attcttagct    29640
cctccgtcgc tttccaaaca caacagctca cacaatttgt acgtgtcggg gttttctcac    29700
gctgcctcat gtacaacgcg aattctgacc ggctcagcac aacctccact tgattcagag    29760
ctaattcgtg tctgcacttc cagcacgttg ctggagtacc gttcttgaga gccttcgagc    29820
acgccttcga aagacacgta aagcagacgc gatgagggca acgggaaagc ttaacaaccc    29880
gggttgcctt gttgctgcag cacgaaacag tcttcttctt tgccgaccgt ccacgtgcag    29940
cgaacttgac agttgatggc atgcccaagc tgctatttgc gcaggtctct ctccttcaaa    30000
tatgcgccca tgatcgctac caatcgcttc ttcgcctcgt cccagcgttt gtcaatcgtg    30060
ttcaacgcac cgtctcgcag cagaagaaac gagtgaccac cttggctact cgcgtcgttc    30120
catggagcag cgccaacgcc accaacagga acccaaacgc cgttgtgtac accgcaaacg    30180
gatgctgcgc tgtcattgca tccaaatgaa ccggaacgcg gctgtctcca atcaagaagc    30240
caagcacacc aagcaccagc accaccgcca gcatctggcc agcgccaatc aacaacttga    30300
agcacccaaa gtacacccct gcaagcactg ttctgggcga cgacgtgccc aacgacctct    30360
cgaatcttgg acacggctca aaagcctgtc cttgtctccc tgcaattggc gggggcactc    30420
gaaccggcag cagcgggtgt aattcagtgc tagaacttga accccccac tcggccaagt    30480 ccatgtcaat gcaatccgct gccgttgcag ccagtgcatt gtaaataaaa gcgtctatgc    30540
agcacaagta aagaccgtg tgcagcagcg cgtgaaagac cgcgacgccg cagccacaga    30600
ggggcatcgt cacgaccgcc agcgctgccc ccgcccacac taacaatgca gcgacaatac    30660
tcagcactgc actgcacccg ttgaagagca gcatcctcgt cacctgactg gccaaagtgc    30720
agggccgtac caagttgcag cctcgcggtt ggcgcaacac gctcacgcga tggcgttccg    30780
gccgataggc gggcggcgac ggaggccacg cgaggcgttg gcggggctgc gaagctgtat    30840
acagtggggt gaagtctgcc acggcctggt acatgtgctg cgacggcggt agcgtctccg    30900
tggcgcggta cgaagcgacg aacggactgc gcggcggcga cgacaagggc atcatggccg    30960
gccagaaatc ttcgattgg tccgattttt tggtccaatt tggtccaaat ttgagctgat    31020
gcgaatagag gggatcccct cctctgttgc atagcagaca attccggcca caagttgata    31080
atcatcatgg gagactcgca gaactggtcg tcgttcgagc ctgaggcgcc caagcctgcc    31140
aagcagccac agacgacgga gagcgacgac atcaagagta gcaagggact gggcgcgctg    31200
acagagcccg tggcggtgcg caacctgcgc aatcgcctca tcttcggcag tttggtgggt    31260
ttcgtcacag gcgccacctt cggaggcagt acgtacagtt aacgtcgctg caatatgttg    31320
caatagcttc tgcattgctg acttgtatgg ctggtagttg acgcggccaa gacgtaccac    31380
aagacgcacg ggaagctggc gcctgcagct ctgagctccg tcgcgcgtgg cgctgcagtg    31440
acgggaggag ccttttcagg gtgaggaatt gcagcgacga tgcgtgtgtt gagcgcgttg    31500
```

```
ctgacggtgt tttgtgtggc ttttggtgca gtttcttctt catgtactgc gggatcaaga    31560
cggtgctggc gacccagcga gaggacgatc tcgtgggtgc gggcattgct acagtggcgg    31620
cgggtctgcc gttcatccgc tcgacggtca tgaagcaaaa cttgccgtac gcactcatgc    31680
tggtggcact cgaccacttc cacgaggagc tcagcgaata ccgtaaatag aggatcgata    31740
gggtcttgct tttccgttgc gttaatggtg ttgtagtgga tgaagcaggt ttgcagttgt    31800
gtgcagctcg atcattgacg gtggcttacc aaaatgacgc aggattgtgt cccatgatga    31860
acttaatttg tgtttctgtg cattacgctt tgcgtgtgca atataggtct ggctagcgcc    31920
aagtttcttc ctgacgccat ggagacgatt taacttcacg cctacagcct ggcgccgacc    31980
tccttggact gcgcaaagag ctgctgcatc tcgacgaggc tctcctcgag caggtggccc    32040
atgcgggcgc cccaactgcc gtgctggcgg cacgcgatgt tgaactggat cgactcgttc    32100
ttgacgctgt aggcgatacc aagaccctcg ggcacgacct caccccagcc ccagccgtca    32160
aagagctcgt tggtcaggtg actcgtggaa atgagccaac gactggccct agtcatcacc    32220
gggtcctcga agaacggcac gcgctcgcca ggctgcacca gcagcttcaa gccgagaatg    32280
tggcggtcca caccacgacc agcgccagcc ttgcgcatgt acgcaacgtg ggcattggct    32340
gcagctagca gcagcttcct cttctcttcc gcagtgacgg caccggatac gtcttccatg    32400
gcgtcggtaa acttcgcgct ggccgtggag caactcgcgc tcgtctcggt gcgtccgtgt    32460
aggaagatgc gagtctgcga tgcctcatac gtggccacgt tcttcttgaa cagcttctta    32520
taggcaagtt ggatcgcaag ctgcacaaac gcgtcgggc tgcagcggaa tcccttgatg    32580
gagcgtgcgc cgtacccgta aaggcctgc acgaacacct cgtggtcgat cacggtctga    32640
tcaaacgcct tctcggcttc aacaatgttg cgaagcgtct gagtcgtgaa tcggaacgtg    32700
agttgcttcg gagcaacgag cgagcgctca agctgtgccg tcgtctgacc acgcgggccc    32760
aggtcggtct ggctgtggtg aagacgcgac agcagcgagt ccgtgtagcg agccatgggc    32820
atgccgtcca gcatcgagtg ttcaccgagc agtccggcct tgccgttctc gaacacgaca    32880
atctgcacgc atttgtcgaa gaagcggttg cggccgttgc catgccacaa tccgcgtgcg    32940
acctcggtac gggacacagg cgcttcatca tccatattga ccactagcaa cgagctctca    33000
atggcacgca gcgattcctc gttcttcggg gacgcccgga tcagctcctc acgagcatcc    33060
gcccaggagt cgcgatcttg ggacgtgagc gcccccacag ccgactcctt ggctcccgca    33120
gcttccagga tcctggccag ctggaagcac agcgcttcaa agcccagcgg ctcctgagtg    33180
cgcggatcca gcagctccag ctggaagaac ttgttgtgcc gcatgaccac ggcgtgctgg    33240
tgcatcttgg ggtcgtagat ccggtacgag tcctgctcgc ccgcgggat ccggcacgcg    33300
ttgaacatgt acttgtaggc tgtggcacac acgggcgtct tgttcttgcc gagttgctcg    33360
ggctcaagcg atccgtccgc aacttggcgc gcgaacagca ccgagcccct cagcagcgcg    33420
gcggcccgtc caatgttgga gcgctgggcc gggtgcacgc tgtctgcgaa atggaagaag    33480
tagctgacgt tgaacaccac ggggtcgcgc acctgcaggt agccgagcgt gttccaccac    33540
tcagccagga agctcgagtc gccgcgctcc ttggctctgg caagcaagcg gttctgcagc    33600
tcgtcaccca cgcccccggg ttgcaggaag gcggcggcca gctctttggc gcgcgtcaat    33660
tcggtgggcg tcacgagcgg ccgcagcgtc tccaggtaca gcgccaccgt gtcacccagc    33720
gcggcacag gcagccgcgg cagcgcgcgc tggaagcggt agagcggacg cgcggggtcc    33780
tccaggtccg cctcggcgcg gtagtcgccc cagcactcgc ggaagccctg cgggccgaag    33840
```

```
ctgccgtgtg gaatgagagc catggcttgg gagatggtcg tgtgtctttc gcggtagatc    33900
ggagactgag gctgaaaggg cacaggttca acgtcaacgt atgcaatatt tccaaacgaa    33960
gcgcaatatt tccaaatgaa gagcaatatt gtgggtttga aaagcgagca gtgacgacag    34020
cgacggacct tagcttaact ggaagatgag cggttcctcg ctggtgcctg tggccgtgac    34080
ggcggcggtg ggcggcttgg cgctctatgg gtttctgcgt attgctcgcg cccgcatcta    34140
cgacgcgacg atcgtgaaat tgaccactgg atggtacgag gaggtgctgg agcggctccc    34200
cgagggcagg aagttcctgg acgtgggcat tggcacagga ctggcgctga tcaacaatgg    34260
ggcgcaactg aagcgcaaga atatcacagt agacggcgtg gactatgacg aggattatgt    34320
gacgcgctgt caggcgctgc tggagcaaaa gcagctgacg acgcacgttc aggcgcacca    34380
cgcgtccatc tacgacttcg cgggcggccc ctacgacgcc gcgtacttca gttcgtcgct    34440
catgctcatg cccgacgcgg tgaaggctct acagcactgt gtggcgatgc taaaacccgg    34500
agagggcaag atctacgtga cccagaccat ccagacgcgc cactcgaagc tcgtggagat    34560
cggcaaaccg ctgctcaagt tcctcacgac catcgacttt ggcagcgtca cgtacgagga    34620
ggagctgctg agcacgttca agaaggcggg actcacgctg cgggagcatg tgccgatctc    34680
tggctcgacg atgacgtcca cgcggtcctt cagactcttc gtcctggaac cgtgaagcgg    34740
gagtgagacc tgctatatgg aaaccgctat gactttcgaa cagcgttggc aatagccaaa    34800
caatgaagct ttgtacatcc ttgtgcagtt caataacacg cttcgggctt ctttctactt    34860
ttgtgcgatc ttgaaccgac accactcact gatttacggc gggggactca aggggggaga    34920
attcgagaga tcttggagag ggatgactcg ctcgaggtgg agcaatgtgc tcccttggt    34980
ggcgacgggt atttgcctct tgcttgcgct aggtttcggt caaggggtgg aagcgtcggt    35040
tgctaacttg aagaggaacg cggagcctca tgacccggtg ccgccactc gaggtctcat    35100
tcaccgacga ctgggagaca aatacaatga ccaggttcgt catctctacg cccggccttg    35160
ttgtaattgt taaccttgtg ttgtacacca gatcgcactt cgtgtactgc catcagatgc    35220
cgatcagctg gacgtgtttg agcttggaag tgacggtgac aagctcgaac tcgccgcgaa    35280
ctcggccacc gccatggcgt acgggctgca atggtacttc aaaacagtac tacgcactca    35340
aacagattgg gacaaccaca agctgcaact tccagacaaa ctaccgaaag tggatgaacg    35400
agtgcgccaa aagcgaagct cgaaattctc gtattaccag aacgtggaca cgggtagcta    35460
ttcactgtgg gcctggaggt ggccgcagtg ggaaaagcat attgactgga tggcgatgaa    35520
cggtgtgtgc tcatatcaat ctattgaagt tgtgtaatac tgattgcata tttactatcc    35580
aggtattaat atgccattgg cattcactgg gcaggagaag gtgtggcaaa atacttttca    35640
caagtactac aacgtgagct atgagggcct cgggaagttt ttcgctggct cagccttctt    35700
gtcctggggg cgaatgggaa acctgcgtgg aagctgggtg aaaggacctc taccccaagc    35760
cttcatcgac aaccaacatg agctccagct acgtattctg aagcgtatgc gtgagttcgg    35820
catgattcca gctttaccag cgttcgctgg acacgttccc gaagatttga agctcacatt    35880
gccaaacgcg aacttcacac ggtcgccaaa ctggggcaac ttctcagacg accattgctg    35940
tgtctacatg attgagccaa ccgatccgtt gtatcgcgag attggcaaga tcttcctcga    36000
agaacagcgc aagttgtaca actacacgtc atcactgtac cagtgtgata cctacatgga    36060
gatggcgcca gagttttcta atctggacga actgaagggt gcagctcgcg ctgtgatcga    36120
cggcatgtca gcggcagacc ccgatgccgt ttggctaatg cagggctggc catttgtgga    36180
cgatccaaat tattggacca ggccacgcgt gaaggcgtat ctcgatggtg tgcctacaga    36240
```

```
aaagctgatc atcctcgact tctacagtga atccgtgcct atatggaaca agatggacaa   36300
ctacttcggc aagagctgga tttactgcgt gctgcacaac ttcggcggaa atactggaat   36360
gcggggagat tgccgacgc tgggcacagc gcctgtgcta gccaaccgtg ccagcaatgg    36420
cactttggtt ggtgtcggct tgactatgga gggcattttc cagaactatg tggtgtacga   36480
ccttacgttg caaatggctt gggtggataa tcctcttgat atgcagaatt gggtgccaaa   36540
atttgccgcg cagcggtacc attctcgaaa tgagcatgtc gaacgggctt ggaactatct   36600
ctcgcggtcg gtttacaatc gcacacttgc atatggcggt gtgaccaaga acttggtttg   36660
cttgattcca cactggagac ttttgtacga caggtttcag cctaccctca tcaagtacga   36720
cccgaaagat gtcgtgcttg cctggaagga gcttcttctc gttggagaag agttgcatgg   36780
tgtagacacc taccgacacg atctagtgga tgtcacgaag caattcctga gcaacaaact   36840
cttggagcag tatgttcgct tgaaggatct ctacagcgcg aaagtcgtgc catctcatga   36900
agtatgtggg ttaaccaagg ccatgctcac tacagtcgag cgcctagagg aaatcctcgc   36960
cacaaacgaa gacttcctgc ttggaaattg gatcgctgat gcactagcac ttgctggcga   37020
cttaaatgtt ggagacgaca ggttgacgaa atctaaactg cgagaatact acgaatatga   37080
agctcgcaac caggtgacgc gctggggcga tgacaacaac gaggctattc acgactatgc   37140
tggcaaggaa tggcaggtc tcgtgaaagg atactacttg cctcgctgga ccatgtggct    37200
caacgaggtc tgcgaggcgt atactgaaaa acgtgacatg gccgtgaagg cgttgaagaa   37260
aaagcgtatc gcattcgagt tgcaatggca gctcagccac gaggtgtatc caaccactac   37320
agtcggcgat ccgcttgcag tgtccaagcg catatacagc gagtatatcg acagctatgc   37380
cgtggttcct tgggatttct ttgggatcaa cacagcgaca tcgtagtgag cttacacgac   37440
aagcttgaag gagagcaacg gtctgtacgg ccagcgagcg taacctgcat gtttagcatc   37500
gttttgcatt tcatcgtact cttgaatact gcttgaactc catggtactt cgaagtatta   37560
cttagccttg gcattgtcat tagtcttgtt gatatactgc tgaaatatta cagtaaagct   37620
cagtaagcgt ttggttcgtt aagcttgttt tgggtttgta gactcatctt gtatgtgaac   37680
aaataagcat tacggtcaca tttgagcttt cgtcccagcc cgcacatagt gctgtggttg   37740
gcgacaatga tcccggtctt cgaaatactt aagtgaaaca agctgaagcc aatgacatct   37800
cttactgtga agcagcattg ttagctaccc ccatttaacc aactgaagga taaactgtag   37860
tcgtttcctg caccagagtt ttgtcagact aattctggta acttcaatat tccttggtca   37920
acacgcttac cactatgctc gagtgcgttt ccactgtga aaaagatcca gaaacaaat    37980 ttggctgaac cattcgctag ccccgatcga gcacaaatga agcaggcgt agcatgaaga    38040 ttccaagttt cctttggatc gtttatcgat ttatcatgaa atatagtaat tctaataccg   38100
cgtaggtgag gacaccacca acctaagatg gcaagacctt ctttatcaag cttctttaat   38160
acattcggtt gggaagataa aagtcggcaa cttcggtgta ttccacgaga atcacggaat   38220
tccgtcgtga aaagaacttg agccgttttg tggacgaaaa cgcttcgttc tctcgaagta   38280
taaagattct acatgtagat tcctcgagag acttttttc gcgaggttta atcttcctgt    38340
gcgctgtgta tttgacatgg gcacgagcaa cactcgcttg acgtgttttt tgcagctgtg   38400
tcgtcgacag cgccggatga gtttaagcta ccctcgctaa catcattgtg tttcggaacg   38460
gctagtgcgg agctgtaccg aaggcgaacg tcaaggtttg acttcgtttg gaagtcttcc   38520
ttgatgagct gtagtagtgc aacatcaatg atgcaagctg atcttaacgg gcggctggcc   38580
```

```
ggaattcggc gtcatagtac agcgatgctc ttcatcaagt ggctggtatc cagcatcgac    38640
accaacgctt gaattgaatc atcgctatcc atgccttgag gattttcgca caaaatgcaa    38700
ttttcagact aacatttctt ggcaacagca atggaactct tcatgggcta gaaaatgatg    38760
agtttcagtt cggtatgcga gagtttgatg aacaataact caagtagacc aagagagccc    38820
cctcgtagac gtgctaacaa taccaataat gttcactcta ccagcaagta gacgtgcttg    38880
cgtcactctg ttttcatttt tggtaatgat ttcccgcttt tacaaataaa ttatttctaa    38940
ggaatgtatc gtcattacga aaatgttcac agtggaggta agaaaagtct gctccaagaa    39000
tgagtcaagc gtacaaataa ggcgctgcta aatgcagctg tgtgcgtagt acgagccttg    39060
agcggagaca atacagcgat gcgcagccct ccaagtggaa ctgcgcggac agaccgcgga    39120
agccatcaac tatgcagcaa tgcacaaaaa ttcgagtgta gccaaaagtc gaaaatcagg    39180
agggcgggtg tccctccagc ctctgcataa cgtctccatt ctccatcgat ctctcgagac    39240
gcgcgaggtg tcgaggtgct gtctctcgca ttcttttttg agtcggggac taaaactctt    39300
gcgtctccac ttgcgctggc ctcttttcct cgctgaccac cggctccgtc ctcataattg    39360
gaaaacgatg gcgccgtccg agtggctggc ggcctggcgc gccgtgcact ggacgtgcct    39420
cggagtcgcg ggcgcgagcg cgctcttcct gctgctgcac tcggccgcgt tccaccgact    39480
caagcggcgc atggccgact tgctgctgag cggcatcgcg ctggccgacg cgggcttcgt    39540
ggtcatggag gcgcttaagc agctgctgca cgcgagctac ttggctcgct acggagaggg    39600
acacgacgga caacgcggct acaccacagg ggactttgtg ctcacgctgc tggggcgctt    39660
cagcttcttc atgtccttgt actggatcgc caacctgtcg ctgctcatgc ggctgggcaa    39720
tatcgaggcg ctgcacgtca aacgcagcct gctgctgtcg tcgctggcct cgctggtcta    39780
cggctgcatg catgctgtcc tgccgacgtt gagcgacgca caggcggggg cgtcgtatac    39840
agcgacggct gtgctactgc tgatgatgca ggctacgccg ctgctactca tcatgacgaa    39900
cctccgcgcc gtgagacggt cgagactcaa ctcgtccatg caggggcgta atgttatcag    39960
gaggttgacg gggtactgcg tgtgcgcggc cgtgttcacg ctgccgtacg cgctggtgct    40020
catcgtgtcg caagatttgg tcgggatcgg cgccgtcacg gagacgtgca actactttgt    40080
gcccattgcc aacgcgctgc tgttcggcac aagtttgagc tgctgttgct gttgtgctac    40140
agcggcagac acggcggcag gaccgccaca agacgggaaa cggtgtgacg atgataccc    40200 gtcgtcgtcg atagatattt cggctggtgg gcttacagac ggcagcgcta ctcctgggag    40260
tacgggttgt tcgggggggtg gcgtgttagg cgtccgagac ggactgctgg cggggggggcc    40320 tattgctgaa atggtgacgg aaggaccagc ggtgaagatc ggcgagggat cgagcgccga    40380
ggtgtacaga gcccagtggc tgggcatcac agtcgcgctc aagtgcctgc gcttccatgc    40440
tggtgctagt tccgaagcag atctgtacat gacgcacctg gccgagctgc gtaccgagtt    40500
cctggatgaa gcagtgctgg ccgcccagct gcgtcacccg aacatcacgc tgtttatcaa    40560
aatgggcacc tacaggggca gcttgtgcct cgtcaagtac gtgctggcta tgaagtgtat    40620
aggacttgga ccgagagatc tgacgtttgt tgtgcctttt gttcgtgtta ccagcgagta    40680
ttgtgcgcgt ggatccatga gagatgtgct tcgtgcgaat ccgctgatgg agtggagcac    40740
taaagttcga ctagctttcg agaccgcaaa aggactggcc ttcatgcaca accgtgagcc    40800
catctacctg caccgcgacc tcaaggcctc caacatcctc gtcaccgcag actggacggc    40860
caaaatcgcg gacttcggca tcgctcgggt tgcgacggat tttactgtga ggaagcagca    40920
catctcgcac aagttctccg cgcagtcgct tcagtcgttg cagtcaattg gtgagagcga    40980
```

```
tgtcatcgtg gacaacgcag catcggagct gatgacgact tttgcgggca cgtggcgctg    41040
gaacgcccct gaaatcatga tgaaccccaa cgagtgccgc ttcaaccgcg aaacagacat    41100
gtacagcttt ggtgtgtcgc tgtgggagat tctgaccaac ggagcagtgc cgttcggtaa    41160
tgtggacttt gatcatcagg tgcggcagct cgttgcagtt ggcgagcgcc caacgcttcc    41220
ccctgcttat atgcggcgcg tgccgcccga gttcgtcgag gtcatgtgtg cctgctggca    41280
ccagcggcca gagaagcgac ccagcgctca agatgtgatg ctgcgacttg gatccttgtc    41340
gtactcgctg tcgagcggct cggagtttta catgtcgtcg cagggaacag cgcgctacat    41400
cttcagcgac aactactacc aggccatgga ctctggccag agttgcccag gactgtggtg    41460
aggacttgga acggcatgga gtggcgtctg taatttaaga gaagtctgca ccaagattcg    41520
cagagcagca aatatactga gcaacgtaga taaattacgt atcaacactg tcacaacctt    41580
ggtgcagttt accacgcacc accatcggcc tccaccatcc catgtgtcac tccggaatca    41640
tccttctcac tgctgctggt cgtggctgtt gcttcctcgg acgctgccag gactcgagac    41700
cggcagaatc cggtcgatct cctcgtcact aattccctgg tccctcaact ggttccgaga    41760
cagcgcaagg acaaccttgg cctcgtactc gtgcttttcc gccaacaact tctccttcct    41820
cgcctgagcc tctaaaatct ccaagttgag tcgttctcgg cgctgttccc gttggtctct    41880
cttgatctcc agctgcagtc gtttctcctc gatctccagt ctccgcttgt tgaacgcaga    41940
ggtcgttgcc gcttgcgccg tggtcgcagg tccttctacg atggaattga ccacaaatc     42000
gtcctcgttg agtgcagcgg cggcactggt ggccgtcgtg ctccaccgcg gtcgatcgcg    42060
cgtcctggcg ggcgattggc gctgtttctt ggccggtggc gcgttgcttt cggccgaatt    42120
tgcgccagtc gtcgttgccg tctcagtgca catgctgtcg gcctctatgg cgtgatcagc    42180
gagctctgag ggcgtcggaa tcgcgtcgga cagcgagctg tgcccaagt  cggttgacgg    42240
ctgctgtgct tcgcccaatg aagagcgcgc gggacacaca cgcagatgcg actgcaggcg    42300
gttgacggca gccgacactt gcttttgaca ggccttgcag tccaccctgt cgaccttggc    42360
gccggccacc cggtatctgt gcccgaagag ttcccattcc ttattgagcg gcctgaccat    42420
tttcgaggaa gtcgttggtt attatttgca tgaaattaac cggtcaatga aaggaatttt    42480
gctcgacggt gattgaacga gagaagaata aaaccggggg attggtggaa agagtagct    42540
tcaacctggg tgcgaatcac tttcatcacc ttctcagcga tccatcctgc gttggatgtg    42600
caacgtgcgg cagcgacggc tgcaggaagc gcaaacttaa gttgagactc tcaaccagag    42660
gctctgactc agtctggctg actgtcactg ttgcacgcag gtgatctggt atgaacaaga    42720
cagtgaagtg actctcttca catgctctcg gacccgagtc gggctgctgc cattcctcct    42780
tttcccacca aacgctcaca agctccgcc  gccggtaaag aagaaaatgt ctcgcgtgga    42840
gtgcaacctc aaagtcctcc ctcacgtctt catggtcgac aacaacaacg tcgtctgcca    42900
ggcggctcaa agcccgacg  accacacggt catcattctc gtcactccgc aggacgcgtg    42960
ggtcaagaaa atgctcatta gcgccaccaa cgtgttcggg tacgagctcc agtgcggcga    43020
caaggctggc gagcccatgc aggggctcaa cgccaacatg aagttcagca agtggaccct    43080
cggcaagggc tgcggagacg tcgccatcca gttcctcaag ccaaagttcc tcggtgtcta    43140
taccgactac gggacgctga caatccccaa ctcgctgcga ggctatacga tcgccttctt    43200
ctggccgaac gacgccgatg gagaccctg  gaacatcttt ctagagaact aacccaaac     43260
ccaacgcgct gtcggtggga ttggcggcgt cgcgacggag gtcgtcaaaa tcggccaagg    43320
```

```
cgcggtcgac ttcagagctc tgtttgccta attccagtgc agcgaaagaa ggattcggcc    43380
tggttgtgtc ctgtacagac aggggtcgaa cttgctccta aatgaccaaa tgaaggtttc    43440
aagatatgct tgtcttgggt actcggattc tcgttgcact tatttccaac cggaggtaac    43500
gttagtacgc tgatgacagc attgcctcaa tgtcgacccc aacagtgatg acagccatgg    43560
taatgatgct aagctaaggt taacgatgtt gaagtcagcc ggttcgttct tgcctatggg    43620
tctcttgttt tttgtgtagt tggtggctta ggtaggtacg ccaatttcaa aactgcgctg    43680
ttcgcccgag tcaaaccttt gccattgagc acaggtgcac gataaacgat ggaagagaga    43740
cacagttaat tctgatgaag gtgacaaagt tctcgagcga acaatgatgg cattactgga    43800
ggcattactg gagctgccca tgtagatagc tggtggtcgt attcaagtac cgggccatgc    43860
acgcgttcac tggtatgctg ccgaacttgg tcgttgaaat tgctttcctg aacgagacgt    43920
tttgatgcga cggcgagtta tcgtgcaagt gtagcaccaa agtaatcgta ctgagatcga    43980
gttcaaggtt caaagcgagt acgctgcact gaggcgtaga catccctgac cagcatgttc    44040
ttgagaactg gttcttgatg agatgtcagg ttaagcaatg caaatcgtcc ttatgtcctt    44100
gagcgctaaa gataacggat cgaaacgaca ctaactttta gtgtcagcgt tcgactcgac    44160
gctaggtagt gcggggcggg gggaaatgga agcgggcca ccagtgttgg acgcgttagc    44220
caagttggag ctcgcgatgc gcccgcaaac ggttccgtca tggctcagta gcgataccaa    44280
ccacgctccc aaggtcaccg ctctcggtcc aaggacgtcc agcgtcgagt tggtcgataa    44340
cgcaacggtg cacggagctg tggaagctgc gatcggtcgt agaaatgaca gcccccacgg    44400
aatttctccg cacaaagaca aaactggtcc catggccccc agttcttcag ccgttcgacc    44460
tcgagctccg attgggatgc acaaggatgc ggttagtgct gtagacaagg aatttctgtc    44520
gaaagggtcg gaacacccgt ctccgaagag atcgaggcag cgtgtgcgac aacaagcaac    44580
cgagtcaaaa agcaggtggg tactgatgtc ttgcagtgca ttatacctgg cgattggcac    44640
gagctcactc gtgcgttgta ggcgggtcaa gcagtcgctt gtagaatcgc tgcggtcgct    44700
ggagttcttt gacaagacga accgaagccg cgaactcacg actaaaatct ctgtcatgcg    44760
cactcatgca gaccctggag gttagtatta aacgttccct gagtgaagct gctgttgctg    44820
atctttggct cttgtggtgc tctctacaga caatgtgcat ttcgtcaata tcgacgatag    44880
cttggaagac agtgaagatg acaaagcgct agccgacaat gcagagttca cttttgtacga    44940 caatggccgc catactaacc acgaggccgt ggaaaaccga gcatcgaagt atctcgcaaa    45000
gccactgggg tcgaagccgt cgccagaccc accgcaagtt ttccaaattc ccgagctgcc    45060
gcatggacaa aaccttgtca tcaacatcct ctcaacatgg ggagatccgt tctacgtagg    45120
gcttatgggt atcgagatat ttgaccacac aggccatgcc gtgtacctct ctgacgtcga    45180
caagcagctt tcagcagatc cacctgacct caatatccaa gatcacgatc gcctcgaccc    45240
tcggacggtc gataagctcg tggacaaaca ctattttacg tgcgatgaac tgcgttcgtg    45300
gcttgcgccg ttctcacgcg gccaaaatca tttttatttac atggacttcg actatccgtt    45360
gtccatttcg atgctgcgta tctggaatta caacacaact cgcattcact cgtaccgcgg    45420
tgcacggtac gtggagattt cgctcgacgg gaagtttatc ttcaaaggag aaatctgccg    45480
cgctcctgga agtgtcatcg aagacatcga cgactgtaac gagtgcatcc tgtttaccat    45540
gaaccaatcg attttacagt tgattgaaaa atacgaaaag cgaaacgaga cactcattga    45600
tcgtgattgt gcaggagaag caataccatc aacaaataca gggcacctgc cttccgtaga    45660
gggtcaaagc agtaccagcg ccacaattgg ctcccccatc ggctcggatc cacgtctact    45720
```

```
tgagagacca aagacaggaa acaagacatc tcgtactgct gccagaggga acatcatctg  45780
ctctcctgac acgagtgacg cagcattccc tattaatcct gtgttcactc ccgtggcccc  45840
gctgcctaaa gggatgagtt accaaacgtc ggcgaaggca gctcaagctt ctcgtccatg  45900
cacagctcca gtcgtgggag ggccgatgac agagcgtcca ctgagctgca aaacgataga  45960
actgatattg gaggcgaact ggggagatcc gtatgagatt gggcttgcag gtctacaatt  46020
cttagacgcc aactacgtac ccttggcaat ttgcttggat agcgttatgg tctccgctcc  46080
ggtcgctgct gacaagatgc aaaagctcat cgtgactcat ggcgcccgcc acctctccac  46140
taatcctgaa gacatgtgga gtgccccgct acaggatgtc ctcacacttc cccccgagcg  46200
ccgtgcagtc atcgtagatt ttcccgagaa agtaagcatt cgagcgctga agtttggaa   46260
ctacaacaca actttggagg actccttcaa aggcaccaag cagatgtcag tgcgaataga  46320
tggcgtccat catacgcgtg tatcgctgcg aaggctcca gggaatctca tggacttcga   46380
ctttggccag ttcctgtatc tacgcagcag ctcatcgttg catggtacag ctgcgatcac  46440
tgctactttt gaggcatttc caactagcaa agaaggtgac ccgctcgcct cgactgcaga  46500
agaagtcgaa agcacaaggt catcgtcacc tgcggcgagt atgggagcgc cacgtaccga  46560
cgcctcgagt ggattcgccg agggatctgc gttctgcaac gcgactttct cgctgtcgca  46620
gtcatctcca ttggtacgaa agaagatcgc catgaagccc atttcggagg ttttccagca  46680
gtaccagacg ccactgttcc cgaccgggta catcatcaag ttcgtgttca cgtccacctg  46740
gggcgacacg ttctacctgg gtctcaacgg tgtcgagctc tacgaccgca caaccagct   46800
catccctctc tgcagtgaga tcgtcgacgc ccaaccacgc gatattaaca tcctgaaaga  46860
accaggcgca acacgacg ttcgaacgct ggacaagctc tacgacggcg tcaacaacac    46920
gtacgatgac cgacacatgt ggctagctcc gcacgcaccg tcgcacccga caaaactcgt  46980
ggttttcttc aatgagccgg tggccatctc caagatccgg ctatggaact acagcaagac  47040
acctgcacgc ggcgtccgcg agttcgaggt gtttctagac gacgtgctga tctaccacgg  47100
gatcctgaag caggcgccgc ctctgaatct gccgagtctt gacggaacgt ccgacgagtc  47160
tgcacttgac gcgtacggac actcgtctat ggagaaccgc cgaatgcgca aaaagtggca  47220
cgaacaagct gaagtcgctg ccaacgcggt caacatgacg cagacgctgc tgttcacgga  47280
tgacctggag gtgatcgagg ccgaggccaa caacattttc atgccccagg acgagctcga  47340
agacagcgtc acgttctacg acaacagtca agtgctgtcc ctctccgacc tgcccgggca  47400
cgagaccatc atgcgcccct tcaaccagcgc aggctggtag aagcgctgct ggcagcaaca  47460
tactataaac ttcaacctac accctttaa atcgatatag atacgtattt ctaacttgat   47520
atttaattcc cggggtttta gccaatgaag tgacggaatc tgctgcgcat cgtagcatgc  47580
gactgccatg agcagcagcg gtctccacgt gcgcacgggc gaaagccccg gcgcgggcgg  47640
acgcagcgcc gggtccacaa tgcgaagcag ccaacagtca cgccctagca gcagccgcag  47700
cagtatggcg tccagtcgcg ggggcaggaa gctcgaggag caagtgcgcc tcgtgggcac  47760
gcactacgta tgtcttaagc aagtccagga ccggttattg cgcggtacct cacagttgct  47820
atgatatgtc ttatcctgtg tatgaccgca tagcaattgg gggcggagat cgggcgcgga  47880
ggctttggta tcgtgtatgg ggcgctggat ctacgtaatg gacgctccgt cgccattaaa  47940
caagtgtcgc tgcgggatat cgacaaggac gagctgctgt cgattgaggt acaagctgag  48000
gtggtgtgtt agcgctgtgc tgttgtgtgt gacgactcta tcctgtatta ttcaacatac  48060
```

```
cagaccgaga tcagtctgct gcgcaaattg aagcacgaga acattgtcaa gtaccacgac    48120
acgatcaaga cgcaggggaa cctgtacatt gtgctcgagt acatggagaa cggctcgctc    48180
gcccagttta tcaaaaagtt cggctcacta tcggagacgc tcgtggccat gtatatcacg    48240
caggtgttga ggggacttgc gtatctgcac gagcaaggtg tgctgcatcg agatgtgaag    48300
ggggccaaca tcctcacgac caaggacgga ctggtgaagc tggccgactt cggcgtggcg    48360
atcaagctga cgagacgca gaaggcaaat tcagttgtgg ggtcgcccta ctggagtgcg    48420
ttgctgctga atggtacttt gtgtagcacc gtgctaatga agtgtgctgt tgtagtggcg    48480
ccggaggtga ttgagatggc tggctggtcg tctgcttcgg atatctggag cgtgggctgc    48540
acaattattg agctacttac gatgaagcca ccgtacttcg acctagcgcc catggctgca    48600
ctatttcgaa tcgtacaaga agaccaccca ccgcttcctc agcgcatgtc accggtagag    48660
acactttgac ttattattgc aaactgtgtg ttgctgactt gttgtttgtt gctgcaggcc    48720
ttacacgatt tcatcatgaa gtgcttcatg aaagagccgc gactgcgagc gtctgcagag    48780
gaactcctcg cacatccgtg gatcgcacag attccgaaaa acaaggtgga gcaaagtacg    48840
cagctcgttg cagagagcgt aacctcttcc aacgatcgtg acgctgtgct gaatactatt    48900
aaactatacg agaaaagctc gtctacaacg gacatcccac cgccaacttc aggcaaaagc    48960
taccgatctc tcagtgtcgc aaatgagcag tccgacgagg atgccgagga ttgggacgat    49020
gagttccgtg tggattctaa ccccacgccg ttcgtgctta gagctgacga gaacaagaac    49080
gatagcattt caaaagcatc ggtggaagct gcgccgagca agtcaaagtt ccagttatca    49140
aaagaagatg cgaacgcact atttgacgac gatgtgtggg atgacgaggg gtctgaagca    49200
agagttttat cggaggactc agccatcctg gatgctagtc acggtggtag cggtgtcaac    49260
atgaatcaga gtaagggcga aaagtcatcg atgaactcgt gggatcgatc atcgcttatt    49320
cctgctcaaa accgcatcgc aaagctacag cagtttgtcg aggatccgga agaagacctc    49380
acatttgatg atattgacga gaagcaactt ttgcaagcag ctgcaaagca acaacgtgct    49440
atggagtcag atcctatcgg tgctacagta gttccagcca agaaacggct cagtgacttc    49500
aaggaggacg ctgatatcga cggtgacttc gactttgaag agcaaccggg gagtttggtg    49560
ttacgtgttg gtggcaaccg tgatagtaat gtgggggtcat cttctggggg aagtgcgcag    49620
gagaatctct ttgacgatga gttggacttc gattattcga ctgctcgtga cactaaccaa    49680
aaggcaacag ctcgagtggt agagctactt tcgttactgg atccaagcat ggaagaccag    49740
gtcatccttg atgcttgcaa taatttggta cgttacgttg aaataacctg cactacgccc    49800
atcttcgatg gagaaggggg tttgataccg tgtgctcact ataaatgcgt gccattctac    49860
aggaagaaat atttgatcag aacgtaactc tgaggcggga cttgatgtct cagcctggtg    49920
tggtgcccaa catcatggag gcgctggaaa tgaagaagat ggacgtgctg catgccgtac    49980
taagggttat caatatcgta agatctgttt gttcgctgtg ctgtgtttgg aatagtgcga    50040
cttactctga ttgctattgc ttgcatccgc agattgtcga gggtaacaaa aagttccagg    50100
agaacttggc actggttgga ctagtgccgg tgattatcaa gctcacgaag cagcacaacc    50160
catactactt gccaggtgaa agcggcagag gattccggat ggataaccca gaggacaacg    50220
aattctcaat cgcggtgcgg atggaagccg ctaagtttgt acggcagtgc tgcaaaacaa    50280
gctcgctcac tttacaaatg ttcatcgcgt gtggcggatt accgtattg gtggactttt    50340
tgaccctgga agataaacca tccaatctta atgacgacgt ggacacgctt cgggtcgctc    50400
tggatggaat cttcagcgtg ttcagcatcc agaccatccc gaagaacgat atatgccgtc    50460
```

```
tttttgtgaa ggcgggtctg ttgaaaaagt ttgtcgtcgt cttttcggag attgttgcgt   50520
cagtgtcagc gagcgatacg cgctccccga aatgcgatga aagtgtgccg aaattattga   50580
aaacaaacgc agaaccgacc aaatccaagc gtggatcagt ggcacagtgg acaatgaagg   50640
agcttcacaa gacttgtgat gtcttcgtgc tattttctca aggagatgct gtggtgaaag   50700
agcatatgtg cgatggtgct gttttggaag gcctactgga agctatccat cctttgccgc   50760 ttttttaactc aggcgaggaa caaaacaagg ggtcgctgcc gttgatacgg cattcggacg   50820
aatttgtttc cgccatgctg aaggttctca agtgtattcg taatctgagc atggagccct   50880
tgacactcga gaaactcgac cgagccgag caatcccgac acttgtgcgt ctattaaacg    50940
aacaagagac agaaggcccc tctatctcag acgcgaagcg gaaagaggtc gaaaacattg   51000
tgctccaatc gatgtattat ctctgtcgga ttaatcgcaa ccgccagact catgccgcac   51060
aggctggtgt gattccatcg cttattaagg tggtccggaa ttccagtccg ctcaagcagt   51120
ttgcgcttcc gatcctgtgt gatctggcgc atgcctcgcc tacagcacga gctcaccttt   51180
ggacgtacga cagcgtgtcc cttttttctgg agttgctgga ggataaatac tggcaaattg   51240
atgccattaa gtccattagc gtttggcttg tgcacgacac ggtgaagatg gagaatgtct   51300
tgctcgttcc agaaaatctg atgaaaatta cggtgtactt ccacaacgct ttggacaccg   51360
agttagagaa cctactggag ccgctgttgg agattatgag tcgctcggtg aggcttaacc   51420
aggcactcgg acgaagcggc atgtttgtga cggagatcct aaagcgactg cgtctcattc   51480
cgaaggcgat tgtgcgcaag aacttgctga agatgctcaa gagtcttttc gagtctcata   51540
catcgcccat ccagttcctt gtggagtaca acctccgccc aatcgtgtat gcgctcgcac   51600
aagacgagaa cagcatgatt cttgtcaagg aaattgcgtc gcagctcctc caagccattc   51660
tggtggctgc gggggtgttt tagatggagt gtacgtgtca gtcctagtga ggacataact   51720
gcactggaca aggctcacaa aaaagtggtc aacgccagcg acaagcgcgc cgctcgaggg   51780
gtaagcggcg agtggagcag tgtgctttat ttattggaaa tggacgtcac ctgtgcttgt   51840
ttgtatgctt gtcatttgtg tgcgtgcttc tgctgttgca gcgacgacag aagaagttcc   51900
ctcttgaatg cttctaggtt gcggtggttg gaggcattga aggttgccag agacgatggt   51960
ggcattttct gcgcacgaga cttggcgagt tcttggtgga cttcttcccg aacgacatgt   52020
tggatcatgg cctttgttgg tggcaactca ccttggcatg aaatgcactt ggctcctaca   52080
agcggtgccg atttctgaac tgcatcttcg atggtagggc tggcttcgcc cctcagcaga   52140
tttgagctgg aatccgtccg cccaggttgg ccttgcagta gcgccttcag ttggcttta    52200 tctaacttgc ggcgcaatct tcggtggata tcaacgagat cgtgctcatc gagtgacgcg   52260
ttggcaacat tctgcacctg gcgttcgagt acctcttggg tccaaagcaa ttcgtccttg   52320 tccaatttt tgctgacgcg tgcgataagc tggttcatct cctctcctag cagtccgtcg    52380
cgctccagtg tctcgctgcg cgtgttctcg agactcgttg tgagcaactc cctcatctcg   52440
ttgttggagg tcatcagctc ctcaatggac ttcttgacgt cctcctcctt agcatatgca   52500
aacgagagct ccatgaaggt atcgaggcgt gagttcatca gcttgaccag cgcaatggtc   52560
gagtcgaggt gaccaagcgc gaaaccgtgt tcctcgatct tgctttgaac gagagtctgc   52620
gtggagcgga gatcctccac ctggtgacgc gagttcatcg cttctgagtg cagcagaagc   52680
agaaagagaa cggaccgtac ttgaaccact acgtcgtgca tgaagagggt caactccgga   52740
atctggttgc cttctcggtg agcttctcgt gtgatgagag ccccttccaa ttctttcagc   52800
```

```
ttggtggtcg tcatgaacac aagatggtcg tcaaagctcg aatgttggtt agaggttgcg    52860
gtgccaccgc cataggcgtc attgtttccg cctgtgtcaa gagcaagtga atgagcagcc    52920
gctttggcca tagctgcttg gcccttgagc ttatcgagtt gctgttggaa gtccaacgat    52980
gtctccacca agaagtctat ctcggacgca gcttcttggg agagaagcgt gttgcagttt    53040
tctatgaagt gcgtgaagat tcctcgcagt agctcaatgc caacatcaag cgctgttcgc    53100
gtagagctct ttgtggactg ctcaattttg ccaagctcaa ccgactggag catcgctccg    53160
ctcattccga gcagcgtgtg gtagatgcgg ttgcaaaatt cggtgatgcg aagaagcacg    53220
tttccatctg aagttcgttg cgaggtcttg atctggtcca ctattttctg aagttccagc    53280
gcagcctcgg tggttcgctg ctcggcttct tgtcgtagcg tgtacagcga aagttccaac    53340
ttctcgtgga gagcaggaat ttctgcctcg ctcacctgcg tcaacagttt ctccgaggcc    53400
tcaaaggcag taacttggtg attgaacttg gaggatactt cctgtagctg cactgatatg    53460
gcgctcgtca ctgcgcttgt cacgctcgaa gttactgagc tagtgcggcg agcagaagtt    53520
cgcagccgct ggatctccac atcaatctcc tgtaactttt cctctacatc gacgatggtg    53580
cgagcctgtg tcttctgcgt gcgctcaagc ttttggactc tgtccacaac aggctggagc    53640
tccatgatac tctcatccag agcattgatg gccgagctgt tatcctgaac gtgccgctcg    53700
aggtactcca gcgatccatc taggcgtgcg gtgttttcct ctagtcgctt cacacgcgaa    53760
cccatggaca tttgctgtcg acgaaagagc gctttctcag cattgatgcc gttcaattgt    53820
cggagccgct gcaagcgtac aagcttggcc agtaagataa accaaagctc tttgactctc    53880
tctttggtga ctggtgggcg tggctcaaca acgacgggtg tttccggtct tggaagtggc    53940
aatgaacgcg acaccagctc gttcccgggg gaaaattcac gtgatgtgac gtctatatcc    54000
ttacggttgg tggttgagcg acgctggcgc cgtgctcgaa cgactgacgt aagcacgttt    54060
ggacgtgagc cggaagatga cgaggaccgg aatagtgcca cctgatcatc cctttccttt    54120
tgctgcgtgg ccaactggga acgatactgc cgtggtaact cctctcgtgt gacttcttgc    54180
tcttcttctt tggcggtact ttcactcgcc gctacgtctt cctgcttttc ttcttctttg    54240
ctgtcttcaa cgactgcaac cggtttgggg gtgataggag tgctgctagg aacttgctca    54300
acgacaacag tctccgtagt gcgttcaccc tccgactgct gacgggaaga ctctggtact    54360
tgttctggca gagctgtatc taggacatca atggggttgtt caacaaccac ttctgggatt    54420
ggtggatcga ccaagtcact tgataccact ggggtggctg gttcggtagc gtggtgacgt    54480
cttcgtaatg aacgccttac gaacttggac accaagacgg tggctttcgc tctaagtgga    54540
gggcctgagg gtgatagtgg atgttgcgta gctggaacgt ccgtcgcgct gtcttgctcg    54600
gatacatcag ggtgggcagg caccacctcg acatcttgct gctgcggtaa tggttcttcg    54660
gtcggagttt ctctcgcctc agcggtgaca tcgagctggg aattctctga ccgaaacact    54720
gggacgaagt ggagagctgc ttttctagca acaggcttgg ctgtctcctc ttcatctgct    54780
ggcgcctctt cttcctctgc agatccatcg ccctcctcgc tggtttcaga gtcaacgtcg    54840
tcgctaccca gcgacttggc cagcatttcg atcccaacgc gcatgtcctc gatgccttgt    54900
tcttgtcggt cggatcgacg catcagctcc ttcacctcca tcttcattct cgacaagtaa    54960
tcaaagcgct tttcgagctg ctcgagctgc gtctggaccg cttcttccgt ttgtcttgtt    55020
ttctccgcca aactgtccgt cgcctcgctt cgcagcttcc caatctcgag actaaccttc    55080
tggtccagag ctcgaagcgt ctcctccagc aaggccctcg ctggtccgtc atcaaccact    55140
tgcgaactct gtagagccac gagcgcctgc tgcatctgct cgttaacctg ctgctgcaca    55200
```

```
ttatgctgca gctgctccat cttggtcgtc agcgtggtca aagcgtccag caccgacgtg   55260
tcgggcagcg ccggctccaa cgagggtacc tcaactacca caggagtcgg cgccggagcg   55320
ttctgcagct ccctgacggc gagtcgcatc gagagctgcg tggattcgag ctgcgccatc   55380
cgctgtgcct gccgctcgtt cgccgctgcc aaatgctgca gttgcgtggt cagtgtggtg   55440
atcacagacg ttagcgcgcc ttcctgtgcg ccagaacgt cgcccatgcc aggcatgaac    55500
tcatccagca agtccatggg ccttcaagat gcaaaaaaga catctgagct tttgaggag    55560
cggccaatag cgtaacggtt ttcgcgccac ttcaacatgc acgtgattgg ctgattcggt   55620
cctgtatact attggttttc tgtgcaaaga aaaaggtcta cgatacagga agtcatggcg   55680
tcgtggcagc actacccggg ctcgtggacg cccgaagagg aggcggctcg acttggagga   55740
cgcacagcgg cgaatgcacc gcctatgcgc ttcgaagacg ccgaagaaac gaagatggac   55800
ccgtttccag gtcgggatgg acgtgcgcaa cgtcctccct cgtctcagta ctatgctgtc   55860
aatactatgg cgccgcagcc tccaattcaa caggaagaga ctcgtcgcca gcaattccac   55920
gcccagcagc tcccagaata ctcgcatcca caaggttacg caaggtaccc cgttgtccaa   55980
gaacattacg ctccgatgtc ttatcgagac cagttgacgt accaagctcc agctccccgt   56040
ccgcaatcga cgtcagtgcg gggccagtgg gtggcggtgg acgagcaaca gactcgtcgt   56100
gggggttgga tggaaggccc cgaagctcca ggagcattgc agatgcgacc tgttgcatcg   56160
tcgactcgac gcaggacgtc agggtttctg acgactacgc tgctactttg tgcgttccat   56220
gtggccaacg tcttcttcgc cttggtggcg tgcggcgtgc tgtgtgcggg catctgctcg   56280
gcggtttcga tgatccccgt gtgctgcatt ggactgctca tcttccaggt gctcgtgtac   56340
attggatttg cgctagcaca atgggatatc acgctcggga actacatcgc gccggcgcat   56400
cagtgcgcgt actcgaactt gctgccaccc ggcaggttcg tgggcaggga ggggctctcg   56460
gtctaccgta tttctccaaa tttggcgttc ttttcgccgc tgtcgctcat ggcgatgctg   56520
tacttcgtgc tggtgaagcc cgtgatcggc gctctgagct tcctgtcggt ggtgctggtt   56580
gttgcgccga cggtgtcgtt catcacatcg ctgacgtcgc aataccatga taactacgac   56640
tccatccaga tctacggcgt tggccccacg tcactgagtc gctatccagg gctgtcgttg   56700
gtgggggcca tttgcgtgac gctcgtgggc gtggcgctaa tgcagctcgt ggccaagatc   56760
tcgctggggg ccacacggtt tttctgctgc gagaagctcg ccgtggcgac caggcatttc   56820
caataccaac cacttgcgag caatgggtac ggaacagctt caacgaggag ctaaccagcc   56880
tggttgccag gggagtaccg ttaccggtat cctttcgtgt ggccagaaaa aggcaacata   56940
ttcacaatca ttccactcaa aatgtatgct gcgccacgaa tgcctctatg gcacaacact   57000
ttccaacttg ctccaaccca cgcagcggca gcgatcaagg tctccaaaca tggtcgagtc   57060
gtcacgcttc agcacccgcc tgtaccccga catcgaggct ccagtcgacc cgagatacgg   57120
cgcagcgtac cctgcagcca actctcctcc gatgacagcg gccgagtcgg agcgctggcc   57180
gctgacagct gcagtgccat cgtacaccca gcaacagcaa gagccgtaca cgcctacta    57240
tgtgcccccg tcctacggag cgccgcctgc tgagaatcgc cactgccatc gccaccacca   57300
gaacgaccgc caccaccgca gctaccacgt gcaagctgac tgcaaccacg aagtcttcgt   57360
cctcttgacc ctgaaactcg ggcttttcca ctcgctcaac gcgctgctgg ggcttgtcgc   57420
tttcgttgcg gtcgtcactg gtgtgcacgt cgctgtcggg ctgatcccgc tgtgctgcct   57480
cggccttctg gtgttccgcg gcgtggtggc tttggtgcga tggcttgcaa cgctagatgt   57540
```

```
caagctgagc aactacgtcg catcgcctgg ggaagaacgt attctcattg cggatgcgga    57600
ccaaccgctg ggagccttcg tggggctgcg actgtctcca gagctgtcgt acttctcgcc    57660
cgtgtcgctg ctgggcgctc tgtatttctc gacggtgaag tttgtactga gcatcgtcag    57720
tttgatcgtc gtttccctgt tgttgcgtt gcccatggcg ctgctcgctt tcagcagcga     57780
cgacgacacc gagtggacta tcaaggtgca ccaccacaag cgagtggata tgcgtgagca    57840
cccatttgcc ttctacgttg tgtggggctg cctctacatt ctcaccatcg tggccatgca    57900
cgtcgtagcg tggctatcac gggctatgac caagttcttc tgctgcgagc gggtgtccgc    57960
gtccgagtac actatcccaa tcgtccacta cccagacgcc gccacaatgt acggctccag    58020
ccgaagcaac ttgtaacaga acacgcagta aattgaccat gcctagtaaa tacatgtagc    58080
aacacaatga aaagaatgt agtaatatca agtgcagaag gcagtagaac gtcgcgacaa     58140
ccaatacatg cattgtcttg cattgtccct atatcctaag ctgtaacgca gtgacatcgc    58200
actcttagga tatatcccca tacggtactg gtgtacagtg tcgaggtgtc gcatttcaca    58260
actggagcgt catggtggac gcgcaggccg tcgtgataca ggctcttcgg gtgctcgtgt    58320
tcctggtgct caactatgtg ctcgcgtcca cgggcttcat ggtcattgtg tttggcgtcg    58380
cattctcgct cgggtcgatc gcgctctgct gcttgggcgt cgtggtgttc cacggtctcc    58440
tgtacctggc gccgctgctc gcgcggctgg acgtggcgct gcacaacttc gtggagcccg    58500
tggaaaacaa actgtacggc cagatcccgc gctacgggga gaacggggag tacatggctc    58560
ggccgtcgct ggccgtgctg ctgtacttca gcacggccaa gctgggcgtc ggcgtgctca    58620
gcgccatggt ggtggtcatc ccgttctcca tgcccatcca cgcgctcacg tcgccgccgt    58680
ttcgagccga gtactttgcc gacggatggt caacctctc ggccttcatt gtggtcgcca     58740
ctgcgctgct ggtgagcggg ctcgtcgcca tgccgcacgt ggccaaactc tcgtgcgtca    58800
ccacgcgtct gctgtgtcgt gaggtgttct ccaccatcta cacgcgcgac ttcgtgctgt    58860
ccatctcgga agcgcctcca gcgtcctacg gcaccaagca gcaagtctga atgaacaaag    58920
tgaacgacaa ttaactgaga cctcagcact agaagaccaa aattgtacta caaccgttgc    58980
ctgataaatc aattccagct ctggtgccgc accagaattt tgcctgcac cagaaattgg      59040 gtatgtcggg acttgatggc tggagccaca taaatacgtc caccgaaata agtcactctt    59100
tcgggaagct tcatcgcact atagtcactc ttcgcaaact gcacatatca tactttttc     59160 gcgcatcacc cttgcacttt tcaacttgca cttgccagca gagctcctcg caaatgccac    59220
gagccaaaga cgcccacgtg accttccagt cgccctccaa gagcccagcg tcgcccacct    59280
acatgttcca ttccaaaccg ccgccgcgtc actgctgccc cgagccgccc gcagtcgacg    59340
ccgagggcct cgttcacgcg ttgctgcgcg tcacgctcaa gctcgtggtc ttccactgga    59400
gcaactcgat gctgggggc gccgccttg tggtggtggg ctgcggcgcg ctgctgtcgt       59460
tcgtactgac gccactctgc ggtctcggcc tcgtgctctt ccgtctcgtg ctgtgcctcg     59520
tagcgctgtt gtcggagctg gacgtggtgc tcgccaactt cgtatcgctg ccagaggagc    59580
acatctccat taagaggctg agcagcggaa gccacgccag cccgcgcgcg tgcggtgaga    59640
cgagcgtcga gcgactcgtg ccagaactcg acacgttctc gccccaggcg ctgcgtgcta    59700
cgctctactt tgtgtcggtt aaggcgctga ttgggacgct cagtagcctc gtgctgtcca    59760
ttgccttctc actgccggtg ggtgcaattt ctcgaggcag tttaggggac aatttccatg    59820
gagttgtggg cctgctcgtg ttcttgctcg cgacgacctt gctgctgggc atcggcatcc    59880
cgctcatgca gtatggcgcg agactgtcgc gagcagcgac ggtctacttt tgctgcgaga    59940
```

```
agtgcgcgcc cgagcaccat caccacggag aacagggtca ttcggctacg tacggctcta   60000
cggacatgta cgcagcagcg tgaggcagca acaaacacgaa tgcggcagtg ctcaggtctc   60060
cagaactttg acgtctgtgt actacatgtt ttgatggaga tgtggaatgg ttaccatgcg   60120
tgccgattaa tgtaagacca cgaagttctc aaacattttc cgtgttatta ccacttcgat   60180
cgtggcttac gttacactgt actatgcgca gcaactcgac caacatacaa cgagcgggtt   60240
gacgcttctc aacaaaaacg actggggtgt ctgggacctt tcacaactta cagcacaaga   60300
cgacacagca gcacactcca gtcgaagctc ttcccaaaac accaattgtt tatcatcacc   60360
tcttcactcg ccagcttact gctgggcgcc gaagtcctgc gtccagtagg tgtcatactc   60420
gctgcaggcg ctgttggtga ccagagcaaa tccgacgttc accacgtcgt ccttgaggat   60480
gttggcgcgg tggcccgcag agttccacca ggacgtcatg acggccgaga cgctcgtttg   60540
gccggcagcc acgttctccg ccgccacgct ccagtcgtat ccctgcgcct cgatgcggtc   60600
ccagggctcc gagccgtccg tgccctcgtg ggtcatggtg cagtgcgtgg cctggtcctg   60660
cgagtggaca ttggccgcgg ccacaagttg cacgtcgatg gtcaacgcgg acagtccgtt   60720
gtccgcgcgg tacgagttga tgcgcgccag catctccgcc gactcggcgc ttgtcagccc   60780
gttgtcgtac gtcgtggacc cggacgtctg ggaggaagtt gagtccgagt tctgatcggt   60840
ttgcgatgcc tggctggtct ggtcgttctg agcaacctgg tcgccctttt ggccggcgtt   60900
ctgtccagcg ctttggtcgg ccgagtcgga gaagcggtcg atgacgtatc cgcagccagc   60960
gccccagtag gccgaggcgg tggccgtctc gccgctcttg agccagcagg tgccgccgtt   61020
gaagtaggtc cacgtccagt gcgtgcactt ggcgtcgtcc gcgcacaggt ctccgcagac   61080
gtccgggatg cccagcaccg aagacgtgtc gtcaccgtag aagtcgcagt tattctgcca   61140
catgacgcgg ccctggctgc cgacttggaa cgcggaggac gagcccagcg ccatcgcagc   61200
gacggcggcg gacagtgtga gcacttggga gcggcacatg cttgcgggat gtctatagag   61260
cagggagaga ggattgtttg gtgcccgatg aattgaaaag tgagagaccg agcaccggcg   61320
tcggactcaa ggtgaaaggc aaaggataga ctgcaggcag agcttcctcc gcgctggtga   61380
acatctggcg gccagttgac gagtacacgc tgccaatatc gttgaggcgc tgtcaacttg   61440
gcgctaatat cgttgaggct gtcaaattgg tgttttgcgg tggaagtgcc gtagtagcga   61500
gtaccagcga gcctgagagc gtcggtggcc tgctggtggc tgtgcgctcc aggactctac   61560
atggcgtgtt ccaaactttg gaatacgctg gcactctcat cgggcttggt ggtggaaagg   61620
cggaagtcgg agcgcatgca caaacgtgag cacgtcatgt tgctaaggca gcgaagcacg   61680
aaagaatgga gctcgacttg cgagagctga atgcgttcac agcgttggtt gtcgtggatg   61740
gcacagcgtg ttgcttggcg accaagtagt gcagagtccc tgtgctgccg gcttctacga   61800
ctcatccacc gaacgatccg gctcactcgg tctccgttgc tgctgagctt ttccgcagca   61860
ccactattat atctatacag cagtggcaag gataatggag accagccgtt cccgtcccgg   61920
tacttgcgtt gaagcggttg ttgaagccac atggcatctt catcgtcgcg atctttacca   61980
ggtggtgagt caacacacac tgggatagcg tgcatgctaa aggcgagcgg ctccaataag   62040
actaacccgc cagcggatcc agttgttgct gtagtaagtg ggcgttgtgc ttcagcttga   62100
tgtgtaaaag ttctcctcaa cggtcgtcaa ctctacaggg agtaaaaatc tccagggcaa   62160
ggctagaaga gcgatggtac atacggagct ctctcaatcc tggcgtttgt gcggcaaatt   62220
ctaccgatgg ccagcttcca gcgaaaacgg atatgctgtt gtgcgtttgt agttttgttg   62280
```

```
aacacttgac gtcgttgaca attactacgg catgttataa tactcactgc tacacatatt    62340
acacgctacg cttacgcact agagtacatc gagatcgttg acatgaattg gctttccact    62400
gagccattta ctgctgcata tcgcttcagc cctggcggcc gaagtcctgc gtccagtagg    62460
tgtcgtagct gtcgcacccg ccgttgatca ccttggcaaa gccaacgttc gtcgcgtcct    62520
tggcgaggat gttggcgcgg tggccgggcg agttccacca cgaggtcatg acctgctcta    62580
ccgacgtctg gccggcagcc acgttctcgg cagccatcgc gaagctgtag ccctgtgcct    62640
tgatgcggtc accaagtcgg gagccgtccg agcccgtgtg cgtcatctcg cagtggctcg    62700
cctggtcttg ggagtgcagc gcagccgcca ctgtcaagcg gttgtccatg gtgagtcgcg    62760
cgaggccatt ctggacccgg tagttgttga tccggcttag catctcactc atttccgagc    62820
tcgagagacc gctgctggag gcgacgatag ctgaggcttg aatccctgc gtttgaacgc     62880 gcacgttgcg agacgtcacg tagccgcagt tggtggccca cttcgacacc ttggcggagc    62940
gggcgccctt cttaagccag caagttccgc tgttgtagtt ggtccacgac cagtgagtgc    63000
aagtcgagtc gtccgcgcac acgtcaccac acatagctgg gatcccgcgc agtgagcggt    63060
agtcgttgcc ggtgaagtcg cagttgttct cccacatgac gcggcctccg ctgccgagct    63120
ggaagccggt ggtggttggt gcgaacgaac tgcaggttat ggcagacgca gccagcagag    63180
cgagaccagt gaagcgcggc attgttttcc gaggtgttgt tgatcggtcc aaatggaaaa    63240
tgaattccag ggcctcgaac tcgcgcactc ctggattgca gagcaatggg ccctatgtgc    63300
acatctattc gaatgattca gtgaatacca acagatgagt gtccgcctcc cgccgcgatg    63360
gaaaaggttg gagcaaacat cggttgtgga tcctgatgtt catcctgatg ttgggtccat    63420
gccacgtcga tcgttaagca ggaatcgcca tctcggtggc taaagttaaa ggagctatgc    63480
agggatgggg aataagggcg actctgtttg tccgtacatt ttaggtagac gttttgatac    63540
cacaagcatg catgggggcc catacaagcc ctgtccatct ttacgggcgt gcaggcaagg    63600
cgttttcgct gtgcagaccc aatatctaca tgtactggac gagtgcagca atgcgtttgt    63660
tgtccacttt tctgttagaa agtctaactt gacggcgttg ccaacttcaa gatcccaaga    63720
tgtgtagtac tgccactcgc attactcaga gcaatagttg ataacgttgc tcgagctgta    63780
tctcgtaacg tttccacttg atatcctggt caacgttcat gcgtgcgttc aacatttact    63840
gcacctgctg ctatttgctc tattcaacga ataattggtg gcggcttgac ggcctgctgt    63900
gcatcgtaga atcctgaggc tgtcgtgctg ttcacgctgg ggtgcagtcg ctcgcataaa    63960
atccttcttt accaaaagcc actggctttt ctgtacatct gtgcttcaac acatgctctc    64020
cgcttttggc tcgcaacgaa gcaacgcaga tggcactcgc aatagtctac aactatacat    64080
gtaatacacc accatgacga ctattcctca tatgtcaatc gcacgcaaac ccggatcttc    64140
aaaggtatgg gtactctact gcaagttaag caagtggatt ggttcatatt taatattgat    64200
cttgatagta gtctacatgg actaagtagc tgcgttcaat acagaggacg cccgaaatcc    64260
tgcgtccaat aggtccggta gtcgctgcag cctccgttcg tggccaaggc aaagccgact    64320
tgaaccacat tcttgttgag gatattggca cggtggccgg gggagttcaa ccacgagttc    64380
atgacatcag ccacagtggc ttgtccggct gcaacgttct ccgcggctgt gccataggtg    64440
tagccctgcg ccttgatccg atctccgaag ttaggaattg tcgttcctgt gtgcgtcatc    64500
acgcagtgac tcgcttggtc ttgagagtga agcaacgcag ccttcacgag ccggtagtca    64560
atggtgagtc cgccgaggcc attttccgca cgaaccgagt tgatccggcc cagcatgtcg    64620
gccgtgtcag cgatagatag accgctggtg ctggtagaag tcgcggtgcg tgacacaacg    64680
```

```
tagccgcaga tagcaccact gctcgttgcc atggtgaagc gtgtgttcgt tttgaaccag    64740
caagtaccgc cattgtagtt gttccagctc cagtgagtgc acgtcaagtc ggccgcgcag    64800
aggtccccgc agatttcgga ggaccctttc agtgcccggt agtcgttgcc agggaagtcg    64860
caattgctgt cccacatgac gcgtccgctg ctgccaagct ggaagtcagc agcgaccggc    64920
gcaagagaaa tggaagcgat gaaagatgct gcggcaatcg tgaagctggt tagccgaagc    64980
attttgactt gagagggga gttggctgga acgaggagaa tgtaaagtga tttctctact     65040
acaagcaaga tccgtgctat ggcggtcgtt gccccctgat cacatggatg gagtgcaaat    65100
agatgctgct agatggacat cctcaagcca ttgaaaagga cgcgaagaag cttcgatggc    65160
ggatcctgat gccctttca ctgcgagtat ttgcatggcg ttttctgggg gctgcgcaca     65220
acgcagggct ggggaataag accccgataa atactgtaca tcgttattat agagtgagga    65280
cgatatataa atgcgtcgtc gccttgaggc gtggtagttc aacttcagcg gaactgcact    65340
ccgacaacag gtacacgtag cttcaagcat gggacaactg aaccaaaaca actaacccaa    65400
aatctgtgaa tgatcagcac gagaaagaca cgagcgtctc tcacgtaaaa tccaaagtag    65460
cctcaagatc cacattgaca ggatgcaggc tattaacgca cgcctggatg tgcagcgtgc    65520
gtcgatctgt agacgaaaaa gacaacaact ttgtgtagcc atttcctccc ccgctcccat    65580
tggtagaaac tgcgtcactg acgtgtcaga cgtaacgtcc catcgaaatg caaatgatac    65640
ccagtttaca aagcgtctga gtatggagca ggtctacgcg ggccagagcc tcttcgtcac    65700
gggcggcacg ggcttcctgg ccaaggtgtg tctctgcact gcttgtcctt cgtcttctgc    65760
ggctgctaac cccttccct ccctcagacg ctcatcgaga agctgctgcg atgcactcca     65820
gacgtcgaaa aggtgccatt tgctccacat tccctctaaa tccgctgtaa attggctgaa    65880
aattgctgtc actttggcag atcttcgtcc taattcgtcc tcgcaagggc gtggcccctg    65940
ccgagcgcct acagaaagag atcgtcgaga gtcgcgtctt cgatcgactg cgggccgagc    66000
gtccacggga ttttgaggcg tttgcggcct ccaagctgca cgcaatcgcc ggagacatca    66060
cgacgccaga cttgggactc agtgcagaag acgcacaact tttgagagcc tgcgtgcaga    66120
tttctatcca ttcagcggct actgtgcagt tcaatgagcc gctggaggtg gcggtggaaa    66180
tgaactgtct gggcactctg cacgttgcaa gattcgtgca gagctgtccg aggaaccgct    66240
gccatttgca tgtgtcgacg gcttatgtga atagcaaccg acgtgatacg aggatctcgg    66300
aggagctgta tccgctggac tttgacgcac atgatgcact gaaggctgtg acgacggcgt    66360
cgccgagtga attggaacga ctgagggtga acctcatggg cacgtatcct aacacgtata    66420
cgcttaccaa gtccatgacg gagcaccttt tggtgagaga ggtcgcgccg gacttcccgc    66480 tggttatta ccgcccgacg atcattgggg cgagttggaa ggaacccatg ccaggctgga     66540
cggaccagat cgctgcggca ggtgctatct ttctggctgc agggatgggt gttttgacca    66600
tgctgcctgg tgatccacga aatgttgcag atattgtccc cgtggatctc gctgtcaaca    66660
gcatcttgct gtcgatctgc gcaaagattc accagcaaga gaggctgagc ttatcgcagg    66720
agccaccttg cccactgatc aagggagtgt cggtgaacaa gcctatggtg gttcattgtg    66780
gtacctcaga tcctcgacag aacccttgc gctggcgtgt gccgtgcatg ctggtgcctg     66840
aatacttccg caagaacccg ccagtccgtg gactcttccc gtccaaattc tctatgattc    66900
caactcacca gagcttccag atacaatggt tcctgacgta tgcgctgccg tcgtccgtgt    66960
actcgacagt tgccaacaag agcgggcatc ctggtcacat caagaatgca gccaggctgt    67020
```

```
ggcagcttac ttggcgtgca cgcaatttgg tagagctgtt caagccgttc acggagaatc    67080
aatggatttt cgccgctgat gctgcagaga agacgctgaa gccttgggca acgaaagact    67140
tttggattga ttcgcatgaa attgcgtggg agcggtatgt ggtcaactac tgtgtcgggt    67200
tgaaaaagta tatgctgcac gaggatgtaa ttgacgtgga catcgagggc gtcaaccaaa    67260
ccaagctcgc gctgagcacg gggcgcattc tggactggga ccctgatcac cacgctatct    67320
cgtttcctgg actactgtcc gatgtggcct gggcgtacac gtccagtcgc aagcctgggt    67380
acaccaaatc cggactgctg ggtcgcgtga tggggattac tgggtggaag aaggcatga    67440 atcacgaggc atcgcacgtc cccaggcctc atgttgagtc gatcggcggc cttcggaaca    67500
gcgttcttga atcggaagct gtccgcgcgg ccatcgaaga acgcgctgtg gcacagggaa    67560
tggatctgga cgacgtggag cgtcaggccg ccagcatgct gagcaccatg gctgcgcaga    67620
tggactacaa ggcagtgcgt aaaatcggct ggctgctgcg aaaggtgtgc cgcaacatgt    67680
acgaccaaat tcacgttgac gagtctggtc tcactcgtat tcgcgacttg ctggctgatc    67740
gacgtgggag tgtcgtgctt gtgcccacgc accggtctta tgtcgacttc ctgctgatga    67800
gctacgtgtt tttcgcctac aacatccccg ttccttacgt tgcagccggc gaagacttcc    67860
ttaacatggg cagtctcacc aagcttctgc gtgagtcggg tgcgtacttc atccgccgat    67920 cttttctcgga tgatccgctc tactctgctg tcttccgcgc ctacacacag tacttggtct    67980
cccaaggcca cacgatcgag ttcttcatcg aaggctctcg cagtcgtagc ggcaagcagc    68040
tgcacccgaa attcggcatc ctcaacacag tcgtcgactg ttacctctcc gagaaagtca    68100
agaacgtaag taccttcagc tcccagcaca ggctgcaatt cgatatcggc gagatgcatg    68160
actgattgtt gtgtggattt gtctcccagc tctacattgt gcccgtcacg atcgactacg    68220
agaagccgtt agaagtgctg ctccaccaga acgagctcct gggcgagggc aagattcgtg    68280
aggtaagaga tctctgtgtc atctttcatt gctgcgtact cataacgcgc tggtggttat    68340
ggtttctagt cgatcagcgc tctggtgaag gccatgcccg ttgtgcgcaa gaaattcggc    68400
tccatctcgg tcaagttcgg cgtgcctctg gatataaaac agcacgtaga cgcaacgctt    68460
gcgcgcgctg aagagcagga ggtgtttgtt cctacctcgg ccatcgtcga agacctcggc    68520
tacgctatta ccgacgcatt gatcacgaat gctacatgtg ccatgtcaca cgtggtggct    68580
accatcctgt tggtgtaccg tcaaggaatc tccaagcaag aacttgtgcg ccaggcagac    68640
tggttacggt tggagatttt acgccgtggt ggccaagtcg ttggcactca gggtcgctca    68700
cctactgtcg tcgtggaccg cgcactcgag ctgctacacg aacttgttac catgcggcgc    68760
aaggatcttg ttgagcctgc cattaccagc gtaagttgtc gttgacgtga cgttcatgct    68820
gctattcgag tgtaatctta ccttcgttgt gaatgctggg ctgcagcgcg agcaataccc    68880
caacatgatt ggcctcggct actaccgcaa caatctgctg cactggttca accgtgaggg    68940
cgtgctggcg tgtgcctacc atgcgttgga cgctttcaac ttgccggctg gggccagcag    69000
cacacgctca acgtcaagca actcggaaga cgcaggtgtc gaccgccagg agctgctcga    69060
tggcgcgctg ttcctgcacg agatgcttat gatggagttt gttcgcaagg acgactctga    69120
ggccgaccgg gctcatctcg cggaggccct cgcgcagctc gagacgcgta acgtgctcgt    69180
ccccgtgtcc gcttcatcgt cctcagcgcc gcgagtggag gcggcggacg gcgcgatgct    69240
gtcgctgctc aacacgcttg tgtggcctta catcgacagc tactgggtcg ctgtcacgag    69300
tctattcgca ctgcgcccac acggcgaagt gacgacggag gacttgctca agcgccttca    69360
gtggctcgcc gagaccatgt accacgagaa gctcatcagc ttctacgagt cttgctcgcg    69420
```

```
cgagacgctg cagaacgctt tggctctgct ggaacgctgg ggcgtccttt ccagtcgtcg  69480
ccgccccagc aagcgcagca cgaacaagcc cgctgtgcag ctcctgagcc tcaccccgca  69540
gttcgcaaag gatggcgagc tcgaacagct cgctctgcgc gtctccaagt tccgcaaact  69600
gcctcctgga gtgcaacctg caacagccag cgagactgaa gtgctcgctc gactgcctgc  69660
actctctcgc atgtagataa caaaccacgt taaggcaaaa gttaaaaaga caagctggca  69720
ttccgatcat atcaaactca cgaggcctgc aaatggcagc gttgtggagc cgcacagata  69780
ctatcgtgct cctccgacgc acccgctgct aacagcgaga agcgagcaag ctgcttacag  69840
gttgccacgg atgcgctcct gcacgtcgcc gatgctgtgg tgggcagcag accaggcgca  69900
gtggaacaga ccctcgcggt ccgtgcgctc gtaggtgtgg ccgccgaaga agtcgcgctg  69960
agcctgggtc aggttggccg gcagacgctc gcgacggaac gtgtcgtagt agttgagcga  70020
gcccgagaac gagggtgcgg ggatgccgct ggccacagcg agcgacacga cgcgacgcca  70080
cgagtactgg cgagcctgca gctcggcggc gaagtccggg tccacgagca gcgagatgag  70140
ggacgcgtcc ttggtgtagg ccgacttgat gcggtcgagg aacttggcgc ggatgatgca  70200
gccgcccttc cagatgcggg cgcactcgcc caggtcgacg ttccagccca tctgcacacc  70260
cgcctcacgg atgaggttca ggccctgcgc gtacgaacag atcttggacg cgtacagcgc  70320
ctggcgcacg tcgtcgatca gctgctgctt gtcgacggcg gggatctcgg acgggcccga  70380
gaggatcttg acgcgaaca cgcgctcctc cttgcgcgcg ctcaggtagc gcgcgtccag  70440
cgacgcggta atggtggggg cggcgatgga tcgctcggcg gcctcctgca cggtccagcg  70500
gcccgtgccc ttcatgccgg tcttgtcgag gatcttgtcc agcacgtagc cgtcggcctc  70560
caggtcgtcc ttcttggcga agatctgggc cgtgatctcg atgaggaacg actcgagctc  70620
gctcttgttc cactcgtcga agacgctcgc gagctcttcg ttcgtgaggc cgcccgcgat  70680
cttgaggata tcgtaggcct cggcgatcag ctgcatgtcg ccgtactcga tgccgttgtg  70740
caccatcttg acgtagttgc ccgagccgat ggggcccagg tacgtcgtgc acgcgccgtc  70800
gtccacctgg gcggcgcact tggtgatgat gggctcgagc gcgtcgtagg cttccctggg  70860
gccaccaggc atgagcgacg gcccgttgcg ggcgccctcc tcaccgccag acacgcccat  70920
gcccacgaag tggatgccct tgggctccag ctcgctggcg cgacgcacgc tgttggggaa  70980
ccactcgttg ccgccgtcca cgatgatgtc gcccggctcc atgaactcgg acagcgcggc  71040
gatcgtcaga tccacgggct tgccggccac cacgaggatg atgaccttgc ggggacgagc  71100
cagggacgcc acaaagtcct tcatgtcctt gtggcccacg agcggcaggt taccctcgtc  71160
cttggcgcgc tgcaccgtgg cgtccacctt gtcgggcgag cggttgcaca ccgacacctt  71220
gaagccgtgc gacgccatgt tgagcgcgaa gttctggccc atgacggcca ggccgtagag  71280
tccgacgtcc gagaggtcag ccattgtact ggaaggaggc ggggagtga tggtctggga  71340 gctgctgaag tgccgagctc tgctgcgcaa attgcggaat gacttgctcg ggggaagat  71400 cctccttgcc ccacgctgag ctgcccgcat gcgtacaaga aaaccggtaa atgacgcggt  71460
tcgaaacgat gacgtaggcg cccaagagac atgaaagact cagcaaggga cctgcgtgag  71520
gcacttgcaa tgaggacatg ttgccgcgcg gagcaagcgc aaggcatagc cgtcgagcat  71580
tgttcaacca cagcaaccgg ccgtcaacgc gccgggtgcg agaccgccca gttggcgaaa  71640
tgatgaaggg ggtccactgt cgaagtactg gggtgcaacg cagcgacctc ggctgtacag  71700
tacagtacgg taattcggta tatatagtga cacattccct cgacacatta gtgtcgagag  71760
```

```
gaatgccaaa ggactaagca ctacataacg tagaggttgc tgctgctgca gctccgttgc    71820
catggttgcc atcgcggatt ttgaagttcg agctgagtga ggtgtatctt aacatgagg     71880 cgtattggct tttctcgttg catgcttact tcgcgactcg agaaacgggc ggtgaaaagc    71940
gtcgatacct atcagcggag cgtcggcatg cctgagcaac aacggcggca acttaatcgt    72000
cacgagcatc atggcgccag gattcgtgga gctgttgtcg tcaatgcggc ttcgaaatgc    72060
cgcctgcgtg gccgcagatg atttcgcggg gtcctcgttt acgtcatgat ctacatgtag    72120
cacaccaagc accaatatta cggggaaagt ctacatcaaa gtgctatgac gtaaaagagg    72180
ctgagtggaa atagtgaaga ccaaaaaaaa agcggagcat ggtttaacaa gattatatgc    72240
tacaaacgag tttatgccgg ctcgacaagt gccaatcctc aatgcaccag cacgacagct    72300
gccagttctc ctcacctgct taagctggta cttgccctgc atactcaccg cgaagcagcc    72360
agttgcgcag aacttgactt ttgtatggtt ttcatggcca gcatggtatt tatatagcaa    72420
taatcccttc ttgtgacaat acagtcgaca atatcgactg tcgcagttca cctgcttaag    72480
cagattggcc ccacaaacat cggaaatggt tgtgcgacaa cgtaagctct ggtaaaccag    72540
cttggcgcgt caacttcccg gcgggattca ggccagcgac agcgctgatt cccggctgcc    72600
tttggctcgt atccgtcgtc ggcaacttgc cctcgacacg cgctgcactg ccaacaatgt    72660
aggcagtgcc tactaggcac cactctaaac tctgtagttt acacgtacac taagcttgct    72720
tggtttggga gcgctcagac atccaaggaa aattggagcc tcaagcagca agtcaggtgg    72780
caacccgacc gctatcagca aaacactgcg aatgtttaag ggatatgttt cttcatcaac    72840
gcgctccaca ggtataatca caatacaaat acacagccat ccgtacgaga cggcagcaag    72900
aagaaaagtg agcactatcg tagtagctcc tgccagcaaa agtgcagcct tgtcttcgcg    72960
tccatcggtt ttggcaagcc ggttctggaa tcttccactg caatttgatt cgccaaaacc    73020
cattctttga acgggttttg acgaatgagc cgccgttgct gacgactggt gcgcagtgcg    73080
tcttgcaccg ccgcgccttc cttcaagctc agaacacgat ttagaattgc gaagtcaagt    73140
gggcccctct cgggggggcgg cttggggaaa ttccccggac accagggcag agagtgccag    73200
cgtccaagcg cagactccct cagcgatgaa gcttggcgga gagggcccgt ctcggcgggt    73260
tggagtcatc ggcggattcg cgaggactga tggtcatact aacagttatg caattggctc    73320
agcggcatat ggcggacgtc gtgccgtcgc cgcttggagc taacccgacg gggattactc    73380
atgttgtgtt ctccacgaca cccaacgacg aagaaattgc cacgggaggc ggtcaggctt    73440
gtgtttgtca acgcagatga cctttgcata tctggatatt gtgtactgta tatgctgtat    73500
atctgagcgc gttgatgaag aaacatatcc cttaaacatt cgcagtgttt tgctgatagc    73560
ggtcgggttg ccacctgact tgctgcttga ggctccaatt ttccttggat gtctgagcgc    73620 tcatagttt ttattgtatg tttgtttact gtggagtaca aggattaaat ttgacatgcg     73680
cgtcgtttga agtctgtgct gtagtggcct ctctaatgaa acgacaacct agtaatccat    73740
ttctaatgag tactcccagt tcacgattga tgtagtcata ggttcctgta gattgaaaga    73800
ggtaaccact ccaacatgat cctttttgcaa cctatctgtc catcaagtct tcttgcttct    73860
tcttgagttc gtcttcattt gctgtttacc cgtggatgca catgatgccc cgactgagcg    73920
ctcgagtgca cccccagagc tctcataagg tgcagacacc gtcgtcgaac tttgaagaga    73980
aagttgcaag ttatacctgc ttgccgtcgc cgtctgcacc ttttgaagat actgtgccac    74040
catcggctcg tggagtgtgc gggctagatc gtcgtcgcac tgagtggctg tacaactatc    74100
cgcgcctcag cttcgtggtc ctctttattg tctgcacgta cattggaggc atctacatct    74160
```

```
ccacggaagt cacgtcgtgg gcactggatg cactgggtgt tcatagcgag ctttcggccg   74220
cgaggcaagt gtatttggca acggctcacg cgttgaactc catgtcagag tgcgtggacc   74280
ggagctcgct gcagtatctt gcaggtgcta agcttcagtt tgaggccgat agcaagcgcg   74340
ttcaaaagat aatcgatgcc aacgacgagg ttcttgccgc ccagaggaac gctacgatga   74400
cgtgtgagtt ccatcttgat gcttttgctc ctttggacga tcactcacac gtttcttgtg   74460
ccaggctcga gcaccttctt gaagactctg cagaagcagg tgaagacagc agcattgggc   74520
gatgcaaact cgacgttgag ttgtttctcc gacaactttt acgcgaatgt ccccgacacg   74580
ggtactcttt cgtcctcccg ggcactggtg cttgctgtcc gtgcaatgct gacgactcaa   74640
gctgtatcgg aagcgcacga caacgtgtcc gaacagcaaa acaatttga acccagctc    74700 tttggtatgt ggtcagccgt cgacacggtc aagacatcca tcgagaaaac ccttggagcc   74760
acaaacacgt tggcttcgaa acagttgagc tcactagcgc ccatcttgtc agacaacgac   74820
ggcagtggtc acacgcaaca atctgcttcc cgccttggac ggttaagcaa aggagtatcg   74880
tctaaactgt cgggcccact gacctcgaca tccacgactg gtctggagac catacgaaag   74940
gctggtagaa cgcttcacaa agccctccaa gttctttcag gcttgcacga cgggttttcg   75000
gatgtcatgg acaccgtaga cgaaacttgg gagttgttgg agaagcagct gaatgccacc   75060
gtccagcaag ccgcacaact tcaaaaggag ctcgcttacg cttcagagtc aacagcacag   75120
cagatcaacc gcacgagtac cgctatcgca acgagtttcg aacaggctca agacgaagta   75180
accgcatcct tcagcatctt gcaacaacag tggcagaatg cagccaaaaa gctggtgctg   75240
gcaggtttca cgccgtggca acgccttgga gatcagctag tagccgagct cactgctaat   75300
cagcgtcaaa gtaccagaac tgagaacgcc attcagcgca gatacatttt gccggacaga   75360
acgacaaact cgaccttggg gcaagaaaaa gaaagactgg ccattgctgc tcgtgacggt   75420
ctttcagcaa acacaacgtc ttcatctgac agcggcgacg agttcgacat tgacacggtc   75480
gtgctgcgcg catcgctggt ggacgtcggt gctttcatca cgcaattgat cttctacgtc   75540
gatattggcc gcctcactat gatggttgcg gatctcgctg tcggattgat caccgagtcg   75600
tattcggaca tgccgatgct cgacatacgg ggaatcacca ccgccgacac aatttgggagt  75660 atctgcgagg tcttcctctg caagcacagc atatcggctg tctgctacac actcgtgaca   75720
aaatcttcgg agctgctgcg cgttctggtg acgttcctct tactattttt cgtggcctca   75780
atcgtcacgg cagggttgtt cgtgtggaaa caagatcaca tcgcgcattg cggaagtgcg   75840
ggtgtttcgc ggttgaattc ctcccagaca gcatttcaaa gtatcactcg tgcattcttc   75900
gagaacagtg gcaataccag taacagagtc gtcgatccac tcgatgagat ccagaagtac   75960
accaccatta tcaacgactc catccgaaat gactacgcag cactgacgtt ggactctgct   76020
gccgtgtgga agaatcagtc gacagcattc gaagacttca gtgactgcac gacaactaca   76080
agcagcttgg ttcgggtgtt tcaagactgc actgagcgcg gtagcagcgg ggaattgggt   76140
cttgctaacg atgcttctct ttcaagtcag tgcttgacga gtagcctacg cagcccctca   76200
gagctggtga ccccagtgac ttctgcagag caaatgagca gcgatgcgcc gttcctcgtg   76260
ccatcctctg cctttgcatc gtgctttcca caagaagagt tggcgcattt gggccgggaa   76320
gaagctgttg gtaagctgca gcacagtctg gcctgtgcga ccgaaaaggc cgtgtatctc   76380
tcgtgtgcat cgtggtggct actgattgtc gttttgtcg cgaaccgctt tacggtgagg    76440
atggtcatca aggccgcggg tatctactgg tggcgcttct tgagtgctga ccgactgcaa   76500
```

```
ttcgtggcgt tctgcagaga ggacggagat ctcgtggcga ccgacaaact tcaaggtgct   76560
atccaagaac aattgcgcga agccaaatgg agaatcgcgg gtcgcttcct tggcattgta   76620
tactccatca catgtgctat taccgtgatc ctcatcactt ttcaaggaat tctgtagaga   76680
aacaccggaa actacgtgta gcgttcgtag ctcaatatat ttccaacacc aggtcaaacc   76740
aggtcgccgt gatcccgcac gctcattaca cttgcttcat tgcattacgt gctctatccg   76800
atcgatgatg cccttccact ttcttactca atcgcgatca tctccgccaa gtcttgcagc   76860
gcgtagccga acgaatcgcc ctcctcgtcc cagctatcaa cgtcggtacc gtcagtctca   76920
accaagtcag agtcgtcctc gaccacggta gcaccaactt cctcctcttc acccttgcca   76980
aagcacacgc ggaacgcacg cacctcgatc gcctgcaacg tcacagacgt gcctttcaca   77040
ggcaaagacc gaggcgacca gccgtacgct tcgtccgtcg tcttccactc cagtccgccg   77100
atctcctcac cctccaccga cagctccttc gtgccagtca aagtcagctc cgtcacctcc   77160
gacaccaccg agttcttcac cgagaacaac gacgagaagt ccaccgtcgc cggctgcgac   77220
agcgtcgagt gctcctccac tgcgtacaag tgcgacagac gcaccagcag acactgcttc   77280
gacagctcct gcagcgtcgt gagacccacg ttcggaggga actcacccac tgctagccac   77340
ggcaccttcg cctccactcc agatgccacg ggtttgcgga acaccgccag aggacggaag   77400
aactgcgact ccatcttcga ccgcagactg cgcatgccgt cctccgcaga gtccacgttg   77460
acgaagaagt tgccgcgcac cgccagaccc ttcgtcacca gcttcttgtt cgccgagtcg   77520
tacacggcct ccgtctcgtt caggtgctcg cccacgccct tgtcgtcatc cgccagcaaa   77580
cgtcggtgca ccatcacctc cacctgaccg tcaaccagac tcgccgcacc ctgcgcacgg   77640
tccgtcacca cgttcagctg ccgcttcgcg tccttaatgt acgctcccgt cgtgatgggg   77700
aagtagttgg ccgccaccgt ctcctgattg tcgtgcagcg tcaggttcca cgtgtcgcgg   77760
tggttgcgca cgcgcttcat gaactccaga ccgttcgagt ccgtgtacag cgtgctgtcg   77820
gacgcgatgc tgttgcccgc gtcgaagcgt acgatgacct ccttgccctt cttatcgtcg   77880
atgggaccg gcccaacggt ccactcgatc tccaggaact cgtcatcgtc gttcacacgg   77940
tactccagtg tgacccactt gccgattttg aacgccacgc gtggtacgct acccaggcgg   78000
ttactaccag aaacaccact cgtctgcagc tccaccatcg tcacgtccgg caccgcagac   78060
gctgccgtgc cgctaccgcc aatcacgggg tacgtctggt tcgagtcggg acggaacacg   78120
tacgcgccag acttgtgtcc gtcgccttgg aatgcctggt agtacgccac gtccagcgat   78180
agcgggatct ggatgttctt cttcttgttg gccaacttcg tgatggaccc cgtcttcttg   78240
ctcacctcgg cgcgcagcag gtggttctcc agcacaacaa cgtcctcatc gtcgctgtac   78300
ttgtcgtcgt cgagactacc agcacccteg tttccacgct catattcgac acctcctcga   78360
acgttgctgt cgtcgctggc atccttctgc ttcaccagga atcgagccgt gctcaacggc   78420
ttcagctcca cactgaatac gaacgagttc ggagccacag acgtctccgg gtgcactggc   78480
acagccacgt acacgttctg ctcgcggagt ctcgcatccc ccgacaaaag ctgcgcctcc   78540
gccgacctgt gcgtgatcgg aactgacagc gttttgcacac tggtacgcgc caaggcgttg   78600
tgcaccagca cctcaaagtc agtgttctgc gtggacacat cacagacgct cgtgttggcc   78660
aacagacaga agtggtatgg ctccttctcg ccgatcacga agagcacctc gttcagttcc   78720
ttctccgcct gactgatgcc gtcgttcagc cgcagcgcgt agtcgtcggc aacgctttgt   78780
ttctccgtgc cggagagacc atcgtggtgc tgcacgagac caacagcccg ttgtagtgcc   78840
accaactcgc tcgagtggtg gctttggtac acggcgtcca attgacgcac ctgctgcagg   78900
```

```
agagtgttgg caacgcgagc gaaccgcttc aaggttggcc gactcgtgaa gaatcccgac   78960
cagtagtcat cttggtcgga cgcgtacggc atgaagtcgt ccgtcttgac gctccaagtt   79020
aaaccttctg catgcttcac gtccgtgtag tacgacaggt tcgagtagag cacgttgact   79080
cgcgcgtcct ggttgacgta gtggatgagt ttgtccatat tcttgaacca gtgtctcgag   79140
ttgtcatact ggaagtcaca gcccatgggg atgaagacat ggttgccctt ggacgcgcca   79200
ccacgcatct tggcgttatt gacgaactgc tccacttcat cgcagacatc atagtcgtgc   79260
aggtctgcat catcctgaat ctcattgcga gtgtcaccgt actcgaattt gccaggaggg   79320
cagtacgtgt cgatgatctc acccgtgaat acctgcgact ccttaccgcg agacttgctc   79380
ggacgccaaa tgaactccag atccttgttc ttcttcctca ggccgtagtc ctggtagtcc   79440
atgcgcgcga agtacagagc gtcaaagccc acgccctgcg acaacaacga gccctgtgtg   79500
gccgagtggc cgaacggatc gatctgccac ccgatgcgcg gactgatgcc gaactcgtcc   79560
atgagcagct ggtggccgta cgccgtctgg tccaccatgg cgatgtagtg cggcgtggcc   79620
tcgtcgtgca tgcaccagcc gccgttgacc gtgaggtcca gccgtccctc cttcacgagc   79680
tgcttgacga cgccttgcac ctcggagccc tgctcgtgcc accagcgctg gaagaaggac   79740
tgctccacga acatgaactg gcggtctggg ttgcgcacga gttcctccac ggccgtgtcc   79800
aggatgtact gcaccttctc catgtagtac tggtccaccc ccatcagcca gccctagcg   79860 gcaacagagt caacatgtta gtatagataa tatagttta gtatagataa tatagtttg   79920 caatgtgctg gtgtgggcgt acgggtcgtc gtgggagtgc gcgatgaggt gcacattgag   79980
tttgttgggg tcgatttggc tggaagtgtt gtacacgccg tcgctgggtg gcgtccactt   80040
gctcgggtcg caggccgcgt gggcggcaga cgccagcagt gccaccgcag ccatagcttg   80100
cacgcgtgcc atcgttctct ccgccttct tcgttcgcgc aactcgatgg ggaaaattct   80160
gatcaacgtt ttgccagaaa gatcgcgtag gtggcgattc aaatttgaat cgcaaacgtg   80220
cgtggttgaa gtggttcgac caatgagagt ggtccgacgg agcagctcga ttaagtgcga   80280
attggccggt tcctgtgctc tgagtcgcac cgtcgtcagt gcacggccgg agcccctcgc   80340
cagcgttgac tccatgcagg gcattgcagg cacgcgggct ttgcagcgag ctcaccacgc   80400
cgccagggcc acaactcgcc gcgtgcgatc gcaggaaata tccacccggg ggggttggat   80460
cgtttagctg gtcgaggcgc cggattgatg gggggggggt aaatatagaa ggaaacgtca   80520
cttgccgcag caatgaccgg atgaatcaag cagcggtgct ggaaaaacgg cgttgccggc   80580
agcgctcggg gcccgagtca ggccgaggac caacaacaag tgcatagctc tggcgagctc   80640
aagcaaatgg cgcgcagagc gcggcggaca tcgccaattc gtcgaaccgc tccatcaac   80700 ttgcgcgaga cccaacgcag ctgggccttg gcgctcagct ggaaatgctt cgcaggctga   80760
agtgttgccg ccactataat ggactcgccg tcagcatggg gctttcgcag cagccagcag   80820
cttgagacgc acgccaagcg ccaaatggct cggactttc tacagccaag ttgaaaaacg   80880
ccaaccatga agccagcgct atgtccacct cattcccctt tccctaccaa agtttcccc   80940 atcggttcga ctcgctcact tcgcgatttt cctccgacgt cggtagcagg ttgatcagga   81000
ctcgaaatgc cgctcctctt gcggccaacg gcgcccagcc cctccatcga cgagctcgcg   81060
ttcgcggtgc cgctctcgtc gcagcgctcc gtgtcctcgg ccgtgtcgga actgccgcgc   81120
tgcgccacgc acgacgact gtcgctgccc cgccgccgcc gcagcacggc cggcaccgag   81180
accgagttcg cgggctgcac ggacgaaacg tgcacggacc cggagcgcca ccgccagcag   81240
```

```
agtttgcgcg tcctcaagcc caaggacgcg ccggaagtag acgcggactt ccgcgactca    81300
aagcgctcgt cgcgcgagac gcaacccgac gacgaccacc tgtccagcga cggcagctac    81360
cagtccgagg ccgagcgcgt gtccagcgtg ctcagctgcg gctgctcgtg cgtggacgcc    81420
aacgagctgg ccatcacgtc ctcagccgtc gtgattgagg accgccagct cgccgtcgtg    81480
gacaaagagc tgcgcgactt ccgaaagacc ttcgtgcgca aattgtactc gcgcttcacc    81540
aaaatctccg gcctcgcacg gaggaagtct gctaccaaac ccgtcttctg agctcgtgcg    81600
tctgcaagga cattgggaat cctgtaggtg caacaagtta ggacactctg ccgtcgggca    81660
ggcggagtgg ccagaagatg atagattgtg cttgggcagc acagccaacg tcgctaatat    81720
ttataaagag ttgttgtgtc atccgtacgc catgcacctt caacaatcgt gctcacaggg    81780
aaacactctt caaagcaacg cgtgcaacac cagcaggttg tgcggaagca acgggcaag    81840 tccagttgta gtctatgagt cattatttc caaaagagca gtgtcaacag ctaccgtcaa    81900
cggcttcttc caccgctaaa ctacagcggt agcgaacgaa cttgcactga atcagtcgaa    81960
cggcttgcgg ttggaacggc ggacgtgcgc ctggtacatc atggagaaca cgagcgccag    82020
gacgaacacg agcgccacca cgaacgcaac catctgcgac tgcattatct gccgcaggaa    82080
caagaagcac aaggtggagc aacccacagc gtcagcgcaa ttgagtcacg aacggtaggc    82140
ctaacgctac agacggcgaa cgtacccgct tcgcgctggc gtcggccacc tcggacggtt    82200
tcttgtgctg gcgcttgagc cgctcgctca tcttggtgta gcgctcgccg ctgtagatgg    82260
tgggccccag cgtcacgtcg aggccgctcg cgccctgctt cgaggcgcca gtggcgcggt    82320
tccgcaactc catggtcgaa ggcaaggtga cgtcgcgtcc tactcacgga agtgcgggtc    82380
aaaacccgtg aacccgatgc tggatttcag cgaatccgcg aatttacagc tcttttcagc    82440
gaaccacagc agctgaaaag cagacccgcg ggaatggcgt gataggtcag gctcccattg    82500
gttaatactc ggtctcgcca aatgtcgcga aggggtcacc tcgagcattg tgcagcttcc    82560
tcgcggcagt tcttcactag cgactgcgtc ggtggcgacc tcgtagagt ccgtctcctc    82620 ctccctccct ccctccccgt atctaagcaa gctaccatca tgagcgagtg gtgggcgacc    82680
atcggccagc ccttcgcgga tgtgcgtggc gtttcttttgc gttccctgcg tatcagagcc    82740
agactgaacg tgatgctgtt gtaggcgctg ctgagtctgg ataccgtcaa gatcaaggcg    82800
gcgttcgcga atgccccgag ctcttactac gagtacatcc gctccatcta cgagcgcagc    82860
cccgagcacg tgattatcga gacgttcctg attgtgttcg taatctacat cacgttcgtc    82920
aagcgtgaca agcccaaggg aacggcctcc aagctctcgg agcgcgagat cgacgacttg    82980
tgcgaggagt ggacccccga gcccatcatc ccgcctgaag ccgtcgtgga cgtcaacaag    83040
tccaagccca ttggcatcgt ggaggacacg cccggcacgc atctcaagct gcagggctat    83100
gccaacccgc tgctgaactt ggccacgttt gacttcctcg gattgggatc gcgacccgag    83160
ctcaaggagg tcgccgtcaa gacgctcacc aagtacggct gcggttcctg cggacccgc    83220 ggcttctacg gaaccatcga cacgcacgag atcctggaga aggacattgc gcacatgatg    83280
ggcacgacag actcgatcac gttctcggac acggaggcca cgtcgtcctc ggtgctgccg    83340
gcgtttgcta aacgcggtga cctcattgtt atggacgagg gctgcaacga ctcgatcctg    83400
gtaggtgcca ccctggcgcg ttgcacggtg ctctactaca agcacaacga cgtggaggat    83460
ctggagcgcg ttctgcagcg cgtcgcgac gaagacaaga ggaagaaccg tggctcggac    83520
tgccagcgcc gttatgttgt gacggaggct cttttccgca accacggcga catgatcgaa    83580
ctgcccaagg tggtggagct gtgcaacaag ttcttcttcc gccttttcct ggatgagagc    83640
```

```
ttttcattcg gtgtgctggg taagtctggc cgtggactca cggagcactt cggcatggac   83700
gtctcggaag ttgctattat ttgcagctcg cttgctggat ctaccgccag cgtgggtggc   83760
ttcagcacgg gttcgcagga agtcgtcgat taccaacgta ttaacagtgc tggctacgtg   83820
ttctcggcct cggcgccgcc cttcacgtcg gcttgctgct cggaggccat ccgcattatg   83880
aaggacgagc cgcagctctt caccaagctc cgcgacaacg ccaagctcgc gcacgacgct   83940
ctgtccgctg gcgtcaacgg cgtgttcgct atctccaagg ctgaatgctc gcccatctta   84000
cacctgcgtc tgcttcccga ggtcgtggcc cgcgtcggca gcgacgagaa ccagcgtgct   84060
ctgcagcgta aggtgtgcga caccgtcatg cagaagtgtc tcgccaaggg cgtggcgatc   84120
tgctcgccac ggtacaagac tgaccagacg ctggagccgc tgcctagtct gcgtgtgtcg   84180
gtgactgcca tccactcgcc taaggatctg gaaaaggcct gcaagaccat cgcaacggag   84240
gccatggcta cggccaaaca ggtgctcgcc actttccctg tggacgatgc tcctgctagc   84300
ggattgcgac agcggaagca ttaaatcgtt agagtttcca aactccgtcg agagagaggc   84360
cgccactttt cctaatgaac tgcttgacgc ttactctgta tcaatgcgtt gccagtagat   84420
agtcttcaac ggtagtgatg cattggcttt aggctgtcga tcgtctacat agcctgcttg   84480
tcctcctcca gcatctcctt ctcgcgcctc tggcggtaga tctcgaactg ctctgcattc   84540
gtgtactggt gcagacaggc gttgagttcc ctgttgttct cgcggcactt gaagacgacc   84600
atgaggccgt tggccttggc gcactcggcg aacttctcgg agacgttgcg gcacttggcg   84660
atggcgatgt cgctcagctc ttgtcgcagt ttctgcagac acgtcaaacc aaaacagtta   84720
gccaatgggg taacggcagt ctcaagcggc gggaggacgc acgtgctcgg cctggttgct   84780
ccacgacagc cgcgacgagc ggaacttgtt cttggctgtc tccttgtcca cgggctgctc   84840
catgatgtcc tcggtctcaa ttaagggtat gcggtgggca tgactccgcg tttccaatcg   84900
caatgtggtg tgcaccactt cagtaatgct atcatttcga tacggtgtgt atcaaagcaa   84960
cttcaacttg tctttttgct tcggagcaga cctagacaca caatggatca ctctaccgcc   85020
gtctgaaagg cgtctcgcgc tagttttgat gcccagggcc attgtacggt gtttagagcg   85080
gcaaactcgt cgaaaatgcg cttcgaaacg caagcgtgt cgcccgtcgg catggttggg   85140
tacgactcgt ggctgagttg ccacttgagc tcgaacgcga tgcgagcttt cttcaagacg   85200
tcctcattga ttttgcgtcc ttgggtgtat gattgacata cctctcctag ccacatgcgc   85260
cagcgaggca agtagtagct ctttacgagg ccagcccact ccttgcctgc gtaatcatga   85320
atggattcgg agttgttgtc gccccagcgt gtcacttgat tccgagcttc gtactcgtag   85380
taatcctgaa gattgtccac agtggcaata tcaccttcgt cgacaaggcc ccgtgcgtcg   85440
gcgatccagt tgccgagcag gaagtcatcg ctcgtcgcta gaatctcgtc caggcgctcg   85500
atcgtgataa gcatgcgacc cgtccaagca cacaattggt ctgctggcac tccctttcct   85560
gtgtacatat ccttcaaatg gaggtactgc gccatgaaat ggtcactaag gaactgccgc   85620
gtgacatcga ccaggtcatg gcgatacgtg tcgacagcat gcagctctgt ccccgcaaac   85680
agtagctcct tccaagcgcg agcaatgtcc atagggtcgt aagtgatcaa agtcggcata   85740
aagccatcac ggacgagttt ccagtgtggt atcaagcaca ccaagctttt agtaaccaca   85800
ccgtaaccca gcgtacgatt gtataccgac tgcagcaaga agccccaagc ccgttccgtg   85860
tgcgcgtctt tgagtgata acgttgcact gcaaagcttg ggaccactc gtccatgtct   85920
agtggagcat ccacccatgc catctgcaag gtgagatcgt acaccacata gttctggaaa   85980
```

```
atgccttcca tggtcagacc cacacctgcc atcgtcccat tgctggcctg gttggccaac   86040
acgggtgctg tgccgagcgt cggtaagtct ccacgcatcc cagtgttgcc accaaagttg   86100
tgcagcacgc aatagatcca gctcttgcca aagtagttgt ccatcttgtt ccacactggg   86160
cttacctcgc tgtagagatc cagaattatc attttgtcgt tgggcacgcc gtccaggtat   86220
gtcttcacac gttccttggt ccaatagtct ggactgttga caaagagcca accttggatg   86280
agccaaactg cattaggatc cgtagccgtc atgctatcga tgcagcgcg cgatgcagcc   86340 tgcagccgca ccggatcagt aaattctggg tccatctcgt tgtaggtatc acactggtac   86400
agcgaagacg tgtagtcgta gagagcacgc tgctcctcaa ggaaagtctt gccgatttca   86460
tggtagagcg ggtctgcggg gtccagcatg tatacacagc agaactcatc tgaaaagtct   86520
ccccagttag gcgagcgagt gaactttgct tttggaaaca gcgacttcat ctcttctggc   86580
acatggccag cgaaggctgg caaggcagga atcataccga attccctcat gcgcgtcagg   86640
atcttcaact gcaacttgaa ctggccatca ataaaggctt gcggaagtgg gccctccacc   86700
caactgccac ggaggttgcc catgcgaccc cacgccagaa acgctgatcc ggcgaagaac   86760
ttgttcaaac cagcagcgct aacgttatag tgtttctgga acgtgttctg ccacaccctc   86820
tcttgcccag tgaacgcaag cggcatattg atacctgagc agcagtggac acacgagtgt   86880
cagtactaag ccctaagtct catcttgcat ctgaaatata tataaaagat acgcaccgtt   86940
gagcgccatc cagtcaatat ggttctccca cttcttccac ccccacgtcc acgaggagta   87000
gctcaccgtg cacacgttct ggtagtacga gaacttgctg ctacgtttgt gccgcacgcg   87060
ctggtccacc tttggtagca cgtagggcag ctgcagcttg tggtcgtccc agtctgtctg   87120
cgtgtgcagt gccgtcttca agtaccattg caggccgtac gccatggcgg tggccgagtt   87180
ggcggcgatc tcgagtttgt cgccgtcgtt acccagctca aacacgtcca gattatcggc   87240
ctcggaaggc agcactcgga gcgttatcta gtatcaatgc attgttagtt tcccattgcg   87300
atctcctacg tgtaagtgat cgtagacagc agaacctggt cgttgaagcg tgcacccagt   87360
cggcggtgga tgagcccgcg cgtcgtcgcc acgacgtcgt gcgcccccgc gctcttcttc   87420
agctggtcga tggaggccgc cgcgagcagc ggcagcagca ggagcgtcac caagattcgc   87480
ttcatcgaat ctgttgtttt gagctcttca accacgtaat tagttgcgta attaaacgac   87540
aaattaataa aactgaagta aatcgctgcg tgtcatgacg taacgaagca gcgcgaggta   87600
atgtcctcga ttaattgaaa aacaccatat tctgcgtcgt acgcactcaa ataatcacct   87660
ttatcaacca ataagataac atctgaacgc ttattggtcg taatggccga ctcattgagg   87720
gttttaacga agaattgggc agctcattta gcctcacaca agggtgctgt cctcgctgac   87780
gtacacttcc cccacgcaga caaggcataa acgctgtccg agcgcgcaga gcacaagtag   87840
gcaagcagaa gacacagcag gacgatggcc ttgcgtaaac gccgctcgag tcccgagggg   87900
agccccaagc acgcgcagaa tgcgttgcca cccgcggtca agcccgcagg aagactgacc   87960
aagttcatga cgcgcgtcgt tgtgggcttc gccatgatcg gcggcttcat cgccatcctg   88020
tacggcggcc acatgtacgc gtgggggctc gtggtactgc tgcagacgct gctcttccgc   88080
gagctcgtga acgtgcgcta ccgggcgcg gccgaaaaga atatcccgtg gttccgctcc   88140
gtgcaggtgc gtgcagctgc aaatggagag ggggaggagg agggaaggta tagactaatg   88200
ctgactcttg tggctgcagt ggatgtggtt cgtggtggcg ctgttctaca actacggcga   88260
ctcgttcggc gccttcatcg agagcagcaa gattcgcttc gtgccgcctg ccatcgtgca   88320
ctacctgcgg taccacacgt gggtgtcgtt caccatgtac gctatgctct tcgtcatgtc   88380
```

```
ggtgctgagt ctcaagaaag gtgcgtgact gtagatttga tgttgagctc gttgtgctgt   88440
cgtacggttg cttcaacgac tgacgctgtg ccgacgaaca ttttggtgtc aacgatgtgg   88500
ttttattgac tgggtaggtt actacaagta ccagatgggt aagttggcag gaatctcgtt   88560
ttgagtttgc agacattcta acttgtgaat ttctcgcttg cagggcaata cacgtggacc   88620
attgtcacgc tgggtttgat cgtcttccag atgaaatacg tcctcacgaa tatcttcaac   88680
ggtacgaatg taacaaatat cccgaccttg tcacaagttg ctaacgggat tcatatgctt   88740
gttcacccct ctaggtctct tctggttctt gttcccgtg tcgctcgtga tctgcaacga   88800
ctgctttgcg ttcttctgcg gcaagctttt tggtcgcaag ttcattaaga cgccgttcct   88860
gcgattgtcc ccgaacaaga cgtgggaggg cttcataggt gctttcgttt gcaccgtgat   88920
ttatgccttt ttttccagtg ccttcatctc gcaggtacga agcaaacacg gtaccgtttc   88980
gcgtattttg tttattgatt gtgttgtctt ttgttcgttt tagttttctt ggttgacctg   89040
ccccgtggag agcttcgagg tgagagcaca gtgtttagtg ctgcaaagca ctggtcttca   89100
tgcagcatac gtgcttatgg taacactgat gtctttattt tgctacagtt caagctgatt   89160
cccgacccac tcacgtgcac acctcgtgac gtgttcctcc ctcattccta cggcgtaccg   89220
gtctacctgg cgggtctaat tggtcgaagc cagatccagc ttctcccgat tcaggtttga   89280
tgttgtggct ggctagatcg atgtatggcg attgctgacg agctgtctgg ttgtgttcgt   89340
gaatgcagtt tcactccatc tggttcgcga tcttcgcctc cgtggtgtca cccttcggag   89400
gtttctacgc ttcggcaatc aagcgtacgt acaacctgaa ggacttcgac tcggtcattc   89460
ctggccacgg tggtgtcatg gaccgaatgg actgtcagct gatcacaaac tgcttcacga   89520
cggtctactt caacaccttc attcggtatg tcgtttctct agtgttcaca cggcccgcta   89580
catcgtgttg ctaacagttg ttgtgctttg tgtgttgctc cctctattgc agttcgtcga   89640
caccgtccgt ggcgctgatt ctgaacctcg tggcgcagtt gacactcgac cagaaacagg   89700
aggtgctgcg agccatccaa gagatgctcc aaggctgaga ccatctcagc attagcacaa   89760
ccatctgact gcttagaagg aggacagaaa gagaaaccat tgccaacggt aacagagacc   89820
atttgccact cccgttcatt ttttctgaag tcgtggagaa caacctaaca gcgtgatctc   89880
atcaccccct gcaaacagcg atgtgaagta gtgcatgaag aaggcaagca caaactattc   89940
gccgggtatc ttgggtgagt acggtggtca gtcctctatt agtattgggt attgtatggc   90000
atttgttgca caagtagaaa tcgcattacc ataacctgga aataacccgc cagtacaata   90060
attacttttta gctcattacc gtaattcgct aaatgttaga ggtgagcgac aggatcaaac   90120
gcaggatgct ctacgaaatt ttgcaggacc aaatttcggg tgcaggatgc ctgcataaaa   90180
ttcttcccag ctggtgacgg atccttagcg ttgactgccc agaaccataa cattgcagca   90240
catgtttgac ctaaaaacga tctggaagag attgaagagc atacatcaag tcgacaacct   90300
gcttctagca catcgtagaa cgaatagaat tttttttttat cctttcctc gcgaacaatt   90360
cttgagtctg cgttgtcctc ttcacctccc gtgtcttctc tgaacgtcgt cctaataaac   90420
gcacgacgta agtgatccac ttccgggggt aggaaacctt ggacccgcct ctctgagagc   90480
agtgatagcc caattccttg tgatgcggac ttctatcgac ttctatcaca catggaagtg   90540
tgaaattgcg aattttttcca ccttgaacag aaaaatcggt actccatttc gctatccgaa   90600
aagttgtaga gcaatctccc cagctttaac aaatccatct tttccagcta gaaaataggc   90660
agaagtagac gccaaccaac tcttgtggcg acaagtttgc ttcctatgac gtcaatcctt   90720
```

```
tcgtgtgaac agtttacttt ttcatcgcca atcacgggct tcaatacatt cttcgagaca   90780
aacgtttcat tttgttcgta ccatataaaa taaacaattt ccaatttcca aatggtagta   90840
aacgcaccgg cagacgagcg cttctgcctg cgcatacgga acctcccggc cgtgctgtcc   90900
accgaggcga tcacgtcctt aatctcccac tacgggtcta ctcgcgtccg cgtattacag   90960
cgccgggtac gtaatgacca gctctgcatg aagggatatt ttcatgtatc aatggccaat   91020 gttttctga tattttgagc agaatgcagc gtcgagcggc aaggaacctg gtgcagcacc   91080
atccaagcag ctgcaaaagg ctgttgctat atttgcaacg cgggaagcac agcagaacgc   91140
gcggcgacgt ctgcattccc tggtattggc tggtcagcac ctgcaggtgg aagtggttgg   91200
cgacgaagct gcaaccgcct cgacagagac gcgaccgcag cctgtgcaga ctggggatga   91260
gttgccgctg aaaggacaac cgccactgcc gaagggtttg cctccaccgc tgccaccgac   91320
accgactccc atgcagaatc ttctctacgc accagcacca ttggctccgc atcttgggta   91380
agttgataca ctattgagct gaaaattatc agtactcatg ctggatgggg tttatttcga   91440
ttgtagtctg cattacgccc cgtcgccact gctggagtac aagtaccca aagcaactga   91500 aggaatcgta cgcaatattg caaatggttt gtggtgctgt gatgatgatt tgttggagtc   91560
aaagagttgg atggatgttc ctaactcgaa agatatgttg ttgtggttgt tttcagctct   91620
tattgcgttg cctcgatttt atattcaagt gctgcatctt atgaacaaga tgaatttacc   91680
gccgccgttt gatgaagatg cgatcccagg aagattttcc actcaccgag atgttacacc   91740
acactactgt gaaagtgagg gtatacgtaa gcgaactcta aagcgccgca gaagcaacga   91800
aagctcgaat gagcaaattg ttgaagagga cgaagaagat gatagcgagg aaggtgggaa   91860
tgatgcagta aaaagcatgg atcacaacaa caccccttggc actgaagaag tgcatttacc   91920
gtcatcacgg ctacaaagtg ggcgtgtcac ggaagattca aagtctgttc aaaaatcttc   91980
tgaggcctcg atccaacctg aagctaattc ttcacggccc gtgcttctcg gtatgccctt   92040
ttcgaaacag aatagaggcc cagaaacgaa gaagagtgcg gcgctcaatg tggcgttcca   92100
acttggaact gatactggaa acactccgag atcacgccga ttgacgcgtc cgggcgtgat   92160
ttcagagaac gaggtgaagc ggcagcgact cgcacaaggg ggtacgtcgt gcttcagtgg   92220
gactgctcgt aagtattggt ctcacacgct gacaccgttg cgtgcaaaca gatttccaga   92280
aggaacctct catggcaacg tactcgcgtg gatcaccatc ggccgttgtt gtggtggaaa   92340
atatcgccca aacagtggat gagaaagact tgcgctacgt attcggctac gttctgccgc   92400
tggaggaggc tttaacgtaa gtgttgctgc tatttcgttg cggactcggg tgccaggaac   92460
gcgttcttat gtttaccatt ctgtggttag ctcgctgaag atcaggctca agccaggaaa   92520
gggttctgca gtaataacct accctgatga agcggtagca gtagcagcag ttgatgaact   92580
gcatggtgta caactggaag ggaaagcgtt gcttgtggta cggtatcgat tttctacccc   92640
atcgcataat ttgcgatatt gatgctcaat tccgatcgca taatttgctt tttgtgaaat   92700
acagagtttc cagagcacct ctggtgtgtc cgaagtgatg ccgagtgtac ggcattggac   92760
tatagaggaa ctggcaagca accgcctaca cgaatcgcaa cttgctctgg agaagagcac   92820
aaagacgtac cagcgaggcg agccttccga cacgctctat gtaaagaacc ttgccaaggc   92880
agtggagctg gcagacctct gcgctgtctt tggtgcagtg ctgcctcccg aatctggacc   92940
tgagtacggc acaacagcgc atttcagcca tattttgatc gtgctgacac taaccacctt   93000
gcggtattct tgaacggtgc agcacgctga atattcgcca tttcacaact ggtcgaatga   93060
aatgccaggc ttttgtgaaa tactcaacgg ttgaactcgc ttccagtgcg ctaaaccaag   93120
```

```
tccatggtgt cgttctcaaa gataagccga tgatcgtggt acgtaaacac tttttcctc    93180
atggtgtgtg tgtgtgctca ttcgattcac atcgcattac tttttgcagt gctttcgtaa    93240
accccaaaca aactaaacac gaagttgcta tcgcagtcca caccttcacc tctaatgccc    93300
ctctcttaaa taacgatagg gaagattctt cacaacttca gggcagcatt cagggaagct    93360
cacgcagttt tgcctcgctg atgctgttga tcacccaaag ataattcaca atgatcgctg    93420
cagacaccgc tttcacctgc gacttcgctt tcagatgcct tgtttgctgg cgcaatgcgt    93480
tcggattgag cttgtcggag acaatgatga gcttccgtgt acggttttcg cgcttgtgca    93540
tttcgtcggg aatgtcatcc atgaatggaa tcaactttcc acccccatg cagatcaacg     93600
agtttagctc cgtgaccggt ggcataggtg aagaaactc cccgatcaag tggaaacaga     93660
aatctgcaaa cagcatcgta ccaacgttcg agcgatcgac ctgtgttggc gcgtacaaaa    93720
aacattataa gcacgagtta gtgtgcatgc agtgccgcgg ctgagcaaca acgaatcaag    93780
atgagatcgt acgtttagag aagtcagctg gagcaacttg tcacgtgttg cccgtgaccg    93840
tttgactgcg tcatggatcc ttcttccctt ccagtgacca tcggcttcat aatttacttc    93900
actcacatag ccgccatggt ctgcgcaaac tggaaggtag acgcataata aagaaggtga    93960
caccccgccc atagtgacgc cgtcagtatc gtaaataatg accttataca gaaccatgat    94020
tgccgtacct tgaagccact catcgctcac gatccaccga ccgcaacca atgccttcag      94080
atacttcaag gaccggatct tgacccatct gccgggcttc gggtcactga acaacttccg    94140
cttaccatcc ttacgcgcct ggggaggaga ctttgaatcc gattcatcca tcgaacgctc    94200
ctcatccttg acttcttcgg cgctaacaca tttcacaatc aaatgtgtca cgtgattgga    94260
ccagtactgg acaacttcag caccaagcag ctcggcccat tcgtctatct gttgcattcg    94320
gttttcctta aatcctgagc acaggaacac catgcctgaa tgcgttgtca gcgccttcgt    94380
tttaggcttg accttgtttt ccgaatgggg cgagggcctt gttttcggag ctccagcatt    94440
cggcgaagcc atgatctcag atggtcgtcg acgttggcgc tttcttgcag aatggcttgg    94500
ggtcgagtcc gaggctatat cctcggcagg tctgcgaata aaagccccgg gcacgcgtct    94560
atccattcca gtgccaatca gaaacttaac gccgtaaaag ccgtctccgt gaaccgtgat    94620
gatacgcgcc gcgcccccac gtttattgat tccactccac tgccgctcaa ttacgtccac    94680
caaggcgccg acttggaaag tttcgatttc aagcggaagc tgcgtttggc catcaaaaac    94740
cgaggatggg tttgccgcta gtccgttggt aggagctatt tttccattgg attgatatgt    94800
tcgctcagat gccccgtttt gcgcagtgtc gtcgaatccg tttgtttcag atcgtcgcct    94860
tttgagcggt gtcagctgct gcttcgcttc aatagccccc atctgtggtt ctttggcgac    94920
ttcaactgta gctgattgtg aacgcagcgt cgcctggtgt tgtgattgcg cttgtaccac    94980
atgagttttc tcttgggctg catctgtagc tgacttccgc cgccgtggct ccagagcttg    95040
ctgctccgtt cgatttttgct gaaatccatc agaaatgtca actgtagctg accgtcgacg    95100
ttctcgcaat gtcagtgtcc gtggcttcgg ctctacagct tccacccgcg cttcatctgt    95160
ggctgcatcg gtagtagacc gccgccgtct tgtagataca gtttgttgct gcaagtcttg    95220
cagttgtgtt tcgcctgcgg ctttatctga aacaagtgga tttcgggaag accgccgccg    95280
gtgcggtgaa gatgatgctc gctgcacctc ttctggctgc atttcggatt caatttcgtc    95340
tataaggatt gcattcttg aagaccgccg ccgccgtgga gttatagcct gttgcatcgg     95400
ttcttctacc ggtgttgatg cttcatccat ggcttcatct gtgattatat ctgattgctg    95460
```

```
acgtcgcgga gataatgtgt gctgctgctt ggcttttacc acttccagtt gtgtttcatc   95520
cacgtctgcg ttcggagccg taatttccaa ggtacactgt ggagataatg ccttagcctc   95580
cagttgtgtt tcatccgctc ctgctgcatc cgcacccgac caccgctgct catccacatt   95640
gtcaatctgc gtcattgtat cctcacaatg aagtctctcc gcactagaac ctgcaatcgc   95700
ttctgccact tgcgtcttcg ctgctctcgg cgctgaaatc tcaaacagcg ctggggacat   95760
gggcgacgcc atctcggagt acaagtcccg tcgacgcggc gacgctctcc tcactggcgt   95820
cgtttgcttc tccgtcttca tcttgaccaa ttgaggccga agcgacgtgc tgccgccagt   95880
gatccaagcg tccatcagcg tctgcgtctg cgatcctggg gagttttcg tctgcgctct    95940 ccgtcgcgga ggtgacctcc tctcgggcgt agtagcagca actttaacag gcttggctgc   96000 tgcaattta acgtcgctcg gggctgtcgt cacctgcttc tccgtcgtct gcttggtcgt    96060
cttcatctcg attgactgcg gctgcttttc cgctgcagca tcctcgggcg cagcgcagag   96120
catctccgtg gcgcatagta gctcctgcac tgtcgtatcg tagcgcagcc gtcgcttctt   96180
ggccggcgcc ttgcagatgg ggcacagcgt cttgagctcc aacgcacggt ggatgcactc   96240
ctcgcagaag cagtggttgc acggcagcga cacggggttg tcgtacgcac acaggcagat   96300
agcgcactgc agttgcgccg agaaggtctc cacgcgcgc tccagccgct tgagcgtcca    96360
cggcggcatc tccgccaggc gaaattgggt cgtgtgctca aactttgacg ttttggtcgg   96420
atcaattttc agcattttg gtccgaagtt ttggtccgag gttttattac agtatctcaa    96480
agcaggaagc gattgcagca acgaggatgt ctctggatga gtcgtccatc ctgatggacc   96540
gcgcgctggt gaccatgtgc ccggacctgc ccgagtcgct ggggctgtac aacacggcca   96600
aagaccagtt ctcgctagca gccatgcgca ccgtgccgct gctggagcac gtggagccgg   96660
actcgcgcaa gctggcgcta ctccgcgatt ggatgcgcgc gtacgagccg gcggaggacc   96720
agccgctgac ggcggagatc agcatggact cgctacgagt gacggccaag cgcgagcgca   96780
aggagcgcga gcgcagctg caggaggaga agcacgcgca gcgcacaagc gagagcatag    96840
ccgagagcga cgacaagaag cgcaagaaac gccagcgcag gaaggagaag cacgcagcca   96900
gggacaagga gagcggtcga ggcaagggca aggacaaggc caaacccaag aagaagagcg   96960
caggtaagga gaagaagaac agcaggacca gggcagcagg ccgcaaacgt cacgtgaagc   97020
tcgacagcga cgacgacgtc ctgtcaattg aggaatcaag cagctccagt gatgaatcgt   97080
cgtcttcgtc cagcgagtcg gacgacagca gagcgaagaa gcgcaagaag tcgtcgggga   97140
acctgccgcc caaggaggtc gtgctgtcct cggacgagga tgacgaagag cccaatgaca   97200
tgttcgacac ggacgacccg gacgtgtacg aggtggagac tatcatccgg aagaagacgg   97260
gcgagagcta cggcgacccg gacttgtacg aagtcaagtg ggaagggtac gatgagacca   97320
cgtgggagcc ggccgccaac atctcgaagg acatgatcga cgagttcgag ggccagccgg   97380
tgcgggaaga cgtgtacacg gtggaggaaa ttgttgatcg ccgcagcaag cgcgagccct   97440
ccacgaagct caagacgcac cagtacaagg tcaagtgggt tggctacgac gagctcacgt   97500
gggaacccgc cgacaacctc ccgcacaacc tacgacgaaa gttcgaccag aagtatgaga   97560
gtcggaagcg ccgacggtcg tgagaagtgg ccagccgtaa agaacgaagt ctgagaccga   97620
agatggtcaa ataccaagtg caaagtgcaa cgagccacta cacttttcta gtatgatggc   97680
tacattatgt attccacgct atgtattccc tctacaagaa cagatcagct catatccctc   97740
tagaagagtg ttgctgtcag ggggacttcc ctcaaagaga acttggctcg caaaggtcaa    97800
aaagctgcgg cgatcgttgc gcgaggacgg ctctatctgc tcgggcacgt tacgtacagc   97860
```

```
gcatcaacac ggcgcatcag gatccccact cttccgcgcg tcttctggta ccttccacgc    97920
gccaatctgc aacgtagatc atgagcggcg tggagagttt gctactcgag agcgatgatg    97980
aagacctggg ggagctggat ctgtccgcca tcacgctaga ggagatccta cgtgaggagg    98040
aacaggccac gaagggcacg caggcccagg gcggcggcgc gcaagacgga gacgagctct    98100
tcttctcgcc cgcgaccttc acattgagca tcgagccagg cccgggcatg gacgtggtcc    98160
ccgcgcccaa ggcggcgcct gtagccgcgt ccaagacgga gacgcacttc cgctcgtcgc    98220
tggagatcgc agaggctcgg gagaagcagc tgctgagctg cgtgggcgtg gagctcatct    98280
ccccgctgca ggtgaagcgt cgactgcgcg cccacgcgcg gtccaaagcc ctcaaatccc    98340
gacgagaggg actcgtggcc atgaagaaga accaacggaa gaagcaaatc gcagagggcg    98400
cgggtgccac tgctgtggct gtggctacgg agaagaagtc cacgggcgtg gtcaaggtgg    98460
agcctatgga ggctattagt cgccagctaa ggaagaacat tgagttcaag gagtacggcc    98520
ccgggtcccc cacggtggtg gcgatccact ctaagttcat tgcaattgga acgtccaagg    98580
ggctcgtgat catcttcgac cacttccaga atatccgaca ggtgctgggg aacacgaacg    98640
acgcagacgg agatggaccc gttacggctg tggacgtgtc gccaggcagt gactatttgg    98700
tgtgcggcta ccagagcgga cgcattgtgc tctgggatat gattaagggt acgtccctca    98760
aggccgtgtc ggatgcacac gagaaccctg ttgtgagtct gcgcttcctc aaggaccaga    98820
agcccgtgct cgtctcggtg gacaccaatg ggctcgtgaa caagctgaat ttctccaaaa    98880
tgatgggcat ggtgtacgtt gtggatgtgg atccgctgta tgacggctcc gcggggaaga    98940
tcttgtccat ttcggtgctt ccacagtctg cgggaaatgc caagatctca tacctcacgg    99000
atcagtattg tctcgctgca ctgagcaccg aaaccgttac gtttatcatt gccatcgaac    99060
cagaggtccg tgtgatctac cgctgggcgc gacctgatga cattgcgccg gatgacccgg    99120
tgctcccgtc gctggccttc gcgtggattt catttccagg aagctcacgt gctctagcgc    99180
cagtgcttgc tcgtggctgg ggtaaccgcg ttcagttctt ggaggtggtt ttcccgggcg    99240
gcaagaacca ctcgcatggg cgccatggct tccctacttt cgacgagcac gaccaaatcg    99300
agtcctcgag cgctgttatg gctgtgcagt ggctaggcga ccaagtggtg gtgtatctca    99360
actcgcacga tgaaatctgt gtgtacgatg tgatgtctcg ccaggagctg gaaatcgtgg    99420
acgtttcgtc cctggagttg gtgtttgcgt cttatcgtgg caagaacgct cgcagtttct    99480
caaacagttt ccgtggttgt tacaacattt tgtacctgct gggtcttaag gaattgcaga    99540
cagctcgtgt gctgccgtgg acccagcgca tcgatttgct ggtggatgat ggcgagtggc    99600
tggaggctct cgcacttgcg ctggatcact acgagggact taagatcgct gcggcggacc    99660
gtgcggccag agatcgattc ccgcctgtgt cttccgtga caagcagaat gatcagtgcc    99720
ttgttgatat cttacatatg tgccagacta accagcgtac tggcgagaag gaggatgtgt    99780
ttcggcatga agagagtgcg gacgaggtgc gttgggtctg tggtgaagtg ccatacccgc    99840
ctgacattgc caaaaagcta gaggagacac tccaaaaagc acgtagcggt gaggtgacga    99900
agaacttcgt gcctattagt gtggctgagc gcgtagcaga tctgctgatg gaatacgtcc    99960
gtcttgccat cgctaacgcg ccgggttcta cagctgccgc tggaggcgag ctgagcctga   100020
acaagatcgg aatgaagctc gacttggcga agagccacta ccagatgctg gctggtgttt   100080
gcattgagta ctgtgctctc atcggtcgaa cagaccttct ctttggagag atctacacgc   100140
gattcaagga tgccaacaag ctcagtgtat tcgtggagtt gctggaacca tatattctat   100200
```

```
ccgagaagct gcgtaacctg tcgccggtgg ccatggaaga gttcgtcaag cactttagtg    100260
atcagggcaa gcttgcccaa gtggagcagt gtttgctcca cctgaatgtg gcagagctgg    100320
acctggatac catcctcaag ctttgtcacg accacgaact gtactcagct ctcatctaca    100380
tttacaacga aggaatggat gattacacga cacctatcga tgtgttgctg gaagcttgct    100440
ccgacgcaaa ggcgtcgaag tcaaagcctg caccagagcc ggctcctcga gctactcgtg    100500
caccttctgg tagcaaagtg agcagttttg catctgcgtt cggggggtact acccgcacgg    100560
ctggctcaaa ggtctcaatt gcgaagcctg ctgggttgtc agcacgcgaa aaagctgaag    100620
aggaagcgct cagtggtcct cgacgccgac ggttgtatgg gtacaaactg ctgttgtaca    100680
tttcgtacgc gttgagcggt cgctcgttcc cgaagcatga accgatctcg gcccaaaagc    100740
taggaaaggt gcgctcgcag atctgctacc atttgttcga acaggcggtg gcggggtcat    100800
caaacccgcg accatacccg cgactcgaga cgcttattga tcttgacgca cgtgagctgt    100860
tcaacatcat gggacgtatg tttgacacac ccagcgttga gtttgaaggc gaaaagaagg    100920
acggttcggg ccgtccaacg agccgatacg actcggctcg caatgctgaa atgaccaagt    100980
gccctagccg tctgtcgatt gtgctttcgc ttgccgaggt aatcttcggc ccgaagagcc    101040
ccttcagctc tgtggagcac gcacacttct ttatgtttga ggctcgtctt ctcagtggcg    101100
gctccatcga accacaggaa tacgctgatg cacgtgccga ggccattggt gacgccggct    101160
ccgctaacag tggcgaatct atgatggatt cgctgatgaa cttcctggcg cttggtcctg    101220
cgtcacttct ttcgaagggc tcatctgcag tcacgcctgc tacctctcag gaggagggct    101280
tcgacaaggc tggacgtgaa gctatgcttg tgcgactact gacaaagctg agcaaagcca    101340
cgtacaacca cgaggctttg ttggcgagtg tcatccgaga gaagatgaac cgcgcagctg    101400
tgttgttata caaggataag ggtgacttta ctcaggcgat tgcctcgtat ctggctgatg    101460
aagaccacga gtaccaggtg aatgctttca gctacatccg cgtggagacc gacaaggcag    101520
tggatggtga agagatggag atgcgcgaca gtaatggagc tgagcctacc cgtcgccgcc    101580
ggaagaccat tgaagaggct gtgcttgccc atgcaccggc tctgatgaag acggacggct    101640
acgcgttcgt gacgttgatt ctgggccagt tcccgaactt gaacaacaag ataatccaaa    101700
aattcctgtc aatgggcaag gagggtgcgg agctcgagtt cctttacctc aagcaggtgc    101760
ttatggcctc atcgaccacg agcggcggca gcccaagcga cgaggccgat gtcgtgaaag    101820
acctgctgga tcgttcgaag ttgcgtatcg ccgacgaccc cgctgtccag gagcgtttcg    101880
ttcgcccttct gtgcgagttc gaacccgccg gtgtgttccc gtaccttgaa tcccacgaca    101940
gctacaaggt ggatgcgtgc ctgcggctct gcaaggagtt cgcaatcaca gacgctgaag    102000
cctatctgct cgaacgcaca ggcgatgtca ccggtgctct tacgcttatc ctgcaaagtc    102060
tggagcaaaa gctcaagatt ctcaagccgg cactacgtgg atacaacgtc tccgctgtgt    102120
cttcgtcgtc gacaggagct tcggacatgc tagtaagcac tggtggtggc actggtggcg    102180
ctggtggatc tagtgggttg acttcgacgt caagacacca atcgtctgac cgcatcattg    102240
acagcgttca ggagggcaag gacgcaacga agacgctgga agtggccttg accatgtgtc    102300
agcgtaactc gctgcgtaac cgagatgagc aagcagaaaa gctttggttc acgctgctgg    102360
acaagctgct gcgtatccag aactctgtga agcgtagcct cagctccaag acctcatctc    102420
gcaacgttcc tgtcactcgg actcacagca gtgcggtaa cagtggacat ggtgctatga    102480
ctgccttcca ggtggcgttg aacgaaatga ttcgtttcat tcttgaacgc atggcttcct    102540
cagtgtcgct gaagtcgatc cttttcaaga tcacaaacga gcatggtcgt ggtgcttttg    102600
```

```
gtgacttccg gcccactata ttcggtatgc tggacacgta caactacgag cagaacattt   102660
accagacagc gaacgcgctc atcagtgtgg atctgttcga ccagattacg acgctgaagc   102720
gagccaagtc tcgctgctac gccccaccgt cgaatgtgtg cggctactgt cacgtcacgt   102780
tgtccaagcc tccttttggt atgggtcaat ctggcgctcc tggcacggag aagtggcatt   102840
tgcacacgtc catggtgctc gttacgtcgg gtcaaacctt ccacgagtcg tgtggcaagg   102900
cttggcagca gggtgtggat accaagactc cggcagcgcg cggagctcct cagagcaagc   102960
tctcgcgcca ccacagctcg atcagtagca tggccagcga tggactggcc ggagaagatg   103020
aagcaggcag ccgtctccag cgtaagcagc cgagcacaag acgctacttg acacgactaa   103080
agacgcagcg ccgcgcatcc cgacgacagg tgtcgcctca cgttgtgctc gaaagcctca   103140
tccgcgagga caacgggcgc aacaagtacc tcaagagctc gcgcgcagtt ttctcgctgc   103200
gcccggaccc ggaggtggct gccagcaagg tgaagaagcg cctggggacg cgcaagcctg   103260
gttcgctccc cgtggcgccc atccagaagg gcggcatcta aggcagcaaa ttgttgaaat   103320
gagggagctg gcggaaatgt gtccaaacat cgttgtgcat gttttagggg ggtaagcaag   103380
aatcaaatgg acccgcggac tgcgggtcaa gtgtgtttag acgttgtgtg ttggcaggtg   103440
ctgtgggggg ccgcagcttg gatctatttt gctttgtgcg cttgcagcct ggggtcggtt   103500
gcgctggaga gcatgagcga aggcaaacct gcagccaaag cgacaagaag cgcgatctac   103560
agcgttggtt cctggcgact cggcgatgat ggatccatcc accggcgcgg tcgattgaag   103620
tactcaaccg gtgacgtgta cgacggcgag tgggtggatg gcaagcgaca cggccaaggt   103680
gtgctcacct ttggtgcagg tggcagctac acaggggagt tcgcaaacgg cctgttcgaa   103740
ggctttggcg tgcttcgtgt gcccaagacg cagcacccgt tgaccaagca gtggctgcgt   103800
ggagagaagt acgaaggcga attcttgcgt ggactcaagc atggccgcgg cacgtggcag   103860
actcgtagcg gggatcagta cgatggcgag ctgaagcagg ggctttatga cggccgaggt   103920
gtgtgcgtct atgcagcatc gggggatgtg tacgacgggg agttcgttcg cggtctgcgc   103980
catgggcgcg gtgagctgcg gtttcgtaat ggctcaacac acagtggtga cttccgtctt   104040
gactactttc atggctttgg tcgggtgtcg tacgggcctg gaggcattca tggttcctac   104100
gttggagaat ttgccgatgg caagcggcac gggcgaggag ttcgcatata cggcaacgac   104160
gaagccaata gaacgaacag gagacgttat gagggtgcgt gggaggatga cgaacctcag   104220
ggcactggtg tgcttgagcg tgatagctgc actgctgtgg ggatgtttga acgtggtctt   104280
cagaagggtc ctggagcaat gcggtttgca aatggcgata cgtacgatgg gaacttcgag   104340
aagggagatt ttcatggaga aggacgcatt gtctaccgtg atggcggcgc gttcgaaggc   104400
acattcctgc gctctaaacg ccatggtaaa ggcaccagag tgttttccaa tggagatcga   104460
tacgtaggcg actgggctga cgacttgatg cacggccgag gagtgcacac gagcacaatc   104520
gattttacgc ctcgcggtaa gaccaagaag ggtggaggaa gtggcaaact ggtttacgat   104580
ggggagtact tcaacggaca ccagactgga gaggctacca ttgtctacgt gttcataccg   104640
tatatgcctg acaccgaaga acggcctgaa acggagcttg catccaagac gcaggaggat   104700
tcagcaaacc agcctcagaa gcagtggccg aactgggaat ggaacggaga gttcgagttt   104760
ccggagggct ctggttgctg gcatcgtggg cgcgggaaaa cgacgtatca aggtggtgtc   104820
ctgcgtggtc gcttccatgg gcagggcgca ctgcgctcgc ctgatgggaa attgtggcgc   104880
ggtgagtggg cccacgggca gcttcaaggg cgtggcgaac gcgtttacct tcctttagag   104940
```

```
tttgcacctc tgacgacaaa gaacacgctg gaaaaggacg tcccgaccat cacgttggcg   105000
gatagtcggc tggggcttta tggcgtggtg cattacgttg gtgagttcgt gaagaacgtg   105060
cggcatggcg aaggtgaact gctgtacacg aacggatatc gacttcgtgg tcgttttgca   105120
aacggcttcg tcgagggcgt agcgtgctat ggcgttggca gacttggagg agatgctcga   105180
tggagatacg gtgagtttgt tcgcggtgag cgcaagcgat ggctcagcga ggaagaggag   105240
gcagtgattc tgaagcagaa gcaagacgag caagctgctg aaacacgcaa gcaaagcctg   105300
ctacgaacgc tgatgccgag gtgacgtgct caaagacctg acaactaaaa catcaacgcg   105360
aacatagttc tattctatca tttgacaagc tagagttctt cgtggcgttc aggtttacta   105420
cctgcctcta cctttgcgcc ttgctgttgc agttccttgg ggaattgttt cacttgagcg   105480
atttcgccca ccaatgtgtc ttcttccact gcctcgcaag cagcaggcgt ctcgaagcga   105540
atctcgtact cgcacatttc gcgctcttcg acggagacga cgcggttggc aacaccgcac   105600
gagaactcga cgcgtgtctg acgctccttc ccatcggcac acggctcgcc gtggttgtac   105660
tcttggacac gcgcgaaacg agccgaatct tcatcgctgg tcagccactg attccagata   105720
cccagaccaa tgggacgggg aacatcttcc tcttcattgt catccgcagc ggtagccccg   105780
accttggttt ggcgttctgc cttggtccac ttcgggtagc ctggctcagt ttgggagaca   105840
ttctggaacg gacacagcac catgacgtat tcgcgcggga taacgttggg cgtcccacct   105900
ttcagctgct tctcgtccac cgtgtgcggg aagcactgac ccacaagctc gacgaacgct   105960
ggtttccagc tcgcgtccga aaaggtgctc cgatcaacta cgcgactctg aacatacgtg   106020
acatactgca ctgtccgcag cacattgtac gactgctcca attgtccctg cagctccggg   106080
ttgtgctgca ctcgctgctg caagtcctca aatgctcgtt gccctgcctg gtacgcttct   106140
gcaagtcggt caaagtcggc attcagctgc ttcaccttgt ccactgcctc cgtcaagtaa   106200
cctttacgaa ctctcatgcc tttttgcacc gcacccagcc tcatcttgag cgccttcagt   106260
ctcttttgcc attggatctc acacgtgtca acacacacgc cctccctctc gtcgctgccg   106320
tcacaacagt cacacactcc atcgcccacg aaagccagcg acaccaacct gtcgtctgct   106380
ttgcagccaa acttgcgatc aattggcatc cttctggagc tcaacagcac gcgggaacaa   106440
gccgaagtgt tcggctcgtc gcttccgtct tcgcagtcgc aatagtcgtc gtccacgcga   106500
tcgaccggca aggcatcgac gcagaatccg ctctgcgcct ctagatatgc ggtatttgca   106560
ttggtgtggt gccctgcgag ccccagaatt gcgtcgtcgt ccatgaaatc ccagtcgtcg   106620
tcttcttcgt cctcatcctc gtcgaaagct tcgccgatcc cgaagcgttt gaagtcaccg   106680
gagctggcag aagccgcggc gacactcggc acttggatgg ccagcaccag catgcacgcg   106740
atggccacga tcacggccag gaagaacgcc agcagcgagc ggcgcacggt acgcggcgcc   106800
atactcggcg attggtgcaa tggcacgagc agctacgaag acattgattg gtggaaaatc   106860
tgctttagtt accttttgaca tcaatgatgt caaccttctt gtctgagttt caccgctcat   106920
aaaagcgttg tggtcgtgct ggcggtggag acttggtggg gcatggagac aggacggatg   106980
cgtttcactg gacgaagagc ggcgattaga ctgggtctct cttctccgtc gctcaactcg   107040
atcaactcgt cttcagtagt cgactctgag gcttcgcggc ttcttttgcc gttctcatcc   107100
agcaggtttc gtcctccagt ctcccacttg tcctcttctt ccgccacgga cacccaatcg   107160
tctgcgaggt tcttttgctc tgcgttatcg atgctttcgg tccccagcaa ctgctgctcc   107220
ccattcggta ggtcgattcg agacacccct ggtaaatggc gactcatgtc aacgaggcgt   107280
gcggccccca ttcgcagcag cttcaccacc atccgaccca caaacaccat caacgtgaag   107340
```

```
aacttagcca taacacccat ggcaaacagc ggactgggga gacttgggac caggtgtcgt 107400
caagaagaat ccctcaactt caacgtccaa tcccatagtg acgtcagttt cttgggccga 107460
aaggacacgg tgtcagcact tcattagttg ctggcacgaa catgacacga agccgctaca 107520 acagggtgg gcaaggcgct ggacactact ctagtagcag tgaaagcagc ttcggcagcg 107580
aaagtgatgt cgaaagtagc tgtgctagtg acgcttcaag tgatggtcta gagctcggac 107640
tgagcgggaa gggcgaggcg gagcagaagt tcaagcggtt gcgccgcatt ttccttaatc 107700
gcccgacgaa ggtaaagaaa agggagagca accaacagcg acggcggagt cccagcagta 107760
gaagatctgg actggagcga agaccactca aggttttggc gacagaacga tcacggtcac 107820
aacgtccaag ggacagcgtc tcaagtaaca gcagcagcac aagcgatgaa aggacgttgg 107880
aaagaccatg caaaccagtg aactcagcgc ggccactcca agcggcgatt gatcaacata 107940
tgcattcgct gtgggaacag atgaagcggc attctgcgca gcgcgactcc agtacgtcac 108000
gtggctcccc atcttgtcaa tgctacatca atttctaaca ccagtgcttg ctagctgccg 108060
gccaggttca gagtatgctc gagcaggccg tggatgaggt tcaatttcta aagaaacaag 108120
aagagcgcgc attagaaagc caagtgaggc ttatccgaga ggtgagcgcg agtacactca 108180
aattgtaacc atgcattttc tcatcagtct tcgtggtttt gatacagagc tacgctttgc 108240
gactggaggt cttccagcag cagtacctga gcaaagtagc cgaaattgaa gatgaaatgt 108300
acgcttcaat ccaaaaacgg caagaagaat gcgatgcaac tgtcctagct gcagtcaaaa 108360
agctccaaga tcagacccaa cacgcgttat tgaaggattt ggctacgatg aatagcgaac 108420
cgatagagga acagttcgac tcaagctcat tctcaaccgg cagcagttca gcgagtcagt 108480
caaaagtgcg tcgacaccaa agcggaccgc ttcgccatga cccactcagc tgcaattctt 108540
ctcacgtacc gccaatggtg aagcacgtat ctccagtttc gaagcagcga cagaaattgc 108600
aagcactcga agagaagctt gcagcatttt cacctgattc gctaattcgt gtcaagaacg 108660
aattggccac atcagtccgt gctgagcgga ccgcagcgaa gcctaaacga gaatccgtac 108720
cgagacgcag gcactcgcaa cgcaaacacg aagatcaaga cacatttgct gacgaatggc 108780
aagtctcgcc gctatcaccg cttcgaaatg gaccatcata ctggaaaaat ggcatttcac 108840
ttgaagcacg agatgtacga gaagtagaca atgctggcaa cccgggcaag catgagcaag 108900
cagcttctgc aacagtgaaa agacgagcac ctgcatcttt cttaagccgg cggttcctta 108960
gaccggaaga ggaggaagag ctgcgccatc tccgaacgag cattggcctc gcaaaagact 109020
ggatggcgat caatagtcag gcgtgagcga gcagagaggc attcacgcag tcaataaagg 109080
agacacgagc acggcaaggt cagacgcgag cgctaaatat tctaattaca cgttgatcat 109140
tgccgagatg ctggccaacg cggccttgtg cttttcgcgc tcgagcagca tcacaaccgt 109200
ggtcttgctg ctcttgtcca cacgctcgcg ctcggtcaac ggagtgtcga acgagaagct 109260
gagctccgcc tcctgctcga ggaactcgtc tcaaagttg tggaagaact tggctgtctg 109320
ctcgtacgcc gtcttggtct tctttccctt tttggcgcca cttgcgccgc cgctcttctc 109380
ctccgtgcag gtggccagaa tcaaaaagta gtccatcttg aagctgttgc gcagctcctc 109440
cgtgtcttcg ttctcgattg cccactcaat gtcttcgtgc agcgccgagt gtagcgctgg 109500
tacgagctgg tacggcaggt tcaccatgcg ctcattgagc acaagtccga cgttcttggt 109560
gctgaggatc tgctgcagct tggactggtc agcgctcgga cacttcttgg ccacgtactg 109620
caagatctgc tgcacgctgg tctcgttggc gaagctcttg aggttcattg ccgtgatgaa 109680
```

```
gccgtatacg tcgtcctccc cttccacgca gaccatagta ccggccgtga cttggcccac    109740
gacggcgttg gccaggccag acacgtcgaa gggttgcgac ggcggcaggt aggccagcag    109800
gaactgcttg acactgtgga aatgagcctc gcgcgggtcc gagaagagaa agtcaacgct    109860
cacgttgcca ccagcagctg cagcggcctc tccgccgtcc atgtcgtcgt ccgagtcctc    109920
gtcgtcatcg gctccagcgg gcgccgcagc gaacgtgaga tcgtcctcac tgtcgctttc    109980
gctgtccgag tcgtcctcca tcatctccac ctcatggtcc tctgcgctag ggccttcgg    110040
gtccagcggt gccttgccgg cgttgcgggt gcgcttattc tggggcggca tgaacgtagc    110100
tacgagcttg attagcaatg gagctgctgg ttggccagcg tcgacttttt gagccaacaa    110160
ttgaaaccgg tacaaaaccg gttgttccgt tgttgacaat ggacggatct tccttcatcc    110220
cgccgccatt cccgttccca gaggcgtggc cgcgagtctt cgcggagcaa cagcagcgac    110280
aggagcagcg gtggctcact cctaccgcac ttcctctagt gcaatggccg gcagcacaat    110340
attatcccta ccctgctgac caaccgattc cagctcaagt gccaccgact gtgacggttg    110400
acgcgcaaga cgaagacgga gaggacgacg gagaggacga gtacgaatac ggatacgtcc    110460
tgagcgacga gtggcgagag cggttccagt cgtcggttca attgcagcaa ccacagccaa    110520
agcgcagcaa gggcaaaaag aagaagaaaa caccgctaaa gaagaccaaa tcgcagcggc    110580
agacagtcaa tgcagaagct gttgccgctg ccagtgcgag ccggtccggc cacttgcagc    110640
gcgagattca agcagcaaaa acgcgcgaac tggcccggaa gtggaagcgg cgaggcggca    110700
ccaccgctgc aactactgac ccgcaggctg cagcactgga gacgtcgctg aacatgctgt    110760
tcgacgagtt ctgcgacgcg ttccagccag tcgtgtggcc gcacgatccg ctccaacgat    110820
aagaagtgca ccacctaccg gtagcgttgt cgggcagaaa ttgtgactac ttgctaattg    110880
catcggtaac ccatcattcc tccaggggcg tcctataggt acgaagccta cagagtccaa    110940
aaacgtatcg gatttccgac ttgtcgtacc ctctgacatc cgtgaataac atcgttaaat    111000
gtgaccctct gcaaagtgat catcggtaat ttgagtgtgg attctcactt tttgtcggga    111060
aaaaggggggc aaaaaacata aagaaatttg agctgtacat gcgccacccg gacatctcgc    111120
aatgaacctc gggcagatga agaacgaccc ctccaacggc tcggcgcaga gcatcccgtc    111180
ccttaagcgc acgctgagcg gcggcgcggc cagcaacgtg ggcggccacg gactgggcag    111240
ccacctgggc gtgggcatga acaacatgaa ctccatcccg tccgtgctgc acgcgacgcc    111300
caacacgaac ccgccgcaga tgctgcgtgc cgtgacatcc tcgggtgtgt acaaccgccc    111360
gtcggccaac caggccttcc cgggccgcag cggaggcctc tcggccgtgg gcggcggctc    111420
ctcagccagc accaacgtca ccgccacgac ggccacgcgc agcgtctccc agtcctccac    111480
catgcaggac tggaggatgt acctgaccat tgaggagcgc caggctgtgc gctccaagat    111540
ccgcgacgct tacaccagtc gctgctccac ctacgaagac ctgctgcaag tggtgaggcc    111600
ccggcagaca actagagggg ttgcagtgct gtgttgatgt tctaatgtgg tgttttttgt    111660
tgttgctatt gttgcaggcc tgcgctattg aagaggagct gctacacatt tcggcgccgt    111720
ctcgtctgga ctacttcaag agcggcttcg agttcgagaa ccgcgtgaaa ctcaagaagg    111780
accagttgca gggccaactg gcggccttgg acgccaagcg gcggtcgccc agcgggcaac    111840
agcagcaggg aagctcaagc agtggcaaca gtggcagcaa acaggtagga tcggccaaga    111900
agcagaggaa ttaggacgtc ctagtggcgc cttgcactat tcagcggcgc ttctgcccct    111960
atcaagaggc tcagcggtga cgaccggagg cccgggctac gtgtgggaag cgataagctt    112020
tcgtgtatat cttgagccca gacgaggagc gacagggaac cagacattag gagagcgctc    112080
```

```
cttgctgagc tcctcatcaa tcaagtaatt ttcgggatca gcggtagaag ctccagcaaa   112140
cgagtcaaga caccgaagtg atgtgcatcg tttagtgtat ttggttgctc ttgctgcggt   112200
tgtgcaggtc tacaggtcta gtatttgctc aagaagaaat gcttcaacac ctccaagtgc   112260
agttgtagca tgctactttg ctgtagctct ggggcgaagg cgttgaagtt agctgcttcc   112320
agctctttca ggtacaaaga ggagctcacg agcggcagga acgcacggcg tgactcacgt   112380
ggtagatcat tccggagcga gcgagcttgg tggaggtgct ccattgcacg acaggcgaca   112440
tcaaacacta caggcgccac cttctctccg agcttgggat cctccaccgc agcgaccaga   112500
tcatccacgg tgacgccatg ctgtacaggt acaaccaaca ccacaagcca acgcttagca   112560
taaggattcc gggaaccaaa tccaagccga gatcatcgat ccgtaccttg ttcatgaggt   112620
cctcgggcaa gtaagactgc tgtcgtgagc tgtgaaacgc tgttcctcgc agcagcgtcg   112680
ccaacccgat agccacaccg gcgtgtccgg ctacgcggtc tgccgtgtcg tcgcgaacac   112740
cgagacactc cagcgtgagg tacagcagcg acgaggccgt ctgctccgcg tagacctcca   112800
gctcccgcag actcagcacg tcctcccggt ccagatcctg gtcgcgcgcg tccagcagcc   112860
gctcgaacca cctccgtgtc aagtcgtgtt cctgaatgcc ctggtccagt gcccgcagca   112920
gcgctgtcga ctgctgcggt cgccccgcac ccgccgaggc tgacacttca tacaaattgt   112980
agatacgctc ccgccaccat tgcatgcgga tcttgcccgt gatttggttg ctgtgcgcag   113040
agtccttgat ggtcgcgatc tcagcgttca gcgcgcgctg tacaacgcaa tatcagcctt   113100
tgctccagca atccacccgc aactaatcaa gaccagggac gtacgatggc gaagaaggac   113160
gggcgagtct ttaccggtag cagcagaccg cacagatacc cgtcgtagtc caatttcctg   113220
atgggcattg caatattaga tatttcacat atttgcagcc gttgtagcgc cttttaaagc   113280
catcatctta ccggactgac tcacgaagct ccaggccttc cttgttgtgt tgcccacgcg   113340
ccgcactgaa cgctctgcgc tgcagcagcg tcgccggacg tcgtaaggag ctcgacatca   113400
tacttcagga gaccgcagcg taaccgccgc tcgttttcg gctaccacca ccgaaacgac   113460
cggtttctac cggtatatcg tagccatttc taaatggagg tacaccacac aatcgcattg   113520
atggctacct gtgtgtacac cacataatac gcggcctgcc agtcaattat ggccaatcgc   113580
gtctgctggc caccattggc ccgctgcctg tcattcggcg cgtatcgcta ccgaagacac   113640
cgcctcgctc gcattgccca ccggaaggtg ctgacttcca tctaccagag ccatgagcca   113700
gctgaagaag cgcgcggctg ccgagttttc gggtgacctg aagcgccaca cggcgcacgg   113760
ccagaccaat ggcgaggagg acctggtgtt cgaggacccg ttcggagacg acatggagga   113820
cgaggagatg gtcgagagcg acgaggaggt cgtggacggt gaggctgcca ccgacaagga   113880
cgtagatatg gacggcgatg agcaggctgg tacgcaagtg aagaaggtgt tcatgccggg   113940
cgtggacaag ctggaggacg acgaggtgct ggactacgac agcagcgcct acgacatgta   114000
ctacgccatg acagccgagt ggccctcgct cagcatcgac gtggtgcgcg caacctcgg   114060 agctgtgcgt tcgcgtttcc cgatgactgt gttcatggtg gcgggcacgc aagcgaccaa   114120
cccggacgac aaccagatca cggttatgaa aatgtcggag ctgcacaaga ctaagcacca   114180
caatgattcg gactcagagg atgaagagtc ggaggatgag gatgagacgg agggcgaccc   114240
ggtgctcgag tcgcgttcca tcccgcaccc gggcggtgtc aaccgcattc gctgcatgcc   114300
gcagtcgtct aacatcgtgg ccacctggtc cgaccgcaag aaggtgcatc tctgggacat   114360
tgccaagcag ctcgagtcgc tggacggcaa ggccggcgcc ccactgccgg ccaagcaggc   114420
```

```
ccccgtgtac acgttctcgg gacacgcaga cgaaggtttt gccatggact ggtctccggt   114480
gcaagctggc agtcttgtga cgggcgattg cagcaagttt atctacgttt gggccaactc   114540
ggagggcgcg tggagcgtgg acaaggtgcc cttcacgggc acaagagct cagtggagga    114600
cctgcagtgg agcccaccg aggcgtccgt gttcgcttcg tgctcgtctg accgcactgt    114660
gcgcatttgg gacacccggc ggaaggcggg cagcatgctg gacgttgctg cccacgacga   114720
cgatgtgaac gtgatctcgt ggaaccgcaa cgtcgcctac ctgctggcgt ccggctcgga   114780
cgatggctcg ttcaagattt gggacctgcg caactttaag gcggacaacc cggtggcgca   114840
cttccggtac cacacggcgc cggtcacgtc gatcgagtgg cacccgaccg acgagtctgt   114900
gcttgcagtg tcaggcgccg acaaccagat ctcagtctgg gatatgtccg tcgaagagga   114960
cgccgaggcc gccgtgcccg tccagggaga gagcggcgag gcgaaggtgg acctgccgcc   115020
gcagctgctg ttcatccacc agggccagac cgacatcaag gagctgcact tccatccgca   115080
gtgcccaggt gtgctcatga gcacggctgg cgacggcttc aacgtcttca agcccgctaa   115140
tatttcgtaa taagacctgc tatcgtttgt gtcaagccca atacagtaga cttttcaaac   115200
gtcgagttgt aattgtgtat tgtacaccac ccgtagcttt atttcttcga agggcggacc   115260
acaacgttcc caggcgacta acgaatcggc cgcaacgcta atcgttccgt acacgatact   115320
caggccactc gtctgcagca tgacaccgct cacagtttcc agagcgtcgt gccttctctt   115380
cctgctctct ctggtcgccg tccaagcaga gcctctggcc atatacggct acggggcta   115440
cggtggggac cacatgcgcc accagggtat ggagtactac gccccggcag accgcggctg   115500
tgccatgtgc cgcaacggag agaactgctc cgtggctgtg cacaaccaat cggccggcgt   115560
gttctgtggc gacgtcttgt ccacctttca gccgtgttgc tgcgccttcc gcaacgagtg   115620
catgaccacc atcttctcgg acgagtgcga gtgcttcgac ggcgcacgcg aggagcagat   115680
catgaccacg aggttctacc tgttcgtggg tctgtccgtg atagcgtggg ctctactggc   115740
ctacgacaag atgtgcgcag gccgtacaa ggtgatgaac agcaatagca atcaccagct    115800
actggccagt tcgccgtctg cggcccgggc gagaggagaa acagtgttg tggacacggt    115860
ggacagtgac tcggaggatg aggaaacagc aaggggccag gatgctgcta ctggttcagc   115920
tactgctgca gtcgcgactg tgagtgttga agttgcagag gatgaagctg acgttgacga   115980
tgatacagcc ccgttgcgtc cagagtcatc ttcaccgagt gttgacgttg aagctgtgat   116040
cgacgagccg cagacccaca gcggaaggca agagcaagat ggttcttcga ttcaaaccgt   116100
ctagttggta tctgtctcgg atgttgctgg ggatttact ggtgggaagg tgaggggt     116160
attgtgaaat gtagtttgat attatggtac acacgatact ctgaggacga cgaggacgga   116220
gaacttcact ctaacgagat ttcttgaagc tctgccagag attccggcag actagtacta   116280
acttcttgca cagcatcaac aggaacagtg acaactacga cttcctctgg caacggttcc   116340
ttctgttcgt cggccacagg aatatctgcg acctcggctt ctgggacatt ggcgaaagtg   116400
aacgcaggcg acgaggttgg tgctggagac tgcaacacca gcagcggtag attgtcgtca   116460
gcgtctgtat ccacttcaga gtctcgccgc cgcttgccga accgttggcg gaaccgaagc   116520
atcttcatgt cgacggcctc gccgtacgcc accattcggt tccgtcggaa gtcgctgaaa   116580
cactccaccc agtggtccac gtacgcggcg aacacaaaga gcgcaagata cgccgacaaa   116640
tggatcagaa tctctgtggt cacggacatt tggctgtcct tcagatgggc ctcggaagct   116700
gcgaagctgt cttgcacctg ctggacttct gtttcgttcg ctgcttcggt gactgaaagc   116760
ctctcgtggc gttgggcttc tagttgcgcg gaccacgccc cgccgcactc gcatgtaagc   116820
```

```
gacttgctgg ttacacggca ctcggtgtag tacggacagc agcacggctg cgtgttagct   116880
tcggcatgca gatctccgca aaatactccg gacgctgaat cgttcgtggc cacggagcag   116940
ttcccgctgt cccgacacag cgagcagccc gcagcgacgc taccaacgct ggaagaaacc   117000
acgcgtacgg ggctgagtgg cactgcgttc tgtccctgtg cggacacctt cgcggcgacg   117060
tgaggtacac tacagactgc gccgagcaac agcaacgcga cggagcgcct cagcaatgac   117120
tccatggcga ggtgcaattg tagaatgcaa cgtggacacg gacacgccgc aattcgtcag   117180
gatctcctag gatggggtca aatatcaacg ctcggcaaag gcgccgtgtg taccggcgtg   117240
cgtttccacg agtgccatcg tgcacgattg ccaggtgggc aaccgcactg cactgtattg   117300
cccgtctaca catggtgcca ctgtccgcga tttcacccaa tgcgcgtcgg gcaaatgtag   117360
tcggtgcaaa tactgaacat gggtcaaggt gagtgtcagg ttgacactgt caaccaccgg   117420
gacactaatt ttgctcctgg cgatgattgc caaggctcat cggccgacct gcatatggag   117480
ctacagtaca tgtacaattt tgatggccat accagtgcat acattgcaaa ctcacgcgaa   117540
ggagttatgg cgctttaatc cttcagtgat acacactttg cgatcaccgc aaaactgtta   117600
gcaacgcagg caacaaggcc gctgaagtga acccgatcg cgacgcagca gacgaagatg   117660
tcaactctgc catcatggct atcatgacag ttccaatgcc agcactcaat gtcagacgac   117720
gggctcctat ccgccagcaa tgccatcttg tatacatgta tacacaatta tacatcgaat   117780
cagtcgtgta tacactccat tccccattca ccttgacgat ggcgtcgaca gctcggcagg   117840
tgacgctgtt actgctcctg acggcgcagg tgggtgtaca acccgtgctc atgggctggt   117900
acgcaagcga ggcgcgcgac gtgcgtctgc gcgtggggt tgtggagttc cttaagctgc   117960
tgctggcgct ggtgccgttg agcctcacgc gtggcgaggg cgggctgctg aaccagctca   118020
agacgtggaa gctgcgcgcc gccatggcca cgacggtgct cccggcgctc atctacgtgc   118080
tgcagaacct gctgaaccat gcagcggtcg tggcgctgga cggcgtcacg ttcaacgtgc   118140
tgaaccagac caagatcatc tggacggctc tgctcgtgta cctgctgctg ggcacgcgcc   118200
agtctccgct gcaggtcgtg tctctggccc ttctttgtgt ggctgcggtg ctcatgacgt   118260
cgtcgtcgga cgcagagcca acaagtgcag agtcgacaga cgccgtagcc ttcacaggca   118320
tgtaccaagc actactgggc gcggtgctct cagcgctggc tgggagtatc atccagagag   118380
ccttgcaacg cgaaaaccgt aatcagtata tggtgacggt ggagctcagt gtgctggcg   118440 agatgacgct cctggctctg gcaattgtgc agggcggact gaaggctgcg acggcggacg   118500
cagactcgca ggacagcatg tgggagggct ggagtttgct cacactggcg gctctgttgt   118560
gtcaagcact gggaggagtt ctggtgggtt ttgtgatccg agactgcggc aatgtggaga   118620
agagcttcgc tgtcgtggga ggaatgggcc ttacggctct gttggagact cacttcaacg   118680 gaaaacccttt cggtcacaac gcgctgctgg ctatggcgct cgtggctatt agtacggcgt   118740
tgtacactct caacccacct gcagttgtgt catctgacga gaaaccactc gcatcgctta   118800
tgccagctga agttggcgtt gctcctgtgc cagtggttgg gccttcatcg aacgtgcggc   118860
attcgaagaa gaagatgagc gctgacacga gggagctgga gccgttcctg gtgcctccaa   118920
cggttgtcac agtcagtagc aatagtgtac atacaagcag cacttctcga caggacatgc   118980
ggcggtctgt aaggcagttg cagtctgcag agatgccaag tactcaacgg gtagtggagg   119040
cgatcgtgtg agcgactacc acttcgatgt accaacaaaa tttactctat atctcaaatc   119100
gatgagatcc cgtcgagttc tgctctgcgt ttgcggtaat gtcttagctg agctgaacgg   119160
```

```
cacgctgcag tgactgcgct aaagcggcac tagaaaattt gtcaagctca tcggtcttcc   119220
ataatgcccc aacgtggccg tctgggcgca cgagagcagc agccttggtc tccgtaaagc   119280
tagtccatgc cttgttgttg gccttatcgc tgtcgtcttt gacaacattc catgagagca   119340
cggagctgaa ggtcgccgat ttctgggcct cagcgatagc agcatcaacc atcgcagaac   119400
caccatcaga acccgatcgc agcacaacca gggatacatg tctcgacact gtcggtgaag   119460
cagacgctga acatgaactg atcacacgcg cagcatcgcg tccggtgacg accagaacga   119520
actgcacgct gccggcattc tccataggct tttcacgttg aacagcaaga cgcatcatat   119580
cgtgagtgga caccttcgca gcacatggac tctcgctagt gcaccaaaag tgcggaaagc   119640
gctcgccaac gcggtaagtc ggagaaaaga tgatgctgtc tccatctcca acctcggtgc   119700
ggaattccac ggactggtcc aacgctgggt cttgcatgag cttcttggcg cgagacgccc   119760
acgaaggtgc gtcgtacgaa aaaccgatat caaagtggta aacatcatg ccgagcgttt    119820 tacggcgtgt cacgatatct tgtacgttgg cacgcatacg attgcccaag gcgctgcctg   119880
caccacctgc atcctcagcc tcatcaagca gtccaagagg caatttaccg acacgcatga   119940
tccgctgcgc aatttcacgc tgcgcgcgca gcgggagcaa ctgcatcggt gccgagttga   120000
tcattttcgc gagtgtctgg gcgttgtcgt gggacacatt gagcgcacgc ggaattttca   120060
tggttcgagc aacattgctc agactgaact gcgtgtttgt cttcgcaata agctggcgct   120120
cacggccgta cgaacgcaac aatgcttgag tgtcgacgtc gttgtcagta gcttggcttt   120180
cagcatccat ctgaatcgca agtgcgagct tccaggccag gttgtgcgtg tcctgcagtc   120240
ccgtattcat gccaaatcct cctgccgggg gaaactggtg cgcggcatcg cccacaagga   120300
acactcgttc cttgccggag tcatagtgtt tggccacacg cgcccccatt ttccattggc   120360
cagctgacaa gatattgatg tcgtcgtcgt tgactttaac gtcgttaggc aggatgtggc   120420
ggacaatttc cgtgcactgg gcaaccgaga atcccaggg gatcgactct tgaggaggaa    120480
agaagggaat ctggaagacc cattcgccct tattcaggtc gtgagcgatc agaatgccaa   120540
caacctcctt attgaactac ggacacgcaa atagcagcgt tgggttagct acagtcatat   120600
gtgtcatgtc gggggaagaa attgcgctta ccacgaagta caacatagca gggttctcgc   120660
gcgccgcctc cgacaacgcc ttgctggtga agtgcacgtt cgcgatactc tgcaggttac   120720
tcgttccagc catgtcaata ccgcagagac tgcgcaccag actgtgcgca ccatcggctc   120780
caataacgta gtcataggac gcttgctcga ccgtgttagt atccctgata aacactcaaa   120840
cgcaaacggc gcaacctgcc atcagtccat gccccgaggc aaactccac actcaacccc     120900 actacaactc acaaatggcg cagtgtgact tctggctgtt gcattgcaga accttccgac   120960
tgcaacttca ggccctccag ctcaactcct cgctcgacac gcaggtcgtt ttcagtcagg   121020
aactcgtcca acagcgtctc gaaacgattc tgagggaagt gcagaaactg cgtcggcgac   121080
aacgccgcca atgacttcct aagactgtca ccattagctg ccgcctgctc aatcgtatca   121140
cgcgggatgc ctgcacaaac agcgaacgtc agtctcacgt cgatggcagt tgccagttgc   121200
aatcatttca cctacaagga ccaaactggt cgatacgcgc gatctcccga gccttgccca   121260
cccccgtgca gtaaacgtag tcacgccact gcaacaaatg catccaaaac tgagccgtca   121320
ctcattgaca catgctccac ttgcagatac tactcacgag cacgctgggc gccgcctgag   121380
cgagcagccg gtcgtggaac tccggcatcg tagcgtatag cacctccatc gtgcgaaggt   121440
tgatgaaatg cgcctgcggg tgcgacgtag ggctgcgctg acgctccacc acgcgagtag   121500
ggacgttata gagcttctca agcatgaaag cggtggccag ccccacggga ccgccgccca   121560
```

```
ccaccagaac gcgcggcttc tgtgcctgca acaattgcga cgccagcgtc atgaatcaag   121620
aagcgctgca agccacgagt agcggggaat gcagacagcg caatgctacg gcgcgttgat   121680
acgcgccgtt cacatggcac acttgccctc tcgaatagag gtccttcgtg tggaccacgt   121740
tggatgagac tcgttaaagt acgaagatag ttttttgcgg agtgattgtc acttcaacgt   121800
catggacctg ttccccgctc taccgctgcc ttctacggga gatgaagcga acaagcggtt   121860
gttgcaggtg atgagagcat ttgaggacca cttcggacgg ctgccgacgg gcgttacgcg   121920
cgctcctgga cgcgtgaacc tcatcggaga gcacgtggac tacgaaggct acgcggtgct   121980
tcccatggcc attgagcaga gtgtctacgt ggctttcgac gtcgtccaaa cggaagaaag   122040
cagtgccaat agtgcagggg tgaggacgtt aagtgtggca aacgctaagt catcatacaa   122100
aagcatttcg ttttctatgg aggagaaaga gcaggaaaac atgcagacac tggagaaaga   122160
gggagcggcc tgggccaagt acgtgctgtg tggggtgctg ggggttcaag atgagcgccc   122220
ggggctgttt ggcggggagc ggagggagct gcagatgctg gtggacggag acatccctgt   122280
tggttgtggt ctctcaagct ctagtgcgtt ggttgtagca tccgcgttgg cgacgagcag   122340
cgcgttgcag acaacaggga taacaccttt cagcagaatg gagatggcag agctctgccg   122400
acgagcggaa catcgtgtgg gcactatggg gggcgggatg gaccaagcgg tggcgtgcct   122460
ggcgcaacgt ggtgtcgcct tgcacctcga tttctcgagc gttcctgcag ccagcgatct   122520
cgtgagtgta ccagatgatg cagctggggt gaccttcgtt gttgcgaaca gtctagtggt   122580
ggcagaaaaa gcagttgatg cagccactcg ctttaacaag cgggtcgtgg aatgcgcgct   122640
tgctgcaaaa atgatagcaa aacgggctgg tatcgagaag tggaaaagcg tacgtctttg   122700
tgtatcctgc gtagatattc gggcgctaat gatgtggacg tttggtgaac agattaatcg   122760
cctcgttgat gtccagctag cattgaacaa tgctcgcggt gaaagcatta gctatactga   122820
gttgcaggag ttggcttcga ctgcttgctc tctgagagag tacaatgttc atgagctcga   122880
agacgaattc ggtgtaccag tcattgaact ttttcagcagt tcttcacttg aggcagctag   122940
caaggtttgg atgtggatgt gcgtacttct tctctgatgg tatcactcac tctgtaacgt   123000
gacacaggaa gttctcatca cagcgacacc acttaaactg cagcagcgag ctctccacgt   123060
ctggagtgaa gccaaacgtg tggaggagtt ccgagaaatc tgtgtctcac tcgcgaataa   123120
tgtgcagcag tcgtcagatc agtcgccttt cacgcagaag caagttgtac aactcggaga   123180
ggtcatgaat gcaagtcaca acagttgcaa gacgttgtac gagtgcagtt gcccggagct   123240
agacgctctg gttgatgctg ctatatctgc tggtgctttg ggagcacgtc ttactggtgc   123300
tggatggggt ggttgcattg tgacgctcgt caaaaaggat gaggtatcca acttcatgaa   123360
aagaatccgc tccagttact accatgatcg aggaagagca gcaacaaaca ctttggacgc   123420
aatgtttgag tccgctccgg cacctggagc ggagattttc tcgccacagc tattgtagtt   123480
tgtactgtca gtaattgttt gattattctc acggagttag caacgagcgg agtttctcta   123540
aatacacatc ctttgcctgt acttcgacct caataagcgc aagctatcac acagaaatgt   123600
aaaaaagtcg gttagtcaac gaaataacaa ctgtaataat gttgtacggc cgcacctcag   123660
ccttacgctg ggctttctct gctggtgtca ttgaaaactg aagaaatgcg aaatcacgtt   123720
tcagattgga caaggtttcc cgtcgctgcg ctatctcctg ctcgtactgc tcaatctctt   123780
tccgcatctg gagcaggtta atacccatta ttgtatcagt tattagggaa aacgtacgtg   123840
agcaataaac gcgtacctca acgttggcag caaagcgatc gagatctaat atgaccctga   123900
```

```
aatacgtatc actcctctgc agtagggtag caacaataca gtaaggtcaa aacgagaagc 123960
agaccgcaag cagcacagag cgactcacat gtatcttctc aaaggccttt ttgacagcag 124020
gtcgtgtctg aacccagcat gaagaaacaa gcgcggcatt cttgcacgga atcacgccaa 124080
tctcgacaac atcctgcatt gcacagtaac tgtgagtact gcctacgaaa gatatcttgt 124140
gtttggccga agcgcacctt tggccgaaga aacagtactt gctgatcaat cagattcaag 124200
aatttctgct cgccttcctc gcgatggtta aatggcagca gcgcctctac agggtcgacg 124260
cagttaagtg gtgtcttgtc tttctggttc agtagctgtt gtggcgatcc aatcagagca 124320
ttaccgcctg ttactgggct cacatcagcc agcgtttcaa ggcatttcca cgtttccaac 124380
gcgttgaaaa cttgtgcaac atcggtagga ttcgatgccc tactggagac ttccatcgat 124440
aagtctggat gattgcttgc agcggattta gcaaggggct gcagacttcc gtctaagtgc 124500
aatacttcaa gcagtccaac ctcggtatct tgcacaaagg tattgcacac ttcttgaata 124560
acggcgaatc gctctccgtg agacgccacg tcattcagat tactgtccat tagtcggcga 124620
caaatctcgt cgatatcgct ccaccaattc cccacagttt ccaaaattac tccaacttct 124680
gctgcacgct tgctgttttg cgcggggtct gcatcatctt ggctgtccga aagcttgctg 124740
cgcgtttgct ctggctcaga taacagcttc aggccgtgca gctcctggaa atcaacaacc 124800
gatcataaca aggaaaaata atcattgtca acttcagctt agtcgaagca agcagggtca 124860 acacatacctg atatctcacg tagttttttcc tcagccgagg tcaaatctac tagtccattt 124920
gcagggcgca gcataatagc aacaaagtcc tgggcgacgt cggaattcgt agcatcgagc 124980
ccactctgat ggcgtgcttc tagccactgc actttggatg tgtcactgt tgaggtggtt 125040 agcagaacca cgtgagccaa cccctcactc gagagttgat gcgtccaatg gagccatctc 125100
tcagcgtctt gatcgctgag tgtgtcaaaa tcccgatgca agaagacggg aagcgtagtt 125160
acttgagctt gatgactatc caaacttgtc ggtgcatctg tttggctctc ttcatcagtc 125220
ttctcactgt gctgttcgtt gtactgaagg tcacgaagcg catctagcaa tgcgtccatc 125280
atcgattcct ctgctgaaac tttcaatccg acgcgcgggt caaaattctc gggtacttct 125340
ccatgcagcg ccttcttcag ttccgaatac cactttgcaa tcgtatgtac tgcaatctcc 125400
agcgtcaaag ttggtgcagt gagtcgctcc aaagtttcgt gtgttggttc ttcgtaggac 125460
ccaagaacct ttgcgccgcc aagaaggctg ctcacacaaa caccaacacc aattcgtgag 125520
tgacacagtc caccaattct gaacagtgac tagccaaacc acgtacgtgt tcgtaacaaa 125580
cgccggattg tcaccggcag aaattgcacg caaatacggg aatttgggcg gcgcactgcc 125640
cagccaggcg gatgcaccgg tcatttttggg cggtttagcc gtcgattccg agatgtttgc 125700 ctcatttttcg gaagatctac gccacctcag gagatgctgc tttgcgtaca cgaccttgtt 125760
gctgtcgtcg tattgttgcg ctgcttcacc gattgctaaa gctgctaggg gcgtcagcac 125820
cgccacagtc acgccgatag atcgagcctt gcgcagcatt ttgccgtgtc aattttgtat 125880
tagatgtagc aggtgatgaa gggcctgttg agggagcgat ataaagggt atatgtgata 125940 gaaggttttg ggatgggtgg accgcactgc accgctttgg attgcatgct gctgacagtt 126000
cagttctcat tttgcattcg ttcgcagcaa ttgctctctc agctgttgtc agtgcttttag 126060 aagtagtgtg catttatcat cggagtggcg tgtgatgtct ttcatgctgg ggaggtttcg 126120
gcctgcccag agtgaattcc tcgtttctga cgaatccgct gaacaagcgg cctcaatgag 126180
accaacctaa gactaaacga ctgatgctct ccatcaaatt cattcgtcg tgcagtcaaa 126240 tgcaatgcag tctctctaag aagtgcctcc agaaagaaag ttgtggatgc tggatagaac 126300
```

```
aatcagctcg accacgtcat gcttaattaa gcgagcacca cgataagacc aagtggtttg  126360
gaagctgaat actttagctt tgctacgtac agtacctact tgtacgaggt cttctccaac  126420
acctccgtaa tgtcgagttg ctctgcgcga tttactcgct accactctcg cttgtggcta  126480
ataaatacca gcggattcgc ccgcttatca ctcgcagctt gcagttctcc tagtactgga  126540
agtggcgtat cttgccattg gcgcctaacg cgaactcatc gccatctccg cttggtcggg  126600
gatcttcact tggtcgaact tcttcacgcc tgccatttgt cttgtttgcc tgacggaacg  126660
gcggcagcat cgaggaactg ctctctgagg ggcttcggtc gtaggtcgtg gacatgtccg  126720
acggactgcc ctcatccatc tcgaagtcat actcatccag cgacgaaagt cgtcctccaa  126780
ccaggccccc accacggcgg ctgccactag gcaagcctac gatcggtaaa ttcgacgaat  126840
caacgtttgc tgggatcaac tccactgcgg cactgcctcg agcgctcagc atgctgatgg  126900
tgtccgtggt acctgcatac ggggatgcga acttgtagaa ttgctcgttg tcctggtgat  126960
catggtattc ctcgctcatc ccgctgctgg tgctgctacg agcggaaaac cgacctcgga  127020
agaagttcgt aatgcgctga cccaggatag agctcggccg atgctccaga tccgaagtac  127080
cgtcaccatt tcgcagcgaa gagaagatgc tgttcgtgta ctcggaacct gacactgacg  127140
ccatcgtggt aaaatcgttc gagttcttcg acatgttgtc cagaattgtt tcgagtattt  127200
ccgcagccag aggcgctgac gggcggactg aagggttctg cgcccagcac tcctcgataa  127260
gctgagcgaa gcgcagaggg caacgttgtc cagggttaat cggtggtcgt tgctccacaa  127320
gcaccttctc gcggacctcg aagtcaaact tagtgtcgct aaaggggacc gcgccatccg  127380
aagcaatttc ccacaaaacc ataccaaacg agtacatgtc cgttccacga ctgtatcggc  127440
agttgtgcgg gtcctgcaaa atctcggggg cgttccatcg ccaggtgcca gcaaacgaag  127500
tgagttcatc cgacacgcta gggttttgct gctcagccaa gctgacagta cgctcgctgt  127560
atcgcacacg gttgacgaaa ttcgatacct tggaaatacc gaagtctgca agttttgctt  127620
gccatgtttc agtgactaaa atgttggaag ccttgagatc gcgatggatg taagtcgggt  127680
tgcgcgcatg caagtaagtt agacccttcg aaatatgaag cgccaacgcc actttgcgcc  127740
gccaactcag tgggaaatgg cgcttgagca cgtccttgag actaccccgt gagcagtact  127800
cggtcaaaat gcccagctta ccctcgaagt atccggcacg catgaacagc gtgatgttcg  127860
gatgccgcag tcgtgagcaa agtcttgcct cctcgatgaa agcttcttct gagttctgaa  127920
taatagtgcg gtacaactcc gcatccgcga catcgcctgc gcctccgttg ggaagcttga  127980
tgaccttcat tgccacttca atccccagcc actgagcttt gtatacactg cccgctgctc  128040
cttcagcgag gaaggccaaa tttgtaagtc cattcagctc ctctagagtc accatctcgt  128100
tgccaacata cgtgctcttc atcgactctt ttccagtgtt gctactggct ccactgcttc  128160
caaaaacggt tcggtacgac gaggctaaaa cgttggcaac gccgttgttg ctgctgccgg  128220
ccaggagacc cgtccccatt cgatctcgct gccgttcgcc atggcgtgag ctgttgctgc  128280
ttgattgcaa catcgtctgg ttgttacgca gatcgttttc gtcctgagga aatctcgctt  128340
ctcctaaatg cctccagccg aacacgatag cgttgaacag cggtacgctg aacagcaaac  128400
aatctgccac ttcgtatgtg gagtagctca ccacatcatg acctagaacg tagcacagca  128460
tcattggaaa ctgcagcacc tgaaccacga ggaagtagtg cataagcttc tcatgagcca  128520
gtcgcagcgc caattgagcc tgaatctccc acgttttcgt agacgccagc gctgcatggt  128580
ccgcgctgtt tccaagtgac ggctctgtca tggctgtagc attgggggcc agatcgcccg  128640
```

```
ctctgctcaa ccgacgtcgc tggatcaaca gcactgcgtt ggcagcaatc acgcagcctg    128700
ccgacagcgc gtacactgcc acaaacaagt agcgcaggca gttggtgagt actatcgtgg    128760
acttactatc tgtgatgacc gcctgagttc tcgccgtcga tagcagtccg cttgcgagtc    128820
ccaccgtcca gataatcaac caacttgctc gcactgggaa gcgtctcatg ggaggactgg    128880
tcccttggtg tccccttgcc cagcgatgtg tgcgcaggac gaaaattgca agcacgacac    128940
cccacagcag cgagaccatg aagctcacgt ggaagacgga ggcgacgctg cgcgccaatga   129000
ctgtcgcac tttgacgcct ggccccatga ccatgtccat ggactggctc acggcgcccg     129060
tgacggagaa caaccagtcg gtcatgacca ccgaatagaa gagcgcaggt cccgtcgcgt    129120
ggggcggcgg cagcggcggc ttcctgctgc gactgcgtcc ccgtctcctc ctggagctat    129180
agcctgggtc cggtatcctc cggaagagaa ccaccgccac gacggacgag atcacggccg    129240
cggtggagat gatgacgagc cgcgccgtct ccagcgcgtc ctcggtcgcc gtcatttaca    129300
gtctgcgcgg gcactggtgt cttctcgtta gcgcagactt gatatacagg gactccgtgt    129360
tgcgctgcga atgaacctgc cgccgcccag tgcaggaaga agcatcgcca gctggtccca    129420
ttgctccgcc tctactcttt gaccgggtct cttccgctag gagcatgctg cagtgtggga    129480
ttacctaaca tacagcatgt gctgacttct tgacccgcgt gacccatctc cctttttggac   129540
caattgtgac taaacgacac aaattttgtg tcggagtgta cttcacgccg tttgattaga    129600
tgctcttcaa ctcagcatct tgtatggctg gagctcgtca ttctccaagt cgctgagcca    129660
agatcaagac tatggacgcc gtcgcgtggg gcccgtacat cgagacgctg cgctcaggcg    129720
cgcagagcgt ggaccaggtg gtggagaagc tctgccggga caacggattg agcgccgacg    129780
ccgcctcctc gtcacagacg acggcgcaaa ttgtgacact cgtgctgcag gcgctggccc    129840
aacaggctgc cggtcactac gtggcgccgt cgctggagca gcagcagagg gaagactccg    129900
ctgtcgcctt tgaccatcac cagcaacgct gcgccgccgt cacgcgtgtc gtggaggcgg    129960
ccgtgagcca gaagctgctg cacgacgaga gcccgctgat caacctcttc agctgggacg    130020
ccttccagaa gcgcctcgcc aacctgcacg ccgccttccc cgagccagag ttcaaccacg    130080
cgctggcagt taaaacgaat cccacgcgcg gcttgctgcg aggcgctcgg gccaaggggt    130140
tcggcgcaga gtgcgcgtct attgcggagg ccaaacacgc gctatcgctc gggtttgaac    130200
cgcgtaaagt cgtatatgac tcgccgtgca agacactggg cgagctgcgc gagatgctgc    130260
tggctggagt gtacattaac ctggacaacg aggaggagat ccgcaaggtg aacgagatct    130320
tcgcggagtt gggactctcg gaggaaacga aaaggaagca cgcggcgcag atcggactgc    130380
ggattaaccc cgtggtgggc ggcggaacaa ttgacgctac tagcacggcg acggtcacga    130440
gtaagtttgg cctcccactc acggcggaga cgaaacccg  actttttgcg atcttcaagc   130500
agaattcgtg gctgcagggc gtgcacgtgc acgtcggttc tcagggctgt cctcttgacc    130560
tactggcggc aggagccaag aaaagcagtgg cgtttgcact tgaggttaac gctcatgttg   130620
gtaacaagca ggtttccgtg ctggacatcg gtggtggcat gcctaccgtg tacgacggtg    130680
gagagcgtga ggcatacgat ttccaagaat acgctgatgc agtgcgcgaa caagtgcccg    130740
agctctttac gagtgggttc tcgtccatta tcacagagtt cggacgcagt atttttgtga    130800
agcctggcat caccgtgtct aaggtggaag ccgtgaagga ttgggcaggc cagcacatcg    130860
cggtgatcca tgtcggagca gaccagtttc cgcgtacagc ctatttgccg gagttgtggt    130920
cacactgtat ctccgttctc gatggccacg gccgccgaa gacgcatcct agcggctcct    130980
acgtccgcca ggacatcgct ggtccgctct gcttttcagg cgacttcctc gccaagcaac    131040
```

```
tacttctgcc tccaattgaa gtcggagatt ttgtggtgat ccatgatagt ggcggctaca   131100
ccatgtcgat gcactccaag tataacagcc gccaagtttc gtcgaacttt gcgtattcga   131160
gctctgccag cgacgtgaat ttttctttgc tgaaggaacg tgagacgact gaggagacac   131220
tagcttgctg gggcctcgac cgtgacgtgg agctgtagct ttacacaggt tagctttccg   131280
tcccaacatt gtgctagctt tgacgagtgc aaggacgggg tttctctatt ttccatgtcg   131340
atttcatgct tattcgtctc ggtagataca cagcgaaatg cggcaatgag ttgcatttca   131400
agccttaagg ttccgcggcg tattccatca gagttgagtg atttaaagac acaactagta   131460
gccgctctcg agcatgctgc gaatatagat cacctggccg aacgcaatac ccacgagcac   131520
gacgttggtg atcatagaca tccacttcac acgcgagttg gtgctctcgg cagctgcaag   131580
taacacaaag cagcacgagt tccctcatca gtgtttcgct acgaacaaga agcaacagca   131640
gcaacagcag tgcccgtacc atcgcgactc agccgttccc ggtgcttgac aaaggaaatg   131700
tcgccacgca aggtgaacac tgactccttg aagaatgcca cctcgtgcat cagttccagt   131760
ccaagatcta aatgatacaa tccacaagtt tgttagtcca agcaatatca atccccaccg   131820
gtcacagcga tggcaaacga accttccacg acgatctgcg ggaagtagtc ctccgcgacg   131880
tggtggatgc cgaaaacaac ggcatcgctg ttctcgtgag catgaatcga gaaggcgacc   131940
gtttccgtct gccgtcgag tttgcgctcg aagatctccg tgatgtcgaa gccaacgtga   132000
ctgccaagct ccgtcacggc attatcaatc acgtgatcgc ggtagccgcc ggtcgcgtag   132060
ccgttcagcg tctcccaagt gacaggatat tgcatgcgct cgggcagcag cgccagagcg   132120
atgtccacct gctgtccgtc cgtaatgctg tccaccgtca gcagcagctt cacgcgcgtg   132180
ttgccgcgga taatgctacg cgagacaccg accaggtcga attccaggat gcccatcttt   132240
gtggcctggc cgttcgtcgt cgtcaccgcc atctgagtgt aggctggtac cgtcgggcg   132300
tccttgctca ccgtggcagc cacattgggc acgagcgtta agctgcgagc gcctgtcgag   132360
atgaagtcga aggaatagaa gagcgtcatg gtggacgacg cgcccttgag cttgcggaag   132420
cacaagtggt agagtccgct ttcgcgcacc gtggccgtgc caaagttgtt ttgctccgcc   132480
ttccacgtga gcacctctcg ctgggatggg ttcctcacct gcattaacgc aacgaagtga   132540
ggaccaacag gccgcggaac cgatgcagta ccacgaaacg taccacgacg tcgacgagat   132600
cgtagctctt gggctccagg actccgaagc ggaagagcac cttgttgtcg gacgcgcggg   132660
cgttcacctc ctccatgaag cattcctgcg caacagagtt agcggtggat tgaggagacc   132720
gtgggttgg gtgggggggcc gaacctccga ccgagacgtc agcgtgaact ggaagcggga   132780
cgcgtgtgaa ctcggcagta ggcacacgca aacagcagt gccagtgaga ggaagctgcg   132840
catagtcgag tgtgtggtgg cgatgtggag caaggagacg tcgctttggc acgatggagg   132900
aggatattgg ctcgcaaaag tgtccgattg ttgcagcaac ataagttggt tggagcaact   132960
ttatgtgggc tcaagtcagc tttctcgatg cgcgatgcag catcgtcgat gcttgcagtg   133020
cggtgaggag aggagaggag tccattcggt ctggcccgga ctaggggggc tcgctgccaa   133080
cgctggagag gattttcatc gtttgtggtt gtcttcgctc gcatttgtaa gttgaatgag   133140
ctcgtctaca aattgcaagc agaggacagc atttgtccgg cgcatgacta cgatattgtc   133200
acgaggagct taccgccgat agtattgcta ttcgcttatc aaaaacgacc acgaaaacgc   133260
ggtaagctgt ctaatgactg gcacttcggg ctttttcatc cgttgcaagc gcattgctga   133320
tagagagtca cggccgattt ggtgagcagc tctgcagtca ttggtattgc cgtctccagc   133380
```

```
tccacacctt ccagcacttc ttccccgtct caggttgcac taacctcggc atcgtcgtgt    133440
tgccaggagt tcgtcgtgtt tgccaatatt cgcttctgaa acagggtgga gaggaacggc    133500
tgcgcgagga gagcgaggcg tgcgtggcga aatgtgctca gagcgatctc gtggtcaaga    133560
ttcagtgggc gatcacgcag cggcagcact tcaagcggta tctgggtgca ggacttttgg    133620
attccgccat gacttatgct ataaatacat gtattatact tcttgctact gtggcggtgg    133680
agctgcaccg agcttgctgg cgttcagcca tcgtgcagcc aagcacacct ggtgacttgc    133740
gcacggcaac ttaccaggct gtggcgctgc gaccggctgc gatcccagca gcatcggtga    133800
ggacgcactc actcgtaggc accgctacgt gtcaatcctt ctcgtcctcg aggtccgatc    133860
gggcgtgcgt gtcctacggg gtgttgaagc ccgcgccgac ttgattcgac gcccaaagcc    133920
agagatttca gacctacccc aggaaatgcc ttaggatagg tcggttcaca cggcgtttgt    133980
ataggtgcgc gtcgacactc gtgaggcccg atcgcaggct gaactgtctt tctcgccgtt    134040
gcggcattgt agcctaccgg catacgtgtc ggccccagtc tctgcaaggc aaagtgtgca    134100
cacgcttcca gtatcctcaa gccctggcgg ttgtcgctca cttcccattt cgccttgcca    134160
tcggttgagc acctcgccta tcaatagtga ggacagaacc ccttcccagt gggagataac    134220
gacgtaaaac ccccgctaca acacacgatg gtcaagttct tcagtccgct ggcgctgtcg    134280
ctcgccgcct ctgccgctgc ggccgccgct ttcgccactc acttgcgctt ccgcccgcag    134340
ccgcccaagc agacccgtc cgagcccgcc acgatggccc cgcgcacggc ccaccagcgc    134400
aacatcgacg agatcaacca cctcgccggc tacgatgtca tcatcgtgtg cacgtccacg    134460
ccgcaccagg cgcgctactg gcaggaccgc ctcatggcca cgcgcggctc catctccccc    134520
aaggatgcca aggtcatcgc cgtgtacgag gactgggacg gcggcgccgg caacggactc    134580
ggcacgctct acgcctacac taaggcggtc gctgccggca aggagctcta cggcatcgac    134640
atctcgtcgc tgctcgcctc gggcagcgtc agcgtcgcac tgtaccacac agccggcaag    134700
ggaacgcgtc tcgcgccgct gcctggcagt gaaaacaaca acaagtctgg cgtcaagctg    134760
ccggccatgg tggaggtgaa tgacaagttc gtccccatga ccatccttga ggctgtggtg    134820
aagcagacgg cgcgtgtacgc ttccagccgc cgtggacgcc tctcggtctt ctggggcgat    134880
caggtgttca tcccgtcggc ggaggtcaag tacgtggcca agcatcacat cgacatccta    134940
gctgcgctgg ccccgatgcc ctcggagaag gagtggaagg agaagggcct tgagaagtac    135000
ggcctgattg tcgtcaacca gcaggacaat gcagcgcagg tggacaaggt cactcacgag    135060
accgcgatcc gtctgttgtc ctccttcggt gagatgaagt cggtcggcac gagtctcggg    135120
tcgttcagcg tggacgccga catgttgcgt gcgctcctga gcgagttctc gaaggaactg    135180
gacgccaagt ccggcaagct tgacagcgac ccgcacttct ggatgccgct cacacttgag    135240
ctcgatgcgt acacggaggt gatggcgcag aagggagtgg agaaggcaga gtccaccacg    135300
cactaccagc gtatgcagaa gatgatggcc aacttcgagg agacccggac gaaggagctt    135360
ggactgtttg gctgtgtcga cgtcggcagc gatgtgtact ggtgggacta cggccagctg    135420
aagctgtacc tgaagaacaa ccgcctggtg accaagccgg gtgtggaggc agattgcctg    135480
cgctcgttcc tcggcatcag caacagcctg cagcacagca acgtcggcgt ggacgcgacc    135540
atcgaggatg ctacggtcct gaacagcgag attggtcacg gcgacattaa gcgcagcgtg    135600
ttgagcggcg tgtgcgcgaa ggaggtgaac gcgcacggtt caatcctcat caacgtgact    135660
gcgcgctcca tcacagcgcc caactgcgtg gtgtacaacg tcacctctga tgaggccgag    135720
ggtctgtgcc ttgaggaggg cagtgtggtc gtgggcgtgc tgctgcccga tggcaagaag    135780
```

```
gtcgtcatgc gctcgagcat ggatgtgtgc ggcggcaagg catggaagac cgtgctggaa   135840
gagaaccagc actctttcga gaagatctat gagctgaacg cggatgcgaa cgtgtcaaag   135900
ctggagcagc tgatccaggc tgagcacttg aagatgcgcg aggtggtcat gtcctaagca   135960
tggcctgagc tagtagtaac gtagataatt ccccccccca cccaccgctc gccggtagaa   136020
actcctaaat gcatttgatt tcttaccctg aacgcacgcg aaccaaagct tcaagccgca   136080
gcagagcttc aattgtggtc aagttccatg ccgtgtagcc accgtgacgc aggcctcgtg   136140
gcagaccttg ttgctgcagt ttgattgcaa atggcgctgc acttgctctt cgctggtcgt   136200
cggagatttt cacaaccccg cgatgccacg tcagaacgct tttattcgga gtggactcgg   136260 agttttgta  ctcgtactta gtccaccctt tgaaccacac cagcgtgaca caagtgacat   136320
tcgtcatcct gataatcgct agtcgaccgc cacacgttcc ggagatgcca gcggacgcga   136380
agcttcagct gctcgtagcg gccctgggcg cgatcgccct gcagcaattc atctctcgcc   136440
gccagcgcca agctgtgcaa atggagaagg tgaagcagca gcagaagcag gtccagagtg   136500
ccgccgcggc cgacgaagac gaggcgtttg tagtggagat cgagtactgc accggatgcc   136560
gctggatgct gcgcgccgcg tggatggcac aggagcttct caccacgttc cagcaggatg   136620
agagcagtcg ccttcgatcc gtgacgctca cgcccaattc gcgccaggga ggtgtgttca   136680
atgtgtacct acgcgaggtt ggccccaacg ccgaccccga agccgagcca gacatgctgt   136740
ggtcgcgtaa gatcgctcgc cgcttcccgg agtccaagga gctcaagcag ctcgtgcgcg   136800
acattgtgtg tccagagaga ggcctcggcc actcggacaa gaagtaataa ggcaggaaat   136860
aggatggaaa ggaatcttct attctctact gaggcgctcg gaatccagcc atgacgcttg   136920
gaagtgatga acgggtcgac cctccgggaa acactgcact aggcctgttt gaacgacacc   136980
atcgtcagcc acgagagaga tcgcagcagc aaatgaatga accaaactca ccgtgcaaaa   137040
agacttcgca tgctcttgcc gatagacgca acacctgcca gactctttgg catgttggag   137100
aacgatgttc gccggccgtc gggatgggtc acgcacttga tagcagatac ttggaattct   137160
cgccatgccc acgggtgcgc cttcagacaa gaccgtacag caaacattag cttggagttg   137220
ctagcgttca tgctaccgaa tgaaatgaaa tcatactcgg atctgttgac tcgtgaaacg   137280
ctgcttggcg tccttgtcga gaatctgcca gcgttagaag tgatgtgaga aatgcatcga   137340
cgaagcttaa acaagaggaa ttacagtcta cgcacgtgtt tcaagagatc gataagctca   137400
ctttccacca cacgatcgcc aacgctgtcc gggtactcaa tggtgtcgtt ctatgcgagg   137460
ttagcccagc aattagtact gtgctgcatt gtaacaacgc tggcagtttt acatacctga   137520
atcctgccgt acaactccgt catcgtttta gcgacaaagg gcggatgtcc atagataaac   137580
atgtacaagg tgactccgca agcccaaata tcaacgggct tcccttgaaa attttctcct   137640
gtcagcatct ccggcgctag agaaagatac atttacttag cacttctgaa aacagtatgc   137700
caacacggtc tacacacgta cccatgaaga tagcagttcc ggcagtttgc ctcatatcct   137760
cattgtcatt tgccatttcc tggatacaac gtcaacggtg aaagttaggc aatattcacg   137820
atggctttcg cacttccgta tcatcttacg tgagaaaccc cgaagtcggc aatcttgagg   137880
ataacctcat tttcgtcgat agttttcagc agcaaattcc ccgttttat atcgcgatga    137940 attatctagc gacagcacat ccgtattaga agtgctgaac gaatgtccac ccttgaggtt   138000
aacaagcgta cctgttctc atgtaggaaa tcaatacctt caatctaaag aggaaggaag   138060
cgattagaag gcaaagttgt tgcgctgtgt tgacgcaaca cggtcttacc aggtgtgtga   138120
```

```
aatacgtctt tgtaagttcc gcgtttagtg gagtacactc tctgagacac aaagtgaaat    138180
gatgtcagtg atggtagcaa tttactgcaa cggtagggcg ataaattcgt acatgtcatc    138240
atccagtacg ggcccaccat ctacaagctc gctgatcatg aagagctctt cgctgtctac    138300
agtcaaattt aaatgagttt caagtctgca agtatcactt tggcgcgcgt gcgtaccgtc    138360
cgtatcgatg acttcacgca gcactacgat atgccggtgt ttgaatcgct tccagatatt    138420
gagctctttc ttgacggatt gcagtgcatt accaaaacgc caacgcgaa ttcgcttgag     138480 agccttctta tctacacact ttgctgcgaa aatctctttt gtgtcgttgc attccacctt    138540
gaagacaata ccgtaagctc ctttgcctag ctggtccatg aacgtgctgt aaaaatgaaa    138600
ccacatcata gatagaaaag taagcacagc gcaatgccca ggaggagcaa gcaaaatcgt    138660
tctcacgtac tactggttca gttgcctccg accgtcagca tctacggtgc taaccattct    138720
cttggtttct cggaaggact ggcctcgctt ccgtagtggt acgattggtt tcattcctgt    138780
caactgttta tcgcctccac tgccttgcat gctcatcgaa gctcgactga gagcgacgat    138840
aggctttaca actaccaaag caggaggatc cggcgatgga cctggttcga cttttcttc    138900 agcaatcgga tctggatcgg gactgagagc gatgataggc tttacaacta ccaaagcagg    138960
agggtccggc gatagacctg gctcgacttt ttcttcagca atcggatctg gatcgggact    139020
gagagcaatg ataggctttc atgacaaccg ggtccggcga tggacctggc tcgactttt    139080 cttcagcaat cggatctgga tcgggactga gagcaatgat aggcttcata ccaaagcagg    139140
agggtccggc gatagacctg gctcgacttt ttcttcagca atcggatctg gatcgggact    139200
gagagcaatg ataggctttc atgacaaccg ggtccggcga tggacctggc tcgactttt    139260 cttcagcaat cggatctgga tcgggactga gagcaatgat aggcttcatg acaccgggt    139320 ccggcgatgg acttggctcg acttttctt cagctactgg gtcggatcg ggactgagag     139380 cgaagatagg ctttaggata accaaaccat gaggcttcgg cgttggacct ggttcaactt    139440
ttccgtcagc tacggggacg ggaccaggaa caacagcact gatagttatt tcgtcgatag    139500
cattattggg tggggatact ggagcttcag ctgcagcctc ggacgatcca gaaaggcctc    139560
ccacctcagt gacgcgttgc agcgggtcta gcctggctgc aggtccatgc ctgttgttgg    139620
gctccaggcc agtcgacgac gcttttcca tcgggaatac gctcaccagc ggtggctgta    139680
tttgataaag ctgggcagct ggcaccagag cagctttgct aaatacaacc actacacaaa    139740
agtgtttcgc gcagacaaag atagcggcat cattcatgta tcacacagga atacttacgt    139800
atatatattt tttgctagaa gtggtggact tttatacaca tggacgccat acacctccgg    139860
cgcccccacc ccacaacaat ccgggttgac tgaagtctag tagtaatcat aatacaggtc    139920
ttggcagtcg agcaacgctt tgacattgtc acgaacgtgt accagccacg agatctgttc    139980
gtcgaggtgg accagcattt cctccagctg cgggatcggc acggagacac gagcgtactc    140040
cacaatctcg acctttggc cacggaaggc gctgcaaaat gacaatgcgt gatagagggt     140100
tagaaaacta aagtcagcaa ttaccaccaa accatggcac cataccagac gcagccgatg    140160
aactctttcc gtgacgcaca gccctccggg atgtttgtga tcggcttctg cgtagccatc    140220
aaactaaagg cttcaaccag ctattgaaaa tatgaacagc gcgcacatgt tagttcaacg    140280
tctccagtac tatggagctt gacgcattca cacaccagtt cgccacggtg aatcgagaaa    140340
tccacaataa cttcggacgg cagtgccggc ttgaagctct gcacaaacca atgacgctgt    140400
tcgtcagtat ctctcacccc ctacaccttc tctgctgaaa accaacgtac gtggtcgacg    140460
tgagagcagt aagggaaccg acgacggctg ggcagccgca ggacgttggc ggcgttgcgc    140520
```

```
agctcctgac agatgcggcc caggctctgg aaagtgcgct gcacgatctc cacgtacacc   140580
tcgacgtcat cattgctggg ctcgtcgtgt atgagctcct gccgctggac gtgcatgaat   140640
tccttgagcg ccgcgagcct ccccacttgg ctctgcacga tgccgtggaa ctcgaggatc   140700
tggttcagca cgcagtactg ctgcagtctg tgggcgtcat gcagacatgg acacctggtt   140760
ataatctgca gaggaagctg catccagtac tactactcgt acgtgctaac gatgggcgca   140820
ttgcgctggg ccttggtcag cttgagctcc accttggtga acaccacgag gtggccctgt   140880
cattaggcga cgcgtatgta acacagcaca tgccaatgcc gtcagtatcc atcctaaatc   140940
agtatgcgtt cgaatctgaa cctacttcca cgcggatgtc ggccttgatc gcgggcgacg   141000
ccgcgccacg gtccgagcgg atgcgtcccc agatgaagtc gatgcgctcc aactcatgcg   141060
ccgcgtagtc gatggccgag ttcacgtctt tgagcaggta gtagcgcgtc tcgcgcttct   141120
gctcggcagg tggcacgaac gtaagcatgt gtactgtact aggttagacg aagtagccct   141180
acccacccat gcgctgagct cgtcgtcggc ttcctggagc gccacgggcg ccgctgcgtg   141240
ctgcgtgagg ctgctggaca tggctgcgat cggactgctc gtgctctgga gtggcggata   141300
gaaggaagaa tggcaggcgt ctgcgctcac tcgcgtgcgc ctcgtgtggt gtcgtccatg   141360
ttgaaccgca cggaaaggac actctgcgga cagccacgat tcagatttga attgtgcgtg   141420
tcgcagacac gctacctttt tgttcactac agcgatatcc ctgtgataca cgatggattc   141480
acttacattt ccaagtcctc ccactctctg aaagcgagta ttgcaggact gtcaccagat   141540
aatctcatga tttggctcag gcttgctgca acgtttcctc gccacaattt tgatcgccgt   141600
ggccaatttc tcccgagcgt gtcacagcca gcaccagctg gcgcgatcga aagcctaact   141660
tgaggccctc gactcgagcg tagcaagtga tggctgtgca tgcgcattgg tatccgccga   141720
aaagttctcg agaagttctc gggccagtcg cacctaaaga tactttttaa gccctctacg   141780
gtatttatat cgcttgaaat ggctacagtt cttgcttcaa catccgagct acgagcagca   141840
tggcgaccac ggaggcggta gcgctggcca tggccatcga ggaaggcaag acgcgcgacc   141900
tgtacaacgc gctgcggacg ggcgagctcg gcgtcaggtg ggcagccgaa aactgaagcg   141960
ttttaatcga ttgacgcgcg tgagacggtc cgttctgatt gttttgctgt tggtgctgtt   142020
gcagcctcga ggcgctgatg caggcgctgt acttcctgca gcacgccgag ttcacgctct   142080
tcgatgtgaa ggacgccttc cgttcctcga ttggtgagaa gtgcagactt tccaccatat   142140
tgccgccttg tcattaacag cgctgatctg acgctgcaca ggggcgagcc aacgcttcct   142200
ggcctaccgc gagttccaaa tcgcgctagg aaagatcgcc cgtgtcaagt attacggcaa   142260
ttgcggcggg gctgacgagt cggttgggac ttcttgggat ggaggagctc cctcgccaaa   142320
gcagcgccca cgacctacgg agctgggggct catgtgctcg cttgtggatc agctgaacag   142380
ccatcgccac cagcttgaca cgttacggag ccacatgacc cgtcccagta ctcttgacac   142440
gctcgagcac aatttgccat tgcttgtcca gagcttccag ctctacggca cgcagaaccg   142500
cctctcaacg aacaccgcgc tatcaatgct ggcaaccata acgctggacg ggttcgtcga   142560
ctttctcaat gcgtacttcg agtatgagga gttcttctcg ttcatcgatc ttgcacgtgt   142620
gagtatcagc cacacaacca ggttgtttgg cgaggttact gatattcgct cttgttcgtg   142680
gatctgttgc agatgtcaac cgaagtgctt tctggcttca ctagcgctag cgctagcgca   142740
ggtgcaaaag ccgactcaaa agatagcaag gaccagctcc tcaaggggga gctgaacttt   142800
gcgcagtttc tggagttgtt ttgccgtgtg gcatctgcgt ttcaccacaa gctgctagta   142860
```

```
aaagagggtg cgcagcttcg acgggctgtg gagtcttgcc gtcttgagtt cagccttgag    142920
gtgctgttgg atcacatgca tatcacgctt atttcgaatg gtggctcgag atcgacaagt    142980
gcctctactc cgcaacagca agaggtttcg accatcacct ccagtatgaa agctctcacg    143040
acagaatcac cccagtcctc tcgtggtgat gaacttccag cgctgattgc aatcgttcag    143100
aatattcgag atgtgcttcg gctcgatgct gctgaccatg ctatatctaa gaagcctaaa    143160
tatcgtgtga agcgcgaggg tagcttggta atgcaaggtc agctgtccag aaggcctagt    143220
agcaaccccc ccgagcagga attgtcaggt agaagccccc caagtgtgca ttcgaccaga    143280
acgcaacgcc aggcaaaagt agaggaaagc ccgaggccgc ttccgcaggt ggctatgata    143340
cgagaagttg tgatgccacc agcacttcct gcagacgtga tccagcagct cgaaagtgcc    143400
ctaaaattcc agaacttggg ccagtacaac gtatgttgct caactattta tcggatatct    143460
attgtaccgg tgacgctagt tttacttacg tacattgtgt atgcaacgca gatggctctg    143520
agtgctctgg attcctgtga gcaacgctat caaaagcaaa tcttgcagcc catcgacgat    143580
gttagcggca tactcgaccc gattcaaacc gaagtccatc tcttttttgc tctccaagcc    143640
gcaagcatac acgatagcgc ccaccgcgac tcacacgctc tgataaaata ctatgaggca    143700
atgaagttgt cgcgccaact tccagcatcg catccaggtc gattgctcgt caaaagctgc    143760
ctgggtgtca ctctatttta cgctggagag ctaccgctag cacaacagtg ccaccaactc    143820
gttttggatg cacgaaaagc tacaaaggtc agtggagctg atgcccgcca ccttccagac    143880
aaaagagcag cgtccaagac tgataacaac tcgaaccgtg ttctcgtcga cactgcttcg    143940
gcaatgaaca acctcgcctg ctgcttatcc caagaccaga gtgattcggc ctcgaaatct    144000
tcggacagcg cgtatctttt gttcaaacac gctcggcagg tctacgtgga tgcttttggg    144060
cccgcgcacc ctcgtgtggg actgatttcg cgaaacttgg atcgcgtacg tgcttgtcaa    144120
aatggtgttg tgagtgatgc ggctgatgcc ctagcacgtg gtgaatacgc acatgtaatt    144180
cctggcagca cattccagat tcaagcgttt gagttcgtag cgaagcctgt gaagagcagc    144240
agtagcaaaa gcagtaaatc cggaggcaag aagaagaaaa aaggagctaa gtaggttgtt    144300
gcaacgtaaa tccaaccatt gttttctttc agcggagatt ccgatgtctt cgacttcaag    144360
aagagaaaat ggaaatgact tcaagcaaca agtacgacaa agtggaggaa aaaaattatg    144420
cacagaataa tgcaagtcta ttcgtgagtt ggtacgactt agtttgtctt cgacttgaca    144480
ggcgacgtga gcagcaggcc aagaagttct cccagcggct tcttccagta cttgtccaat    144540
gcgaaccaag ccacgcagaa gtatagcacg cgagcttcca agattcgttc ctccttcgaa    144600
acgaaatggt tagcaacgtg agccacgacg ccaatgatac cgctggtcgc aacaatctgt    144660
aggatgaatc caaaggcgcc tatggataat tccaccacac ggtgcgtctg gccgtagttc    144720
gtcaagtagc ggagcaccat accgctagcg tacaagttgg cagtagaaat cgcaaggaac    144780
ccgagtgggt gtgcatttgt attcgtctgc cattccatca ccagcttagg gatcgtgaca    144840
gccttcaacc agctaacact gagcccaacg actgctttca gcagaggaat cgggatacgg    144900
aggccgtcga ccactaccctc aacaaggaag taaatgggca ccacgagtct cacggtctct    144960
tcaatctgcg gcgcagcgcc gaacacaggg cgaatgatgg tcgttcccag taaattggca    145020
gtgacggcag cgaacagcgc gcgagcgtgg cgaatcatcg cctttcgcag cgacggcgga    145080
cgacgtgcca gctcgggggg agtcacaaag tccgtgagtt gggtgcgcac agccaagcag    145140
acccagacga tgaacgaacg cttgaggaac gactggagct ctggggactg cacgtagatg    145200
actcctgtcg tgaactcgaa ccaaacaccg gcgagggcca cggtgatcac cagcaaattc    145260
```

```
ggcaaaaagc tgaagcatat ggacaaccac aatggggacg aaccagcaac gccattgcgt   145320
ttgcttgggg tggtctgggg gggagatgga gtcttggcga cagcacggcg cttggccatg   145380
tcgattgagg gatgcaatgc aacggagact gaaggtcgga acttcgagtc ggacagttga   145440
cgcgacgaca cgttgcagaa tcgggaaacg gaggaaacta tatatagcag gttttgtaa    145500 tagacattgc gtggagttgt gttttcgtga cggttcagta taaactatga aaggctttat   145560
ggatcctacg acgcgacgag catgtgtcaa aatggaaatc agtgtgcttg ccacgccata   145620
ccttggcttc ctttgtacat ttcaccgtcg ttgtctgtag taccaagtgg taaaactgtg   145680
caatcgccaa ccacgcgaag atcggttgct ctgggcaccg aaactggaaa agaaggcaat   145740
acatacaaca tctattacaa taactccact gcgtttcact accaagtcac agttttcttt   145800
ttgatagact cgatgagctg cgctggcagc aattcgcgac tgaagaagga aagcgtcccg   145860
aattcctcta tcacttgcga gctgtacatg tacgccaccc actcccacaa gcacccacca   145920
acttgggccg catggaacag agtctcggct tcttcctgca acgctgattt cgggagcggt   145980
ggcgcacact cagccgcctc tgacagcaac tcgtaaaact ctgtggagag ttgagtcctc   146040
atcatgctcg gcaggagact cacgtattcg tcgaacgtgc gcagcgtgaa ggtactatcg   146100
aacttaggct cgttctgacc gcgattgcga tgcttgtcgg tcgctttcga agtcttcatg   146160
tatgcaaagc gctctttctc gctgcagcta gtaatccatt cgtgaccttc cgtctcgata   146220
cgctcggcga acagatcata tttctgcttc agctcttcaa atacagttgt gaatggagat   146280
tgccactccc agtctttctt catcttcggc cactcacggt caatgcgggt gtgatatgtc   146340
gaaaggtacg tgaacaaaga ttccttgacg tcccagatag ccaagaaggg attgcacagc   146400
cccagaccac caaggttcaa cggccaataa atccacgctg ctggcatcgc tggacctgga   146460
ctctgacgcc tcctcatgat ctgctcacgc aggtaaccta gcgcatcgcc gtcagtcttc   146520
ggaaatacga gcttgtgaac gcggcggagt gtagataacg cctcgtcgat gtgacttaac   146580
ccgaaaattg gggacgggtt cccaaagttg cgcaggaaga agaacatgta cttgttgtac   146640
acgttaatcc acgcgaatgc tgaggttgca gcagccaaac ggtctgccat ttcggttgcg   146700
aacgcctcca cctcatcttg acggatatcc actgacccat ttgaccgcag ctcaagcaga   146760
ccccacctaa ttggagtcgc tggcagcggg gctggaccca cctttgcttc cgtggtgttg   146820
gatccagcgt tcaagcagat tgacccactt ttctcttcat tgaatttcag accgacgcac   146880
cgggcatagc gctgcatttc cttccaggct cgtagcacct tcgcctcatc ggcatcaaag   146940
aagcaaatat cgtcatgcga ccggtacaag aaaatatccg atgacgcaag cacgagataa   147000
tccatcacaa acaactccac ctcagcgagc agcatagtca tcattcggct gacagggagc   147060
cctcgctgca tactcttggg tttcgtgaaa ccagggaaaa tcagcggaat ttgtgtgtat   147120
cgccggaaca cgctcaacat atcatcatgc acgcccaaaa agcgaaggca cgcaaagaca   147180
gcttcgcgcg cgacagacgg cccgaagaac tcgaggtctg tcataacggc cacgagaggt   147240
gacggctcct tgccctcgct ggctagaatt ttctgtaggt gcgcttccgc tagcacacga   147300
cgaatgatat cctgtttgtc tgatttctgg tcctcgtcgt cgccgtcgtc ggatgccgag   147360
tcatcttcat cgtacggacc gcgcctccca tctttcatag actccggaag agcaaacaac   147420
tgaaatcgtc gcatcatgtc ggcacgaaca gactccacgg atgtcaaccc gctcatccgt   147480
gggtcatcac tcagtgagtc gagtagtgct cgaagtaccg ccttaatttc gatgctccac   147540
ttgaggccga tgtactggaa gagcagcagc gtaattgcat cttcctgtag cagacagcgg   147600
```

```
aagcggccgt tcatgccacg ttggatgtcg acgtgaactc cttcttcagg ccatcgccac 147660
tcactcacat tgctcaactc aatcgtaagc acttgggaca gctctttcat aacctgcttg 147720
ttgcgctggg catcggtgaa aagcgccgta acatcaggat tcaggaaatc cttgttacgt 147780
agcagcgcgg ccacacagca cttgacatct tcttcggtga tagggatttc cccacgcagc 147840
atgctgtcgc caaactggcc caaacgactg cgcgcctggt gcagcgcatc ttgctggcgc 147900
tgcgtcttgg cccgggagaa ttcttcgcgc tcctggaaca cctcggtcgt taaaaacgcg 147960
tacacttcgt cctccgacac gccgctactc tggaaaaagt aggactccag tcgctgctgt 148020
gtttcttccc tcgacagctt tgcaagtggt tcattgtcgg cagcccctcc accgacagca 148080
gacgacttcg gttcaccgcc ttgtgggcgg tccgcctctc tgtctttttg gtcgtgttcc 148140
gtctcctcca gcgactccat gagcagttcg cccagcagct tgttgtgctg ccagagactg 148200
cgacgctgcc gaacttctcg caggagctgc tgcttgcgct gttcgaccac cgtgtcggtg 148260
ctccaggggt cggcggctgc gaactcgacc agctccccgg tgttttccaa ccctcgtgc 148320 accttggtct gcacgacctg caggtccttt acaccctcgt acagccctcc cagttgttct 148380
cggccggtcg aagctgcgcc agtcttggcc aatagcgcct tgtagtgcgt ctcgagcttg 148440
cgctcgtgtt tggtgagttc tcccaacttg atctgcgtcg acagcttgag cagctggaaa 148500
tgcgctgtcg cgggcttctg tgaggtcgcc attgcaatga gaagaaaaa cacgtgagca 148560 gtaggttgca aaatgaagag taaggacgaa gatccgcttt tgaattttgt acccacacat 148620
tttaccatca ctcacgtata ttgtacaaaa aggcaacttc aacgctgtga tcatttttat 148680
cgctgctgta cagataattc gtgctgaggt tagcgatgac ctcagcacat tatctccagg 148740
atctgctcgc tgcggcctgc tttcagaatt ttcattggaa agtcgtttcc tgatggagtc 148800
gtaatgtcca cctgaatcga acgttgttgt actgggatcg ggtagggggg acctgggcg 148860 cgacaagcaa cgctggtgaa gattgctgct gaagtcgtcg cttgcggcag ctcgtgtata 148920
tgctgatacc cagcacgacc gccatcccag cgatgcgtgc agcgatctag tctagctcag 148980
agcgttgctt ggcgccattc cacttgagct gcttcgtgcg ctactggagc tcctgcctga 149040
gggatagttg ccaacgactc tcccagcgga ggttaaggac cctgcaagtg ttatgggggg 149100
gaagctgctc tgacgctgaa aagccaggag cgtccacagc actattacag ctcttcatct 149160
cagcgccatg ctgctaacgt tcacagtttc gggcggtgtc gcatggtgga gtgcaagttt 149220
tcgtgcgtgt cgagctctcc gggacgtgga ccctgccatg actacgacac cacggctcgc 149280
ctttacttcg ccttttcacg aggcaagtaa tgccatgact tgtctacttg gaaaatcgag 149340
ctgaacggag accgaagcta tctactgctc gtaggagtga atagaatcta agccaacaga 149400
atagtgcacg agagcgaata gaagaagtat cattcttcgc tgacactttc gtcggcctag 149460
aagtctcctg caaactcgcc accaccgaaa tcgccgccgc caccgccacc tgcatcgccc 149520
agagcttcac caatgagcag cccacccagc aagcctccag cagcgcccat tgccacggca 149580
ccgcccattc ctcgatttcc gccacgtcgg tagtcgcctc catagcctcc atggccataa 149640
cctggttggc cgtaacctgg ctggacgtag gtaggctgag catagcccc ctgggcgtac 149700 accggctgcg cataggtccc aggagcgtat ccctgttggg ggtagccacc ctgggcgtaa 149760
actggttgct gggcataggt cacgcccgct tcaggtgggt agtcaccgtg ccgctgttgc 149820
atgcgccgct tgcggatggc catcgaggcg ccaccgccta tcaaggcgcc aacgacaaag 149880
acgccgaggc ctatccagat ccagtaggac ggacgcttgt tgctcttctg gcacgtgcac 149940
tcgtacgtgt tatccgagga gcagacatca ctggcggggc agcagcaggc acgtcggttg 150000
```

```
ttggacgagt ccagccacga gttgcagaac ttgccggcgg ctccgttgta ggcctcggag   150060
cagtcgcccg agtcgcggca gatttcgcac tgtgacttgg acgaggaccc ggatgcggat   150120
gagttggacg cgacgatggt ggcagccgtc gagccgctgg ccgactgtgc cgtcgcgaca   150180
gacacgagcg ccaccaccac cagcagctgc actgccagaa tgcgcaggac actacggcgc   150240
ataacgaact tgacgaggag gttcttccag cggtgtgtgt cgagaaatgg acaaagtttg   150300
tctaataaaa gaggtgtgct gaacggtttt gacaggatat gcgtaagtac cccgctcgcg   150360
gcgacatgga gtccacctac aatggatacc cggcttcgtc cagaatatcc atccgcgggg   150420
ggaatcacac gtgatgcggc atcatgtccg acatgttggt agcggatttg tgctagggca   150480
ccttgctgtc gaaggtgtca ttaaggtgtt gaaaatagcg aaacccctta atttcagata   150540
gcgcgcaata tggcgatcgc ttggggccgg cgcgtgctga cggcgctcgt ggggatcccg   150600
acggcgctgc acctgctgag ctcggacgcc ggcatgctgt gcctcgccac gacgctctgc   150660
tgcctgtcgc tcgtggagtt cagcgccact atctgcccgc agatcgtgcc gcagcccaag   150720
gcgacgacgg agaggatggc gcatcgcctg ctagtggtcg cgtcgggcgc gctgctgtgc   150780
ttgggcgcgt ggaccggaac caaagtcgtg catggtgagg agattgcagt tgctgttact   150840
atgaatatgg aggctgatgg aagttgtgct gctcttctgt tgcagacgcc ttgatgctcg   150900
gagtgacgct gacaatctcc gccttcaca ttgcgaccgc caagacgatg gaccaaacag   150960
gttaagtcct gcaggtattg caggttgtag cctatactaa tgggtggtcg tgcgttgtgc   151020
gttttcgtgt tgcagcgctg accaagttgc tgctggacct gttcgcgctg ctatatatcg   151080
tgagcggttt cagtcacgct attctgctgc ggtacagctc cggcaaatat ggtcttggac   151140
tgcagatcct ggggctctgc tgcgcctggg tctgcgacag tggcgctctt gtggcaggct   151200
ccttcatggg tcatgcgaag ctggcacctg tagttagtcc aggcaagact ctagtggggg   151260
cgatagctgg agtcacctcg agcatcgcga cggtgctggt gatgtttatt ctcccgcagc   151320
tttccagcgc gctgccagtt ttcgggcaat ggacacacga cctgctgcct cctctagaag   151380
tggtgtctcg tacgcaccag gtagtacttg ggttggtgct tggagtgttg tgcatcgttg   151440
gcgacctggt cgagtcgtac gtgaaacgcg tcgccggtgt gaaagactcg ggagctttt   151500 tccccggcca tggtggctgt ctcgatcgca tggacagctt cctgtttgtc gcgccgtgtc   151560
tgtacttcta cagtcaattt gcactcccct aagcccaaca attaggccag agctgctgct   151620
tcgcatcaat agagactcaa aagactccca agcttactgt aatttgcgat tacaatgtgg   151680
cgtccacagc ctcctccacg atggattcga cgggcgcttt cttcttgccc ttgccactct   151740
tcttgatctc gggtttcgat ggttcgcttg ttggtagagc cttttgcagct tctgctgctg   151800 ccacctgtgc gggatcgtta atgtcgattg tatccaccgc cttcgtcttc gagttcctcc   151860
gcaggaactt ctgtcggtcc ttccgggacc cgcccaactt gctcgagtac tggcggatac   151920
ggcccctgca cgccgatcca caatataaaa catttaagta tactgcaagc caaacatagc   151980
agtatgttat ccctcattgc acacgtacgt gatgacggct gtgtcgggtt cgctgagctt   152040
gaaggacgtc ctgcgcatgg ccatgctgaa gtcggtgact tgtccatcac cgacgccatg   152100
cagcgcgtcc agtttggcag cggcttcagc ttgctgcgg gcaatgtcgt catacacgca   152160 ctttcattc tccttggtgc gccagtagta gatgcccacg cagagcagca gcaggatgga   152220
catgttggac ccgaaggcag actacagcga gaagcaacgc aagaaagagg tcagcaaaac   152280
agagataccg ggattgacgc tgcttgacgc accttgacca tcccttcgc gatgatgccg   152340
```

```
aacacgaaga gcagcagcag gtactgcgtc cggagctcca tgatgctgcc tgccttgcca   152400
cgtcgtttct tgcgctgtct tgggcttgaa tcggacttag taagaggctg ttatcatttc   152460
gacacagttc gtgtacaaaa caccaagctg cagagctctt cgtcttgcaa gtggttcagg   152520
tcgcacggag ctctaccgca agtctcatgc ctctacgttg cgacaatgct cgagcttttc   152580
ggtggtgctg cgattactgg tcgccaacca cggaagttag caaaatcgca acatttttca   152640
acgtgcatta gtaagttatg ctccatggcg cgccttatac atacaaggta ggtgaggctg   152700
ttggaacgcc agcctcttct actggctcgg cggagatctc tggcgctaca ggtttcggat   152760
gctcctgcga atcggatagt ccgttcacgg ctcgtcgaag cccaggaact cccataccaa   152820
gtgcattacg ttctcgtcta gcggctcgcc cagcgaaaac ctctcgaaca cgcgtagcac   152880
ggccaggcgc tcgaacaggt agttttcatg ccatgtagca cagtcgcccg tgaactcaaa   152940
gtctccgagt tccggaggga actcgttgcc gtactcgatg gctaagtgct ccaaatgcac   153000
gttgtactgc agggcctcca gcagcgcacg cgtgccgata cgtcgatgt cgttgaacag   153060 caggctgaga tctgtgagcc aagagtcgag aggggactga ctgtcgctga tcagcagcat   153120
ggcaagatcg aacgcgccgc ggaaaccaag catgttcgag tccagattga gactccggat   153180
gcggcagcgg cccttcttgt acgcctccag caacggggtg atgttcatga gttggcagtc   153240
ggacaggttc agcgtcgtta aatatggcga gaaatagata atccggtgca ggatctccgt   153300
ggctgggatg ccgaactggt cggggctgcc gatgcggttc tcgctcagat tgatgtcctc   153360
cagtcggtcg ctgatacccg tcatctggaa gaagagcgtg atcagtggca ccaccatgcc   153420
ctcagcgtcg gaggcctcga tcatgttcca gaacgatact gagcgcatga gcgtcgccgg   153480
cgagcaaatc cgaggcgaca tgccgatctc cgtcatctca atggcgcttt ggcgcggcac   153540
ccatccgagt ccgaagccag gaacaacaac acacaaccac ttgcgcagaa tacagaacac   153600
ctctagcagc tccttctcca caagaaggtc gctgtatact tcgtgctgtg acagcttgga   153660
cgtcggcagc ggacgcaccg tggtgcccct cttgataagg gcgaacacac gacggtgcgg   153720
aatgcccttg agcagcgcgc gcttcacgtc ctcgcgcagg atcttatcgc ggttgctctt   153780
gctgtaacgc tgcaaggctg ctgcgtactc ggggatcagc agaatcagcg ccgggtggcc   153840
cccagccatg atcccttcca cgacacggat gtccttcatc cgcatcatgt tgcgcgatag   153900
gtccagcttt tcaattcggg cggtcgagtt cgggtggaac aggccgaaca ccagccagcc   153960
ccagcacagg tgcaggtcct cctccttcac ttgggcgggg tccatcagtt cctgcaagtc   154020
gatgttctgc acggtgttcg agtagtgcat cgccagccg atgctggcga agaaagtgtt   154080
gtccatggga cactcacgca cggcgatctc cttcacaagg ccgcgctgct cctcgggcag   154140
ctcggcagcc atcgagttgt acttgatcac gggatgcacg gcaaagatgg cggtgcagaa   154200
ccggcggaag gccacacgat gctggtagat gaagttggcg tccagcgtgt cgatgaggtg   154260
gatctgtcgg acgtgcgcca tcttgtcggt gatgaggcgc gagagcgaat tgagctgcac   154320
ctcgttcatc tggaagtggc gaagcgtgag aaactcgatg accttgccca cctgcgtgcc   154380
ctggtacacg tagcggcgca cctcctgctc ctggatggtg cgcagcaggt gcttgaggtc   154440
cacgaagtcg tgcgcgagct cgaagctcag gccgtggtgc tcgtcgcggt ggtactcgca   154500
gcgcacgaag tagtcttcgt cgcaagagca gaacgggagc ggctccggct cgctctccgt   154560
ctccgaatag gtgcctgtgg agtcgtggta tttgcgcccg gaaccacccg ggggcgagct   154620
cgtggggccg tagtacgctg tcttgccgct caccatgtcg aggcgcggcg tggtctgcgg   154680
ctgcgggtag cgcggggttgg tctgtgggaa gggctgcatc cagcggcgga cgcggcactg   154740
```

```
gcggctagca acagcgcgag cgtggggag  aatcgaagtg accgccacga ggccagccgc  154800
gcgtctcgct tcctgtcact gcgtgcgcgt gcagcagcaa ttgaagctgg ccgtatcgtt  154860
gcggctttt  tgcggcctct cttttgattg gatcagagcg gagatgccag tttggttcga  154920
aagtgacgta aacctcaaat taaagatctg tttgaggtgt tttcgacggt gcgtgtacgc  154980
gtgagacttt gtgctagatt ttaatgctgc aagggaggct ttggatgctg ccgtgtgga   155040
tcctgcctat gccgtggtgc tcgaccgtgt gcacgacccc cacagactta caatcgcaac  155100
tgactgcatc cgctgcagtg acacacatct atgcaaaaca atagttttga agaaaaatgg  155160
caggttgagg cagcaatacc tcccagcggc ggctctattt gagtgcagta ccctcaaata  155220
gatgcaatac gctgctttgc aaggctttac aatgccatgg cgttacgcac gcagtgaccg  155280
ggcgaatgct attgccgccg tacctatcat ccgacggcaa gcgatggagc caccgcggc   155340
gcgtggcaca ggcatcgcaa cgctgccagc cagccagcca tgtccaacca aaccatgcca  155400
gcttcgagtc cagcgtccat cactgcgagc ctcgctgctg gcggtggtgg cgtgcttcct  155460
gcactgcaag caagtcaaaa tgactcggag gcacgcgtgt ctcttgcgcc ccattaagtg  155520
cgaccgctcg atatgtcggc gatcttcggc ggtcgcgact ggagatgtcg cctcgtcgcc  155580
gggttcaagc cctgccgctg cgaatgaacg ctggccgcga ccaccgcgcg ctcctggtta  155640
tgccccagcg tggtggcagc gcactcggct gtacgtcgcc acacctacgc tcgaagaggg  155700
cgggcggcga gcaccgtcgg aacgattgca acggacgctt caatggtgga acatgaggat  155760
agctaatagg cgagggtgct gctggtcgat cgcctgccgg aagcataact tgcctgtcca  155820
gtgaattgta cagcgtgccg gagccaagct ctagcacttt tctagaactg cttgcccgcg  155880
gttggtggcc tcttcgaagc attgcgacgc cgaattcact gtcgccctcc cgagggtctc  155940
atatccgcca cgtagtggtc tagacggcaa cgccgtttac ttaaggcaga caccaaccac  156000
cgcacaaagg atacacgcgc cacacttcac tgccttctcg tctactcgaa ccattgttct  156060
cgcattgctc gatcccacgt accctcaggc ggcctcgcgg tgacgttgca cgccgaccc   156120
tctgctgccg ttcgtcactt gcgtcgtcga tcaccaaagt ctgccctttt cgccgacgtc  156180
taccacgatc gctttacgac ggtttcctct tgttccctgc ggtgatgtat aacgagtgaa  156240
ggcactcgga caataaggca gcgctgtcgg ggtccccgac tcgggggggtc acggtcaagc  156300
aagaatgagc tctttgcagc tgaaggtttg ccaggacgat gggtagcttc aagcagaaa   156360
atcaggcagt ttttcgcgtc tccacgcaat ccctaccgct gcggcgctga gttgccagcg  156420
atccctgcac gccctgcaat gctcgcccaa gctgtgcagt gattcactgc cactagcaga  156480
ctgccagtgg ttaagtgact gccccttgtg ctgtgcagca atgttacact gctacgtttt  156540
cagacaattt gcctgaggca aatacactga tatttgcaag aaaaaacttc aaggagcatc  156600
cctacccctt ccatgatgtt caaattgagg cggctccact cttaaatgag ggtatgtgtg  156660
ggtgggtatt ttccctatcc gtaccggaca tatttcggac cacttgccgc acatacaaat  156720
tcaagccaat aagcaaaaag caccacttca gcgatcggcg cgaactgcca ccaataatag  156780
tctttgggcg ctgaaaatcg cgcacaaagt aagaggagaa agccagcttt cgaaaaaaaa  156840
aacacacaca cgctttcctc agatccattt tgacgttaca acatctcccc aaaactcccc  156900
caatgaccaa ggtcccagtc gagacgtggg atctgctgcc attgccgctg tcgctggcgg  156960
cttgagtgag cgcaaggcca ccaaggctta cggcgtctct cgtgggcctc ttcaccagcg  157020
catcaacgga cgtgtaccgc tcgaagctcg cacagggact cagctggact acactactga  157080
```

-continued

```
aggcgctgac cgaggcgtcg tcgagatggt gcgctaccgc gcgctgcgta gaatgtgcgt   157140
ggagtttgaa gagctgcgcg gcatgctcca agtacatggg ggatgcggcc tttgactaat   157200
gactttccta acgacaaatt cattcagcgc tggcttgcca aacactacct cgcactactc   157260
agcttttgga cattgaccgt gcttcagctt ccacagctga tgtcgtctcg cactacttca   157320
ataaccccca gcgcgtcatg aagaagctgg atctgtcgga caagcccaat cgcatctgga   157380
actgcgatga gactcctctt tccaatttgc tgcaagttac tgagcgtcaa aaccgggtgc   157440
tgcgagaact agatctgaat gtggacgcgc tcaatgtcgt gaatctgctt cgagcacggc   157500
ggtagcacca caagctaaaa agcggaaaag aggagactgg gttgacgaaa attactctgg   157560
agggcagctg ctgagctacg cgatgatggt tgttgcggct gctgcaaaat cagcatcaat   157620
agcccaaaaa aaacgaacaa ggagtctgct ccgaagcaaa aacgtgccca ggatgcgatg   157680
aacctgcacg acaaagccga ccaccaaaca gacaggtcga agaagacact cgaaaagtgg   157740
gaacgtgctg ccgtgaaacg ggagcgaaaa acagaacgag ctgcagcaca acgtgcgaag   157800
gcaatgcgaa taactgccga gcgcgcgcag cgactgaacc aggagaaggt gggggagcaa   157860
gcgaccgatg gttgtatgct cttggtagtt gtgtgagcag actggcatac aaaactcaat   157920
agtaaagctg ggtggtccga aatctgtcca ggggtgtatc gacagatata caaaaatagc   157980
ataattcgct aagtggtccg taatatgtcc agcacggata cagtactttc acaatagact   158040
acaactgtag acatgccaac gttggaggcg tgcgaaatct actgtgggaa cataacggcc   158100
ctcttcagtt gttgttctcg acgtcgggtg tatccgcggt tttacacctc ggacgtccac   158160
ggccacaaac gacatcgcag ttactccccg tcggcacccg ccgtttagtc actctttcga   158220
attaagaaat gaccacttga ctccacattt gcggctttac cctccacctt cactgagtag   158280
ctgccacgcg cagtgcgggg tgaacggcaa ccgcaacgct cgcaacaaca gtaaagtctc   158340
accacaaaac cctgacgtat taagtaccag caaggaccag cacaacttcc caagtcacac   158400
ttgtgaagca gatggatagg ttatacttgg attaatgtta caccgttgac aatgacttag   158460
atcggcgttg aagtttaaaa tgatcgctgc agggagctgt gcgctggtca agataccgct   158520
ggatgtacaa gttctagaac gacgctgagg ggttacgagc acatcaaatg ctgctgcgac   158580
gtatacgttt tagcacgact agctccctac gccgtaaacc ttaaagctgg catgtttacc   158640
gaaaatatcg ggaagaacag aggtttgtct gcacgtggta ggataaatgc cgtgtgcatt   158700
acgctggtgg atcatcagaa tgcacacagc atcggatttg atggagcacc accgcgtcaa   158760 cggggttgcag ctcgatcaag ttcagggacg gcgatgacag tgaccgcacg ttcaccttaa   158820
gcggaacagt gcgagtttag tgtttgcggc tctgaacgct atactggtga agtgggcatc   158880
taactgcaag agatttggcc agaacgcgtc gggccccaca agtatctatg aaagctcagc   158940
gagtaccatt cacacgaaac ttggacctgt aataatgtga ggtagaagag taaatactga   159000
aggcgtcgag caacgtcaaa actcgtgtat tattgtacca gtggtcttaa ctatgacaac   159060
agtgatagcc tgtaaaagga gtatacaaaa tttagcgcca agctcccct atagccttat   159120 gctggcgcat tttcaacaat aaagaggata tccctgaccg tatcagcctt gagggcacca   159180
cgtcgtttaa taaccgtatt accggccgtg aaaatgcgc gctccgaagg cactaacttg   159240
gcgatacaat ccaaccactt acgaacaaga ggagcaatag tagcaaaatt tgaatggttc   159300
tgtttccacc acgacaaagc cggcggatat tgttttgctg tatagtaaca actgcctcac   159360
atgaatttcc tatatagttt gagaacacca ggccacaatc tgcaaatacc ttctcatctg   159420
tcaccccgac ctgtttttt taatatttta tgcgtacaac agctttagta agttttggtt   159480
```

```
gaatctgtct cttgggttgt tcagcatttc ctccgagagc gaagaacttg gtatatcaca   159540
gccaaaaggg ataactttat tttttagaat caagaacatt tggcgaataa agacaatttt   159600
cgccttctca aatgtgtcgt cagtgaaaat ctgggcgtta gtcatgtaga gatggagcag   159660
cgaaatccag agaaggtcac tctctttctc cttatagata tgcttcttta gtagtgctaa   159720
aaggctctga cgaacggaat gcaacgttcg gagtattcgt ggagcgaagg acgcttcatt   159780
cacgcttgtg tatagcacgt caaacataca cttgttatcc aacattattt tgagcaactc   159840
aacgacaagg tgaagtgata tcaaagttgg ataagtttca ccatcaaggt ttttgtcgt    159900 gacgctaaat ggcgccaata gctcaatgag gcactgaatg gtgaaccact gttcagcact   159960
agtgaagctt attttttttc gatgcggcat catcaaattc cttcacccct tttaccgaca   160020
ccaggtaggt aaaacaaatc tttcaccgcc gaatggagct tgataaaccg ctggagcata   160080
tccaaagagc tattccatct ggttgggcca tcaatcttca cttttagggg ttccttcggc   160140
tcgattggag ttcatccagt cggttgcgtc ctttttgaga gcggtgaaaa tactcagtaa   160200
gtttgtgaaa attgtgaaca gatttgcggg tcgactccat atcgctgaaa ttgacttccg   160260
tgtcaccaac gctcgcaaca tccgctacaa actgtgcaac ttgtgcgaaa agagatcaat   160320
gtcagagcgc taactaaatt atctagttca ccataggctt gcatgccgtt ttccagaatt   160380
tccaaccgat catctatcca ggaaaactca atttgatttt ttgaaacaga ttgcgaatag   160440
ggaccaatat ctaagacact tttaattgtt ttgccactgt taactccagc ttgattccca   160500
ttattaataa cagtaccatc cgcatctacc gtcaccttgt ttatcatatc ttcactttac   160560
atcaaaagcg cagctacaac taccaaatgc agggaatgag cagtacaaaa tctgtgcgta   160620
agaccaagtt ttgagcatgc actcgtaata tttgatgctc catctcttaa aaagcgcacg   160680
caggttttga ggtcaagacg ccaccacgta aaacaatgag agagcgtact tgcaattgag   160740
tccccatcgt gctttcccgg aatgagtcgt acttcgagag ttcatgattt catgttgaac   160800
aacgcatcca cataatgaag cgtaaagctg atgtagcttt cacattttac tgatgtccag   160860
atgcttgatg aaacagagaa aaaagcgcac ttctcgtcac ttgacagcat atgtctgagt   160920
gtcaaccttg agtcagaggc ttgggaatgg atccgatccg taactgtttg gcagatgga    160980 acggcaagaa tctcctgtac actgttggtg aattaaccag tcttgatgaa ttcacgatca   161040
ccaacagcct cctcatgtca cgactgaccc atttcaccaa tatattctcg aaacaacgct   161100
ggtcggattc ttctgctgat tcagatctgt ttctcaggct ttgacctctt cctctcgccg   161160 aatatttttcc tcaaacattc tcagggcatc aatatgaagc ttcctcatgt ggggacgaac   161220 cttatttta tattttatga atggcactcc ctcattgcag ctcaatcaaa aaaaagcacc    161280
gggcctggtc gcgactgagc ttttctcttt tcacgcctgc ttgctgctca ctcgccacac   161340
ataccatgaa ttgatactac accttctccc tttggcttgg cactggatat gttcgtccgg   161400
tgggacattg ctgcacattt ctgaggactg atatcttct gctagcctga gcgagtgact    161460
ccgacgcaaa agttgctgat ggtgatgctc gcaacgattt tggtcttaat gggggtgatt   161520
tcgtacactt ccgcgtcgct cgcgaaggca ctcttgaagg agttgtccct gatggtgtca   161580
ttcgatatga tttggtcgag cgtgtccttg gtcgtgatgt tgctccagac ttttttttgac  161640 ggtgtcgtgt gtacctgcgt tgctgacgac gtatctcctg cacgttttga tttcttgctt   161700
gatggttggg agtgtggatt ggttctgctt cttcttgagg gagtcgtaga acagctcgca   161760
tctgctacgg tctgatcatc catggcggcc gtgtgtccag cctgatcgat gggaggtctg   161820
```

```
atcagagaat gagccagcta ccactgagtg aagctctcga agcaaagatt tcgaagaagg   161880
attggtatgg gcacgaaact tgcgaatctt tctgcccaaa gctaccgcga agcgcagtcg   161940
gtcttgtttg ccgactcctt cgaaggcttt caatataaca gctgatgtgg catccaacat   162000
ggaactgctt tgattggcta ccttaaagac tttttgccaa ttaaacgact acaatagccg   162060
gggtgtcggc tgtgtgtatc cgcgacgtcg tttgcaaagc tggacgtcca gcccgtcaac   162120
gtccagatcg acgtcaaagg tcgggacgtc gacagcattc ctcttcagtg atggcctcag   162180
acaccgccgc ttgttgcggt tgctgtgtct gtcctcgctg aatttcagaa tgagggcta   162240
tgtacgtttt cgtggcacct ccgaaatggc tacatcccca tattattggg aaacagtgtc   162300
caagctttca tagtaacccc agcatttcgc ctgttctgaa ggcgttgctt gacaccgacc   162360
tgcttgcctg caccaaactg cgggaacgac gccggaactt cgtcaccacg acggcccgtc   162420
agttttgggg tccgaagggg gatacataga ggacgggagc ggcaaaaatg ccaaaatgg    162480
gcactgcgct ccgtctacga acccatttct gaaagatttc tggaaaaacc aaccgacact   162540
tgctcaatct ctctgccact attcagcctg ccccgagact gcgcattgat cacgtcgagc   162600
tgctcacgcc gcacgccgcc acaccacagg tgctcgcctc catctttgtg cctttcttcg   162660
cgtgccagtt tcgagtgcca catcgccgat cgttcgccgc tctcccgtcc agtctacgca   162720
ttcggttggc cgccagctga aagcagcggc aacagctctc ctctcttcct ctcgcgcaca   162780
gttccgcctg ccgcgccgcc gagaagaaga gcgagcgaaa cgcagcgact gagcagcacc   162840
attggccagg ccttcttctg cctgcagacg cggccgcagc cggtggcccc gttcgcgagc   162900
gggacagtgc tgagcttcca cgcgcctggc gaacccgacg ccgtgcgcga acgcctcgcg   162960
cgtctactga gcctctctgc agccatgatg gccgaacccg acgtgctgac caaagccgat   163020
agcgacggcg atgccagcga gaccgccgat gccttccgcc ccgcggacga cgacctgcag   163080
caactcacgg tgcagtcgct cccctacgtc aagtgccgcg agagcgtgag cgccgtgttc   163140
agcttcgact cggcggcgcg tcgccgtgtt tcgctggcgt ccaacgcgac gtccgacacg   163200
gccaattcgt cgcctgaaca cgccgacaag ttccccacgt cgctctcgta ctcagtcccg   163260
tccaccgcga tagtgaccaa cacgccgcgc ggccggcccg ccgtggacgt gatcgctacg   163320
tacatgaaca cgtgtgacca gcgcacggtg aaatcggagc tcatgcgtgc ccacgcgcac   163380
tttgcctcac ctcagggtac ggacatgctc ttttgctctt gcctgctgtg gttgaagttg   163440
aaggccattg cggcgcagac gaaagaactg actgtagtga tttggtgttt tgtcgttgac   163500
acgtttgtgt tgcgttgttt gttgctgctg ttggtgaagg tggcccgccg tcgcgcatcc   163560
gttcgtcttc cattatgagc aaggagggca gtgctgaatg gggctggttc gccgacatcg   163620
actcgagtag cgaaagctgg ggtggcgatg gttccatcca ctcgctgcgg cgccgactaa   163680
gcgctgactt gggactcatc gacgtgggca acgtccacgt cctgggtgat gaacagacca   163740
acacacgcat cacagcagcg cacaagacgt ttacaatagt cacggaaggc aacagcaagg   163800
tggtctcagc tacagtgtcc attcccaagt tccgcattgt gcagtcacgc tccggcgccg   163860
accgccacgc gcagtattta atcaccctca tgctcggcaa ggagctgtac gcagactggc   163920
gtcggtactc ggagtttggt gaactagtga agacgctgga tgaaaagcgc tacacgcgga   163980
cacaagatgc ctgggcagga atcgagacgc gctggttcaa tcggctagaa ccgtcgtatt   164040
tgcaccagaa atgcatcaca ctcgagaact tcatgcgcga gctcatgtac gagtcgaacg   164100
agccgaatgt gctgatcaac ttcctcggcg gctatctggg taaggttaac gcgcggccta   164160
cggaccccgt ggcatatcgc ccagcagctc agctcccgaa ggagcttcgt ccaccacagc   164220
```

```
cgcaacacga gcgagagctg ttcgagaaga tgtgggctga gaactttaaa cggtcacatg  164280
tggagtactc gacaagtggg ccggcgaccc aggcggctag ctagacagtg agctggctgg  164340
aggagtgatg aaggcgtaaa ggctccgtct gatgcccgtt atttgattat tcgtttaaga  164400
ggttgcccct gcgcccttttt ctagtggact ctttctcatt tagtcgttgg cagagctatt  164460
gacagagcta caggaacctg cttttgaagg cagcagcggc gtccgaatag cagagctcgt  164520
gttgatagac aattaggtcg gggatatggg agatgtcacg caagtagaag aactgggcga  164580
gtcgcgtttg cgaaacgagc gggaacaacc acggagagac ctgtgtgcag catcaccacc  164640
acaacataag catcacgtcg aagcatacca ggccgactaa catgtaaacg aaccgtcgaa  164700
atcagcacat gccaggcaaa gccgacgatc acgccaacaa atgcaccaac agccacttgg  164760
tccttggtgt gatagcccaa gcgcactcgc gagtagcagg tcgccgctgc cagcaaaatg  164820
cagccgacaa tcgtgatcca ctgctcgatg tagcggtgcg agttcaacct gcaatggaga  164880
cattcgtcag ttttcctgtg atccacggca tctcagcgtg acggacctcg aacacgtgta  164940
ggcgacagca ttcgaagcga agtacgagat gaattgcgag tgagccgagg gcattcccga  165000
cccgctcatg cgtgcgccgt caggccgttg ctggttgatt gtcttcttga gcaccttgtt  165060
aatcacttcg ctcaccacct gccaccacca aattgagcgt tagttcggta agaattggct  165120
ggcaacgcat tgattgagat acctggccga aaaacatgct gatgctgtcc aagtcgcgct  165180
gggaggcgac cagcgtcacg tgcatgaggg tcacgaacct acgagagcgt tttcgcgtta  165240
gttagctaga gagcatgata ttgacggcgg aagtggatcg tacactggcg agagcgtgaa  165300
gagcgccatg atgaggccaa accggtcggt cgggtcatac atgacccacg taagctcgaa  165360
ggccttgagc gccttgccct tggactccgc aaccctggtc atggcgtcgt gcggtggtcg  165420 cttctgaag ttgttgggga gagttcgtgc taccggatgg tcctccacga tttgcactga  165480
gcattgcagt gcctggtctc gtggttgcta ttgatattgc ttcgccaaca ttatcggccg  165540
tgactttggt cggatggagc gtgcctgaat tcgacaatgg ccctcgatga agaaggaaaa  165600
ccattgctgc actttcatta caattgattc tgagtaaaca aagcacaact tctaggggtg  165660
tccacgtaac aagttactga gacttcttgc taggagaagc aacaggggcc ttggagcggc  165720
agatttcgtg ttggtagacg gtcaggtccg agatgtgtga tatgtcgcgg atgtaaaaga  165780
acttcgcgag gctcgactcg gccacgcgtg ggaacagcca cggagaaacc tattcaacca  165840
aaaccacagc aacatcagct actctcacat ttgcagtcac cggaaaagtc aaaacagagc  165900
cttctcgtac cgaggagacc aacatatacc acacaactcc agtgagcaca ccaaacaccg  165960
cgccaactac tacttggtcg gtggagtggt agtttaggtg aatacgcgag tagcacgtca  166020
gcaccgccat catgatgaca ctgaagatcg tgaaccactg ctccagtcgt cgacgcgagt  166080
tcatcctgat acacgacagc aaaggtcaca tcatcgcaac tcaatcaact taagggctac  166140
agtccgcgca cctcttccac gtgtaaatca cgacgtatgc cgcaaagaat cccatgaact  166200
gagagtgcgc ggagggcatc cccggtccgg tcatgtacgc gccttccggt cgcggctgat  166260
tgatgaattt cttgagcacc ttgttgaaca cgacgctaac cagctaccga gccacgttac  166320
cagcgtcagc gactgcatca atcaagcaat atattgcaat agcaattgat atttacctgc  166380
cccacgagca tacttatgct gtccaagtct cgctgcgagg cgacgatcgt gaggtacgtg  166440
atgaccagga agctatatgt acaacagggg gtcagcatag caacccagt cgcatcgatg  166500 gcagtaaaca cacatgggag acagagtaaa gagcgctagg acaacgccca gcgggtccgt  166560
```

```
cgggtcgtac acgacccacg tgagctcgaa ctcctgcacg cgcttgaccg catccatcgt   166620
cgacgtcacg tttgctattc accccccaagt acgcaaaccg gatgtagcca tgtcactttt   166680
acgagtgcag ttgtagtgac cgtcagagca atcatgactt cgcaggccac gagactcgag   166740
agcctcttcc tgctcgtgcg aggtacacaa cagtcaacag accgaacttc tacttgcagc   166800
agctgcctgt gtgcttcctc tatctaatgc ggtgcatttc gtgttgtttg gacagacgga   166860
agcagcgcgc agatccgcga gaacgcggcc gagaagctgg gcgaagtggc tgcgcgctct   166920
ccggagttct gcgcctcgat tctgcagcag ctgcgcccac tgatagtgca ctcggaatgg   166980
gacatccgtg tggctgcatc caagtgtctc gatgtggtgg ccagatccct acatcgtgag   167040
gacgggaacg tcgcggatct cttcgcgttg gtctcccgta cgtgaacggc gtagaaatga   167100
tgcaatagag tcgacgcatt aacttgttat ttatattgca gttggcagtc acgaagcttc   167160
cagtgtggcg ctgaatctcc agacggtgga tatcaagaag gtggtgcatg aaggcgcgcc   167220
gttgctgcgg agtggaggag aggtgagtta actgctgcct ttaaacaggt gattgaaact   167280
aactgagaac gtgttgttct acgtaggaat accaatacgc gacgaatctg acggaggaag   167340
aacgacgtgt tcatgcggcg aggcagcgac gtctattgtt gcggcgtctt agtggagcgg   167400
gaggacctat ttggaaaacc cgagaggact cacttaccaa gcagctgctt cccagactca   167460
acagagatcg tacgtgttgg agtggaggtc ttttgtgcgt gtttactgat tggtagcgat   167520
gactgccgta cgggtgtggt tacctgcaga tgcacaggaa atcgctgatg acattggagc   167580
gagcgaagag caacccaacg ttggtgagaa ccctgccaaa ggtatcaatc ggaagcaagc   167640
gagtgaaatg ttatcgattt caacaagatc aaaacgtcag ctagctgatg gtgcagctga   167700
gtttgggagc aaagacaaac gggcaaaagt agatcacaac ggcgatgcaa atgatgcgga   167760
catgaactta ccagttggga cgagctctga cgagcaattg gacgagtcgg aatcacagac   167820
caagggttcg attgtcgcaa gcttggtctc ggatcttttt gagagcatgt ttgattccaa   167880
gtgggaagtt cggcatggtg cactcttgtc gttgcgggaa atgttattag ctgcccattt   167940
caccgctgca gttgaagcag tccgacccgc gacggacgag agcatgcagc gaggcttcgt   168000
ggacaagtgg ctgaagaat gcctaatacg gtgtatgtgt gtacttgctt tggatcaatt   168060
tgtggattac tcggcggacg ggtcgatctc tcccgttcgc gaggtttgct cgcaggtttt   168120
cggcattttg cttggaagtc tttccagcca agatacactt gtcgggtatt tacaagtggt   168180
gcgtacactg tttaatggat cgacatggca ggcttgccat ggtggcctgc ttggactgaa   168240
atatcttgtt cgagctcata gcagtcacgc ccaagcgcta attcctcttt tctttaacga   168300
tatcgtggca gcattctctc agctcgattc ggaggaggat gttctagttc tggccgcaga   168360
aatgttcaca gattttgtcc tatacttgga tcaggttgaa agcataaaca tcacgaaggc   168420
tgcgctgttg ttgtggggat ctctgaagtt aacgaaaag gctggcctgg ttactgccag   168480
tatagtccaa gcactaaatg cctggtacaa tcattctcca gtcgcagagc tcttgcaaag   168540
tgacagtgca gtcaggtcag cgctttggga gaatttgtcg tacacaatcc cgatgctcca   168600
tcaccactcg caatctgttc gagcgtccag tgcaacatgt gtagcggcca tctttcagg   168660
ggggtcttta ttcttgaggg aaaactcggt tagctttgct cattttttc tgccgcatt   168720
gctgcttcaa ataattctgg aaatgaacga gtccgtccag caaagcttgc ttgctgcctg   168780
gaaaaaggta gtgagcagtc tgtctaccaa cgagctgctg atgactgtaa ttgctggaaa   168840
aattccattg tggatgaaac tgttgtggtc tacggacgaa atctattgtc taaatgttga   168900
aatggtgaac tctgacggca ctgtatccgg tagtgtcgtt agcgatcctg ccggccggat   168960
```

```
aatacgagac aatatgtctt ctcgtgtggc tttcggagag gcgatcggtt ttgctatttc   169020
ccatgtgcct ctttccagcg cgtgtatgac tgaattagta gagcttgtct gcgagggtct   169080
gtgtggtagc tccggtgaac agcagtgcgg agttctcgta gccctgtcaa gatgggggtt   169140
ctttgaaaaa caactgagac aggaaagtcc agaggaacaa gcccggcgag ctcggcactt   169200
gcaagataca attgggccct ttctgagctc gttcgctgga aatcattgga ggacacttca   169260
gcctgatgcc ctgagcgaag aaaaattagt gctctatagc gagcaagctg gatcgctgaa   169320
acgtgttatg cagatggaag ctcgaattat tgagatattc tcctctgtgg gtattgcgct   169380
ccagccctca gaaagatcgg gctcgtcatc tacagcggaa atttcacgcc agatcgctga   169440
gcacattgct ctttttccct acgagaagtt gcaagaccat ccgaacgaat acgaattggc   169500
tcatttcaag cggcaagacc tctttcttgc tgatgatctc gtgcagcaaa gtttctctcg   169560
ctgttatcac cgaatacaag gtcttggtag cagtgcactc tgcgaaatac tgccaatccc   169620
caaaaagagt gggtttctag tcaaagcact catgagttcg atcaaagaag aagatgattc   169680
agcattccgc acgatttcat cacaaacggt tgcagccttt gtggtcgatc aagcacaagc   169740
ccaaaagaag tgcgtcgcga aaatcatttc gaacctctgc aacagcgcgg cggcattggt   169800
aggcgtatcg ggtggcccct tggataacat tattggattc agtagttcgc cggagaaccc   169860
gagtgattct gtttctcctg gtgttttcaa aaagacaaag atccgagctg atggggctga   169920
ggctgtgctg cgcaaaatct gcaactacgc aggagattct cttttcgatg tctgtcacgc   169980
attggaggat gccatttcta aggcttggaa ccaaccaaac gtagacgagc cgacaattca   170040
acggtgcatg tatttgatcg tcttagtggc accgcatgtg aagagcagcg caatgacaac   170100
atgtttgtca tggctttgtc aacttgcaca actgacacag aagccatttg ttgaaaatca   170160
aacgcgaggc atcgtggctc atgccattgc tattatttgc aagtatgctc aaggacatca   170220
tcgcaaaaac gcgatgctcg tcgtgtatga atccatcttc gtgatatttt caaacactgg   170280
tggcgctgac gtcttaaaat cggaagctct agaaggcgct gtgatggtgc tcgaccgcat   170340
tgtccgctcg cttggagcgg agttgacacc gtatgttccc agcttggtac actatgcgat   170400
gaaaaccatg agctcgcaat tcaaacttgt tcgaacgttt gctgccgggg tgtttgcgga   170460
cttggtcccg ttgattccac ttcaaatgga tcttgagctt cataaatctg accagctact   170520
tccagtctcg ctgaggacga ttgtgaatca gaatgctgtt tcacgtagct tcctggagag   170580
cttcacggaa gggaaggctg ttcagcatac caatgtgaag ccctggcttg ctccagagac   170640
ctctttgcgc gtataccagc agcatggcgt agactggcta tgcttcatgg ccaggaacaa   170700
tcttcatggg atcctcgccg atgatatggg cctcggaaag acactccaaa cgctttctgc   170760
catggctgca acactagcaa tgacatctac agcccaaagc aaacgtccag cgaggccttg   170820
tctcgttgta tgcccaccga ttatcgtgca tcactggatc caagaagcca agaaatacat   170880
tccaggatac ttcgcatctg tcatcgacta ctcagtccca gcaagtgacc gaaaagtgtt   170940
gggtcacggc aaaaatatcg tgatatctga tcacggcacg actttgatcg tgactacata   171000
ctcgatcctg cggacagaca tcaaccgctt gggagatatt gactactctt ttgtggtgtt   171060
ggacgaagca catttgattc ggaatccatc gacagcgtta ttccgtgctg tatcgaacct   171120
tcacgcatca catcgtgtgg ccttgagtgg aacgccgctg cagaataacg tcacagacct   171180
gtgggctctg ttcgagttcc taatgcctgg atacttaggc gactttactt tattccgtcg   171240
cgagtttgtc cttccaatca caaagtcaaa agagcgcaat gcaacgtcaa agcaaaagga   171300
```

```
gctcgcagcg attgccatca caaaactgca ccaaaaggtt ctgccattta tactgcgacg   171360
aacgaaagac caggtgctgg aagagcttcc accgaaaatc atctcgaacg tgctactgcc   171420
gttaacttcg ctgcagaaac gtttgtactc gctggcgtcg tcatctgaga gcgatccac    171480 aagctctgtg gcatcttctc ggtctacgaa ggtggccgag ccgaaaccat tgacgaacgt   171540
gctaacaaat cttcaattac tgcgcaagat ttgtgtacat ccagcgctcg ttgctgacaa   171600
cgcaatctct ttggggctta atacgaagga aacgggggcc ctgcttgact ggaaaagctc   171660
aggaaagatg actggattgc gcgatctatt ggttgagtgc tgcgatattg cagcatggac   171720
tcaggaaggt cgccaaggac ctgcaactga aggtgatgac gatagcaatt tttctcctca   171780
tcgatgcctg gtgtttgccc acctgcagaa gacgctcgat ctcaccgagg aaatgatgcg   171840
ggacgcatta cctggtgtaa cttatcgacg cctcgatgga caaacacctc acgccaagcg   171900
tgcagacatt gtacagcact tcaatgccga tccgtcaatt gacgtcttgc tgctgactac   171960
gtcagtgggc ggtttaggac tcacccttac tggcgcggac acggtgatct tcatcgagca   172020
ctcgtggaac ccctttgttg atctgcaggc gatggatcgt gcgcatcgca ttggacaaaa   172080
gcgaaccgtg cgggtattcc gactaatcat ggagaagtca cttgaggaac atattctgaa   172140
tctgcaagag ttcaaagaac aagtagctgc tacggttgtg cagaagagtg atgctcagag   172200
cagcatgaat acgaacacga aaggagtcct caacttgctg cagacgtcct catcagcggt   172260
ggctgccaag gagcttcgcg cgtcagttac agcaaaaacg gcaggtcaag atgatccaag   172320
tgtagcagca gcccttccac agggagccca agagctgcta gaccagattg gtgagctatg   172380
ggatgagtcc caatacgact cgttagcgtt tcctgagccc atccacgagt aaccatgcgc   172440
ataacgattc agactcaatg atggctctac aaaaatatct cctatgtatt ggatcatcgc   172500
tgggatctcc agaatctgga gtccaggtga gcagaccacg ccgagttggt ttactgggca   172560
tcaataaggc tttcgacgtc gagctggatt atatccgcgt cacagtccta tggcagaaaa   172620
gcaaggaggg gagacaacgt gagcgaacct ttacgcgtaa tagcacttgc acagctgtac   172680
aacataccaa aattgacgcg acgttggggt tggtccgacc acggtcaccg tgcacgaact   172740
ctttaacgta ggttcctgcg gatgtggtga ggcgcaacat catgtaatgc ttgttcagca   172800
cctcacactt ggcagcatgg ataatcttcg gcctcgtcat cagggttcgg cgatgcagca   172860
cgcgaatagg agtttgctgc tgaatggtga ggtcttgaat tgcatcaatc ttcgcaacgg   172920 actcggggt caattcacct tccgaccaca caacgcagct gataatggaa gcaaatgcga    172980
gtttgtcagt ctaacctgag gtagtagttt gtcccaaggt aaaacactca ccagtaggtt   173040
ttcttctttg agtctgctcc tgcctgcagc ccagcgaaat agtccttcgt cgagctctta   173100
acctggacaa tctcgacagc accattgttt gcggcattca cagccttctg aattccatcg   173160
tactctgatt gattcaggta cgctttcttg gcgtctgcag gcaaaacaaa tacggttgag   173220
ataggccaag tctaataccg ctacataaac gtaaagttgc agcttaccca aaatctccaa   173280
gatgaaaggc cttccgtttc ctagcatgcg cacgtcgaca tcttcacgac ctgctgtgtg   173340
aaacttgtag cctgcaccct tgaagaatgg cagggcgatg tcaccgatgc actcttccac   173400
ggaggattcg cccattcgct cgccgtcaag aacccacggg gtctggctga gtccacgctg   173460
gaacttcaga tatcttccct gcatgtacac cggatcgcgt tcaaacgtgg caacagcgtg   173520
cggggcagta gtgatccgag tcggtggact cttaatagtc tcgggcatgg acgaaagcgt   173580
ccccaacgcg cgggaaactg caccgaaacc atcaaagacc gggggagggc cacgaccgcg   173640
cttcttcgtt tctagttgtt tctgccgaag aggaagcagc gaacacacgt gagttattgc   173700
```

```
acccaagcac cagacaacgt gctcaccata ccctgatcga cggaatctgg cgcacgtcgt   173760
cggcagattc gtcatggttg atgtcgatca gcactgcaaa ctcgctgccg ttcgcgcact   173820
cagcctggtt gagcatcttc gcgataaaag gcgccaacaa agactattca cgacattccc   173880
aaccgcaata gacgtaagtt cataccatcg atcgcaaacg cccgtagttg tttgtacctt   173940
gagcacatct ttcatatcga acggcgtttt gcgcgggaag tccgccacat ccgagcgcaa   174000
gaagtgcagc agcgagtact cgcgcagaag caccacactg gcaacttga tgttgagtgc   174060 gaaggccttg acgtcgtagt cgcttttctc tgccatttgc ttcaggtctt ctaggatctt   174120
cgaatggaac gccccgttca agacgccac gcagcatgta cagcctagag aaataaaaca   174180
caaattcaat tgcaaatggt gaataaattg caacaaaacc cacaacagcc tcatttacac   174240
atgctaacga accggaaact tcctgcggct cgaaacccga gacgccactc tccttggcaa   174300
gctcatgcac cgcatccacc agcttctgct ccagcatct gcagcggcaa acatcatcaa   174360
agaagcgcgc agggtcagtc agtcgtgtgt cactgtgcag ctgggcacat catggtgatc   174420
tccggcccca cacgcacgtg taaatgtcca agtcttcgac gtaggcgaag cgcaggcagc   174480
agcgcacaca gacgccgagc tctctcgcgc gcaaaagtcc cgtggcggac agcaggccgc   174540
cacgcagcgc acccgagacg tccatggcga tgctgctcca gtcaagtgtt gatgttgatc   174600
gtcaacagag agcagggact ttcgaccaat tggcgacgtg gtatcgaccc gttttcgacc   174660
aattgtgaag gtgagctcgc cacgtttacg acgcatacaa atcgcaagtg tgactcacgc   174720
gctcccgctc tcggtcacag tcgccgatcg ccgtagcggc atcgcaaggg gggaaagccc   174780
agtcgcagtc agtctcggac gtggcggaca gaagaaagca atcgcagcca tgccgagctt   174840
ctgccccaag tgagttcgtc tgcctctagt ctgcagttat atgccaatgg gagctaacga   174900
acgcgctgtg ccgtgaccag atgcggggac tttgtggaag cggacgcttg cgagaagtgc   174960
ggcgagaagg cggtgcgtga cgttggttta ggcgcggttt taggcgcagg tgctgacgtt   175020
gtagctgcag gtgacgaccc aagagaatcc gtggagggcg gcgtccaagg ttcccggcgg   175080
agagcccatg agcgttcccg cggtgcccac ggccttcacc gccgccgcgc gtatcaaaat   175140
gatggggtgc gtcctcatta gcagtcttag agacttttga ctgctatcag tgcagcgact   175200
gacgccgtgt gtttgattcc ctcgcgtcgt gcctatgtgt gtgcgtgcag ggtgcagccc   175260
ctgccggagc ccgcgcgcaa agagcaggcg gaggcacgct tcaacttcgt gccgcaagat   175320
ccaagcacgc agctggcgct ggccaagggc gatgaggtgg atgtcgtgcg caaggacagc   175380
gacggctggt ggttcgtcat caaggacggc gagaagggcc tcgtgccggg ctcgtacctg   175440
cacatcgaga accccattat ccccgtcacg gatgcggcga tcctcgcggc acgtgagacc   175500
tccaatcagc ggttcatgga gatgcagcaa agctcgggag caactggaca gggtgccgag   175560
ccgggagtgg aataccagtc gccgctggga ctcgaagcgc tcgcgatcgc agactcgtgc   175620
gcgcccaagc cgcccaatgg gcctgccgc gctgatgcca gtctggcgg caccgagttt   175680 aagccgggcg aagtgcgcaa gttgagaaaa tgctacgcct gcaaggagac gattctgggc   175740
cgcacgaaag tgtgcaagga ccagatattc cacgaaatcg taagtggcag tggtcggctt   175800
gcttaaaaca cagtgtgtat gctgattgcg atggtgttta tacagtgtct gctgtgcaaa   175860
ggctgccgcg agtcgatcga agagggcgag gacttcaccc tcatcaagaa aaaggttcac   175920
tgcaagcact ttctagggaa tgctactggc tgagcgctga ccattgtgtt ggaactgtag   175980
gcctaccacg ctgaatgcgc taaagacgtc aaccactgca tggtttgcga taaggtattg   176040
```

```
ctcgctgctg caagcgtttc ggtgttttgc gaaaagttct cacgttgatg catgatgtag   176100
gaaatcttgg gccgagtgta ccgagctggc gatggcgcat tccacaagct ttgcatggtt   176160
tgttcagttt gcaacaaaca agctaaagaa ggtaagcaac gccgttaaac tggaactgaa   176220
ggatggtgga gtgtgcaagc ggatgaaact caaattttga tgttcactta ccgtttgacg   176280
tgacagctgg atcgaagttg gaaaacgacc tcctcatttg cggtgaatgc gtcgcggaga   176340
agggtaagcg catcttacgg tgcaatggcg agtcgaacaa taatgctaac aactacaatg   176400
tggcatgctt gcagagagaa aagagaggga ggagagagaa gccgccctcg aacgtgagcg   176460
ggctgctgcc aaagcgaagg ctgaaaagga ggctgctctt gctgcagcac gcgcgttgga   176520
agaaaagaag gagcgtgaag cacgcgaagc acagaaggct gtcgaagacg ctgcgcgcgc   176580
aaaggttgag gcagaagccg ctgcggctgc ggctgctcgt gcccaggctg agaaggaggc   176640
agcagaggcg gaagcgttgc aaaaggctgc tgcagctgct gtggcaaacg gcaacgggcg   176700
gtctggaacc gacagtctgc gatccagcac atcaaatctt gatgagtttg atttggaagc   176760
tacacccatc gacatgtcgg gtcagaataa tcgtatctcg gaagtatcgg atctggactc   176820
gattcttagc gacggcgatt acgctggata catgggaagt ggccaacggg agtcgctacg   176880
cttgtcagag gttctagacc tcgagtcgta tgatgaccgt ttgtccgact tgagcggcat   176940
ttcagaggga ggtgctggta gaccacgacg ctccacaatt gaaaggaccg tgaacgaaaa   177000
cgcagaggcc ttctcggaag atgaagacga tcgtgagctg tgtggtggtt gcggacttgt   177060
cctggaagga gaagccgttg gtgcattgaa tcagtacttc cactatgagg tacgtgtttg   177120
cacactgtgg agttcatcat gttagaaatc gtttgacgaa caacctatgc tgcttgtgct   177180
gaacagtgct tcaaatgcag tcactgcagt cgtgttattg cggaagatga tggctatgca   177240
gagaaagaca accaggtact cttcttcttg aatttggtac cataccctgc cctggaaact   177300
catctcacat cttgcttttt gcaggctttc caccaagcat gctaccaggc tcgattcgga   177360
aagaagtgcc atcggtgcag caaggttctc aaggggaaaag tcgtcaaggc cctcgatcat   177420
ctctaccacc cggattgctt tgtgtgcttc aattgtagtg cttctctttc aggtacatac   177480
cataatagcc cgctggatcg tatgtgtgaa ctactcaata ctaacacagg gcgtgtgtga   177540
tgttttatcg tccagcagag agtttcttcg agcacgaagg tcaagccgtt tgcgctaaat   177600
gcaaacacga agcaattgct ttggacgaac caagcctccc gtatgtcgtg tgctttctgc   177660
tttaactagc actgcctacc aactaaattt gtgtcatatg ttttgctctg cagagagaac   177720
gtggcaccag tgtctaaagg cattgctggt tatcggttcg acgcccagga tgacacacaa   177780
ttgactattt atccgggcga cgaagtcact atccttcaga aggtttgttc atttagaagg   177840
cggctcttgc tgtaaacgct tcctaacgtt ggcatcttgc attgtgtgcg acaggacgac   177900
gatggctggt ggcttgtgga tttgcgaaac aagcgtggtt acgtgccagg ctcctacttg   177960
atcgagcgcc caattgaaga gccaaagccc cagccgaaga agaagaagag tgccttcaag   178020
agtaagccca acgtacacc gggtctttgc agctcgtgct cgacgcaaaa cccggcgag    178080 gcacgcttct gccgaagctg tggcaacaac ctgaaggcct aactggcgga tgggtaagaa   178140
tgagaaagta acatgcaaca agcgacagtt tgtttagagt acgcgggcgg acgagaccaa   178200
ccggccttat gagccgtgcg atggagtttc ttttgcgcgg cagtggctgt tagatgcttc   178260
gtgtttgctc ttgtgacaag agaatgtcgc tctcgtcccc tgtgttcttc atcatgtagg   178320
tgtttgcgct aaggaaatta actgtcactt cagcgtccca gttttcgtga tgttgtcttc   178380
acttgagtat tttccaacga gaccaccgag catatcgagg ctggaggcga tcatgtggag   178440
```

```
taaagtgacg aaccgctctt ctgcagcttt cctattggcg agcgcggaat gcagtctcgg 178500
cgcaccgttc gcatctggga tcgggtgcag ccatccctct ggcatccctt ggcatcgttg 178560
gagcagtcgc ttatggatgt ggaagtgatg gctcgtcgag tgttctcacc tcactttccg 178620
acgtttgcgc cgtttgcgtc caacgcgatg gcggaagtgt atgacagtga cgacgagttt 178680
ttcaaggacc tgccaatcaa gagaccggag caacagacaa agcagtgtt agaggctgca 178740 acgccgcgtt tctcttaaga gctactacag cgctcaacgc caagatgcag tgcagacaac 178800
gcagcaatga agaggaagc tgctgcgaca ccttcgactg gtgaaggcac cgctgcgcca 178860
agcccatcgt acagtgccgt actcatacag ctacttcgag tgtagtggcc accgtatcgg 178920
cactgctcgt cgacgctatg aagactcgac ggcgaggctg aaggcgacgc acgagcgcga 178980
gatcgacgtc aagaaggtca agatgttgtg gcagcggtcc aatacgcagg acgagggcgg 179040
gcacgagacg atttgctcga gtggcaatcc ggaggagttc gagagggaat ggaccgacac 179100
accgcttggc cgcgcggagg acgagaagct ggccaagtgg atggaggagc gagagcgcag 179160
cgtgtacgtg gccttcggca tcgagtacaa gccagtgatg gagcccaagg tgaagcaaaa 179220
tgacacgacc ccagaggagc gcaaggtggt ggaagagggc gggaaggaga cgatccagga 179280
aatatccaag aggagacgac gcccccgcag ttcttgtcgt gaagcagccg accaggcatg 179340
aagagagtgc cgctccctca tcttgaacga tcgggatcat gttgaagtct caagatttga 179400
gcgctgaaaa caagagtaaa gcttcacaaa aggcagcttc ggtatgttac aaattaattg 179460
gtgtctgctc tcgttcgcgt cttctcctcc gcttcgcttg tctcccccgt ctcgctcctc 179520
tccttggctc ttttcctatt tctccgtttg tgcgagcttg gattttgtga tacttccgct 179580
tccgcatcaa gctgtgggtc cccgtagtat cgaaatgcaa attgttcatg ttcattctga 179640
acgagatctg caaggcatcg cccagtccag acgtcgacag gatactatta gtgcagcgag 179700
ggactacatc cttgccacga tccacggacg cgagtgtcag cgcatgaaga cgatagcttc 179760
gctgattaag aagtccaaga cggagtgcga gagcctcacg tacgttggtt cctctctttc 179820
gctggtccct atcgtggtta attcacggta tcttgttgtg gtttgtagtg tctgtcattg 179880
ctcaaaaggt tgtccacggg ctggagaaag ttgtacgttc agactgaagt ccgtcttgct 179940
cggtcgtccg cctcatttgg agtgatttct gtgctgctgc aggaaatgtg ttcgggttgc 180000
caagatgcga tgcgccgtcc aaagctggtg gcgttggccg acgccgacag caggcgacgc 180060
ggttcccttg gtgcgtgttg gtgtcagatg ggagactaca tgtaagctta tagccatctg 180120
accgttgttc gtggtctcca tcagccccga gctcgaacca actgcgcgag gagcaaaaga 180180
tcctcgagat cgacgtcaag cccggctgga aggacgacac caaggtgact tttgaaggtc 180240
aggacgacgc gctgcccggt cgaccagctc aagacatcgt gttcgtcatc aagcagaagc 180300
cgcacaataa gttcacgcgt gatggcgaca acctgctgta ccgcgcctag ctgtcgctgc 180360
gagacgcact gctgggcagc ggcacgttga ccatcaagac gctggacgga cgcgaggtgc 180420
ccgttcctct gggaggcgtc gtcgctcccg gtacgcggat ggtgatcgcg ggcgagggca 180480
tgccgctgca gaagagaccc tcgcagcgag gtaacctcgt ggtggagttc gacgtgcagt 180540
tccccaccaa actcacagag gcgcagaaga gcatggagcg ccaggtattg taagcttacc 180600
agttttgtca ggcgcggttc cgaagcccca ggccgcgccg caagatcata cgccagcgcc 180660
agctgagtgc gacgtgcttc ggtgtgcgag cgtcatccgt ttagaagcac caagatgaac 180720
aacaaggacg ttgcttttgt ccaaatacgt acacgctggc acatttcaca aatgcttacg 180780
```

```
atgcacccca ccctttttaag cgcgtggcgg cgacgcacca ctaccaccac agtgcagcaa   180840
cagcagcagc ctagtcgcgc atcgaacacg gacagcagca gctcgcgcag attgttgccg   180900
aacttcttct tgtacacggg cttgatgtcg cgcagcacga tgtggtagcg caccacggcc   180960
cttacgcatc atagcaatgc cttcgttgac ttcgctcatg ggcatctgtt gaacgagttc   181020
aaccacatcc tacacataaa caacgtgatg cttggattcg tactttacaa tctcaaaatt   181080
gtattttagc tacccatcat ccgagctgtg cctccagtca ttccccttc caacgtcatg    181140 gacgagcagc aggacgagcc catgctcaag ccctgcggcg gcggcgcctc agacgccagc   181200
gctgcgcctt cgccatacca gcttaacggg ttcggcgtgg acgcggctac gggcgagtcc   181260
aagcgctggc tgcagagcct ggagaaatgc atccgcgcca tcgtgagcat ccgcctgctg   181320
agcgtgcgcg ccttcgacgg caacggcgcc agcttcagcg tggccacggg attcgtggtg   181380
gacatggaga ggggcatcat cctcacgaac cgccacgtgg tgacgcccgg accggtcgtg   181440
gccgacgcca ttttcctcaa taaggaggag gtggatcttg tgcccgtcta caggtgatga   181500
ctcaccctga ccccatgaac agaggggaga tgggctcatt gcttttttct ttgctgtttg   181560
gccgtaggga ccccgtgcac gactttggct tcttccactt cgaccccaag aaggtcaagt   181620
tcctgcagct ccacgagatc ccgctgcgac ctgaagaggc caagagtggg tgacgattaa   181680
cgcacgagtt tctgcatttt aaggggacgt attgacgggt tttggtgctt gttgctgtga   181740
cttctttagt cggtgcggag attcgtgtgg tgggcaacga cgctggcgag aagttgtcca   181800
tcttgccggg tatttggcc aagttggacc gcgacgcgcc gtcctacggc tccagcacgt    181860
acaacgactt caacacgttt tactttgcag cggcagcag cactagcgga ggatcgagcg    181920
gctcgccggt gctaaacatc gatgggtgcg ctatcgcgct caatgcgggt ggagcgaaga   181980
aggcggcgtc gtctttttac ctgcctctgg accgagttgt gcgagttctt ggacttattc   182040
agcagggcgt gcccgtgccg cgcggcacaa ttcagactat tttccgtcac acggcatttg   182100
atgaagtgcg tcgactgggt cttttccggcg aaacagaggc gctggtgcgg caacaatttc   182160
cgcaggagac agggatgcta gtgatagacc aggtcatcca gggaggaccg gcgcatgatc   182220
agctgcggac aggtgacgtg ctgatcaagt ttgccgatca gtacggggca acgtttctaa   182280
acattgaaga gttcctggat tctcatgttg gagagaccgt cgaagctcag tttcagcgcg   182340
gagaagaaca gtatacagcc accctgagcg tccaagattt acattctatt cgccagaca   182400 gatatttgga aattggaggt ggcatcgtgc atgcactttc ctaccagcaa gctcgcaacg   182460
cttcactacc tgtcggtggc gtgtatctgg cccaagcagg tcatgtgttc atgaaagcac   182520
atttggccca gccctgcatc atcacatccg tggcggggca acccactccg acattagatg   182580
actttgcgcg cgtgatggcc tcactgccca acggatttcg tacggtattg cgctacttca   182640
tgattcgcga tcgccatcgt gtccgcacag ccttcatcat gatggatcgt ctttggttcc   182700
caatgcagat gtgtacgcgc aacgacgagg acgggctgtg gtattccaag tcatatattc   182760
aggatgatac gtcatcactt gtggcagcta cagactccaa tccgacattt gccccagcgc   182820
cattaagctt tccgggaggc aatgcactgg gcaagaaaac gttgctgtcc cttgtaatgg   182880
tgtcatttga cattccttat atgattgatg gtatttcgag ctcaagctac cacgaatgg    182940 gagtcgtggt cgatgctgag cgaggctttg tgcttgtgga ccagaatacc gtcccatcg    183000 cgttaggcga tgtgttgatt acgattgctg ctaccgttga gattcctgcc aaagtggttt   183060
ttgtgcacca agtccacaac ttttcgatcg tccagtacga cccaatgca cttggtgctg    183120 tagccagcca catcaaaaac gtagtgctgg cggataagcc gttggaggtg ggcgagacag   183180
```

```
ccgattacat cggcctcagt agtaactgga ctgtggttac catgaagtct gtggttacta    183240
aactagaccg tcttgtgctg cgcgatttcc agccgccgcg ctacaaggcg tgcaacatcg    183300
aagtcctgca tttcgatcgt atcacgaagt ctgtaggcgg tgttttcatt gacgaccaag    183360
gcgctgtcaa cgcactctgg cttteattta gctaccagga cagtgccggc cgcaaggaag    183420
tctttcgtgg cctgccagtt gagattgttc ggcccatcat tgacgagctt cagacgtctc    183480
gtatcccggc atcaatcaac atcctaccgg cgcagttgtt gacgtactcg ctctcgaagg    183540
cgcgttctgg tcttggactc tcggacacat ggattcaaaa actcgaggcc tgttacgaag    183600
acaagcggca ggtgctcgga atcaaaagat gtgctgctgg tacggactgt gccagtaagc    183660
ttgagagcgg cgacttgctt ctagctgtcg atgggcaggc tgtggtgcgc gatgcagatg    183720
tagagcgcgc ggttgatggt aaaacagagc tgaaggcttt ggtggtgcgt gatcagaagg    183780
aaatgatagt tactgtaagc acatctcagc tctcagcgat gggcacagat cgtgtaattg    183840
tctggtgcgt tctcgtcatt cagagtccgc actacgctgt cgcaagcctg gctatattc    183900
cggaagaagg cggcggtgtg tactgttcgc ggtggtgcta tggatcccca gcgcataagt    183960
acggattgcg agcaaccatt tggcttgtgg aagtcaacgg tgaacctaca cgcacgttag    184020
acgatttctt gcgtgtggta gaacgcctgg aaaaccgaga atcggtgcgt ctgaaaacga    184080
tttccatcac acgaagccta aggtattcac gctcaaaacg gactatcact actgcctac    184140
gatcgagctg cacagagagg aatgggactg gaagtatgtg gagcaccctg tggtcacata    184200
agtgttgtcc tgagtgcagt gaagaccacc gcattcaata ttcttcatca gcccccaac    184260
ccagaaatca agaaatgaga agaccccgaa gaataataca tagagcacac tacacagagt    184320
gcgaccgcac cgccatcgct ttgaaatata cacaggtgcg tgtttgcctc acatcccgat    184380
gactattatt aggaaaccag cttggactct tacttccaac gtcgtgttgc acagctcaaa    184440
agcagatggg gacggtgggt gttcaaattg aagatttaag cgtgcgttgt ctaccggcaa    184500
ggacagaaga ctgctccgag agtgaaggta ctgtgtacat tgcccaacag gagcagcagc    184560
gatccaacac ttcagctcaa gacgacgaga agctcgatgt tatccaaaca aagatgttca    184620
agcgacgacg acttgcaact gctgtcctcg atggtgaccc gggacgtgcc ctcccaccaa    184680
agtgttgcaa gcgctgcaag agcgatttga acggaaaact tatggtgcgg tgcgctacgt    184740
gcccattccg gtgtcacttg tattgcttct cacctccact caagcagcac cctgggttcc    184800
tgatccggcg gcaacaacag caaattggtg gccaaaatga tgatacttcg ccaatttgga    184860
agtgtgaaaa gtgtgaaggc acgtcggttg tatttaatgt caaccccaga ccttcgtcag    184920
tgacgacatc atcgacacgt agaagctccc tcgtgaagcg caaaaacgac acacaagcgc    184980
agtcaaccac tactacgaca attacggaag aaaaggacgc aggatggatc caaccgcagt    185040
ggataaaaaa tgccgacgtt gtgtttgatt ggcatcgctt tcgagcagaa aaggccaatg    185100
tacttcgcca ccacgagact gacgctgatc aaaagcgtag tggtgttgac gaactggttt    185160
tttattcgaa atcctatgcg ctgatgaaaa aagttgcagc aatttggcgc ggacttgtat    185220
taaagcgacg atatcgacac cagcaagaac tcgaagcgaa agccatgaat tatccaggtg    185280
tgaagcgcaa ggtaatgtgt gtgcgaatat caaccgagaa agacacatca gactttagca    185340
aggaggagtt gtgtgcagaa gaggaagacg tggatctggt tgaggacatg aaccggtaca    185400
gaccatactc tcggagacct ccacggcttc caattctgtg ggaaggagaa cctccaagcg    185460
cattaatgtg ttggactacg ggtgagagat ccgacgttgc tgatgtcttg gctgagatcg    185520
```

```
aagagcgggt gtgcttagcg tttgaggatg ctgatgcacc tcccacgaaa gaaacgataa   185580
ttgctaccct cgaagatgtt actgacacaa actcagcggg atgcaccgtt gctaacgtca   185640
aaggtgttaa cattcgcaca gctgctgcga ttattcagag gatattcgct cgccattgta   185700
tttggcgtcg aagaactgat cgagccaatc gacaacgacg cgtgatcgaa gaagcgaaac   185760
gcaaagcgaa ggcgcggtca tcggttgctc tcttacggac gtgcatccag tttattgttc   185820
tgcttgtcag aatgcttagt caggctcaaa agaagaaagc aatgctgttg gtgctacacg   185880
atgcagctga agaaacccaa gtaaagaata gcacgttgac gaaggagcag gatggaaacc   185940
aagatgcagc acgtttagct cgagagcgta cacagaaaat gtctgttgtg caaattcgtc   186000
gtttttttcat tcggcgagtc cacccgtacg tgaagctgaa gaaaactgtg atggcacggc   186060
gaatacagcg ttggtggaaa cacaaaacat acctgtgcaa gtggcgggag actgcaatta   186120
cgattcgact ttctcataga agtcagtcat gcacccgaat tcagcggttt tacaggcaga   186180
cccgggctcg agctcaattt cgcgttttga tcgaaaaaca cgcactgaag aaactacggc   186240
gagccctaac aggctggttg attttacgtc ttgctagaaa ggaagctaaa cgtagtgctg   186300
cgtacgaagc tgcacagctc acattgacag aagagagctc cataccgcaa gacgcgcctc   186360
tggatgaaat ccttgagaag cgaggattgg acctctacga acagggcgat ttctggaatg   186420
ctgcatcgat acttgagcga ctttgtgaga tgagaacagg gaagttaacc cgagcattgc   186480
aacaagcact tgcatattca caccacaggg catggtacac atcttacgac cagtttaacc   186540
tgcatcgagc gtatgagttg tactgcgact cacttgaggg ctcaccaaat ggtgacccac   186600
gtgtagatcc ttccgtacta catgaccttg cgatcgtaat gatgcacatg gaacactttg   186660
gcgactcctt gcgcttgcta gccaagctga tcgagtactt cgcacgacaa cctcagtttt   186720
cactttggct gctacttgcc gctgtacaat tacagcaacg cggcgagtgg gaacaaagtg   186780
tcgggtatct gacgtatctt cacgacttcc cccccactcc gtatttggag cgagatatac   186840
tggcattgtg tgcaatcgga tacgaacaat taggaattgc agcggctaaa tcgtctgagg   186900
gacgcaatgc aaactccaat tttgctcaag aggcatggcg tgctgcttta cgacaatgga   186960
atctcgagaa agttactgct ggagaagctg acggaaccgc gcgaagtcga ggaaatgggc   187020
gtacgttgac gttacgacaa aagtgggaac tgctaacaaa cctggggcaa cgagctctag   187080
agcagggtca ttatcttttg gcttgcaggg tttacatcta tgccttagaa cgtgaatcac   187140
cggcttctga cctcacttca ccttctccgt acgccagcta ctacaaacaa gaaaaacata   187200
cagcctggtg gaatcttgcc gatgcgtttc gccaccttgg gcacctcgat ttgtatttaa   187260
ccgctgcaca gcgcagccag actggcagct cagctgaaga agtcgacgaa aacctgcaag   187320
aaagctggcg agagcttgcg agccaacagg catccagttt cgagaccgaa ctaaggacac   187380
tgacagtgct tgaaaaactg cgacaactag ctggtatcgc taagtaatgt gcaaaatgaa   187440
atgtgtatta cggagatgta gatagaattt aatcgtcagt tgaatgttgc cggacgttca   187500
cgtcgtctgt atcttcaatt gtagatgtca actctgccat gagatgttca tcgtgcctgt   187560
gatgtcctcc tgcatttgta gatgcggtca ttcgcctgcg ttgagacttc cgcctgcgtg   187620
gaacggcatc ttcgtttgat ggctgcgcct gaatgaaggt actttgacgt tgtgcgcaat   187680
tactttgcg ctcagatcct cgtcgctgaa tatcttgtaa agctgcgagt gcatcgcgtt   187740
ctttagctcg catcgctaga ccacgggcgc cagccagcgc acgattaaaa tgcagcggat   187800
tttgtgtcat agtcgcaacc atctcgagct cgtcgtcgtc gtcatcgtca ctgtcatcat   187860
ctccacgctt tccaccctgc tctttatctt tttggttgcg atgccagtga ctaaaaactt   187920
```

```
tctgcacccg agtaatacgt ttgtagtagt cgggtcgaag cgctacaaca agctctgtta 187980
tcagaactag tgcaaagtac acacaacttg cggctacaag aagtgtggtg gcaacggcca 188040
gcatttgtgc cgaagtactc gtgaatccag tatcgttact tccaagccga ccgctttcaa 188100
acattacgcc ggccagtaac acgagagaag cgctgaacag gagacacgcc tccactgtgt 188160
tgtgatccca gagatatccg accacgttct gcggttcttg tgatgcgagg atggcttcat 188220
tagctccacg aagtcctgaa gtgggcggag cagaactacc agtcacacca ttcccccat 188280
ggtcaccatg gccgctcttc caggcagtta ccgtcgaagc gtgcatttca agacgcaggt 188340
gagctggttg aatgaatgcc tctcccttgg cttttgcacg ccgagtttcc aacaggactc 188400
gtttggcata gtccgctaag acccgctgtg tctcatagac actcatgtat gggcggcagc 188460
gtacttgtag cgcgtagttc acaaacaata caaaggtcgc tgttgccagt tggaacactg 188520
ggtcttgacg gaacagaagc ccgatacctg cgagtaggaa cttcctcagg ataatgagca 188580
ccatccagta ccagtagccc ggcttgaatt gataatacaa ttttgaaaac ttcttgcgga 188640
acacccagca gtttggattg gttcggcgac ttgttcctct ctgcatagcc cgtagaagct 188700
gatcttccat gaccaacgct cgattacgag acaacgtcag aagtacaaag agtggatagc 188760
ccagcgaata taccacaaat gccagcactg cgtacgggaa gagctgcatg tgcaacccgc 188820
ctggtttgaa gcactgagta taaatggcca ccatgtacag cttccgtcc gacgggatcg 188880
atccgacgca gttgaagata tccaatgtcg ttcgtgtgag atacaagaaa agataataca 188940
tcatcacaag cgttgatccg aaaagctgcg gcaggtgcga tgttagacgt gtgcgtcgtt 189000
tctttataaa gcgtttgtaa gcgtaaagag ctacaaagac cccgagcgcc gtggccgcca 189060
tgacaagtgg gaacacctcg atgatgaacc acttattcac aaacgagacc tggagtgaaa 189120
aacactcggg tgcaatcagc tccaaattga ggttgaatgc agacagagtc gcgaataaat 189180
taatcaacga cgttggccac gaaatacgag cgttgccgaa gatggagagt gtctggaagt 189240
aatcgatacc gatagatagt agaccaaggc tcactccttt tcgagtaaga agataactca 189300
cgatggatgc aacactaata cagacgacca caattgcgac cgaccccac ttgttctccg 189360
ggcacacgtt gcactctgaa ttgagcttgt ggtagtttgt ctcgcattcg ccgcaccta 189420
tgtcagtata accctccgcg catttgttgg cacctaggca cgcatacatg ggatcgcatg 189480
cgaggacaac ctcaccttca cgccagtagc caggtttggc taacggcatc tcgtccccac 189540
cagcacaagt agcccctct ggacactcgt cgcagaattc cgtcgaagtt cggtagtaac 189600
ctggactgca ttgaaacttc agctgtgttt gactggtagc agacatcacg ttgccaccta 189660
ccgacagaat aatgctcgta acaccagcct tcgttttggg tggataccat accaattctg 189720
aggcactcgt ccagactacg gtcccggttg agttctctgt tgatacgttt gtggaggcaa 189780
ttgaactgtc ggacactaac tgccgatgag acgtgtcttc aaaaatactc gagatacttg 189840
gcaagtagga gatgcctggg gaactcaatt tgcgggatat tgactgtact gtatctgacg 189900
tatcgtccga gccagcaaaa taaatggtaa ttgcatcatt ggggaaacaa ccaaagtcgg 189960
tacccttgat cgtgatagcg ttggctccat ttgcatcggg ctgatttggc atctgagcag 190020
tgatgacggg ctgattgtac gaaaatgtta aggcgttact ggattggttg tcaactataa 190080
cgtagaccaa aacgtcagca ccataccag caggcacact tgtcacaatt acaaagtcag 190140
agtggcttgt gaaatcttca gacacatcgg gtgcaggatc tgttgtctca cacatcattt 190200
gagcccctgt agtgtcgtta cagacctcaa ggaaaccaaa cgtagggctc acgacgtaca 190260
```

-continued

```
gcgatggata gcagacaaac gtatcagtat caatacaggg accgctggtc gagtattcac   190320
atgtgtcgga tccacaagcc ctcgggtgag aactttggct atcaacgcgt gcatcccggc   190380
caccaataag cactttagca cgagttgatc cgaaattttt accgtaaaga gagatggtgt   190440
aacctccgca agtcgacaag ttggtcgtat tggtttcgta gccgatcagc tcagggctct   190500
gatagccgaa tgcgattgat tgttcgcaa gctgaagccc tgatacagtc atattgacaa    190560
tacgtgagat gccttgtcct ggtggcaagt tgaatttgat gtttgaatgg ctgaagtaca   190620
cgatgtcatc gctcgtaata ttcaccgatt ccatcacgct atcggtgctg gccagctcga   190680
ggtgccaatc aaacgtctgg acaccaaagt ttttgccggc aagtgtgata gctactctct   190740
cgcacagctc cgtttctgca ggacaggcac gtgaggctgc ctttgagcaa gtgcccgggt   190800
tgactttcat agccaccgca ctaacggtg gatccaccat cacattgagc caacctgcag    190860
gtgttgggtt cactgtcgcg gtactagcac gataaatacg ttcatcactt tgtaacaatt   190920
gccaaacccc accggtgaat agcagctgta catttgtcgc tacatcactc atgtacactg   190980
gcttgttgct ggagtacaca tctgcctctg cagtgactgt tactttttgc aacacccat    191040
ttagcagtgt ttccacgcaa tagctaccaa gctcggtggt agttgagctt gcttcgagga   191100
aattgcactc aaacggtgcc aaaagcgttg cgcaggacg tctggatca gtgcagctgc     191160
aggaatacccc agaggtcggg ccattgcttt tactaatgct gtagacgagc gggggtcat   191220
agctgaaagt cacattcttg tcagcattaa cttgaccact gacagtgact acgattgtat   191280
ggccacttcc ttggccctcg cttgtcatgc aagtaatcac tgcatgctta acactgttga   191340
ttgtgcatga aaaatatca ccaattaaaa cggtatgagc gcctgatagc tcgcttgtcc    191400
cgaaattctc gccttggatc gtcatcaagg aaccaccttc ggtggtagcg tcaaccactt   191460
cgacattata aatcacaggg gcgttgtagg aaaacaccgt tgcagtttct tggttccccg   191520
cggtcaactt tattgtgtag ttctgcctt ccccaggagg aatagtgact gtagcacgcg    191580
agtgatcata cgacgtgatt tcaagtgaaa cagttctgtt ggaattccca gtcatcgaaa   191640
tgactggcgt ggtaccgaag tttgatccaa cgagagaaac aacctttccg gttgtagaag   191700
cagaagtggc agagcttccg tcccaatcca cgtttggcgg aatataactc aaataccgtg   191760
gactacttag agttatacct cgtgttacaa gaagtggaag catgacgcct tgaccactcg   191820
gcactgtgca cgaaatcagg cggatattgc tcacccctgt gacccccca gacagaagta    191880
tgctggaagg gatgaccgga gtgctcaccg cgacattggt acaattgttt ccacccactg   191940
ttacccgggg actacggcca acatacttcg tgtatagact tagtgtagct ccaccactag   192000
ttgctgattg gtagctaaac accccgaca taacgggagt agttgctact gttcggaata    192060
agctcgtgtt gccatccaat cggtgactcg ttgtacaatc cagtaccccg caggtcgagc   192120
taagtgtgta ccagtcgaga atggacggat catcccagct gaacggcgca gaattactca   192180
gcagcttctc tctgccaatc acaatggtca cgtatcctag acggcctacg tactgcggga   192240
ttatgatggt gttatgagac caagacaaaa cctcaactga agattcatag ctagcacctt   192300
ctaggttgct tgcggtgata aggtacttg acactatcac gcgccccgag gtatagaaat    192360
tgtttccagt aatagtaagt cggatgcaag aaggtagaca ctcagtgggg ccttcgtccg   192420
tagataccga gtcaatcaac ggaggcccat agctaattgg ctgtggtgca cttctttgaa   192480
cactcgacgt accgaccaac acttgcagcg atccaccata gccataaccc accggtacac   192540
gaatcacaat gtactcgctg ctgttgctgt cactaaaatc tccaacccca attataggaa   192600
tgcgataact tgacaaactt gcttgcggtg gagtgaactc aacgcgtgct gctgcgaaag   192660
```

```
gcacgttcgc cccaagattt tctccgataa cagtaatctc cgtagtccca tcagttgatg 192720
caacggaagg gtacaatgag taaaccacag gcggtgcata tgagctcgtg gcagtcgaca 192780
atcttgattc ttgatcaccg actgacacca tccaggatag attcgcccct acaccaggaa 192840
cagatgtgca aatgattgtg gaatcattgt gctcgagcac ttccttcaca tgatagtctc 192900
ttcctgaatt tccatacgaa attccatcga tgactacagt atcgggccca aaattgcctc 192960
ctcgaagaac gactgcctgc ccaccgcgaa ctagagcgtt ggttgcccca ttaccctcaa 193020
tcgaagtgat aaatggtctt gaataactaa tcgtgggcgt tgcgctggtt aaaccatcga 193080
ttgtgactat ccaagcaagg cgattgccca caccaggtgc ggtcgtacag aggatccgtt 193140
cgtggtcgac cacgatggca caatcctcag ccgtgaactc gtcaccattg acgccatatg 193200
tcacactcga aatggtggat gcattgatgg tgccaaagtt cttgcccgtg ataacaactt 193260
gctgatcccc acttgtcttg atttcggttt ctccatccgg gcgaaacact tttgtcacaa 193320
tcggtcctgc atacgatgag ttgtgtgcag tccacaggga tgcttggcct tcgatggtga 193380
cacgccacga gtggaacgag ccactaccag ccacagacac acactgtatc aaattatgat 193440
tggtcggatc gttgtatttt cgtttgcagt tgacactgcg aaggatcgta acattgtcga 193500
aagagtactc gacaatgggg tccgtataga cagcaccgtc aggtccgaag ttttccccgc 193560
ggagttcaaa gaccgttcct cccgcggtag gaacatcttt gaagcccatg acttcaaaga 193620 gttcggggc cttataagaa gttgtgattg tagtagtcga gtaactcttc tgatcatcca 193680
cggaaacctg ccatcggaat aatcctccag ctccgggttg agataaacag gataactgca 193740
cgtgatcaat gacaacctta cagtcatcaa gctcaaacga gtgaacgttg ttactatacc 193800
acacagtgac tttgccacat ccctgacacc cgtatccagc tccgttcacc attacgatgt 193860
cacctccggt ggtcaacatt ccggcagcca cagttacatc agaaatagtc ggaaacgcat 193920
agtgacagct agatgcgaaa gcggtgctgg cctgaccgcg aactaccaca acgaatgcga 193980
gatcagcgcc tgtaccaaca acactgcgac acgcgatata atgacctgtt gcatcttcgc 194040
gtacctcaca gctttgggct tcgaattcgg agccatatac aacgacaaga tatgcatctg 194100
cgcttgttat ctgcgttgac cccaggtttt caccataaat cctaatattg tttgtgttgc 194160
taccatcggt cggtagcgca ctgttgcaga caacagagcc tataaccgga acaccatagg 194220
atgccagggg aaccgaggag gatgcttgga atacggtttc tccaatagtt gggacctcca 194280
ttaccaaagt aacgttccag tatagatttg cgccaacacc tggcgttgac gtgcatgcaa 194340
ttccggtgtt cccattaacg agcccacagc ttgtagcgcg gtatagtgca gtggctccat 194400
acgccccata ttccacgatg agctgcttga ttacaactga gttatcagct cgttgcttga 194460
acccaatgtt tgaaccagtg agtaagaacc tttcaccccc cttcgtatcg aggtctgagg 194520
agctggtatc cataagtctg aacgtatcaa tagtagtatc tagaacgtca accacttcga 194580
ccgcgacctg ttttacaatc gtaaacgcat tgaaaccact agaatcacga gcttcaacgc 194640
tcactgtata ggcttgaaca gcctcgtagt ctatcagccc atctactatc aaatcaccgc 194700
ttgcagcatc aatgcggaat acattcagtc ctggtggata cacatcgatc gcgtaccgaa 194760
ttgtcttgaa ttcgtcagag taaatatctg ggtctgccgt cttgatttga agcaagaccg 194820
agttaattgc cgtattttcg aaaacagaat atgtcgctgg aaccccaata aatgaatgaa 194880
tctcatttac atcctccact tcaactgtga taccagccac cgcagtcagc ttaccagcat 194940
cctgagcaat caaagtgaag ctgtagactt gtcgtacctc gaagttaaag ctttgtttga 195000
```

```
ccacaatcct agcacacagc tcgtggctat agtcctcttc aacttgtacc gcgaaaagag   195060
agcaatcagc tgtatttgca cacgaaatcg tgtaagcaag tgaataacca tcgccttcgt   195120
caggatcagc cgcactgata caacgcggaa gggctagatt caccgcttca ttctctttta   195180
tctggaacgc gtaagactgg tcactgaata caggtgcctc gttgacattt atgacctgaa   195240
cagtgacgtc ttgtgtactg cacatgtgtg ctggatcaca tgccgctact gtgcatacga   195300
atgcgcgttt cttctcgaaa tccaaagtgc gtcctgcacg aagcgtcaga gcgccatttg   195360
ccaatccaag gataaacatg tctgaacagt atgtgtcggc tttcgactgc aatgtaaact   195420
gaattgggtc gctgtctgga tcactgacaa aatgagatag ggaggccccc gcttgcattc   195480
ctgcccctga atttcagct atcacgagtg acgacggcaa cgtgcttaac cagacaggtg   195540
caaagtttga ctttgtcgtt agaacttgaa tgagtccgtt acccgaacag tgatcatagc   195600
tggtgtcggt aacagcaact ttcacatagt attgagccgg gtataccagc tcggcgttta   195660
aagggttccg accaagtcta agttgacctg tcagcacgtc tattagaatc aaacccgctg   195720
aagcatttgt ctccaagatg ctgtacgtga gagtatcgga acatcttgg tctttacccg   195780
gaagtggata gccaatttga gtggtgacag aggatcgctc tctcaccgtg aatgttaaag   195840
aagccagcac ggggcagtca tttgcgttga aacagtcac agttatacga ctctcagtat   195900
atagagacgt tgttttcact gtcttgtctg aaattcgaac tgtaagcaca tattgagact   195960
gagtttcgta atctggcagg gatgatcctt tccaaactaa gcccacttga ccgttgatgc   196020
atacagtcga ttcaagaacc cctgcggaga ctaatccatt tactgtcgtg tcatccacca   196080
actggaattg tgcgctagtc ccgataattt gatagaacga gcacgatgca ctgtctggat   196140
cagtagcgct aaacgtgcac gcggctgtgc cttgttcgtt caaaatagtc ggggtattct   196200
ccactattac acaagtaaca tcactcatca aaggcatctc ggggacatca gtaaccgtta   196260
ctgtgacgta gccacttcca cataaacttg tctgcgctgc atcgcaaact cttatgttaa   196320
gattgaagcg agtagggtcc ttctcaaagt ctagagagcg tgttgtcttc aaagaccccg   196380
tctgtggatc aatttggaac ggtgcaaagc tatccacaag ggcaaaaata ttgtctgagc   196440
tgcgatcagg atcaacatac cttgctacta aaacactagt actagcagcc atattctctg   196500
ggacagaccc attgatgcca gtaacaacct caggaggctc gttttcgtcg agtacggtga   196560
ctgtaacgtt tagataggac caatactcac cgtcagaata cgctactttc agctcatact   196620
gagctttgct ctcaaaattc aaagacacaa gtgtttgcag ctgaccatca cttcgaatcg   196680
aaaactctga ttcgttttcca ctggaaatac cttcttttat caaaaaccca taactgctcc   196740
ccacaactcc atcaacgtcc acgatttgaa taggtcttcc aactaaggac cctggagaga   196800
gattttcttt tatgacgaac atatctgcca gcagagtggg gggttcgttg acattttgga   196860
ccgataaagt aataatagta gatgtaataa ttggcccaca ctgagactcc tccagtagca   196920
tgtggcatcc cactccattg tcttcgactg taatttcaat atagagtact ggcattgttt   196980
catagtcaaa aggagccatc gaatacagcc caccgttccc ggaaacgcga atataatcac   197040
tagcattcgt tcgaaagaac agctcagaat tcttatcagg atcagtggcc actacagtcc   197100
cgataaacgt tccattaggt tcgttttcta gtatactttg agaactagag tgagcgaatt   197160
gaggagcctc atttacatca agtatcgtga cctccacgat tgcttgcgac tccagagcaa   197220
caggatatcc tgaatcaata acacggacgc caaaggaata gcgattggta ctttcgtagt   197280
ctagattatc ccactgtact accagttgcc cagagcagct ttcgagccga aatgcaaac    197340
cgccagcatt tcgattcacc agctcatatc gtaaattctc ggtctgacca cgatccggat   197400
```

```
caatagcacg catgggcgtt ccaaatggta gccccgatat ggaattttca ggtacgctga  197460
atgaatagta tgcttgctgg aaaattggag gttcgttaac atccaagact ttgatctgaa  197520
tttcgcggtc actgtacaga ccagctatat cagaaacctg gatgcgaacc atgaccaatg  197580
aattcttctc gaaatcaaaa cttgaactat tgcgtacaga cacatgtcca gccggcgtca  197640
ataaaacgtc tggtgatgga aatgctagtt gaaatgctat ccgatcgttg aagtcgggat  197700
cactaccaac aagctcacca accatggtac aacagcggg attctcttga atctcgaaat  197760
aactatcaga aaggatgggt gcctcattca catcatcaac aaaaacaaat aatgtggcct  197820
ctcccagtaa ctcctcgcta tcgacaccaa tcacaacgac ttgcaatggc tggtcgcggg  197880
aatcaatgtc ttcgtaattg agcgtcgggt tagtgagaac cagctctcca gatgccgtga  197940
caccaaacca atcgctcttt gaaccatgga gaaaaaaatc taagaagcc ggatacgcac  198000
caaaatgca cagcatgctc gttgatgttg tgtcaggtat ctcaaacacc ccgaggacgt  198060
ttttttttat atatatatcg aaaataagcg cacttgcact actttgtgct attgcagttt  198120
gaccgccact ctttatgaat gagttcttcg atacccactc tggaacaagg tcagcatcct  198180
gctcgaccaa aacaaacaaa ctgcctcggc tcgctaaaaa cagcgcggta ctcgacaaag  198240
acactgctgt aggtgtggat atcacgaagg catttgccag ctgaggtgga atgtctatcc  198300
attcgaaatc agaagaacca gagaatacag atccttttc tttcagactt gacactatag  198360
cattgcctcc agctggttcg gtcaacgtca aatagtattc atcgtcgtgc tctggatcgg  198420
aaacattaat atagcctaag ctagttccaa ttactgcgtt ttcatacacg cggtacgctt  198480
taccagtgag aacaggtgct tcgttgatat tcaaaatgaa tatccagacg gtggtaatcg  198540
cagttgcttg gccatctgag cactgaacac tgagttcata ttgccgttgt gtctcgaaat  198600
caagaaaagc tgtttccgca tacacaattc cacttttatg ttctacactg aaggctgccg  198660
tatcgttaag aatgttgaaa tataactcgt caccgatgtc ttcatcaaag caaggaatca  198720
cccccagttg ctctaagttt cgcgagtgtg tagatgcggc tggtttcgat actaccgact  198780
ctcttgctgt aaagttgaca ggctgtagca ctggcggatc gttcacattc aaaaccgtaa  198840
ccagaagcgt tgccgaaaca tgaagtcctg caacgtcggt tgcaacaacg ttaacggtga  198900
tcgacggtgt agtttcgaag tttatcttgt aatcgtcgac tactgttagc accccagttg  198960
ctgcatcgat attaaactgt gaagagtccg cattttgcaa cgaaaacttc aatatatcac  199020
caaagtcttg gtcgatggct tttacgtatc cgacgatcgt accatgtgcg ctcatttctt  199080
tcacaactag agactgctct ccagaaaattg ctggagcttc attcacatca ataacactaa  199140
tcacaatgtc gttgctgcaa gcgagtgagg caccagtact tggaacatca ttcgcttgat  199200
aacgaatgcg atacagactt tgtgtttcaa aatccgcgaa agtaagttga ttcgcagcaa  199260
actgaactac gccagtggcg taatcgaccg cgaacgatcg actatcattt gtggaaatca  199320
attgaaaaac gtgattttgc ccagcatcct tgtcttgcac tactatctgg cacaaacctt  199380
gcgtcccagg cagtcctctg ttaatcaaag gagaattttc cagtatccaa cactgaaagg  199440
gcgggcaaat tggaggctca ttgtcgttta cgaccgagat aatcacattg gtggaattcg  199500
ttaaccctga tgaatcagtc acacgtgcac taagctgata agcttcattg ttgtctgcat  199560
ataaaacccc ttgctttatc agggatatta ctcctgagtc agaagatatc gcaaagatac  199620
tgctcacatc tgaggttgca gtatcctcca tattccatcc atactgaatt gtatcgttca  199680
aatcgggatc tgtagcttgg acgacaccaa taagcgagcc tccaggggcc agttcatgaa  199740
```

```
cagatagctc atatgaagat agtctgaaca caggcgattc cggtgcatcc gataccataa   199800
ttgtaaaatt gaaatttgtc gaggtgttat ccgatgcggt cactgccct cgtatggtta   199860 gcattggctc aggcccaccg aaattcacct ttctcatggc ttcgtagtca agagctactt   199920
tcgttgttgc tacccaacca tcagcatcaa ttgtgatggc attagcgata ggacgcgaat   199980
cttgtagaga aaatacaaac ttgtctcctt ccgggtccat gccctgaagg tggcccaata   200040
catgaccact tgcagagttt tcaaatagca caagatctga cgctgacgct tgaagaagta   200100
ctgggggctc gttgacgttt agaacaaata tgaatacggt tacggtatct gaaagaaagc   200160 cttcccgt atctgtgacg attaactgca cccggtgcac ccgcgcactc tcgtagtcaa   200220
agagctcgcg actgtataac aggctacagt ttcgatcggt atcttgaacc acccgagcga   200280
aggaagctga attttcgtca atcgaataaa acagtcgctg gtcactgtcc tggtctatcg   200340
cttcgaagtg atgcaagata gatccaactt ccacgtcctc atatacttgg aggcagacgt   200400
gctggttctc ttcgtagcgg ttatcagctg tgccgtcttc acgaactaag cagttccggt   200460
gtatctgtgg tctctcattt atgtccacaa ccctaatttc gacttgtgtc accactgagt   200520
ttaaagctgt gtcttcaaca gcaacctcaa acgtatacag cgattgagtc tcatagtcca   200580
aatctccggc cacatgaatt tgacccgtat tgtaatcaat tgtgaaaggt actccgttgg   200640
cctcatcagg tagtattgag aagtgcaaaa cgtcataacc atccggatca aatgcatcga   200700
ttggtacgcc gaccaaagca tataggggcg tgttttcttc aacagactgt tccaatacgt   200760
ttgcgacgtg gggtggttca ttgacatcca gcacatcaat aattatgctg cacgtggaag   200820
acaacgacga taccgtaact tgtcccgcag agtcgtttct atagacaaaa ctatcaccaa   200880
tctttacggt tatcgtatac atggccacat tttcatagtc caaagtgcct gagcgttgta   200940
actttagcca gtaggcatta ccacggggct gaacctcaaa aatatcgaaa gcaatgtcac   201000
ctgtatcact gacaacttca aacactgtaa tcgtgttttt gatagatgaa tccggatcat   201060
tccacttaag aggaccgaac ctctcggatg ccgaggcatt ctcaaaaaca gaaagtctca   201120
tgtcttcaca gatcggcatg tcattgatgt cgatgatttc tactggaatt atatccgaca   201180
aagttttaag accagtgcga tcggttgcac ttactactag ctcgtatcga tcgtttattt   201240
catagtcgag agaattagat ttagacaacc gcacttctcc atcacacgag tgtatcataa   201300
aaatatcgac agatactccg ctctgatcca atgcagtttc gatctggtat gaaataacgt   201360
cgtactcgtc aggatcataa gcagctccca cgatacccac aactgtccct ttctgtgaat   201420
cctcagcaat actcattttt gcctgcgatg tgaatactgg tggttcgttg acgtccacaa   201480
catcgattcg cactatcgcg cttgagcgaa ggttatggct gtccaccca gtaatataga   201540 gatcgtaata cgactttagc tcgtagtcaa cagggttcag cagcgatatt aacccatcat   201600
tcgaaatatg aaaaacattc gatgagtttt gtgaaagtga cgtggaatcg ttttcggggt   201660
cccagaatgt cacccgagcg tggctaccat cagttgctct cacccagtct agctcttcat   201720
tgacagattc tggcacccaa aaccggccag gtttgataac cggaggctca ttaatgtcaa   201780
gcacaagtag ctggactgtg gcagtgcatg tgaggccacc tccgtccaca gctccgacct   201840
taaatgatat ttggcgttga acctcgtagt caaaagggtt gtttactacg atgtcaccca   201900
tttctgaaac aacgacggtg atatctgtca ttccgtcacc gatcatgtaa taactcaaca   201960
acccccaaga aattgaggta tttgcatctg gatcgatcgc cacgactcgc ccaacagtac   202020
caatcgtgtt ctctgttatt gaaaatgtca tgataggctg ttcaaaggtg cacttctcgt   202080
tctcgttcat cacatcaata atcaaagtac cagtagcttg cttggtcggg ctgccgtcat   202140
```

```
catgaacttc cacggctagt tgtatactac gtacgaactc atagtcaaaa gcactgccgt   202200
caagaactat gatggagctt gagaccatgc ccacagttac cacgtcgttt tttggcctca   202260
aaacagtgga gttgtcccgc agaaccaaag tagtttcaat caaagtgaaa aatggttct    202320
ggttgaaatc ctcgtcggta atgcgtataa ccccacgat agagctttga cttgggttct    202380
caatgatcga aaaatctgta gcgacaatgg ttggagcatc atttctgtct aaaacaacga   202440
tgtctaatgt cgctgtagta aacagattgc cactatcaga tactaccact gaaaagagt    202500
agtgcccctt tttctcaaaa tcaagctgtt gtctcgtacg ataacccccc gtagttaaat   202560
cgatactgaa cgttggatca acaatctcaa aaatcaatgt gtcactaaaa tcggggtcga   202620
atgcaaccat ctgcccagtc aaggtttcac taagagctgg tgacgtgaac acagaagacc   202680
caatctcagc attttcagcg acatacagcg tttgaggata tacctgaggt ggttcgttaa   202740
tatcttgaat acgaacagac accgtagaaa agctccataa tcctcctggc ccattgtctg   202800
tcgcagcaac tagcaccgta aagagttgtt gtctttcaaa atcaagggct agttggttac   202860
ttacgaccag gctcccatct ccaccaaatg ataatattga aaaagcgcct aagtcatttc   202920
catttgcgat ggtatacgta atggtgctgt tttgatactt atcactgtcg acagcggtga   202980
tacgcccgac tagtgtttga actggtgcat tctccacaac gctgaacatg tatcgatcag   203040
cttgaaaaac gggtggttca ttgctgtccg tgacagtcac gattactgtt gtatcagcat   203100
attccttctg ttcatcaatt acacgaataa ataggcggta atactgctta gtttcaaagt   203160
ccagcagttt tgtaagagtg attatacctg ctgctgatac catgaatgca ccctcatctc   203220
ctgggtcggt gtctaccatt tgaaaaccca aaacagagtt ctcatcaaca tcagaagctg   203280
atagaatgcc aatcatgcta cctttggttg ccgtctcagc gaccgcaaac tggtacaatt   203340
tctgtgagaa aattgggggc tcgttcacgt caataacagc taaaataatc gttgccgtat   203400
ccgcaaggtg caatgatgaa gtattggcat tgtatgcgct tgtatcagga aggacaacgt   203460
agacgacaca cacccgcatg gtttcatagt ccaatccgcc agttgcaagg gtaagttgac   203520
cacatgagtc aagccaaaat gtagtacggc gaccacaagt cgtgtttgta atgaccatct   203580
caaccgagca tcccacaaca gtattcaagt tttcttcgtc aacaacaaaa gcagtgagag   203640
gcttaccgat agcactacca acatcaatat tctcggttac atcaaattga atcacttcat   203700
ggtcgaagta tggcggttcc aacacgttaa taagattaac gctgtacctg gatctcgtag   203760
tcagattccc ttggtcttgt acacaaatat ccacccaaag cgatggcaca tattcgaaat   203820
tgagagcagt ggagttctgt acgataatct ctgcgccgtt gaagcctcta ttttgaacgc   203880
gaaatgtttg tgagtggctt tgctcgcaaa cccaaaactg gtgcttgtcc ccgttgtcgg   203940
gatcgtgaac cagtatgaat aacacaactg tttcatctgg cgaattctca cgtagaagtg   204000
taggaagaga tccctccagt ataggaggct cattaacgtc cgttatgtag atcacgctct   204060
tggaaaccac agtgaactct ccatcagatg ctcgcacaac gataggaagg ctattcccga   204120
aagaagactc aaaatctagt gagctgtcac ttttaagcat taactgccca gaagatgaat   204180
tgattctgat gcaggccaac acaggttcac ttgaaccaac gagatcatac tcaataatgg   204240
aatcgatatc ctcgtcgact gcagtcaccg ggtctcctat ggctgaccca ggtgtaaggt   204300
tttctggtac aaaaaaattg aaggaaccaa ttttggtgg ctcattgacg tcgtcaatgt    204360
atacaacgaa atcggtttca tcagataagc cgccatggtc aataacacgc acacgtaact   204420
tgtacacgga cttggcttca taatctagac gacccgacag actcacttga cctgaccgta   204480
```

```
aatcgatggc aaaggttgtc tgattagtga tcacaagctc aaaggaaaac acttcatggc 204540
cattttttaa atcgggatcg atagtgctgt cgacaaaatt tcttcccaca agtgtactaa 204600
taattgcatc ttctcgtaca gacgtacttt ggactcggat tgttggcctc tcgttaatat 204660
cgataacctt tacagtaaca ttggtaatcg agaataatcc aaacgcgtct cccgctctta 204720
ccagtaaagc gtattcgctt gtttcctcgt agtctagctg ttccgcttgc tgaaatatta 204780
cgcctgtcag ggtatcaatg ccaaatgatg ttggggcccg tggaactcca ctctccggtg 204840
actccgaaac gatgctaaaa aaaattgtgt caccgtctgg atctcgagct ttcacagcag 204900
gtaaaacatt cgttaaaaca ggttggtttt ccgaaatatt cagttgcatc gactcaacga 204960
tgggtggctc gttcaggtta ttgaccagaa tgttcacgtt tagaacgctg ctttcggccc 205020
ccgactcgtc cgtcgcgata atggaaagca cgtaggttga cttgaattca aaatcaagcc 205080
cgtcatgcat taacacaact ttgttaccca caacgttaaa catgtccagc tggccaacca 205140
agcggatttt cacagcatct gggcggccat cattgcgagt gtcggggtca aaaacagtaa 205200
gatttcccgt tgcttcagcc ccagaacgtg agttctcatc tatgtcaaaa gctgtagcga 205260
ggagctgagg cttttcgtta acatcacgta ctacaatgtc aagtctctgc ggggactag 205320
tcaaacctcc caaatcgctt gcttgtacca ttatcgacca aatacgttgc tcttcgtagt 205380
tgatattctg gggcatgttc acaacaatct gaccttgtgg ggtaatatta aaaggactct 205440
tttgatcatt ttccacgata tcccacgtgt gtatcttcca agatatgttc gctgctccat 205500
ttttgtcttc atcttgaacc gtgagactgc acacaatctt cccaactagt agatttaatt 205560
cctgttcatt taagtgataa ggaaattcgt ccatttcaca tgtccgagga gacactattg 205620
tcggtgcatc attttcgtca gataaaatta ctgtagcaga tccacatcct tctaaaggtg 205680
gattcccacc atcctttgcg catacagtaa ttgtgagttg ttggttaact tcgtaattga 205740
gggcagtgga gttggcaact gataacattc ctgaattcga atcaatacgg aaatttagtg 205800
cttctgtatc tgaagtgcgt ggaagataat acataaccct ccctgaaaaa agggttacag 205860
tatccggatc agtcccatca atgatacaaa ttgatgtccc gggtggtgca ttttccgcca 205920
gaaagcatgt tgcatcgtgc acaactggag gctcgtttac gtcctcgata tccactgtga 205980
ccgtcgaaat tgatgacagc cctagacgat cagtaactgc aatcgagagg gcgtatttac 206040
tctcactttc aaaatcaagt tgatcaatat ttgccgtgag ttcaccagtg tttttgtcca 206100
caaaaaatac tggactaact ggattgccct cgatgatagc aaagtgaacg gtatcgctaa 206160
catcaggatc catgtatgga accacaccgt cgacaaggat aacacgtgag actgataaaa 206220
gcaaatacga aagttagaat taacaacaaa agctagagac ctgatgaaat ttaaatgaaa 206280
gcagaccttg ggtaacagtg atttcaagaa cagaagccat tgccgagctg cggtcgtatg 206340
aacttacttc ccctattcct cccctgata ttaaaagga tacacgagta gtgttaatca 206400
tgtccgccat aacaggttcg ataattgacg ctaagttagg tgaccaaata gtagttgctg 206460
aagcctcact ttccacagtc cactccacga aggcaggatt cccaaaactt tccaagctat 206520
cagttgaaat ccacgaattc tgagagctcg tcatcacgcg aatctttagt gaaaatgggc 206580
caatctttcc agatggaact gtaaggcgta actgcgctaa tgaaagttta gcgataaaag 206640
ctggaagtat aacaccctga aattgaagaa caacacccac tgcagttttg ctaaaagggt 206700
catatcccat ttgaagagtt gttcgcgacc agtccgtcga atatacgcca gccgcgttct 206760
ttttgatgct ataatcgtct cgagacgaaa taatcggaaa tacaaagatc tcggtcgtga 206820
gcacacgcaa atgatcagaa ttaacaccta atgtcagtgc atacacacac acgttatact 206880
```

```
cactacacac atgacatcac atattagcgg agtggcttct ttcttacctt ctggaatact 206940
aagatggcga ttttctgtca aaggactctc gttaatatct ctggccgtta tcgacaccac 207000
acagctcgaa cttagtgtcc cgaggccgtt gtggtaagca ccgtcatcgg cgacaacaat 207060
agtcgcaact gttgtgttgt gcgcggccga ttcgaagtca aggttgttct cgcgagttac 207120
aaatatctgt ccattggtcg gatataccccc cagaaacgaa tgttcaagtg caaaagtgaa 207180
gacagttcca atatctgtat cactcacgta cgtcgtaagt ggcttcccaa caagcgctcc 207240
aactggagag ttttcatcca tggcaaatac aatgtttcct ctacagtttg gtggggtatt 207300
gtttacaagt acatccacca aaactgtagt agtactaaaa agctgcttca tatcatacac 207360
gctggccatc agcataaatg aaaaaccttg cttaagagct tgtatgttct gtggtgaaac 207420
cacactgact tctcccgttt gcgggttcac agaaaacaca ccaataccat ttatagtggt 207480
agcagtcagt aaggtttcag atggctggag tgagaacgac aatgaatccc cgtaatcagg 207540
atcaatagct tgaagtacgc caattacgga tcccgtcgcg cgtaacgag atacggaaaa 207600 ctggataagt ctttctgttg caggtacaaa ggatggaggc tcgttgcagt cctcaacatt 207660
tatacgaaga acgctagacg tacacagggc aaacgggtcg catgctcgca gggtgacctc 207720
gtagagagac ttctgttcgt agttcaacga ggcctccaaa gtcagttcgg gtgtggcgat 207780 attacgatg gcaaaaacgc cagcattatt atctctgacc acttggtatg atagctgctg 207840
acctgcgtct tcgtcttgaa cattccatac aagcactgtg gttccaatag ccgcatcttc 207900
tctgacggaa acgcctattt caacggcact agtaggtact tcattgacgt cttgaatcgc 207960
aataacgaaa tgctcaattg aagacaaagt gggggttcct ctatctgata cgcgcacatt 208020
tatccaagct tgatggagct ctaaaagctc aaaatttagt cgttttggat cctcggctat 208080
tatgaacccg cttttagaat ttacagaaaa caatccagct ggagattgat cttcaatttc 208140
aaacacgaga gtgctggtct ggttgaagtc tgggtcgtaa gcgtggatgg cataaaaaga 208200
agtgttacag ttttcattca cttgaacttg ctcactagct atgactgggg cctcgttgac 208260
atccacaaca cgaattgtta ttggacacgt actgcaagca ccgccagcgt cacagactga 208320
aaatgcaagc tgatacaact cacgcgattc ataatcaagg acaagcgct ctgaaacaat 208380 agagcggccc ttgaactgaa atccagaagt ctcctctta tcgattatag tgaaggtcgg 208440
aatgttccca agatcctcca aatcagggtc gtagctatcg accgggggtt ttaaaaccat 208500
tcctccggga ctattctctt cgacatatct cgtttccgat tgacaaatgg gtggctcgtt 208560
aatgtcgaac acgttgataa taactaaaac acaagattcc aacaaactgt cagtggcaca 208620
cacttgaagt gagtaaacac tctgggattc ataatctaat gatgctgttg aagatacgat 208680
aatttgtcct gtggttgatt taatctcgaa atcgtctgaa ccacctgagc caccagatga 208740
ctttatgaaa aagctcaggt ggctatttgc atctggatca tatgccgtaa gtgatcctac 208800
gacggtataa cttgctgcat tttcctgaat tgccaaatta aattgactct gagcaaagct 208860
gggtggctcg ttcacatcaa cgatagagac tgaaataggc acagccagtc gtgctttgtt 208920
aggatcataa acagaaacag tcaaactgat tgtgtttagg acttcttcga aatctaatgg 208980 gttcttgaa cgtagctggc ccgtacaacc atcaacagaa aaaacggcg aaaactctga 209040 ggcatctaaa acatagctca gcgtattgtt ctcaggatcc caaatattag aagacaatga 209100
agctccaatg gccacccccg tgaccatatt ttcgaatacg ttaaattgaa taataccttg 209160
ggaaatcaat tcgggggctt cattcagatc aacgacgtca ataataatag ttgcgttgac 209220
```

```
agtaaagcta gtatccatct tgtccacttt tactgtcagt gacattaatt gatcaaattc  209280
ataatccaaa gggctgagca ggaagagctc gccagttatc ccatcaattg caaatttgtt  209340
gtagttctca cccagcgaga accttaattt ttctcgagac gttcggtccg gatcagaagc  209400
attaattagt tctaatgatc gcgggacaac tccattttca aacacgcgta aactgtgcgt  209460
ttcaggaacg tgagggggct cctcttcgtt taaaacagat acaaaaatgg tgctttccgc  209520
tgtcaataga ccttcatctg tcacttgcac ttgaagagca tactcggctg tggtttcaaa  209580
atctagcata cccggattca gaactgtaat atccccgta tcggaattga tcgcaaatat  209640
gtcgctagcc agcaagcgaa aatggagtaa agaccaattt aaattcgtat ctgggtcaat  209700
tgctttgact gtcataacca gctccccttt cactgcagat tcgttgatat atccgcgttg  209760
gccagttgaa atcacaggca cttcattcac atcggtgagc tctataaata ctgtagtata  209820
taatgttcgc tggtttggag cgtcatccac aataagcaca acacagctaa taatggccgt  209880
accttcaaaa tcaaacgctg acggattccc gacgagtaag ttactggaaa ggcgctcaat  209940
tataaagggg caatcacgcg taagaatttg agcaccggat ttctctccct cttcaacaga  210000
ctcgatttcg aattgtccga tcaaaaaacc cttttgggga ttttcagcga ttgtaaactt  210060
cctggttgta gttaaaggtg catcgttcgc atcaaccacg tcaattccgg ttgccatatt  210120
atcactgagg ccaaattcat cataaacttc ggcagtaaac tgaagagacg actgcaattc  210180
aaagtcaatc catcgccggc gcactgaaat ggatccggag cttgaattaa tttgtatgcc  210240
tgctggtcgg tcagattctc gaagtttaaa gcgcagcttg ttttcttat ctgggtcagt  210300
tgcagatagg ggatgctgca agtaaaaatc taagggaagt aggaattagc aaccacatta  210360
aggtgtttcg aatcatcgga aatagaaaac gtaccagaat ccgggccata catctccaaa  210420
cgcaggcaag tacttcctga ccagcctgta gggattattc tgacttgttt cgcaatcacg  210480
ttagggagca ccacgctagg gttgaccgat gagtccatac tagatccaaa tgccacgaag  210540
tttatgcttt ttgtatcacc ccccacaaga ggtgtaaagc ttgatgtttc tgacagcctc  210600
catgctaact ggaaagtttg tagatatcca gtctggccat ttttatcact tccagggtag  210660
acttggatgc gagatacgat tgtcggttta ggaaaactaa tttgaaccca ctcatttgcc  210720
gaaccggatt tagcgcacca agatccattt gttgtgtcac tacgaatgac atcgagccca  210780
ccatagccgt atccatgcat ttcgctgttg tcaaggtaag aactagctgt tatagaacca  210840
gcctttatca ctcgtcgcgc tgattcacct attaatctgc tttcggcacc tagtgcataa  210900
actcgttaga agtacgacat cacacttcct gaacgttaca tgaacttgga caaatacgta  210960
cttttagagc agcatgcaag gtttgcattc tcagcgttct gttctacctt tccagcagaa  211020
tttgagcaag caggtgctgt catagtgcct tgggtggctg aaggaaacgc tattgagcta  211080
tagtgagggt caacacagag cgaatcaaaa tcctgcggat cacacaatcg taaatttttgg  211140
ctgctgcagt aagtttgccc cccagcttgt gtgatttggt cctttgtccg cttaaagaaa  211200
gtaggaactg tacacgtcac acacggcatg gttaaacctc ctgctgaaca tagttgcagc  211260
aacacgatgt aggacaaacc tgaataagag acgagttcct gaacttgaaa aagcgctatt  211320
gctccagcaa agtagtgaaa ccgtgatatc caccccgtaa acctagcact ttgcgctgag  211380
agaactgcct cttttagcgat agtaggtgct ccaaggaacg ccatcgatat tgtgtccagc  211440
tctccatcaa tgaaaatacg aagatgttgg tcgtttaccg taaatatgat ggctatataa  211500
tgccagctat cgtccgatat atacttctga gagtcgatag caaaggaatt cgtcgaaaca  211560
ctcagttttc cgtcactgtt gatcgaaaca ttgaaatatg cggtacccat tggatcacgc  211620
```

```
agaagcaaaa tgttcgtgtt agtgcttcgg gtgcgaacac ttgttgccgt actaaagtct   211680
aggtcgccaa acagaaagtc aaaattttca ttgcttaata gatcgtgggt aatatttcca   211740
aaaaatattc ctccgctggc cgtatagtgg acattcccat tgacccctcc gctaagttga   211800
gctgcttcag taaatgttgt gattgtcgac acaatatcaa accgtggtgg ctcattaacg   211860
tcaactacag caattgtaat tttaccgcat cctttcatta cagaaatata attatttctt   211920
tccccatcat cgattgcgca aagaacaaag gaccacaagg gctgagtttc aaaatcgagc   211980
gaagttcccc aaattgagat atctgctgca gtcctgttca ctggacgaaa tcgaaatttg   212040
tccgtatcag ggatggtaaa gaacgataaa acgcttcctg cataagtgtc aatacccag   212100 acacggccaa tagtactgcc aatctcaacg ttctcaggca cgctaaacac aaattctcct   212160
accacaggcg gtgaatttac actgcttact gaaattatca attgttgatt tttctctgag   212220
gtgagtccac tgccattgtt atcgatcgct tcaatctcga tattgaatgt ttccaacgcg   212280
tttacttttc ggaccatagt tatcactcca gcgctgctca tagcaaacac gccattcgaa   212340
ttatcactga tgattttaaa ttgaagttcg tctacgacac cgtcaggatc caaagcgctc   212400
acgcgatgta ctacgccgtc cacattggca gattcgggaa tatttagttg aacaatcaat   212460
ttagtaaaaa atggcggttc gttaacatcg gtgatgccca cgtgtaccat aaaacttacg   212520
atattcccac cattgtcaat aactcgacaa gaaagatgag ccattgtgac agcttcgtaa   212580
ttaagcccct ctgagcttag aacataaatc tgccctgtag aactcatgcc aaacaattta   212640
tccgatggag cggaagacac aatttcaaaa agcgagctgt ctccaacatc ttggtctgaa   212700
aagtacatgc tcataggatt tccaaccgtc gatccattcg gagtatttc tggaatactc   212760 agaataacgg gatcttcgac cagaagcttt ggaggctcat ttatatcact tattagcaca   212820
gtacacatct gtgatattga taggcggccc tcactcatac tagaagtatc agacaccgtg   212880
accacaacgt caaaacgttt ttgctgctcg aaatccactt ttgctcctct tacctccagt   212940
tgcgcgttcg aggccgacga atgcacaatg cgaaaagctg tgctattatc gtcagctgca   213000
aagttcgagg tatacgtgaa agtaagagtc tgattttcag gatctgaccc ttccaaatac   213060
gctacaatag tacccagtgg tgcattttct gaaagggtaa gcacattcag agatactgta   213120
ggtggctcgt tcatatcaag cacattgatt ataatatcaa cagtaaccgt aaaattatcg   213180
ctgtcagtta tcttcacttg gaactgatac tgagcaacac gttcataatc aatagcagca   213240
tttgcagtga caaaagttg acctgtcgtt acggatattc caaatggaag ttcttgtccg   213300
atggcaataa ttacaaattc aaaagaatca gcactgcctt caggatccaa cggcctgagg   213360
gcatcaccaa cgagagtata cgcccctgaa tttcattca cataaaaaac ttggggctc    213420 gacaagacag gtggttcatt cacatcgagt acgttaatat tcacccaaat actcgttgac   213480
agctccgtat ccgttgcctc aatcagtact cgatataatt gtttcgtttc gtaatcaagc   213540
aacttactct ggcttagcac aaattggcca gtcgttttt caatagtaaa tgcaccgggt   213600
gaatcttgct gcagtatcgt gtactgcagc atcgacgatg aatcctggtc gatagcacga   213660
actggacgcc caacaggtgt gctttcgtca ctgttctctg ggattgatat atcgatttgt   213720
gcactgacaa tcgagttaag attttgaacg gagactggca tccattcccc agactcaatc   213780
tggaattcta cagaaatagc gtggtttgat ggtgcataaa ggtatagcat tatgtcgtgt   213840
cttccacgtc gtagatctcc agcgtcaact tcgtcgctat actgcagatc aaaaccaggt   213900
cgagtcaacg ccttccccgt aaacacgagc ctgtcaatca tgaatacagc gtttaatttg   213960
```

```
acgctgctaa ggatacgaaa gactgtattg gcttttgatc gcaaaagtaa gttccatccg   214020
atgacagcag catattcgcc ttcaaatccg ttcgggcaga atgcaccatt actgaattcg   214080
gtaatacttt caatgttccc acaacaatac ccaagtggct gactagctga tagaatcatt   214140
gtcgcaagtt ccattccttc cagcttggca aaggtgtctg cgctagccct tttagtttta   214200
acagttagcg agtagtcaat cgtgaaaatt ggtgcttcgt ttacatcgcc aattacaact   214260
ttaatcaatg ctgatgcagt tagcgatggc gtagcactgt ctctaactgt aacttcgatc   214320
tcgtacgaag ctgtccactc atagtcgaga gaattcgagc gtgtaacgta gatttgtcca   214380
ttacaagact ggataccgaa aagttcgtgc ccgtcatcct ttgtgatcgt gaaactcaaa   214440
cgctggccaa tatctggatc tgaggccaac ataggagcac ccactaaggc accttctgaa   214500
gcattctcat caatgtttac ttgcatggga aaaataactg gtggttcgtt cacgtcaata   214560
attttgacag taaacatagc actagaacac aacttcattg agtcgcaggc aagtagcgag   214620
aatgaatact ctgctttgac ctcataatcc agatttgctc taaaaacgac aagttcattg   214680
ttgtcaaagg caaaaggtaa cttgctggca ttgcctccaa tggaatatat cacggtatct   214740
ccttccggat cgacagcaat tacactcgca tcattcacga tgacagtatc aatggcgcta   214800
ttctcttcga tatcagcacc atacagtttg aaaatggggg cttcgttcgc gtcgacaaca   214860
cgaatttcga tttgttcagt tgtggaaaga cctgcgaggt ctgttgccgt aacgccaagg   214920
aaatacgatt tacaaacctc aaaattaaat gcagatgtat cgatggcaaa gattcttcca   214980
gtatcaccat cgatacgaaa cgatgaactt acgttgctac tgatcaaaga aaagcttact   215040
cgatcgtttt tgtcaggatc actagcagaa acgtttagca gagggacgga aggatcttga   215100
gccgattctt tggtgaactc taaaattgac ccaacttgac caggtactat aaaaggaggc   215160
tcgtttatat ctatgatata gacagtgaca acaccacttg acgtacacgg ctccacagca   215220
tcatcagtga cgtaaattgc gaggtcaact gacgatagtg tttcataatt caataccgac   215280
gggtcagcga ctgtaacgac tccggagtat ttgctaatta caaatatatc tgattccagc   215340
gagaatgtca gcctcccaaa tgcatggagt ccataatctt catccattgc attaatgtta   215400
tcaccaattg acgagccgac agcactgttc tcattaatgt agcgtacctg gtttggaacg   215460
cagggacaat catttgtgtc gatcacattg atagctagcg ggcaacgcac agtgttgact   215520
ttgtcactga ccaagagatc aagcgcatag tagggttttg cttcaaaatt aattaacgcc   215580
aggtctttta caaagacgga cccagtagag tttgtataaa atgttccgtt cgcctccatt   215640
gcaaatgaca gtggcttgtt ttcgggatct attgccccac tttgcaataa ccatttatta   215700
taccctgcta gctgttcttg aacatataat atttggattt caccacaaac gggcggttca   215760
tcaacatcaa gtactcgtac taccatccta caaacaatgt agtttgcgga tgaatagtaa   215820
acagcaaatg tcagagaata ggtggactgt tgctcatagt cgagcggcac cagattattc   215880
accgaaattt ctccagtcgt tgtatttagt gtaaaaggca ctagtggttc ttgcagagaa   215940
aagctgttcg gaacatacgc ttcaggtaat acttttactc gacccacgat agcccccacg   216000
gcattctcag atactgccaa attctgatct ttttccaaac aagtaattga cggaggatcc   216060
gaaagcatgg tgaccacaca caacacttga acgtggttgt agccgtcact cacaataatc   216120
gacattacta cttggggtat agtggcgaat gcaccactac ctgtcttatt cacgcgtaat   216180
acttgatcat ctgagatgac aaaacaatcc agatcaacag acgaagtagt aattgaaaac   216240
gtaagagtct tcccttcagg gtctctcata cccattgcca atattggata cccttggaac   216300
gcactgcgat gcatcgatcc attgacaacg gtcagtccga taggtggctc gtcgacatca   216360
```

```
atcacctcta ctataacaac gcaatttcca ctgagtccac ctggatcagt aaccagtaca 216420
gcaacgaaat ggtattgctg agcctcaaaa tccatcagct gctgcaaaac cagtctgccg 216480
gtattgtcaa cagaaaaact gtcagtttca tttttgacgc gataggtaaa cgttttatca 216540
gtagcgtctt catcagtgac gagtagtgct ccagagagta gcgtgtttac tggagcattt 216600
tcattgacat gaatacgcgc acacaccacg ctcgggggt catttgcatc cagcactaca 216660
acgataattg aatatcttgc gactatatca gtgtcaacaa tcgtaagatt gatataatga 216720
tttggttttg cttcaaagtc aactccactg ctatccacgt gtaagtatcc acttgaagag 216780
tccaagtaaa aggtacctgg cgtactttga gacatcaatg agaattgtaa acttgttgaa 216840
ccctcagggt catcaaatat taaagccatt gaaggctcga tggggagcc aacaggcatg 216900 ttctctacca cttcaagtat tccgttcgcc agtagcaaag gaggctcgtt ttggtcttgt 216960
acctcaatat taaattcttt gactgttgat aaagcttcta gagatgaatc atgaactgca 217020
accaccactt gaaacgtttt cttaaggctc gccacgtcca atagtcggta ccagttgtca 217080
tttctgagtt tcaaatcaat cacatgccct gctcgaagac gaggaagctc aaatcttata 217140 gccctatag catatgcgtc gctctgcttc tccgtcacat tcacagctaa aaacaaatta 217200
ctagatacat ccacgcgtac cagtagtcta tcacgcaagg gcagacttaa tttgttcgca 217260
ttttgctcaa tccgggagta aagaaactcg acaatggtag ttgttttga ttcactaata 217320 aattgaactc cggtaatggt caccgtatcg tccagcccaa gcgtagcact aacgagcacg 217380
ttatcaaaga gaaatgcctc atagtcaaag cacgatgcct tcaaaacgga aagttgacct 217440
gatagcgatc caatcgccat gcaaccgctt atactttgcg aagcaatcga aaacaacagc 217500
ggtgtatcct ggtccgggtc gtatgcagca attgggagcc ccaccggaga accgacgggc 217560
acattttcac gcaattgaaa agaagtgctg atgatgactg ggggctcatt aacatccaga 217620
acgtgaactg tcaaatttgt gaaagcactg agtgatccac tatctatcac ttgaaatagg 217680
aggctgtatg aatcgcattg ctcgaaatcc agtgcctggc gaaggatcaa atcgttttcg 217740
ctctcactgt attcaaatgg gcaccctgaa ggtatacaag atataaaagt gatcgttaag 217800
gtgtcattgg tgtcttcgtc tgctacggag agtacgttgg tcaaactcaa acttgtgaca 217860
cttccctcgt tgatatataa atctgacgaa aaaattgttg gaggctcatt gacgtctgtt 217920
atatcgatag tgacgtcaaa aagcgtcgat tgaatcggat ttccgtcgtc aaatgcccta 217980
actgtgagta catactgtgt ctccttttca tagtttaatg aagcgcccaa ctgataaact 218040
gcgtacgaat tcgtcccacc acaacttttt ccaggtgtat cgttgcaagt caaattgcac 218100
gtcgtttgat ggagttggtt ttcttgttcg ccaagtgcca gcttactaca ccagcactca 218160
gaattgacac ccaacgccat aaatggatac gcaaagcatt gctgatagca cctgctgtaa 218220
ggtgctgtgg tatcgctagt aaaagaaatt gacgattcac tctgaagttg tgaaaaacaa 218280
ccaatgaaca gctcgggccc ttcactaatc aaaagttgcc ctgttgccgc gtttaaagcg 218340
aaaaaattat catcgtttcc accaacgatt tcatacgaaa cttgctgtcc tacatcccga 218400
tcaattactg tcaggacatc cccaattgta ctaccaaccc gagtattttc gcgtacttcc 218460
ctgctctggt tactcccaaa gggggctca ttttcatcaa gtatgccgac tctgacgtac 218520
cctgaagcag aaagtggatt ttcgatacgt aattctgtga ctaaaagttg tagcgaatag 218580
accgggtacg tttcgtagtc cagcttttca cgcacaacaa tcacgattt attctggatg 218640 gagaatacat cgagataatt gccatcaacg attgaaacct ccaaatcatc gttttccgga 218700
```

```
tcgtacagag caatatctcc aaccaacacg ccaattttg cggattcgga aacgtgaagg    218760
atggaactag gtaacagtgt cggcgcttcg ttcacattta tgacccaaat ggtgattgct    218820
gtcgttgtca acaagttgcc actgtcttgt actgatactc ggagctcgta ttgaccccgc    218880
gtttcgtaat cgagtccatc gacatttcgt ctgatgtatc ctgtcgacgg attgatttca    218940
aatgcaccac taaatggatc gctttgtaaa aaatacgtca ggttactagt acccgtgtca    219000
tcgtcatcag catttacata ctgtaccggg gctgcatatt gtttggttag tgttatggaa    219060
caaacatgta cgtcaacaaa acataaaact taccgtaaga tataaagcgt gagcacggct    219120
tgttggtgct tttcaggtac gaggacgatt ccatgtctg agatgaggag tcccaatact    219180
gaatagcaac agttgaaatg tagtaattct gttggcaggc ggtgtcgaga atcactttgg    219240
atgcatcaac tggagtccta aaactcattt caatccatat ctttgaatcg gctgttgtat    219300
ccccagtgat gtatgcggca gtagttacat ccccatcgat tgctttgtca atgctggacc    219360
cgtcagatga tctagcagtc aataaatcag ttattaagtt aactcgggtg cgctctgaaa    219420
accaagcaag ctcagcaatt ccgaaagaag ttgccccgcc atcagataaa acagtgaggc    219480
gccagttgtg tgccacgttt ccaattgaac cactaatcag tgggccatcg acatagatgg    219540
ttttgctctt ctcggaactc tccatattgt ttccatgtgc tgtagcgtct accaaattgc    219600
cgtcaaatct agaaaaatgc aatatttgaa caaattagaa aggttatgat tggaatagct    219660
gcctagatga atgataaaca ataaaccaac ctgtaataag caagaatatt ctgctggtac    219720
gggcttaaag accgggcaaa attggctctt atactctcaa aagacttaac ctggctccac    219780
agtcgcagct caaataatca aaaacgtaca gtacaattaa aaaaaatcat ggacgtttaa    219840
atgaaggcaa aatacaaacc tcatcgattg agaactgaaa cggttttcct ggacatcgaa    219900
ttccagaaat gcagtttcca acaatgagag ttgatgatag gccccattga atgcccacgc    219960
aagaaataat ttgccgtctg acaacaacaa ctccatccat atacaccatc agctggcctt    220020
ggatattatc gaaagtcacc gctacgtggt accagacttg tggtgtaagt acaacttcg    220080
tgtcaattgt tacaccgtga agcgtcacaa ggagcctatc tcctgtatat tccagtaaca    220140
aaccctttag tagtactgca ctgtccctcc atgccacaag cgatccctcc tgagtgtcta    220200
tgtataccca actctccaag gtgaagtcta taatggcagc ttcaacctgt tgttcttggt    220260
gtacgtacaa cgtgtcgttc gaaatcagaa gcgccccact tgatgaaata ctagtgatgc    220320
gctcgaaccc ttcgcaattt gcacatgcgt cgcaagaaat gggcttgaga gtgtataagg    220380
tgcactcagc tgaggtgtag ttgtacacgc ctgactcgca ataggctttc tggacacatc    220440
gctgcataca acttccataa gacactattg gagatgattc gattgtcgct gtgtcatcat    220500
taatggtgca tgcgcctctt gaccgaaatc tagatgtagc aattgtgtgt tcaggaacat    220560
tttcgtcaat gaaaaaatgc tgatttgctt caaagtaggg agcttcgtta agatccgtta    220620
cagcagcacg caacgacagc agcgttccag cttcagcctg atccgatact gatatatcta    220680
ttggataaga cgaccgagtc tcataatcca gaggctttac cagtttaacg ttatagactg    220740
tggaatttat ctgctccagt gcgaacgttg aagagggtc tgatatctgc actgtgcaaa    220800
catcaccagc gtcttcatcg aaaacaacta cttcaccaat tactgtaccc accgtagatg    220860
attcaggaat gtctacgttc atcgttgtca ggctaggaaa tgaagcgagg aatgaagcct    220920
ggggcggatc attggtatcg atcacctcaa tgtttaacgc cacaaatgag ctcttcgccg    220980
gccgaaacgc atttctgaca ataagcgtta agttgtaggg gggacgttct tcaaaatcga    221040
gcacttcaat tgctgaaatc tgacctgtaa aggactcaac ccgaaaagta acactgctat    221100
```

```
ctacaagttc gaagatgaat gatgtcgagt cactccgccc tgtatctggg tctgtacagt   221160
atttccagat agcgtctccc acatacgtgt ctctgatttt attttcggga gcgctaacaa   221220
agatacctaa cgagcaaacg ggagactcca attcattcaa aatatcgata ataaatgtgc   221280
acgtgccagc gagtggggtt gcggcgtcat ctcgaacccg aatcgttagc gaatatagcg   221340 ccttttctc ataatcagga gccttcgtgc ccactgtgac agccccactc gacgaatcta   221400
tttgaaatac gtcatcatca tctccagctg caatgtaaaa tgaaaccgta tcgattgcat   221460
ctgagtcact tcctatgaca gtaccaacag ctgtaccgta aggcacattc tcgatcaatt   221520
gagtgtgcgc attggtgcac ttaggtggat gattaatatt tcgtgatagc acaccgattg   221580
tcacttcact atacgcagat gaattcactg tgtccgttac acgcaatgtg atgttaacgc   221640
gttgatcgtc aggtacatac gcgtctggcc gcacagatag ttcgcatgac gtggtgtcgc   221700
tgctggttac aatcttgaaa ttatcagttg agtccgccga gatggagcac tttcctccaa   221760
tctgtcccgg atctctgtca tgtattggta aggacacggt agcataagaa ccatccccta   221820
gttgactaat gtcaacatga taataactct gcgctgtaat agccccaaca aactgtgggg   221880
gtgagggtat cattttgaca gcgatatcaa ttggatgaga gagcccacta agcccatctg   221940
ggtcagtggc ttgaataacg aatgagtatt cgctgacaat ttcagcattc agttgtgaat   222000
tcacagtcag cttccccgta gattcagaaa tagtgaattg gtcaagcgga ttaccggagt   222060
gtattgagta cacaagtttt gtcgattggc cggtgtcttc atctgaaaac aaacatattg   222120
aatcaaggat cgccccaaca ggtgtggttt cgggaatggt aacgccatct acgactcggt   222180
tcacaacagg cgcatcggga ccatctgtaa tttcgacaag atttggacca atctcggcgc   222240
acatgcctaa tggatcgcag gcactgatgt tggcccaag cgaatgaatc gataacgcct   222300
cataatcaag ttcagctatt gtcaccagga aactaccgtt gataccaaaa agctccccaa   222360
atttgccagc tgaatgaaca attgtatacc tgatattatc gccttctggg tcgactgcgt   222420
cgaacgctaa aatcacagtt ccgacaggaa cattctctgc cacttgtttc gtaaagggtg   222480
atccagtagg agcttcattt acatcaacaa cctgcacagt cattgttgcc tcatcgctgc   222540 tgccttttc atcataaact gtaactgata tctgaattgc aggattcgtt tcaaaatcca   222600
tcggttttga ccataactga gaaccttgaa caaacagaaa gtcgctcgtg acgttaatt   222660 gaaatgtcag gactgcacct ttgtcctcat caacagcaaa agtacctaga tttcctacca   222720
agcacgtgtt cccgatgcag ttttcggaaa cgcgaaaaac agcacttgtt agaactggag   222780
catcatttga gtcgtcaca gcgatgcgat aatcacacac tgtttgaagc cccgttttat   222840
ccgtaaaacg aacagtgaag ggcacggtgt cctggacttc gtagttgaga tgttttttca   222900
acgtcacttt accagtggaa gaatccacat caactgttcc tatcgggatt tgagataata   222960
cttcacatat cagatggtcg ccggaatcgg ggtcgaatgc gtacccactc aactgtgcaa   223020
ctccagtctc aatcgaggta ttttcagcca cattaaatga aaaggataca caacttggtg   223080
gctctggcat atcttggatc acgataacca cgttagcgtg agattccaag ccaccaccgt   223140
cctttgcaac aacatccaat acgaattccg ttgtactttc atagtcaata gcgttgatcg   223200
caacgatatt accatcccga gtaatgacaa agttgccatt cccaccacta gatatagata   223260
aggtatgcgt gtcgtatgca tctggatcaa tgacaccaac agcaggcatg agagttgcgg   223320
gaggtagagt attttccttc aatgctcgag aaaaattggta gccgctaatg atgggtgcct   223380
cattgacgtc taccacattc acatggattt tacacgccgc aaacggtgca ctcgctgagg   223440
```

-continued

```
tctcttggat catgagtgtt atttcgtatg cgttttgatt ctcgtagtct aatgccttca 223500
tcaggattaa atgtttctgc tcgttcagtt tgaaaaggtt tgtagaagtg gtcgatgtct 223560
ggaggttata cgtcataccg attgaagaag atgcgaggct aaaactgaca tccgagacaa 223620
atccagggtc atttttcgtgg atgctcagaa tgtgatttct gtcgacacaa atcgaatctg 223680
ggaacacaaa cgacagctta cgagcaccac ctgagcaact atagcccgtg gacacctttt 223740
tgtattcgaa tcggcgatca ttcacagaac cctccggaat agaatagtaa cccgctggga 223800
cattgatagc attgtaatac gagattgctt gtgatagcgg gagtgccatc tgcaagttgt 223860
aacgtgatcc tggggtgact acctcgaacg tcgctggagt agtactgtca ttgacgccaa 223920
cgaacaaaaa gcccgaggct gtagagttag tactaatctg agatatgccg tacccggtta 223980
tccaggtact caaactcgac ggaattttca cgatacttgt accaatgaga acagcaatat 224040
ccccagcacc catcgcagat aacgtgggca tataattatt agacatcgta gcgtcaacag 224100
tagtgtcaaa catcttcgtg ccaagtgccg agtacactaa aatatgtaag atatttgctg 224160
tatctgctat agttttcaca gtttctccgt tgacatagac actacccgtg caagttgggg 224220
cggcaattcc gcataccgcg atatcgatat ctaatgagat agactggccg tcgaaacgat 224280
cgcaacgcaa gttacgaaag cttgcatcgg tagattttcg gaataaaatt gttcttttga 224340
ctacaaactg tgattcagct gcgataatgg acaaatagtg ttgggccccg gacgatgaca 224400
caaacgcaaa tgtgaatgta ccatttcgtg agcgaggaac cgcgataatc ccatctagca 224460
gtacaacagc accccaatca aatccagcaa cgggcagttc gaactcgtag gtgatatccg 224520
tctgtgaatg ttcgaaataa gaaatcgata tgttgtgtgc aaacccagaa gaccaccctg 224580
tcttaaacgc agtcaggttt acatctttga actcgaaaac gtctatagaa acagccgcag 224640
aactacttgt agcagcaaaa acaccttgcg taagggcgtc gtccgttgaa cctggttgtt 224700
tcgataaagg tgcgagaaga tatgagattg atgacgaagt caaaactact tggtcagcgc 224760
cactgggaga atctgggcat cggcttacgc ttccagcctt acaaacacaa ccttgcgcac 224820
atcgaccaga gcaaagtgag ttgatgagac ctacttgatc gccgaatcga gtaggtggac 224880
actgatatgc tgtgcctcgt cggcaataat accctcttgg acaggacagt attccagatt 224940
gttgctcatt caccatcgat ccgacagagt aataaccagg tggcacaatg atagggccag 225000
tgtttccttc tgggcagtac acatttctag aggggcaagg cgctaacgca gtgtaggcac 225060
aaggggcccc gctggagggg cagtagaaac cagcggggat tgcgctacaa ttttgttgac 225120
ctggcttcga aaaagttcca ttcgtgcaag gaacgaaatc tcttcgagcc atctgatcaa 225180
atggacccgc ataaccctct gggacattca acattcgct tgatccagcg tcagcaaagg 225240
tgccaacaga acacttagct ggtgttgttg aaccgcttaa gcatttgaaa cctgatgggc 225300
acgatatgca cgctgcaaca cctgacaacc caaccgacgg cccatacgtc ccggcagggc 225360
acatcgtaca tccgttcgag tgtgattctg aataggtacc cgccggacac tgtgaacagt 225420
cgccactctg tgaactcgtg tagcctggtg ggcatctgtc cggccgtaaa agtaattttg 225480
aggagtcata accatccacg ttatcccata ctatactccc cgttttctga caccagcttt 225540
gcgcccatgc agcgtaggat gtgcaaatgg gtagcatgtc aaatggcgcg tttaaatcgg 225600
atctagttgc actaagacag tctgcatacc agaatccgct ccggcttcgc ctcgcacaat 225660
tttgactcgc ggacagatca ttatcctggt ctggtgtgct gaaatacata ttactaagcg 225720
gggtaagagc atccgttgca taactcgccg tcgaattgta ccctcgcaca gtcaataagt 225780 attttttcctt ttcgcttgcc actcgaaaat cactataaaa cgcggaagtg tccttataat 225840
```

```
ctttggatac gacgatgatt gcctcggtga ctcgtgctgt gatagtagcc agaatatcat  225900
ttccaatcca ccactcattg gcagaaccaa gaccaaaccc gtcacgatac tcattccaat  225960
tgcgattgaa agttgtcttg ccgtttacac ggcgttgtgc aactatccat ccgtcagagc  226020
aaggaagaag gactggatca acatttgggt cgagttgaat atagtactgg ccatctggat  226080
tcacatcacc gttggcagca cgctcgctct tcaggtgcat gcatgaaacc gcgggatttg  226140
ctaacgatag tcctagaggt gtcttaaacg atgattccac ctcaattgaa acttcgtcaa  226200
tcccaaaggc actgatgttc aacgaaccaa aatccgtttc aaaacgtagt tcgtttgctg  226260
ctccgctaaa tcctctcaca gcaaatcgct cccttccacg gtagaagtat gcctgttgcg  226320
ctgaggtcga actctgtccg tagcaagcat aggtcactga ggtatcaact gcagctgtc   226380
gaacaagttg ggtaccaagg taaacccgaa tagtcctcgg ttcagagctc ttgagaagaa  226440
gtgctaccca gtaaagtggt tcaaacacaa aatagtatgt gaatttgacg cgcgcgttaa  226500
atggtttgtc gctcttgttg atggggctca atgttttcct tacaaaggat ccgacccgtg  226560
agaatgatct acctccaaga attacgattc cttgacaaag ctggtaccac ttgtctgcac  226620
cgctccaaga agttacccag agattgtcat caccgcttcc aataaaagag tcttggagag  226680
tgacactcca agaggttgat ggactaacgt cgttggtaga acacaagtat ctagtcgttg  226740
ccagtccacg aggatcaaaa ctaaaagata agccgtctga cacactttgg ccattgaaag  226800
cagaatgcat gcctatccac cttcgttcgt ctggtgcatt cgcaggcgat acagtatcac  226860
aaatgctacc gttatcacgt aaccaccatt ttcctccatc ggttgctgtc caatcgagca  226920
cagtttcgtc atcacttggt aggtcaatac tatcgccaac gtaggcattg gttactccgg  226980
gaactgtcga gaaaagagt gctccatatt tcggtgcat tgatataaaa tgccccgaag   227040
accgcggtac cacttgttga agacccatga tcttacaact atcactgtct tttgggctag  227100
cactgctcag acaattgatg tcactgatgc ccaaatcaca cggcacaatc gtgtatccct  227160
caccgctatc agcggtcata ttgcaaaacg catcatatat tcctgctgac gtcgctatga  227220
catatcgtcc agttgccgca tctggggcat cgactttgat agcgtggcaa gtctgaggca  227280
tattcaaatg aatagtagcg gcacccgagg tattatatgt gcccaattgg acactttggc  227340
gaaagtctga tgctgtgata gcataacatg ttccatccgt atttgcgaag cctacacagt  227400
cactgcttga ttggcaaatg catcggcagc gctctttcaa tgtgtacgtt tgagaacaaa  227460
taccagttcc gcacgcgtcg cctttgcatg gggttgcaag agatacattc tgtccaagtg  227520
cccactttgt gttgtgaaga atcgtccacg cattccccga ataaccact tcctgggttc   227580
ttacaaacgc cacgcgagtt ggatctgtca ctaacgagga cgaattgcga gtcatataaa  227640
ggttgcatgc cttcgtagca atgttgtata cgcctactcg gcatagacca tgccgtgaac  227700
agcgtgactg acacatttct tgcgacagca aggcacctct ctcgaccgtg acaatttgta  227760
gttgcacccc ttttaactgg tacccagaac tcgtcgatgt tttaacgtca actgttactg  227820
tgtgggagcc tgcaacacaa tcgataatag agtgcattgt caaaggctca cacattcctg  227880
acaacactgt ccccgccact gaagagaaat ctccatcaaa gatcgggttt ccgttttcg   227940
atatgcgcgc acgaaatact tcggtggctg cattgcggca gatggtacca ccaacacgaa  228000
ttatcaatgt gcttgaggaa gagagtacta ccattttgga gaagatcgtg ctattcaagg  228060
cagccgtgct gtcgctcaag gtttcagtag ctaatgaacc ccctggaaca aatgtggctg  228120
tcgttctgct accaataatc tttccagtct tcgttccttg gtattgataa ctgagcaaga  228180
```

```
tactcagtgc gctggctgtt ggaacgctag taaagtaaga aaattcaaga ggcacaccag  228240
aagggtcaat aaatgattca tccaagcgaa actgagaggt gactgatgta gtgcttgtgc  228300
cgaacccaag gtcgagacga aacgttttca cagtactttt gtccacgaaa aatcttcccg  228360
taaaagaaca catgagaacc ccacttgttg caggcgtcag ggtcatactt aagccaggta  228420
ttgcactcca tagtgtgcta accgctgtag caaaagaaac ttgagatgcc cttgcactag  228480
cccacatcga agttggaaga aacgagaagg acactaagga cgaggtattt agcttagcac  228540
tcggggtatc tgtcgtcgat agcgctgcta agtgcaatgc gaagcgtccg tcaacaggtg  228600
cactttggaa ctgtagtact gatacccctc tgccaacatt gctagctttg ttagcttgtt  228660
cagccgtaag cgtagctgat atcgtaaaat caggagcagc aaagggagtc cattttgtga  228720
gttccgtaat gagagcagcg gtggaaacga gtaccgggtt ggatccttcg cgactgaaat  228780
atagactcga tgcttcaaac tttgcagata atccgtaaac cttcaacaca tgaaaaccgg  228840
gtgtgatttt catgtcaact tgggtggttt tcgtgaggac acctttccaa tacccagtct  228900
tgcccatcaa atcttgcatc accacaccat ccaggaccac gacagcgccg ttaccgagcc  228960
gaaagggcag acctaaatac cacgaccagc ttgtattaac tgggctagac tccacaaagt  229020
ccacttgcat cagaaaaccc acgtttgtgt ccacctgctt gaatctgccg caaagatcgc  229080
tctgagtgtt caataaaggt cccagtacag atagttctcg ctcacaaaac ccgtcgcttt  229140
ccacgggtgc aggggcagcg tcaaagtctt tcagaaaagt tggcccttgc ccagctttgt  229200
acgctgttgc tgagaatggt tttgacgcat aagagatctt tgcgtatgga ctcagtgaag  229260
cttcaaaacg gaaagcattc gagtgtgtca gttgctgttc tacatttcca attgcaataa  229320
ccagatacgt actggggtaa tttagtcgcg attcgagtac attttccgtg taatatcgag  229380
catcctggtg tgagtggtaa tggcaaacaa caatgcgtta ggtgttttta ataccaatgc  229440
catggttggt cagcaaactg ataacctaca gttctgtagt tgacgtgggc gacaagtact  229500
ccaccgctcg gagtcaccag actcgccgtc ctgtccccat ccaaattgtc atacacgacc  229560
gacggaagaa ctgcaattga attagccttt atgaaaatga cgaatactgg ggggaggggc  229620
ttcgcttaca tggcgtgagc tccacgttcg tgtctgtcgg acgagagttg acgaaggtag  229680
tgaagctggg aggtgcgcat gccccagggt ggaagagcag agcccatccg gcgagcgtcc  229740
acacgggtag cgagcggaga agcatgagcg ggctctgggt tctctcgctt ggggtgtggt  229800
ccgaagatcc ctcgaaagat ataccggact gtattcttgg accaaaagtc tagtaaaaaa  229860
aaagcctata ttagaacaaa tgtagctact ttaacctgca cggaggcact gtgagcttgg  229920
tgacagcatg actgctgctt ctgccttgtc gtcagtctga tggtcttggc ttgcctcttg  229980
gtcagatcac tactccgcct ccttgcgact gccagtgacg tagccgtcat cggcagcctc  230040
agccgtaccc cccccccccc atccgggagg gcgttacccc agcctgacca cgacacgact  230100
cagacaggaa ggccttggca atgccgagtc agcatctccc agcttgcgcc gaacggtaga  230160
ctggaccata ttaatccgac gggcaatctc tctcgtcgag agagctggcg ggggcccccct  230220 gatcgctgct gcgaccgcag caatagtgtt ctcgggggc gtggcggccg gctagttcgg  230280
tgcactaaaa cctctggcgg tcggtgtaag gcatccctca cgcactgctc gctcaggtgg  230340
ttctttagcg caatggcctt cacaatagtc cccttgagct gcgtccccgg tggtgcatca  230400
ccgtctcgcg gtcctcgagg atttgcgcgt gctgccccgg cgtgatcgta gccttgctat  230460
tcttcttgga gctagacggc atgctggtgc tggaagatcg aagtggccat gcgataaggc  230520
tgatcgaagc tcgagctatt actgagttac gcatatggag ttgcttctac taagttgcag  230580
```

```
tattgttact ctacctcgac ggccaccagt tcgggctcca gaggttgacg acgatcacag    230640
acaccttgaa tgctgctaca ccttcctcta gtgccgcagc atcttcttct gcaaccgctg    230700
catcggatcg agtaccacac caattgtgac ccctgcagta ctttcagccg ttagtgttgt    230760
ctcggctgct tctcctttcc ttatgtaggc aggctcaaag taagctcaat gcagttgttt    230820
tataggcatg tattggcgta ttccaccgct tacagttgct gaagaaggtg tgcttggaac    230880
cacgcagact ccttacattg gtgggtgtgc caatgcaatt acgatgaagt gaggccctgg    230940
cctcgactaa tctggaaagg ggtgtcgtcg gctgtcactt ggtgcatctg acagtgattg    231000 cccttttcgta cagaccgggt gcagttctca gcctcgcacc gccgaccgcc accgtgagag    231060
atgcagtagc cattgccacg gtccttcttc ttgcagcctt ccatgatgca gcggcgaatt    231120
ccgccgtgca agtagcatag tccaagacgc tgcgtcccct tcgagcatcc tggaacccgg    231180
cacttcttac cacctccatg tgctcgacaa agccctccac cttgtgaact cttgtcgcaa    231240
ccctgcactt ggcatcgtgc gccgcccccg tgggtcttac accggttgtt tgattgcgct    231300
cgtcgagtgc atccttctgc tatacactgc ttcgctcgac gagttccttt cgatttggta    231360
gacgaagtgg acgacactgt cgaagatgaa gacgtgttcg aaactgtccg cagagtcggc    231420
gggggcagcg gcactgatgg tgcgaagtac ggcacgttct tggcgaggag ttgacttcca    231480
aatggcgacg gaacgggaag gaggaaattg agtggtaacg gattcacacg cccaggggta    231540
gtcgagattg taaacgagct tggacaactg ctggtcgtct aaaagaggg acgcgctgat    231600 cgtgtccccg gaccgacgat gtcgtcccag gactcacgca agaaggagtc catgaccggt    231660
gaaaagtcag gcagctcgct ctcctgtttg atgaatacat ctccagccat gggtgtacgg    231720
ccattaatgc ggatcttcaa gtcaggcgaa agacacgaag aaacaccggc tggaaatcca    231780
gatacaccag cagctagtgg gtgctgcaca ttagcggcga gaggcgactc cgtgtcttgc    231840
gggttgaagg catcactcag tcccgtgagg ttcaattcga gattgtcttg gtcatctctt    231900
tgaaatgccg atgtgggtga ggtggctgcg gagacagcgc ccgtgttatc gagcatcatc    231960
atcgtgcttt cgaagtcgtc gtcgtccagc aggtccattg atgcagacag attcaaaata    232020
tccccaatgt tgtacaacga cgcgttacca ctggtgatag gcgaagtgcg aggatccatg    232080
gctggcggta tcgtctagga ctgaagttgg gatgcacttg cggtacagag cgaaattgga    232140
tgtgagggag aagcctacct gttagaggca aacgctgtca tagttggtag aatgaataag    232200
gtccgggatg ttggcgtgtc ctgatgagca gcgccttcgc catatgcccc ttgtatcttc    232260
cctccaagcc ttattagcga ttctggtgta gctgggtgag atggcgagtc acagcgtcaa    232320
gcttcacgtc atgcacacca ttttgtgttg agtataaata tccctcccga ccaggtcaac    232380
acccccagtg ttgacaacga gaactgggtt tagtactttg aagtcttctg tatgttagca    232440
aaacattcaa aaggaactca aatctgccac caatgctgaa ttcatccgag cctcgtcaat    232500
cagaaaatta tcagtacctc ttaacaccat taagatgctc taaaggataa acgactgctg    232560
gatgagctca ccttgagtct tcagagcgca cccgtacatc attttgctaa gctcgttgag    232620
aacgaagtct cgtgtgcgtt cgacatcctc aactcgaccc gctagattag gctcgacctc    232680
tgcataaatg cgcaggtagc tacgcaccac ggacgcaacg cgaggattca cctcggatgc    232740
agtgatgact gtccatgatg gtgatcgaaa ttcaagccct tgtgtctgca gaatgattga    232800
gtccgctttt accagaacaa tccgctggga ctccttcgaat ttgcgagaaa aatggctccc    232860
gttaatctca atgtcgctct gttctccccg tagtgtcatg acgaagctct tttcgagcga    232920
```

```
gttgggctta cttccgcgta gctgttttat tagaggacac atgctagtta atgacaaaaa   232980
gaaacagcga agaaacactg cagaacacgt acgtagcgat atcgcttatc ggggatgtcg   233040
tgcaccgtat ttaggtcctt ccacaagatc gaagatgctt gttggatcga gcattcgact   233100
ggagtcacag tctcgatctc aattaccttg ccgtactgcg tgttattgtt cacgttcatt   233160
ttggacgaaa ccaggcaagg ctggtcccac ccgagtccgg atttcgagtc gacgtacaag   233220
ttgtccgcgt gtttctccaa tatcttgagg agccctgggc tgttgtccaa aggttgtggt   233280
ggtcgataaa tcggaggcga accaccaaac acgaggtcaa taccctgcgt gagtaccaaa   233340
gggattagtt tcaccagggc acaaagctgc atcaagtcaa aagatacctg ctaatacgta   233400
cgtcaagaac actgcgtctc tgcaacaccc cacgaagaga ctctaccact tgcctctggt   233460
ttgccaggat aactttcagc tgcttgttgg tgttttcgga ctgctgtc                233508
```

<210> SEQ ID NO 39
<211> LENGTH: 493
<212> TYPE: PRT
<213> ORGANISM: Simmondsia chinensis

<400> SEQUENCE: 39

```
Met Glu Glu Met Gly Ser Ile Leu Glu Phe Leu Asp Asn Lys Ala Ile
1               5                   10                  15

Leu Val Thr Gly Ala Thr Gly Ser Leu Ala Lys Ile Phe Val Glu Lys
            20                  25                  30

Val Leu Arg Ser Gln Pro Asn Val Lys Lys Leu Tyr Leu Leu Leu Arg
        35                  40                  45

Ala Thr Asp Asp Glu Thr Ala Ala Leu Arg Leu Gln Asn Glu Val Phe
    50                  55                  60

Gly Lys Glu Leu Phe Lys Val Leu Lys Gln Asn Leu Gly Ala Asn Phe
65                  70                  75                  80

Tyr Ser Phe Val Ser Glu Lys Val Thr Val Val Pro Gly Asp Ile Thr
                85                  90                  95

Gly Glu Asp Leu Cys Leu Lys Asp Val Asn Leu Lys Glu Glu Met Trp
            100                 105                 110

Arg Glu Ile Asp Val Val Asn Leu Ala Ala Thr Ile Asn Phe Ile
        115                 120                 125

Glu Arg Tyr Asp Val Ser Leu Leu Ile Asn Thr Tyr Gly Ala Lys Tyr
    130                 135                 140

Val Leu Asp Phe Ala Lys Lys Cys Asn Lys Leu Lys Ile Phe Val His
145                 150                 155                 160

Val Ser Thr Ala Tyr Val Ser Gly Glu Lys Asn Gly Leu Ile Leu Glu
                165                 170                 175

Lys Pro Tyr Tyr Met Gly Glu Ser Leu Asn Gly Arg Leu Gly Leu Asp
            180                 185                 190

Ile Asn Val Glu Lys Lys Leu Val Glu Ala Lys Ile Asn Glu Leu Gln
        195                 200                 205

Ala Ala Gly Ala Thr Glu Lys Ser Ile Lys Ser Thr Met Lys Asp Met
    210                 215                 220

Gly Ile Glu Arg Ala Arg His Trp Gly Trp Pro Asn Val Tyr Val Phe
225                 230                 235                 240

Thr Lys Ala Leu Gly Glu Met Leu Leu Met Gln Tyr Lys Gly Asp Ile
                245                 250                 255

Pro Leu Thr Ile Ile Arg Pro Thr Ile Ile Thr Ser Thr Phe Lys Glu
            260                 265                 270
```

```
Pro Phe Pro Gly Trp Val Glu Gly Val Arg Thr Ile Asp Asn Val Pro
            275                 280                 285

Val Tyr Tyr Gly Lys Gly Arg Leu Arg Cys Met Leu Cys Gly Pro Ser
290                 295                 300

Thr Ile Ile Asp Leu Ile Pro Ala Asp Met Val Val Asn Ala Thr Ile
305                 310                 315                 320

Val Ala Met Val Ala His Ala Asn Gln Arg Tyr Val Glu Pro Val Thr
                325                 330                 335

Tyr His Val Gly Ser Ser Ala Ala Asn Pro Met Lys Leu Ser Ala Leu
            340                 345                 350

Pro Glu Met Ala His Arg Tyr Phe Thr Lys Asn Pro Trp Ile Asn Pro
        355                 360                 365

Asp Arg Asn Pro Val His Val Gly Arg Ala Met Val Phe Ser Ser Phe
370                 375                 380

Ser Thr Phe His Leu Tyr Leu Thr Leu Asn Phe Leu Leu Pro Leu Lys
385                 390                 395                 400

Val Leu Glu Ile Ala Asn Thr Ile Phe Cys Gln Trp Phe Lys Gly Lys
                405                 410                 415

Tyr Met Asp Leu Lys Arg Lys Thr Arg Leu Leu Arg Leu Val Asp
                420                 425                 430

Ile Tyr Lys Pro Tyr Leu Phe Phe Gln Gly Ile Phe Asp Asp Met Asn
            435                 440                 445

Thr Glu Lys Leu Arg Ile Ala Ala Lys Glu Ser Ile Val Glu Ala Asp
        450                 455                 460

Met Phe Tyr Phe Asp Pro Arg Ala Ile Asn Trp Glu Asp Tyr Phe Leu
465                 470                 475                 480

Lys Thr His Phe Pro Gly Val Val Glu His Val Leu Asn
                485                 490

<210> SEQ ID NO 40
<211> LENGTH: 460
<212> TYPE: PRT
<213> ORGANISM: Bombyx mori

<400> SEQUENCE: 40

Met Ser His Asn Gly Thr Leu Asp Glu His Tyr Gln Thr Val Arg Glu
1               5                   10                  15

Phe Tyr Asp Gly Lys Ser Val Phe Ile Thr Gly Ala Thr Gly Phe Leu
            20                  25                  30

Gly Lys Ala Tyr Val Glu Lys Leu Ala Tyr Ser Cys Pro Gly Ile Val
        35                  40                  45

Ser Ile Tyr Ile Leu Ile Arg Asp Lys Lys Gly Ser Asn Thr Glu Glu
50                  55                  60

Arg Met Arg Lys Tyr Leu Asp Gln Pro Ile Phe Ser Arg Ile Lys Tyr
65                  70                  75                  80

Glu His Pro Glu Tyr Phe Lys Lys Ile Ile Pro Ile Ser Gly Asp Ile
                85                  90                  95

Thr Ala Pro Lys Leu Gly Leu Cys Asp Glu Glu Arg Asn Ile Leu Ile
            100                 105                 110

Asn Glu Val Ser Ile Val Ile His Ser Ala Ala Ser Val Lys Leu Asn
        115                 120                 125

Asp His Leu Lys Phe Thr Leu Asn Thr Asn Val Gly Gly Thr Met Lys
130                 135                 140

Val Leu Glu Leu Val Lys Glu Met Lys Asn Leu Ala Met Phe Val Tyr
145                 150                 155                 160
```

```
Val Ser Thr Ala Tyr Ser Asn Thr Ser Gln Arg Ile Leu Glu Glu Lys
                165                 170                 175
Leu Tyr Pro Gln Ser Leu Asn Leu Asn Glu Ile Gln Lys Phe Ala Glu
            180                 185                 190
Glu His Tyr Ile Leu Gly Lys Asp Asn Asp Glu Met Ile Lys Phe Ile
        195                 200                 205
Gly Asn His Pro Asn Thr Tyr Ala Tyr Thr Lys Ala Leu Ala Glu Asn
    210                 215                 220
Leu Val Ala Glu Glu His Gly Glu Ile Pro Thr Ile Ile Arg Pro
225                 230                 235                 240
Ser Ile Ile Thr Ala Ser Ala Glu Glu Pro Val Arg Gly Phe Val Asp
                245                 250                 255
Ser Trp Ser Gly Ala Thr Ala Met Ala Ala Phe Ala Leu Lys Gly Trp
            260                 265                 270
Asn Asn Ile Met Tyr Ser Thr Gly Glu Glu Asn Ile Asp Leu Ile Pro
        275                 280                 285
Leu Asp Tyr Val Val Asn Leu Thr Leu Val Ala Ile Ala Lys Tyr Lys
    290                 295                 300
Pro Thr Lys Glu Val Thr Val Tyr His Val Thr Thr Ser Asp Leu Asn
305                 310                 315                 320
Pro Ile Ser Ile Arg Arg Ile Phe Ile Lys Leu Ser Glu Phe Ala Ser
                325                 330                 335
Lys Asn Pro Thr Ser Asn Ala Ala Pro Phe Ala Ala Thr Thr Leu Leu
            340                 345                 350
Thr Lys Gln Lys Pro Leu Ile Lys Leu Val Thr Phe Leu Met Gln Thr
        355                 360                 365
Thr Pro Ala Phe Leu Ala Asp Leu Trp Met Lys Thr Gln Arg Lys Glu
    370                 375                 380
Ala Lys Phe Val Lys Gln His Asn Leu Val Val Arg Ser Arg Asp Gln
385                 390                 395                 400
Leu Glu Phe Phe Thr Ser Gln Ser Trp Leu Leu Arg Cys Glu Arg Ala
                405                 410                 415
Arg Val Leu Ser Ala Ala Leu Ser Asp Ser Arg Ala Val Phe Arg
            420                 425                 430
Cys Asp Pro Ser Thr Ile Asp Trp Asp Gln Tyr Leu Pro Ile Tyr Phe
        435                 440                 445
Glu Gly Ile Asn Lys His Leu Phe Lys Asn Lys Leu
    450                 455                 460
```

<210> SEQ ID NO 41
<211> LENGTH: 1491
<212> TYPE: DNA
<213> ORGANISM: Arabidopsis thaliana

<400> SEQUENCE: 41

| | |
|---|---|
| atggaattca gttgtgttca ttttcttcaa aacaagacga ttcttgtcac aggcgcaacc | 60 |
| ggtttccttg ccaaagtttt tgtggagaaa atattgagag tgcaaccaaa tgtgaataag | 120 |
| ctgtacctcg tggtgagagc atccgacaat gaagccgcga cgaaacgctt acgcacagag | 180 |
| gcattcgaga aagatctttt caaggtgtta agagataatc ttggcgatga gaaattgaat | 240 |
| acattgttgt ccgaaaaagt gtcccggtc gcaggtgata tcgcgatgga tcatttaggc | 300 |
| atgaaggact ctaatctaag agaacgtatg caaaagaaa tcgatattgt tgtcaatgtc | 360 |
| gcagctacaa ctaatttcga cgagagatat gatattggtc ttggaataaa cacatttgga | 420 |

```
gctctcaatg tccttaactt cgccaaaaaa tgtgttaaag ctcaattgct tctccatgtt      480
tcaactgctt atgtttgcgg agaaaaacca ggtctcctac ctgaaaaacc gttcgtcatg      540
gaagagattt gtaatgagaa tggtcttcaa ttggatataa accttgaaag ggagctgatg      600
aaacaaagat tgaaagaact caatgaacaa ggttgttcag aagaaggcac tactttctac      660
atgaaagaac tcggcatgga aagggcaaag cttcatggat ggccaaacac atatgttttc      720
accaaatcga tgggagagat gcttcttggt aaccataaag aaaatcttcc tctcgtcatt      780
atccgtccca cgatgatcac tagcactctt tttgaaccat ttcctggttg gattgaagga      840
ctaagaactg tagacagtgt aattattgcg tacgaaaagg gagtgctcaa gtgttttctt      900
gtcgatgtaa actcggtttg cgatatgata ccagcggata tggtggcaaa cgcgatgatc      960
gcagctgcag ccacacatgc tggaggttca aaggttcaca tggtgtacca agttggttca     1020
tctcaccaaa acccaataat atatggagag atccgtgaaa ttttgttttg ttacttcacc     1080
aaaaactcgt tgcgcagtcg caatggctca atgataactg tctcgaaaat gaagctgata     1140
ccaactctgg ctttgttcag cctctacatg accatacgtt acaaactacc tgtccagtta     1200
ttaaaattgg ttgatataat atatccttcg agggaaggag acgaatacaa aaacaaaaac     1260
cgcaagatcg atatggtgat gagattggta aagctttacg agccttacgt actcttcaag     1320
ggcatattcg acgataggaa tactaaaaac ttatgcgcca agcagaaaga gaggacaac      1380 agaaattcag aaaatttat gtttgatttc gaccctaaaa tcattaaatg gaaagattat      1440
cttataaatg tacacattcc tggcctcatc actcacgtgc ttaagaagtg a              1491
```

<210> SEQ ID NO 42
<211> LENGTH: 1584
<212> TYPE: DNA
<213> ORGANISM: Arabidopsis thaliana

<400> SEQUENCE: 42

```
atggctacca caaatgtcct cgccacgagc cacgccttca aattgaatgg tgtcagctac       60
ttctcctctt ttccccgcaa acctaaccac tacatgcctc gtcgtcgttt atcacatact      120
actcgtagag tccaaacttc gtgtttttat ggtgagacgt cttttgaagc tgtaacgtcg      180
ttagttacgc ctaagacaga acaagtcgt aacagtgacg gaattggaat cgtccgtttc       240
ttagaaggga aaagctatct tgttactggt gcaacagggt tcttgccaa agtgttgatt       300 gagaaactgt tgagggaaag tcttgaaatt gggaagatct tccttctgat gagatccaag      360
gatcaagaat cagcaaacaa gagactctac gatgagatca taagctcgga tctgttcaag      420
cttctgaagc aaatgcatgg gagctcttac gaagctttca tgaagagaaa gttgattcca      480
gtaattggag acattgagga agacaatcta ggatcaaat ctgaaatagc aaacatgatc      540
agtgaggaga ttgatgttat tatcagttgt ggtggtcgta caacattcga cgacagatac      600
gattctgccc taagtgtcaa tgctcttgga ccggcttacg tgactggtaa agagagggg      660 acagtactag aaactcctct ctgcattgga gaaaacataa cttctgactt gaacatcaaa      720
tccgagctga aactagcttc agaagctgta agaaagttcc gtggcagaga agaaatcaag      780
aaactcaaag aactcggttt tgaaagagct caacactatg gtgggaaaa tagttacaca      840 ttcacaaaag ccataggtga ggctgtaatt cacagcaagc gaggaaactt gcctgtagtg      900
atcataaggc ctagtattat cgaaagctct acaatgagc ctttccctgg ctggatccaa      960
gggacaagaa tggctgatcc aatcatcttg gcttatgcca aaggccagat ttctgacttc     1020
```

```
tgggcagatc ctcaatcttt gatggacatt atacctgttg acatggttgc aaacgcagca    1080
atagcagcca tggcaaagca tggttgtggt gtcccagagt tcaaagttta caatttaact    1140
tcttcatctc atgtgaaccc catgcgtgct ggcaaattga tagacctctc tcatcaacat    1200
ctgtgtgact ttccattgga agaaacagtg atagacttag agcatatgaa aatccacagt    1260
tccttagagg gtttcacttc tgctttatcg aacacaataa taaaacagga aagagtgatt    1320
gataatgaag gaggaggatt gagcacgaag ggaaagagga agctaaacta ttttgtgtcc    1380
ttggcaaaaa catatgagcc ttacacattc tttcaagctc ggtttgacaa caccaataca    1440
acaagtctga tacaggagat gtcaatggaa gagaaaaaaa cgtttgggtt cgatatcaaa    1500
ggcattgact gggagcatta cattgtcaac gttcatcttc caggtctcaa aaaggaattt    1560
ctttctaaga agaagactga gtaa                                           1584
```

<210> SEQ ID NO 43
<211> LENGTH: 1628
<212> TYPE: DNA
<213> ORGANISM: Ostrinia scapulalis

<400> SEQUENCE: 43

```
gaaaacagtc tagaaaaatg tcagcaaata ccatggaaac tgatgaacaa tttactgata      60
attcaccaat tgtgaatttt tactctggaa aatctgtttt tgttactgga gctacaggat     120
ttctggggac ggttttagtc gagaaactgc tgttctcttg caaggaata  aataatattt     180 acattttgat aaagcagaca gaagacctga ccattgaagc gaggatttta aattatttga     240
attcgaaggc ttttcataga gtgaaaaata caaacccaga gttgatgaaa aaattatac      300 cgatatgtgg gaatttggaa gataaaaatc ttggtatcag cgacagcgac atgaaaacgc     360
ttctagagga ggtatccatc gttttcatg tagctgcaaa attgttatt  aaaatgagct      420 tgactgcagc agtcaatata aataccaaac ccactgaaca gctcatagcg atttgcaaaa     480
aaatgcggcg taatcccatt ttcatctatg tctctagcgc atacagtaat gtaaatgaac     540
aaataatcga tgaaaaagtg tacaacactg gagtaccttt ggaaactatt tatgatacgc     600
tggatacaga aaatacacga ataacggata tttttttaga taaaagacca aatacgtata     660
cctattcaaa agctcttgca gaagtagtag ttgaaaaaga atttgatgaa tcagcagcca     720
ttgttcggcc ttcgataatt gtgtcttcga ttcgggaacc cataccggga tggttgagcg     780
gttcgcacgg attccctagg gtagtaggag cagcatgcaa ggggctcctc ttgcggtggc     840
atggggacgg tacagttgtc tgcgacctta tacctgtaga ccacgttgcg aacctcatca     900
ttgcagcagc atgggaatcc aatgaaagac ggttaatggg caacaaagga gtcaaggtat     960
ataactgttg ttcaagccta cggaacccaa tagacgtgat caccgtagtt aaaacttgca    1020
taaaatacag gaaatatttt ggaactcgca ccatgtccat atttacccca cgatttatta    1080
tgaaaaagaa ttacttatc tacaaattgt tgtacttcac ctgccacaca ataccggcag     1140
ctataataga cggcttcttc tggctcactg gacggactcc aataatgctg aagaccctgg    1200
acaaactcag caaaatctct tctgtcctgg agtacttcac gcaccaccaa tttatattcc    1260
tggacagcaa cgtcagagga cttctcagaa ggatggaggg cacagacaga caaacgttta    1320
attttgatgt cactgaaatt gagtgggagc cgtatctaca aactttgtg cgcggcatcg      1380 caaataatta cgactatagt atgtaatata gtattgaggt ttgatattga ttgaggagag    1440
gtgaaattta gcctatgtta ctcgtgaata atgtagcttt cgaatggtga aagaattatt    1500
aaaaacggtc cagtagtttt tgagcctata aattacaacc aaacaaacct aatattagtg    1560
```

```
tagatttgaa tttgaaaagt gaggtataaa atcttgtcat tactgtcaaa aaaaaaaaaa    1620
aaaaaaaa                                                             1628
```

<210> SEQ ID NO 44
<211> LENGTH: 559
<212> TYPE: PRT
<213> ORGANISM: Unknown
<220> FEATURE:
<223> OTHER INFORMATION: Synthetic polypeptide encoded by DNA from
      Actinobacter species

<400> SEQUENCE: 44

```
Met Glu Lys Ile Trp Phe Ala Glu Tyr Gln Lys Thr Gly Ile Pro Glu
1               5                   10                  15

Thr Val Glu Leu Pro Pro Glu Asn Thr Ser Leu Val Asp Ile Phe Glu
            20                  25                  30

Arg Asn Phe Gln Lys Phe Gly Ser Arg Asp Ala Phe Ile Phe Met Asp
        35                  40                  45

Lys Ala Leu Thr Phe Asn Glu Leu Glu Ala Ser Arg Lys Phe Ala
    50                  55                  60

Ala Tyr Leu Gln Ser Leu Asn Leu Pro Lys Gly Ser Arg Val Ala Val
65                  70                  75                  80

Met Met Pro Asn Val Leu Gln Tyr Pro Ile Val Ala Leu Gly Val Phe
                85                  90                  95

Arg Ala Gly Leu Val Leu Val Asn Val Asn Pro Leu Tyr Thr Ala Arg
            100                 105                 110

Glu Leu Glu His Gln Leu Asn Asp Ser Gly Ala Glu Val Leu Val Ile
        115                 120                 125

Ile Glu Asn Phe Ala Ser Val Tyr Gln Thr Ile Leu Gly Lys Thr Pro
130                 135                 140

Val Lys His Val Val Ile Ala Ser Val Gly Asp Met Leu Gly Thr Leu
145                 150                 155                 160

Lys Gly Thr Leu Val Asn Phe Val Leu Arg Lys Val Arg Lys Gln Ile
                165                 170                 175

Pro Ala Trp Asn Val Pro Gly His Val Lys Phe Asn Ser Ala Leu Asn
            180                 185                 190

Lys Val Ser Pro Ser His Tyr Lys Arg Pro Asn Leu Thr Leu Ser Asp
        195                 200                 205

Thr Ala Val Leu Gln Tyr Thr Gly Gly Thr Thr Gly Val Ser Lys Gly
210                 215                 220

Ala Glu Leu Thr His Arg Asn Leu Val Ala Asn Met Leu Gln Cys Asp
225                 230                 235                 240

Gly Ile Phe Gln Ser Lys Phe Gly Ser Gly Asp Ser Ser Lys Asp Asp
                245                 250                 255

Lys Met Phe Cys Ala Leu Pro Leu Tyr His Ile Phe Ala Phe Met Val
            260                 265                 270

Cys Ala Met Tyr Gly Met Tyr Lys Gly Gln Ala Asn Ile Leu Ile Pro
        275                 280                 285

Asn Pro Arg Asp Leu Pro Ala Val Ile Lys Glu Leu Arg Lys Tyr Gln
    290                 295                 300

Pro Thr Phe Phe Pro Ala Val Asn Thr Leu Phe Asn Ala Leu Val His
305                 310                 315                 320

Asn Glu Glu Phe Lys Gln Leu Asp His Ser Lys Leu Lys Ile Ala Met
                325                 330                 335
```

```
Gly Gly Gly Met Ala Val Leu Pro Ser Thr Ala Glu Ala Trp Lys Arg
            340                 345                 350

Ile Thr Gly Val Thr Ile Ile Glu Gly Tyr Gly Leu Ser Glu Thr Ser
            355                 360                 365

Pro Val Ala Thr Val Asn Pro Pro Ala Ser Ser Glu Phe Ser Gly Thr
            370                 375                 380

Ile Gly Ile Pro Leu Pro Leu Thr Asp Val Ala Ile Leu Asp Asp Asp
385                 390                 395                 400

Gly His Pro Val Ala Leu Gly Glu Gln Gly Glu Ile Ser Ile Arg Gly
            405                 410                 415

Pro Gln Val Met Lys Gly Tyr Trp Asn Arg Pro Asp Glu Thr Ala Lys
            420                 425                 430

Val Met Thr Ser Asp Gly Phe Phe Arg Thr Gly Asp Ile Gly Val Met
            435                 440                 445

Asn Asp Arg Gly Tyr Val Lys Ile Val Asp Arg Lys Lys Asp Met Ile
450                 455                 460

Leu Val Ser Gly Phe Asn Val Tyr Pro Ser Glu Ile Glu Glu Val Ile
465                 470                 475                 480

Ala Lys His Pro Lys Val Leu Glu Val Ala Ala Ile Gly Val Pro Asp
            485                 490                 495

Glu Lys Ser Gly Glu Val Pro Lys Leu Phe Ile Val Lys Lys Asp Pro
            500                 505                 510

Ser Leu Thr Thr Glu Glu Val Leu Ser Phe Ala Lys Glu Asn Leu Thr
            515                 520                 525

Gly Tyr Lys Arg Pro Arg Tyr Val Glu Phe Met Asp Glu Leu Pro Lys
            530                 535                 540

Ser Asn Val Gly Lys Ile Leu Arg Lys Asp Leu Arg Lys Thr Asn
545                 550                 555

<210> SEQ ID NO 45
<211> LENGTH: 562
<212> TYPE: PRT
<213> ORGANISM: Haemophilus influenzae

<400> SEQUENCE: 45

Met Glu Lys Ile Trp Phe Gln Asn Tyr Pro Lys Gly Ser Glu Lys Phe
1               5                   10                  15

Leu Asp Thr Ser Lys Tyr Glu Ser Ile Leu Asp Met Phe Asp Lys Ala
            20                  25                  30

Val Arg Glu His Pro Asp Arg Pro Ala Tyr Ile Asn Met Gly Gln Val
            35                  40                  45

Leu Thr Phe Arg Lys Leu Glu Glu Arg Ser Arg Ala Phe Ala Ala Tyr
        50                  55                  60

Leu Gln Asn Glu Phe Lys Leu Gln Arg Gly Asp Arg Val Ala Leu Met
65                  70                  75                  80

Met Pro Asn Leu Leu Gln Tyr Pro Ile Ala Leu Phe Gly Ile Leu Arg
            85                  90                  95

Ala Gly Leu Ile Ala Val Asn Val Asn Pro Leu Tyr Thr Pro Arg Glu
            100                 105                 110

Leu Glu Leu Gln Leu Gln Asp Ser Gly Ala Val Ala Ile Val Val Val
            115                 120                 125

Ser Asn Phe Ala Ser Thr Leu Glu Lys Val Val Phe Asn Thr Asn Val
            130                 135                 140

Lys His Val Ile Leu Thr Arg Met Gly Asp Gln Leu Ser Phe Gly Lys
145                 150                 155                 160
```

```
Arg Thr Leu Val Asn Phe Val Lys Tyr Val Lys Leu Val Pro
                165                 170                 175

Lys Tyr Lys Leu Pro His Ala Val Thr Phe Arg Glu Val Leu Ser Ile
                180                 185                 190

Gly Lys Tyr Arg Gln Tyr Val Arg Pro Glu Ile Ser Arg Glu Asp Leu
                195                 200                 205

Ala Phe Leu Gln Tyr Thr Gly Gly Thr Thr Gly Val Ala Lys Gly Ala
                210                 215                 220

Met Leu Thr His Gly Asn Ile Ile Thr Asn Val Phe Gln Ala Lys Trp
225                 230                 235                 240

Ile Ala Glu Pro Phe Ile Gly Asp His Ser Arg Thr Arg Ser Ala Ile
                245                 250                 255

Leu Ala Leu Pro Leu Tyr His Val Phe Ala Leu Thr Val Asn Cys Leu
                260                 265                 270

Leu Phe Leu Glu Leu Gly Val Thr Ala Ile Leu Ile Thr Asn Pro Arg
                275                 280                 285

Asp Ile Glu Gly Phe Val Lys Glu Leu Lys Lys Tyr Arg Phe Glu Ala
                290                 295                 300

Ile Thr Gly Val Asn Thr Leu Phe Asn Ala Leu Leu Asn Asn Glu Asn
305                 310                 315                 320

Phe Lys Glu Val Asp Phe Ser Ala Leu Lys Leu Ser Val Gly Gly Gly
                325                 330                 335

Met Ala Ile Gln Gln Ser Val Ala Thr Arg Trp His Glu Leu Thr Gly
                340                 345                 350

Cys Asn Ile Ile Glu Gly Tyr Gly Met Thr Glu Cys Ser Pro Leu Ile
                355                 360                 365

Ala Ala Cys Pro Ile Asn Val Val Lys His Asn Gly Thr Ile Gly Val
                370                 375                 380

Pro Val Pro Asn Thr Asp Ile Lys Ile Ile Lys Asp Asp Gly Ser Asp
385                 390                 395                 400

Ala Lys Ile Gly Glu Ala Gly Glu Leu Trp Val Lys Gly Asp Gln Val
                405                 410                 415

Met Arg Gly Tyr Trp Gln Arg Pro Glu Ala Thr Ser Glu Val Leu Lys
                420                 425                 430

Asp Gly Trp Met Ala Thr Gly Asp Ile Val Ile Met Asp Glu Ser Tyr
                435                 440                 445

Ser Leu Arg Ile Val Asp Arg Lys Asp Ile Ile Leu Val Ser Gly
                450                 455                 460

Phe Asn Val Tyr Pro Asn Glu Ile Glu Asp Val Val Met Leu Asn Tyr
465                 470                 475                 480

Lys Val Ser Glu Ala Val Ala Ile Gly Val Pro His Ala Val Ser Gly
                485                 490                 495

Glu Thr Ile Lys Ile Phe Val Val Lys Lys Asp Asp Ser Leu Thr Arg
                500                 505                 510

Asp Glu Leu Arg Asn His Cys Arg Gln Tyr Leu Thr Gly Tyr Lys Val
                515                 520                 525

Pro Lys Glu Ile Glu Phe Arg Asp Glu Leu Pro Lys Thr Asn Val Gly
                530                 535                 540

Lys Ile Leu Arg Arg Val Leu Arg Asp Glu Glu Ile Ala Lys Arg Pro
545                 550                 555                 560

Lys His
```

```
<210> SEQ ID NO 46
<211> LENGTH: 562
<212> TYPE: PRT
<213> ORGANISM: Pseudomonas aeruginosa

<400> SEQUENCE: 46

Met Ile Glu Asn Phe Trp Lys Asp Lys Tyr Pro Ala Gly Ile Ala Ala
1               5                   10                  15

Glu Ile Asn Pro Asp Gln Tyr Pro Asn Ile Leu Ser Val Leu Lys Glu
            20                  25                  30

Ser Cys Gln Arg Phe Ala Thr Lys Pro Ala Phe Thr Asn Leu Gly Lys
        35                  40                  45

Thr Leu Thr Tyr Gly Glu Leu Tyr Lys Leu Ser Gly Asp Phe Ala Ala
    50                  55                  60

Tyr Leu Gln Gln His Thr Asp Leu Lys Pro Gly Asp Arg Ile Ala Val
65                  70                  75                  80

Gln Leu Pro Asn Val Leu Gln Tyr Pro Ile Val Val Phe Gly Ala Met
                85                  90                  95

Arg Ala Gly Leu Ile Val Val Asn Thr Asn Pro Leu Tyr Thr Ala Arg
            100                 105                 110

Glu Leu Glu His Gln Phe Asn Asp Ser Gly Ala Lys Ala Val Val Cys
        115                 120                 125

Leu Ala Asn Met Ala His Leu Val Glu Gly Val Leu Pro Lys Thr Gly
    130                 135                 140

Val Lys Gln Val Ile Val Thr Glu Val Gly Asp Ile Leu Pro Pro Leu
145                 150                 155                 160

Lys Arg Phe Ile Val Asn Phe Val Val Lys His Ile Lys Lys Met Val
                165                 170                 175

Pro Ala Tyr Ser Leu Pro Gln Ala Thr Lys Leu Thr Asp Ala Leu Ala
            180                 185                 190

Arg Gly Ala Gly Lys Ser Phe Gln Glu Ala Ala Pro Gln Ala Asp Asp
        195                 200                 205

Val Ala Val Leu Gln Tyr Thr Gly Gly Thr Thr Gly Val Ala Lys Gly
    210                 215                 220

Ala Met Leu Thr His Arg Asn Leu Val Ala Asn Met Leu Gln Cys Lys
225                 230                 235                 240

Ala Leu Met Gly Ala Asn Leu Asn Glu Gly Cys Glu Ile Leu Ile Ala
                245                 250                 255

Pro Leu Pro Leu Tyr His Ile Tyr Ala Phe Thr Phe His Cys Met Ala
            260                 265                 270

Met Met Leu Thr Gly Asn His Asn Ile Leu Ile Thr Asn Pro Arg Asp
        275                 280                 285

Leu Pro Ser Met Leu Lys Asp Leu Gly Gln Trp Lys Phe Thr Gly Phe
    290                 295                 300

Val Gly Leu Asn Thr Leu Phe Val Ala Leu Cys Asn Asn Glu Thr Phe
305                 310                 315                 320

Arg Lys Leu Asp Phe Ser Ala Leu Lys Leu Thr Leu Ser Gly Gly Met
                325                 330                 335

Ala Leu Gln Leu Ala Thr Ala Glu Arg Trp Lys Glu Val Thr Gly Cys
            340                 345                 350

Ala Ile Cys Glu Gly Tyr Gly Met Thr Glu Thr Ala Pro Val Val Ser
        355                 360                 365

Val Asn Pro Phe Gln Asn Ile Gln Val Gly Thr Ile Gly Ile Pro Val
    370                 375                 380
```

```
Pro Ser Thr Leu Cys Lys Val Ile Gly Asp Asp Gly Gln Glu Val Pro
385                 390                 395                 400

Leu Gly Glu Arg Gly Glu Leu Cys Val Lys Gly Pro Gln Val Met Lys
            405                 410                 415

Gly Tyr Trp Gln Arg Gln Glu Ala Thr Asp Glu Ile Leu Asp Ala Asp
        420                 425                 430

Gly Trp Leu Lys Thr Gly Asp Ile Ala Ile Gln Glu Asp Gly Tyr
    435                 440                 445

Met Arg Ile Val Asp Arg Lys Lys Asp Met Ile Leu Val Ser Gly Phe
450                 455                 460

Asn Val Tyr Pro Asn Glu Leu Glu Asp Val Leu Ala Thr Leu Pro Gly
465                 470                 475                 480

Val Leu Gln Cys Ala Ala Ile Gly Ile Pro Asp Glu Lys Ser Gly Glu
            485                 490                 495

Ser Ile Lys Val Phe Val Val Lys Pro Gly Ala Thr Leu Thr Lys
            500                 505                 510

Glu Gln Val Met Gln His Met His Asp Asn Leu Thr Gly Tyr Lys Arg
            515                 520                 525

Pro Lys Ala Val Glu Phe Arg Asp Ser Leu Pro Thr Thr Asn Val Gly
            530                 535                 540

Lys Ile Leu Arg Arg Glu Leu Arg Asp Glu Gly Leu Lys Lys Ala Gly
545                 550                 555                 560

Gln Lys

<210> SEQ ID NO 47
<211> LENGTH: 562
<212> TYPE: PRT
<213> ORGANISM: Pseudomonas aeruginosa

<400> SEQUENCE: 47

Met Gln Pro Glu Phe Trp Asn Asp Lys Arg Pro Ala Gly Val Pro Asp
1               5                   10                  15

Ser Leu Asp Phe Ala Ala Tyr Arg Ser Val Val Glu Val Phe Glu Arg
            20                  25                  30

Ser Cys Lys Lys Phe Ala Asp Arg Pro Ala Phe Ser Asn Leu Gly Val
        35                  40                  45

Thr Leu Ser Tyr Ala Glu Leu Asp Arg Leu Ser Ala Ala Phe Ala Ala
    50                  55                  60

Tyr Leu Gln Lys Gln Thr Asp Leu Gln Pro Gly Asp Arg Ile Ala Val
65                  70                  75                  80

Gln Met Pro Asn Val Leu Gln Tyr Pro Ile Ala Val Phe Gly Ala Leu
                85                  90                  95

Arg Ala Gly Leu Val Val Val Asn Thr Asn Pro Leu Tyr Thr Ala Arg
            100                 105                 110

Glu Met Arg His Gln Phe Lys Asp Ala Gly Val Arg Ala Leu Val Tyr
        115                 120                 125

Leu Asn Val Phe Gly Lys Leu Val Glu Glu Val Leu Pro Asp Thr Arg
    130                 135                 140

Ile Glu Tyr Leu Ile Glu Ala Arg Met Gly Asp Leu Leu Pro Ala Leu
145                 150                 155                 160

Lys Gly Trp Leu Val Asn Ser Val Val Lys Ser Val Lys Lys Met Val
                165                 170                 175

Pro Asp Tyr Arg Leu Pro Gln Ala Leu Pro Phe Arg Gln Ala Leu Lys
            180                 185                 190
```

Gln Gly Gln Gly His Ala Leu Gln Pro Val Arg Val Gly Leu Glu Asp
            195                 200                 205

Val Ala Val Leu Gln Tyr Thr Gly Gly Thr Thr Gly Val Ser Lys Gly
210                 215                 220

Ala Met Leu Thr His Gly Asn Leu Val Ala Asn Met Leu Gln Val His
225                 230                 235                 240

Ala Gln Leu Ser Gln Leu Gly Lys Asp Gly Leu Pro Leu Met Lys Glu
            245                 250                 255

Ala Gln Glu Val Met Ile Ala Pro Pro Leu Tyr His Ile Tyr Ala
            260                 265                 270

Phe Thr Ala Asn Cys Met Cys Met Met Val Ser Gly Asn His Asn Val
            275                 280                 285

Leu Ile Thr Asn Pro Arg Asp Ile Pro Gly Phe Val Lys Glu Leu Lys
290                 295                 300

Lys Trp Arg Phe Ser Ala Leu Leu Gly Leu Asn Thr Leu Phe Val Ala
305                 310                 315                 320

Leu Met Glu His Pro Gly Phe Lys Asp Val Asp Phe Ser Asn Leu Lys
            325                 330                 335

Leu Thr Asn Ser Gly Gly Thr Ala Leu Val Ser Ala Thr Ala Glu Arg
            340                 345                 350

Trp Lys Gly Val Thr Gly Cys Thr Val Val Glu Gly Tyr Gly Leu Thr
            355                 360                 365

Glu Cys Ser Pro Val Val Thr Thr Asn Pro Tyr Gly Glu Gln Ala Arg
            370                 375                 380

Leu Gly Thr Val Gly Ile Pro Val Val Gly Thr Ala Leu Lys Val Ile
385                 390                 395                 400

Asp Glu Gln Gly Asn Glu Leu Pro Val Gly Glu Arg Gly Glu Leu Cys
            405                 410                 415

Val Lys Gly Pro Gln Val Met Lys Gly Tyr Trp Gln Arg Pro Glu Ala
            420                 425                 430

Thr Glu Glu Ile Leu Asp Ala Glu Gly Trp Leu Lys Thr Gly Asp Ile
            435                 440                 445

Ala Val Ile Asp Glu Asp Gly Phe Val Arg Ile Val Asp Arg Lys Lys
450                 455                 460

Asp Leu Ile Leu Val Ser Gly Phe Asn Val Tyr Pro Asn Glu Ile Glu
465                 470                 475                 480

Asp Val Val Met Ala His Pro Lys Val Ala Ser Cys Ala Ala Val Gly
            485                 490                 495

Ile Pro Asp Glu Lys Ser Gly Glu Ala Val Lys Leu Phe Val Val Ala
            500                 505                 510

Arg Asp Pro Ser Leu Ser Val Glu Glu Leu Lys Ala Tyr Cys Lys Glu
            515                 520                 525

Asn Leu Thr Gly Tyr Lys Ile Pro Arg Gln Ile Val Leu Lys Asp Ala
530                 535                 540

Leu Pro Met Thr Pro Val Gly Lys Ile Leu Arg Arg Glu Leu Arg Glu
545                 550                 555                 560

Ile Ala

<210> SEQ ID NO 48
<211> LENGTH: 564
<212> TYPE: PRT
<213> ORGANISM: Bacillus halodurans

<400> SEQUENCE: 48

```
Met Val Asp Val Glu Asn Arg Glu Trp Phe Asn Ala Tyr Pro Lys Glu
1               5                   10                  15

Val Pro His Thr Ile Asp Tyr Pro Asn Gln Thr Leu His Asp Leu Ile
            20                  25                  30

Lys Glu Ala Ala Thr Thr Tyr Pro His His Val Ala Leu His Phe Leu
                35                  40                  45

Gly Lys Thr Met Thr Tyr Gln Leu Phe Tyr Glu Gln Val Gln Arg Phe
        50                  55                  60

Ala Ala Asn Leu Gln Gln Leu Gly Leu Gln Lys Gly Glu Arg Val Ser
65                  70                  75                  80

Ile Met Leu Pro Asn Cys Pro Gln Ala Val Ile Ala Tyr Tyr Gly Val
                85                  90                  95

Leu Val Ala Gly Gly Val Val Gln Thr Asn Pro Leu Tyr Val Glu
                100                 105                 110

Arg Glu Leu Asn His Gln Leu Ile Asp Ser Gly Ala Arg Phe Ile Val
            115                 120                 125

Cys Leu Asp Val Leu Tyr Pro Arg Val Ile Lys Ser Arg Glu Gly Ala
    130                 135                 140

Pro Leu Glu His Val Ile Val Thr Ala Ile Lys Asp Tyr Leu Pro Phe
145                 150                 155                 160

Pro Lys Asn Met Ile Tyr Pro Phe Ile Gln Lys Pro Lys Pro Lys Gly
                165                 170                 175

Lys Ile Gly Tyr Gly Ser His Val His Arg Phe Val Pro Met Ala Gln
                180                 185                 190

Ser Gly Ser Thr Asn Pro Thr Pro Val Arg Ile Asp Pro Lys Glu Asp
        195                 200                 205

Leu Ala Leu Leu Gln Tyr Thr Gly Gly Thr Thr Gly Val Ala Lys Gly
    210                 215                 220

Val Met Leu Thr His Tyr Asn Leu Val Ala Asn Thr Ile Gln Cys Arg
225                 230                 235                 240

Lys Trp Met Tyr Lys Trp Arg Asp Gly Gln Glu Arg Thr Leu Ala Val
                245                 250                 255

Leu Pro Phe Phe His Val Tyr Gly Met Thr Thr Ser Met Asn Leu Thr
                260                 265                 270

Leu Met Thr Gly Ser Glu Leu His Ile Val Pro Arg Phe Asp Pro Leu
    275                 280                 285

Gln Val Leu Lys Met Ile Asp Lys Lys Ile Thr Met Phe Pro Gly
    290                 295                 300

Ala Pro Thr Met Tyr Ile Ala Leu Ile Asn His Pro Asp Leu Lys Lys
305                 310                 315                 320

Tyr Asp Leu Ser Ser Ile Glu Ala Cys Ile Ser Gly Ser Ser Ser Leu
                325                 330                 335

Pro Ala Glu Val Gln Gln Thr Phe Glu Gln Leu Thr Gly Gly Arg Leu
                340                 345                 350

Val Glu Gly Tyr Gly Leu Thr Glu Ala Ser Pro Val Thr Asn Cys Asn
                355                 360                 365

Leu Val Trp Gly Glu Arg Lys Asp Gln Ser Ile Gly Val Pro Trp Pro
    370                 375                 380

Asp Thr Asp Val His Ile Arg Ser Leu Glu Thr Gly Glu Ser Leu Pro
385                 390                 395                 400

Ser Gly Glu Ile Gly Glu Val Val Val Arg Gly Pro Gln Val Met Lys
                405                 410                 415

Gly Tyr Trp Asn Arg Pro Glu Glu Thr Asn Ala Thr Leu Gln Asn Gly
```

```
                      420                 425                 430
Trp Leu Tyr Thr Gly Asp Met Gly Tyr Lys Asp Glu Glu Gly Tyr Phe
            435                 440                 445

Tyr Ile Val Asp Arg Lys Lys Asp Met Ile Ile Ala Gly Gly Phe Asn
            450                 455                 460

Ile Tyr Pro Arg Glu Val Glu Val Leu Tyr Ala His Ala Lys Val
465                 470                 475                 480

Gln Glu Ala Val Val Ile Gly Val Pro Asp Glu Tyr Arg Gly Glu Thr
                    485                 490                 495

Val Lys Ala Phe Ile Val Val Lys Glu Gly Glu Ser Val Ser Glu Lys
            500                 505                 510

Glu Leu Asn Asp Tyr Cys Arg Thr His Leu Ala Ala Tyr Lys Val Pro
            515                 520                 525

Arg Lys Tyr Glu Phe Arg Asp Asp Leu Pro Lys Thr Met Val Gly Lys
            530                 535                 540

Val Leu Lys Arg Val Leu Ile Glu Glu Thr Lys Lys Gln Gly Ile
545                 550                 555                 560

Lys Gln Ser Ser

<210> SEQ ID NO 49
<211> LENGTH: 513
<212> TYPE: PRT
<213> ORGANISM: Bacillus subtilis

<400> SEQUENCE: 49

Met Asn Leu Val Ser Lys Leu Glu Glu Thr Ala Ser Glu Lys Pro Asp
1               5                   10                  15

Ser Ile Ala Cys Arg Phe Lys Asp His Met Met Thr Tyr Gln Glu Leu
            20                  25                  30

Asn Glu Tyr Ile Gln Arg Phe Ala Asp Gly Leu Gln Glu Ala Gly Met
        35                  40                  45

Glu Lys Gly Asp His Leu Ala Leu Leu Leu Gly Asn Ser Pro Asp Phe
    50                  55                  60

Ile Ile Ala Phe Phe Gly Ala Leu Lys Ala Gly Ile Val Val Pro
65                  70                  75                  80

Ile Asn Pro Leu Tyr Thr Pro Thr Glu Ile Gly Tyr Met Leu Thr Asn
                85                  90                  95

Gly Asp Val Lys Ala Ile Val Gly Val Ser Gln Leu Leu Pro Leu Tyr
            100                 105                 110

Glu Ser Met His Glu Ser Leu Pro Lys Val Glu Leu Val Ile Leu Cys
        115                 120                 125

Gln Thr Gly Glu Ala Glu Pro Glu Ala Ala Asp Pro Glu Val Arg Met
    130                 135                 140

Lys Met Thr Thr Phe Ala Lys Ile Leu Arg Pro Thr Ser Ala Ala Lys
145                 150                 155                 160

Gln Asn Gln Glu Pro Val Pro Asp Asp Thr Ala Val Ile Leu Tyr Thr
                165                 170                 175

Ser Gly Thr Thr Gly Lys Pro Lys Gly Ala Met Leu Thr His Gln Asn
            180                 185                 190

Leu Tyr Ser Asn Ala Asn Asp Val Ala Gly Tyr Leu Gly Met Asp Glu
        195                 200                 205

Arg Asp Asn Val Val Cys Ala Leu Pro Met Phe His Val Phe Cys Leu
    210                 215                 220

Thr Val Cys Met Asn Ala Pro Leu Met Ser Gly Ala Thr Val Leu Ile
```

```
                   225                 230                 235                 240

Glu Pro Gln Phe Ser Pro Ala Ser Val Phe Lys Leu Val Lys Gln Gln
                245                 250                 255

Gln Ala Thr Ile Phe Ala Gly Val Pro Thr Met Tyr Asn Tyr Leu Phe
            260                 265                 270

Gln His Glu Asn Gly Lys Lys Asp Asp Phe Ser Ser Ile Arg Leu Cys
        275                 280                 285

Ile Ser Gly Gly Ala Ser Met Pro Val Ala Leu Leu Thr Ala Phe Glu
    290                 295                 300

Glu Lys Phe Gly Val Thr Ile Leu Glu Gly Tyr Gly Leu Ser Glu Ala
305                 310                 315                 320

Ser Pro Val Thr Cys Phe Asn Pro Phe Asp Arg Gly Arg Lys Pro Gly
                325                 330                 335

Ser Ile Gly Thr Ser Ile Leu His Val Glu Asn Lys Val Val Asp Pro
            340                 345                 350

Leu Gly Arg Glu Leu Pro Ala His Gln Val Gly Glu Leu Ile Val Lys
        355                 360                 365

Gly Pro Asn Val Met Lys Gly Tyr Tyr Lys Met Pro Met Glu Thr Glu
    370                 375                 380

His Ala Leu Lys Asp Gly Trp Leu Tyr Thr Gly Asp Leu Ala Arg Arg
385                 390                 395                 400

Asp Glu Asp Gly Tyr Phe Tyr Ile Val Asp Arg Lys Lys Asp Met Ile
                405                 410                 415

Ile Val Gly Gly Tyr Asn Val Tyr Pro Arg Glu Val Glu Glu Val Leu
            420                 425                 430

Tyr Ser His Pro Asp Val Lys Glu Ala Val Val Ile Gly Val Pro Asp
        435                 440                 445

Pro Gln Ser Gly Glu Ala Val Lys Gly Tyr Val Val Pro Lys Arg Ser
    450                 455                 460

Gly Val Thr Glu Glu Asp Ile Met Gln His Cys Glu Lys His Leu Ala
465                 470                 475                 480

Lys Tyr Lys Arg Pro Ala Ala Ile Thr Phe Leu Asp Asp Ile Pro Lys
                485                 490                 495

Asn Ala Thr Gly Lys Met Leu Arg Arg Ala Leu Arg Asp Ile Leu Pro
            500                 505                 510

Gln

<210> SEQ ID NO 50
<211> LENGTH: 558
<212> TYPE: PRT
<213> ORGANISM: Marinobacter algicola

<400> SEQUENCE: 50

Met Asp Phe Glu Gln Phe Tyr Gln Asp Lys Tyr Pro Ala Gly Val Ser
1               5                   10                  15

Leu Asn Val Asp Leu Asp Lys Tyr Ser Ser Met Val Asp Val Phe Asp
            20                  25                  30

Gln Ala Val Asn Lys Tyr Ala Asp Arg Pro Ala Phe Ser Ala Val Gly
        35                  40                  45

Ala Thr Leu Thr Tyr Arg Asp Leu Asp Thr Gln Ser Arg Asn Phe Ala
    50                  55                  60

Ala Trp Leu Gln Asn Lys Thr Asp Leu Lys Pro Gly Asp Arg Ile Ala
65                  70                  75                  80

Val Gln Met Pro Asn Val Ser Gln Tyr Pro Val Val Val Phe Gly Ala
```

```
                    85                  90                  95
Met Arg Ala Gly Leu Ile Val Val Asn Thr Asn Pro Leu Tyr Thr Thr
                100                 105                 110

Arg Glu Met Glu His Gln Phe Asn Asp Ser Gly Ala Lys Ala Leu Val
            115                 120                 125

Val Leu Ala Asn Met Ala His Asn Ala Glu Lys Val Leu Pro His Thr
        130                 135                 140

Gly Ile Glu His Val Ile Val Thr Glu Ile Ala Asp Met His Ser Pro
145                 150                 155                 160

Leu Lys Arg Thr Leu Met Asn Ala Ala Val Lys His Leu Lys Lys Met
                165                 170                 175

Val Pro Ala Phe Ser Leu Pro Gln Ala His Lys Leu Pro Ala Val Leu
            180                 185                 190

Ser Ala Gly Ala Arg Glu Lys Phe Ser Pro Val Glu Cys Lys Lys Asp
        195                 200                 205

Asp Ile Ala Val Leu Gln Tyr Thr Gly Thr Thr Gly Val Ala Lys
210                 215                 220

Gly Ala Met Leu Thr His Gly Asn Leu Val Ala Asn Leu Leu Gln Val
225                 230                 235                 240

Arg Pro Met Met Glu Asp Ser Val Glu Glu Gly Thr Glu Val Val Ile
                245                 250                 255

Ala Pro Leu Pro Leu Tyr His Ile Tyr Ser Phe Thr Leu Asn Cys Gly
            260                 265                 270

Ile Met Leu Glu Ala Gly Ala His Asn Val Leu Ile Pro Asn Pro Arg
        275                 280                 285

Asp Ile Pro Gly Phe Val Lys Glu Leu Lys Asn His Arg Phe Thr Ala
    290                 295                 300

Phe Leu Gly Leu Asn Thr Leu Phe Val Ala Leu Cys Asn Asn Glu Glu
305                 310                 315                 320

Phe Lys Ala Leu Asp Phe Ser Ala Leu Lys Leu Thr Ser Ser Gly Gly
                325                 330                 335

Met Ala Leu Thr Ser Asp Thr Ala Lys Met Trp Gln Arg Val Thr Gly
            340                 345                 350

Cys Glu Ile Ser Glu Gly Tyr Gly Met Thr Glu Thr Ser Pro Val Val
        355                 360                 365

Thr Phe Asn Pro Asn Ser Ala Ile Gln Leu Gly Thr Ile Gly Leu Pro
    370                 375                 380

Ile Pro Gly Thr Gln Val Lys Thr Ile Asp Asp Gly Asn Glu Thr
385                 390                 395                 400

Pro Leu Gly Glu Pro Gly Glu Leu Cys Val Lys Gly Pro Gln Val Met
                405                 410                 415

Arg Gly Tyr Trp Gln Arg Pro Glu Asp Thr Gln Lys Ser Phe Thr Asp
            420                 425                 430

Asp Gly Phe Leu Gln Thr Gly Asp Ile Ala Leu Ile Gln Glu Asp Gly
        435                 440                 445

Tyr Ile Arg Ile Val Asp Arg Lys Lys Asp Met Ile Ile Val Ser Gly
    450                 455                 460

Phe Asn Val Phe Pro Asn Glu Ile Glu Asp Val Val Ser Gly His Pro
465                 470                 475                 480

Lys Val Val Glu Cys Ala Ala Val Gly Val Pro Asp Asp Lys Ser Gly
                485                 490                 495

Glu Ala Val Lys Val Tyr Leu Val Ala Thr Ala Glu Gly Val Thr Glu
            500                 505                 510
```

```
Asn Glu Leu Lys Glu Phe Cys Arg Glu Arg Leu Thr Ala Tyr Lys Val
            515                 520                 525

Pro Lys Ser Phe Val Phe Arg Asp Glu Leu Pro Lys Thr Asn Val Gly
        530                 535                 540

Lys Ile Leu Arg Arg Glu Leu Arg Asp Glu Ala Asn Ser Lys
545                 550                 555

<210> SEQ ID NO 51
<211> LENGTH: 558
<212> TYPE: PRT
<213> ORGANISM: Marinobacter aquaeolei

<400> SEQUENCE: 51

Met Asp Phe Glu Gln Phe Tyr Gln Asp Lys Tyr Pro Ala Gly Ile Pro
1               5                   10                  15

Arg Glu Ile Asp Leu Asn Lys Tyr Lys Asn Met Val Asp Val Phe Glu
            20                  25                  30

Gln Ala Val Gln Lys Phe Ala Asp Lys Pro Ala Phe Thr Ala Val Gly
        35                  40                  45

Val Thr Leu Thr Tyr Arg Asp Leu Asp Thr Gln Ser Arg Asn Phe Ala
50                  55                  60

Ala Trp Leu Gln Asn Lys Thr Asp Leu Lys Pro Gly Asp Arg Ile Ala
65                  70                  75                  80

Val Gln Met Pro Asn Val Thr Gln Tyr Pro Val Val Phe Gly Ala
                85                  90                  95

Met Arg Ala Gly Leu Ile Val Val Asn Thr Asn Pro Leu Tyr Thr Ile
            100                 105                 110

Arg Glu Met Glu His Gln Phe Asn Asp Ser Gly Ala Lys Ala Leu Val
        115                 120                 125

Val Leu Ala Asn Met Ala Asp Asn Ala Glu Lys Val Leu Pro His Thr
130                 135                 140

Gly Ile Glu His Val Ile Val Thr Glu Ile Ala Asp Met His Ser Pro
145                 150                 155                 160

Ile Lys Arg Thr Leu Met Asn Ala Ala Val Lys His Leu Lys Lys Met
                165                 170                 175

Val Pro Ala Phe Asn Ile Pro Gly Ala His Lys Leu Pro Ala Val Leu
            180                 185                 190

Ser Ala Gly Ala Arg Glu Lys Phe Thr Pro Val Asp Ile Lys Leu Asp
        195                 200                 205

Asp Leu Ala Val Leu Gln Tyr Thr Gly Gly Thr Thr Gly Val Ala Lys
210                 215                 220

Gly Ala Met Leu Thr His Ala Asn Leu Val Ala Asn Leu Thr Gln Val
225                 230                 235                 240

Arg Pro Met Leu Glu Asp Gln Val Glu Glu Gly Lys Glu Val Val Ile
                245                 250                 255

Ala Pro Leu Pro Leu Tyr His Ile Tyr Ser Phe Thr Leu Asn Cys Gly
            260                 265                 270

Ile Met Leu Glu Ala Gly Ala His Asn Val Leu Ile Pro Asn Pro Arg
        275                 280                 285

Asp Ile Pro Gly Phe Val Lys Glu Leu Gln Lys Gln Lys Phe Ser Ala
290                 295                 300

Phe Ile Gly Leu Asn Thr Leu Phe Val Ala Leu Cys Asn Asn Glu Asp
305                 310                 315                 320

Phe Gln Asp Leu Asp Phe Ser Gly Leu Lys Leu Thr Ala Ser Gly Gly
```

```
                   325                 330                 335
Met Ala Leu Thr Ser Asp Thr Ala Lys Met Trp Gln Arg Val Thr Gly
            340                 345                 350

Cys Glu Ile Ser Glu Gly Tyr Gly Met Thr Glu Thr Ser Pro Val Val
            355                 360                 365

Thr Phe Asn Pro Arg Ser Ala Ile Gln Ile Gly Thr Ile Gly Leu Pro
            370                 375                 380

Ile Pro Ser Thr Val Val Lys Thr Ile Asp Asp Gly Asn Glu Thr
385                 390                 395                 400

Pro Val Gly Glu Pro Gly Glu Leu Cys Val Lys Gly Pro Gln Val Met
                405                 410                 415

Arg Gly Tyr Trp Gln Arg Pro Asp Asp Thr Gln Lys Ser Phe Thr Asp
            420                 425                 430

Asp Gly Phe Leu Lys Thr Gly Asp Val Ala Leu Ile Gln Glu Asp Gly
            435                 440                 445

Tyr Ile Arg Ile Val Asp Arg Lys Lys Asp Met Ile Ile Val Ser Gly
            450                 455                 460

Phe Asn Val Phe Pro Asn Glu Ile Glu Asp Val Val Thr Thr His Pro
465                 470                 475                 480

Lys Val Val Glu Cys Ala Ala Val Gly Ile Pro Asp Ala Lys Ser Gly
                485                 490                 495

Glu Ala Val Lys Val Tyr Val Pro Thr Lys Glu Gly Val Thr Ala
                500                 505                 510

Asn Glu Ile Lys Glu Phe Cys Arg Glu Arg Leu Thr Ala Tyr Lys Val
            515                 520                 525

Pro Lys His Phe Glu Phe Arg Asp Glu Leu Pro Lys Ser Asn Val Gly
            530                 535                 540

Lys Ile Leu Arg Arg Glu Leu Arg Asp Glu Ala Asn Ala Lys
545                 550                 555

<210> SEQ ID NO 52
<211> LENGTH: 597
<212> TYPE: PRT
<213> ORGANISM: Mycobacterium tuberculosis

<400> SEQUENCE: 52

Met Ser Asp Tyr Tyr Gly Gly Ala His Thr Thr Val Arg Leu Ile Asp
1               5                   10                  15

Leu Ala Thr Arg Met Pro Arg Val Leu Ala Asp Thr Pro Val Ile Val
            20                  25                  30

Arg Gly Ala Met Thr Gly Leu Leu Ala Arg Pro Asn Ser Lys Ala Ser
        35                  40                  45

Ile Gly Thr Val Phe Gln Asp Arg Ala Ala Arg Tyr Gly Asp Arg Val
    50                  55                  60

Phe Leu Lys Phe Gly Asp Gln Gln Leu Thr Tyr Arg Asp Ala Asn Ala
65                  70                  75                  80

Thr Ala Asn Arg Tyr Ala Ala Val Leu Ala Ala Arg Gly Val Gly Pro
                85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
        115                 120                 125

Tyr His Gln Arg Gly Glu Val Leu Ala His Ser Leu Gly Leu Leu Asp
    130                 135                 140
```

```
Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
            165                 170                 175

Asp Val Glu Arg Phe Ala Thr Thr Ala Pro Ala Thr Asn Pro Ala Ser
        180                 185                 190

Ala Ser Ala Val Gln Ala Lys Asp Thr Ala Phe Tyr Ile Phe Thr Ser
    195                 200                 205

Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
            245                 250                 255

Thr Val Ala Val Ser Ser Val Ile Asn Ser Gly Ala Thr Leu Ala Leu
        260                 265                 270

Gly Lys Ser Phe Ser Ala Ser Arg Phe Trp Asp Glu Val Ile Ala Asn
    275                 280                 285

Arg Ala Thr Ala Phe Val Tyr Ile Gly Glu Ile Cys Arg Tyr Leu Leu
290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
            325                 330                 335

Phe Gly Val Ala Arg Val Cys Glu Phe Tyr Ala Ala Ser Glu Gly Asn
        340                 345                 350

Ser Ala Phe Ile Asn Ile Phe Asn Val Pro Arg Thr Ala Gly Val Ser
    355                 360                 365

Pro Met Pro Leu Ala Phe Val Glu Tyr Asp Leu Asp Thr Gly Asp Pro
    370                 375                 380

Leu Arg Asp Ala Ser Gly Arg Val Arg Val Pro Asp Gly Glu Pro
385                 390                 395                 400

Gly Leu Leu Leu Ser Arg Val Asn Arg Leu Gln Pro Phe Asp Gly Tyr
            405                 410                 415

Thr Asp Pro Val Ala Ser Glu Lys Lys Leu Val Arg Asn Ala Phe Arg
        420                 425                 430

Asp Gly Asp Cys Trp Phe Asn Thr Gly Asp Val Met Ser Pro Gln Gly
    435                 440                 445

Met Gly His Ala Ala Phe Val Asp Arg Leu Gly Asp Thr Phe Arg Trp
    450                 455                 460

Lys Gly Glu Asn Val Ala Thr Thr Gln Val Glu Ala Ala Leu Ala Ser
465                 470                 475                 480

Asp Gln Thr Val Glu Glu Cys Thr Val Tyr Gly Val Gln Ile Pro Arg
            485                 490                 495

Thr Gly Gly Arg Ala Gly Met Ala Ala Ile Thr Leu Arg Ala Gly Ala
        500                 505                 510

Glu Phe Asp Gly Gln Ala Leu Ala Arg Thr Val Tyr Gly His Leu Pro
    515                 520                 525

Gly Tyr Ala Leu Pro Leu Phe Val Arg Val Gly Ser Leu Ala His
    530                 535                 540

Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
```

```
                           565                 570                 575
Gly Tyr Val Pro Tyr Ala Glu Tyr Pro Glu Glu Val Ser Leu Gly
                   580                 585                 590

Arg Arg Pro Gln Gly
        595

<210> SEQ ID NO 53
<211> LENGTH: 600
<212> TYPE: PRT
<213> ORGANISM: Mycobacterium tuberculosis

<400> SEQUENCE: 53

Met Arg Glu Ile Ser Val Pro Ala Pro Phe Thr Val Gly Glu His Asp
1               5                   10                  15

Asn Val Ala Ala Met Val Phe Glu His Glu Arg Asp Asp Pro Asp Tyr
                20                  25                  30

Val Ile Tyr Gln Arg Leu Ile Asp Gly Val Trp Thr Asp Val Thr Cys
            35                  40                  45

Ala Glu Ala Ala Asn Gln Ile Arg Ala Ala Leu Gly Leu Ile Ser
        50                  55                  60

Leu Gly Val Gln Ala Gly Asp Arg Val Val Ile Phe Ser Ala Thr Arg
65                  70                  75                  80

Tyr Glu Trp Ala Ile Leu Asp Phe Ala Ile Leu Ala Val Gly Ala Val
                85                  90                  95

Thr Val Pro Thr Tyr Glu Thr Ser Ser Ala Glu Gln Val Arg Trp Val
            100                 105                 110

Leu Gln Asp Ser Glu Ala Val Val Leu Phe Ala Glu Thr Asp Ser His
        115                 120                 125

Ala Thr Met Val Ala Glu Leu Ser Gly Ser Val Pro Ala Leu Arg Glu
    130                 135                 140

Val Leu Gln Ile Ala Gly Ser Gly Pro Asn Ala Leu Asp Arg Leu Thr
145                 150                 155                 160

Glu Ala Gly Ala Ser Val Asp Pro Ala Glu Leu Thr Ala Arg Leu Ala
                165                 170                 175

Ala Leu Arg Ser Thr Asp Pro Ala Thr Leu Ile Tyr Thr Ser Gly Thr
            180                 185                 190

Thr Gly Arg Pro Lys Gly Cys Gln Leu Thr Gln Ser Asn Leu Val His
        195                 200                 205

Glu Ile Lys Gly Ala Arg Ala Tyr His Pro Thr Leu Leu Arg Lys Gly
    210                 215                 220

Glu Arg Leu Leu Val Phe Leu Pro Leu Ala His Val Leu Ala Arg Ala
225                 230                 235                 240

Ile Ser Met Ala Ala Phe His Ser Lys Val Thr Val Gly Phe Thr Ser
                245                 250                 255

Asp Ile Lys Asn Leu Leu Pro Met Leu Ala Val Phe Lys Pro Thr Val
            260                 265                 270

Val Val Ser Val Pro Arg Val Phe Glu Lys Val Tyr Asn Thr Ala Glu
        275                 280                 285

Gln Asn Ala Ala Asn Ala Gly Lys Gly Arg Ile Phe Ala Ile Ala Ala
    290                 295                 300

Gln Thr Ala Val Asp Trp Ser Glu Ala Cys Asp Arg Gly Gly Pro Gly
305                 310                 315                 320

Leu Leu Leu Arg Ala Lys His Ala Val Phe Asp Arg Leu Val Tyr Arg
                325                 330                 335
```

```
Lys Leu Arg Ala Ala Leu Gly Gly Asn Cys Arg Ala Ala Val Ser Gly
                340                 345                 350
Gly Ala Pro Leu Gly Ala Arg Leu Gly His Phe Tyr Arg Gly Ala Gly
            355                 360                 365
Leu Thr Ile Tyr Glu Gly Tyr Gly Leu Ser Gly Thr Ser Gly Gly Val
        370                 375                 380
Ala Ile Ser Gln Phe Asn Asp Leu Lys Ile Gly Thr Val Gly Lys Pro
385                 390                 395                 400
Val Pro Gly Asn Ser Leu Arg Ile Ala Asp Asp Gly Glu Leu Leu Val
                405                 410                 415
Arg Gly Gly Val Val Phe Ser Gly Tyr Trp Arg Asn Glu Gln Ala Thr
            420                 425                 430
Thr Glu Ala Phe Thr Asp Gly Trp Phe Lys Thr Gly Asp Leu Gly Ala
        435                 440                 445
Val Asp Glu Asp Gly Phe Leu Thr Ile Thr Gly Arg Lys Lys Glu Ile
450                 455                 460
Ile Val Thr Ala Gly Gly Lys Asn Val Ala Pro Ala Val Leu Glu Asp
465                 470                 475                 480
Gln Leu Arg Ala His Pro Leu Ile Ser Gln Ala Val Val Gly Asp
                485                 490                 495
Ala Lys Pro Phe Ile Gly Ala Leu Ile Thr Ile Asp Pro Glu Ala Phe
            500                 505                 510
Glu Gly Trp Lys Gln Arg Asn Ser Lys Thr Ala Gly Ala Ser Val Gly
        515                 520                 525
Asp Leu Ala Thr Asp Pro Asp Leu Ile Ala Glu Ile Asp Ala Ala Val
530                 535                 540
Lys Gln Ala Asn Leu Ala Val Ser His Ala Glu Ser Ile Arg Lys Phe
545                 550                 555                 560
Arg Ile Leu Pro Val Asp Phe Thr Glu Asp Thr Gly Glu Leu Thr Pro
                565                 570                 575
Thr Met Lys Val Lys Arg Lys Val Val Ala Glu Lys Phe Ala Ser Asp
            580                 585                 590
Ile Glu Ala Ile Tyr Asn Lys Glu
        595                 600

<210> SEQ ID NO 54
<211> LENGTH: 548
<212> TYPE: PRT
<213> ORGANISM: Mycobacterium tuberculosis

<400> SEQUENCE: 54

Met Ala Val Ala Leu Asn Ile Ala Asp Leu Ala Glu His Ala Ile Asp
1               5                   10                  15
Ala Val Pro Asp Arg Val Ala Val Ile Cys Gly Asp Glu Gln Leu Thr
                20                  25                  30
Tyr Ala Gln Leu Glu Asp Lys Ala Asn Arg Leu Ala His His Leu Ile
            35                  40                  45
Asp Gln Gly Val Gln Lys Asp Lys Val Gly Leu Tyr Cys Arg Asn
        50                  55                  60
Arg Ile Glu Ile Val Ile Ala Met Leu Gly Ile Val Lys Ala Gly Ala
65                  70                  75                  80
Ile Leu Val Asn Val Asn Phe Arg Tyr Val Glu Gly Glu Leu Arg Tyr
                85                  90                  95
Leu Phe Asp Asn Ser Asp Met Val Ala Leu Val His Glu Arg Arg Tyr
                100                 105                 110
```

```
Ala Asp Arg Val Ala Asn Val Leu Pro Asp Thr Pro His Val Arg Thr
            115                 120                 125

Ile Leu Val Val Glu Asp Gly Ser Asp Gln Asp Tyr Arg Arg Tyr Gly
        130                 135                 140

Gly Val Glu Phe Tyr Ser Ala Ile Ala Ala Gly Ser Pro Glu Arg Asp
145                 150                 155                 160

Phe Gly Glu Arg Ser Ala Asp Ala Ile Tyr Leu Leu Tyr Thr Gly Gly
                165                 170                 175

Thr Thr Gly Phe Pro Lys Gly Val Met Trp Arg His Glu Asp Ile Tyr
            180                 185                 190

Arg Val Leu Phe Gly Gly Thr Asp Phe Ala Thr Gly Glu Phe Val Lys
        195                 200                 205

Asp Glu Tyr Asp Leu Ala Lys Ala Ala Ala Asn Pro Pro Met Ile
    210                 215                 220

Arg Tyr Pro Ile Pro Pro Met Ile His Gly Ala Thr Gln Ser Ala Thr
225                 230                 235                 240

Trp Met Ala Leu Phe Ser Gly Gln Thr Thr Val Leu Ala Pro Glu Phe
                245                 250                 255

Asn Ala Asp Glu Val Trp Arg Thr Ile His Lys His Lys Val Asn Leu
            260                 265                 270

Leu Phe Phe Thr Gly Asp Ala Met Ala Arg Pro Leu Val Asp Ala Leu
        275                 280                 285

Val Lys Gly Asn Asp Tyr Asp Leu Ser Ser Leu Phe Leu Leu Ala Ser
    290                 295                 300

Thr Ala Ala Leu Phe Ser Pro Ser Ile Lys Glu Lys Leu Leu Glu Leu
305                 310                 315                 320

Leu Pro Asn Arg Val Ile Thr Asp Ser Ile Gly Ser Ser Glu Thr Gly
                325                 330                 335

Phe Gly Gly Thr Ser Val Val Ala Ala Gly Gln Ala His Gly Gly Gly
            340                 345                 350

Pro Arg Val Arg Ile Asp His Arg Thr Val Val Leu Asp Asp Asp Gly
        355                 360                 365

Asn Glu Val Lys Pro Gly Ser Gly Met Arg Gly Val Ile Ala Lys Lys
    370                 375                 380

Gly Asn Ile Pro Val Gly Tyr Tyr Lys Asp Glu Lys Lys Thr Ala Glu
385                 390                 395                 400

Thr Phe Arg Thr Ile Asn Gly Val Arg Tyr Ala Ile Pro Gly Asp Tyr
                405                 410                 415

Ala Gln Val Glu Glu Asp Gly Thr Val Thr Met Leu Gly Arg Gly Ser
            420                 425                 430

Val Ser Ile Asn Ser Gly Gly Glu Lys Val Tyr Pro Glu Glu Val Glu
        435                 440                 445

Ala Ala Leu Lys Gly His Pro Asp Val Phe Asp Ala Leu Val Val Gly
    450                 455                 460

Val Pro Asp Pro Arg Tyr Gly Gln Gln Val Ala Ala Val Val Gln Ala
465                 470                 475                 480

Arg Pro Gly Cys Arg Pro Ser Leu Ala Glu Leu Asp Ser Phe Val Arg
                485                 490                 495

Ser Glu Ile Ala Gly Tyr Lys Val Pro Arg Ser Leu Trp Phe Val Asp
            500                 505                 510

Glu Val Lys Arg Ser Pro Ala Gly Lys Pro Asp Tyr Arg Trp Ala Lys
        515                 520                 525
```

```
Glu Gln Thr Glu Ala Arg Pro Ala Asp Asp Val His Ala Gly His Val
    530                 535                 540

Thr Ser Gly Gly
545

<210> SEQ ID NO 55
<211> LENGTH: 565
<212> TYPE: PRT
<213> ORGANISM: Pseudomonas fluorescens

<400> SEQUENCE: 55

Met Ile Glu Asp Phe Trp Lys Asp Lys Tyr Pro Ala Gly Ile Ala Ala
1               5                   10                  15

Asp Ile Asn Pro Asp Glu Tyr Pro Asn Ile Gln Ala Val Leu Lys Gln
            20                  25                  30

Ser Cys Gln Arg Phe Ala Asp Lys Pro Ala Phe Ser Asn Leu Gly Lys
        35                  40                  45

Thr Leu Thr Tyr Gly Glu Leu Tyr Glu Leu Ser Gly Ala Phe Ala Ala
    50                  55                  60

Tyr Leu Gln Gln His Thr Asp Leu Gln Pro Gly Asp Arg Ile Ala Val
65                  70                  75                  80

Gln Leu Pro Asn Val Leu Gln Tyr Pro Val Ala Val Phe Gly Ala Ile
                85                  90                  95

Arg Ala Gly Leu Ile Val Val Asn Thr Asn Pro Leu Tyr Thr Ala Arg
            100                 105                 110

Glu Met Glu His Gln Phe Asn Asp Ser Gly Ala Lys Ala Leu Val Cys
        115                 120                 125

Leu Ala Asn Met Ala His Leu Ala Glu Thr Val Val Pro Lys Thr Gly
    130                 135                 140

Val Lys His Val Ile Val Thr Glu Val Ala Asp Leu Leu Pro Pro Ile
145                 150                 155                 160

Lys Arg Leu Leu Ile Asn Ser Val Ile Lys Tyr Val Lys Lys Met Val
                165                 170                 175

Pro Ala Tyr His Leu Pro Lys Ala Val Lys Phe Asn Asp Val Leu Ser
            180                 185                 190

Lys Gly Gln Gly Gln Pro Val Ala Glu Ala Asn Pro Asp Ser Gly Asp
        195                 200                 205

Val Ala Val Leu Gln Tyr Thr Gly Gly Thr Gly Val Ala Lys Gly
    210                 215                 220

Ala Met Leu Thr His Arg Asn Leu Val Ala Asn Met Leu Gln Cys Lys
225                 230                 235                 240

Ala Leu Met Gly Ser Asn Leu Asn Glu Gly Cys Glu Ile Leu Ile Thr
                245                 250                 255

Pro Leu Pro Leu Tyr His Ile Tyr Ala Phe Thr Phe His Cys Met Ala
            260                 265                 270

Met Met Leu Ile Gly Asn His Asn Ile Leu Ile Ser Asn Pro Arg Asp
        275                 280                 285

Leu Pro Ala Met Val Lys Glu Leu Ser Lys Trp Lys Phe Ser Gly Phe
    290                 295                 300

Val Gly Leu Asn Thr Leu Phe Val Ala Leu Cys Asn Asn Glu Gly Phe
305                 310                 315                 320

Arg Lys Leu Asp Phe Ser Ala Leu Lys Val Thr Leu Ser Gly Gly Met
                325                 330                 335

Ala Leu Gln Leu Ala Ala Ala Glu Arg Trp Lys Ala Val Thr Gly Cys
            340                 345                 350
```

-continued

Pro Ile Cys Glu Gly Tyr Gly Met Thr Glu Thr Ser Pro Val Ala Thr
        355                 360                 365

Val Asn Pro Ile Gln Asn Ile Gln Ile Gly Thr Ile Gly Ile Pro Val
    370                 375                 380

Pro Ser Thr Leu Cys Lys Val Ile Asp Asp Ala Gly Val Glu Gln Pro
385                 390                 395                 400

Leu Gly Glu Ile Gly Glu Leu Cys Val Lys Gly Pro Gln Val Met Lys
                405                 410                 415

Gly Tyr Trp Gln Arg Gln Glu Ala Thr Asp Glu Met Leu Asp Ser Glu
            420                 425                 430

Gly Trp Leu Lys Thr Gly Asp Ile Ala Leu Ile Gln Pro Asp Gly Tyr
        435                 440                 445

Met Arg Ile Val Asp Arg Lys Lys Asp Met Ile Leu Val Ser Gly Phe
    450                 455                 460

Asn Val Tyr Pro Asn Glu Leu Glu Asp Val Leu Ala Ala Leu Pro Gly
465                 470                 475                 480

Val Leu Gln Cys Ala Ala Ile Gly Val Pro Asp Glu Lys Ser Gly Glu
                485                 490                 495

Ala Ile Lys Ile Phe Ile Val Ala Lys Pro Gly Val Thr Leu Thr Lys
            500                 505                 510

Glu Gln Val Met Glu His Met Arg Ala Asn Val Thr Gly Tyr Lys Val
        515                 520                 525

Pro Arg Ser Val Glu Phe Arg Asp Ala Leu Pro Thr Thr Asn Val Gly
    530                 535                 540

Lys Ile Leu Arg Arg Glu Leu Arg Asp Glu Glu Leu Lys Lys Ile Lys
545                 550                 555                 560

Ala Lys Ser Ala Ala
            565

<210> SEQ ID NO 56
<211> LENGTH: 547
<212> TYPE: PRT
<213> ORGANISM: Escherichia coli

<400> SEQUENCE: 56

Met Lys Val Thr Leu Thr Phe Asn Glu Gln Arg Arg Ala Ala Tyr Arg
1               5                   10                  15

Gln Gln Gly Leu Trp Gly Asp Ala Ser Leu Ala Asp Tyr Trp Gln Gln
            20                  25                  30

Thr Ala Arg Ala Met Pro Asp Lys Ile Ala Val Val Asp Asn His Gly
        35                  40                  45

Ala Ser Tyr Asn Tyr Ser Ala Leu Asp His Ala Ser Cys Leu Ala
    50                  55                  60

Asn Trp Met Leu Ala Lys Gly Ile Glu Ser Gly Asp Arg Ile Ala Phe
65                  70                  75                  80

Gln Leu Pro Gly Trp Cys Glu Phe Thr Val Ile Tyr Leu Ala Cys Leu
                85                  90                  95

Lys Ile Gly Ala Val Ser Val Pro Leu Leu Pro Ser Trp Arg Glu Ala
            100                 105                 110

Glu Leu Val Trp Val Leu Asn Lys Cys Gln Ala Lys Met Phe Phe Ala
        115                 120                 125

Pro Thr Leu Phe Lys Gln Thr Arg Pro Val Asp Leu Ile Leu Pro Leu
    130                 135                 140

Gln Asn Gln Leu Pro Gln Leu Gln Gln Ile Val Gly Val Asp Lys Leu

```
                145                 150                 155                 160
Ala Pro Ala Thr Ser Ser Leu Ser Leu Ser Gln Ile Ile Ala Asp Asn
                    165                 170                 175
Thr Pro Leu Thr Thr Ala Ile Thr Thr His Gly Asp Glu Leu Ala Ala
                    180                 185                 190
Val Leu Phe Thr Ser Gly Thr Glu Gly Leu Pro Lys Gly Val Met Leu
                    195                 200                 205
Thr His Asn Asn Ile Leu Ala Ser Glu Arg Ala Tyr Cys Ala Arg Leu
                    210                 215                 220
Asn Leu Thr Trp Gln Asp Val Phe Met Met Pro Ala Pro Leu Gly His
225                 230                 235                 240
Ala Thr Gly Phe Leu His Gly Val Thr Ala Pro Phe Leu Ile Gly Ala
                    245                 250                 255
Arg Ser Val Leu Leu Asp Ile Phe Thr Pro Asp Ala Cys Leu Ala Leu
                    260                 265                 270
Leu Glu Gln Gln Arg Cys Thr Cys Met Leu Gly Ala Thr Pro Phe Val
                    275                 280                 285
Tyr Asp Leu Leu Asn Leu Leu Glu Lys Gln Pro Ala Asp Leu Ser Ala
                    290                 295                 300
Leu Arg Phe Phe Leu Cys Gly Gly Thr Thr Ile Pro Lys Lys Val Ala
305                 310                 315                 320
Arg Glu Cys Gln Gln Arg Gly Ile Lys Leu Leu Ser Val Tyr Gly Ser
                    325                 330                 335
Thr Glu Ser Ser Pro His Ala Val Val Asn Leu Asp Asp Pro Leu Ser
                    340                 345                 350
Arg Phe Met His Thr Asp Gly Tyr Ala Ala Ala Gly Val Glu Ile Lys
                    355                 360                 365
Val Val Asp Asp Ala Arg Lys Thr Leu Pro Pro Gly Cys Glu Gly Glu
                    370                 375                 380
Glu Ala Ser Arg Gly Pro Asn Val Phe Met Gly Tyr Phe Asp Glu Pro
385                 390                 395                 400
Glu Leu Thr Ala Arg Ala Leu Asp Glu Glu Gly Trp Tyr Tyr Ser Gly
                    405                 410                 415
Asp Leu Cys Arg Met Asp Glu Ala Gly Tyr Ile Lys Ile Thr Gly Arg
                    420                 425                 430
Lys Lys Asp Ile Ile Val Arg Gly Gly Glu Asn Ile Ser Ser Arg Glu
                    435                 440                 445
Val Glu Asp Ile Leu Leu Gln His Pro Lys Ile His Asp Ala Cys Val
                    450                 455                 460
Val Ala Met Pro Asp Glu Arg Leu Gly Glu Arg Ser Cys Ala Tyr Val
465                 470                 475                 480
Val Leu Lys Ala Pro His His Ser Leu Ser Leu Glu Glu Val Val Ala
                    485                 490                 495
Phe Phe Ser Arg Lys Arg Val Lys Tyr Lys Tyr Pro Glu His Ile Val
                    500                 505                 510
Val Ile Glu Lys Leu Pro Arg Thr Ala Ser Gly Lys Ile Gln Lys Phe
                    515                 520                 525
Leu Leu Arg Lys Asp Ile Met Arg Arg Leu Thr Gln Asp Val Cys Glu
                    530                 535                 540
Glu Ile Glu
545

<210> SEQ ID NO 57
```

<211> LENGTH: 546
<212> TYPE: PRT
<213> ORGANISM: Salmonella trphimurium

<400> SEQUENCE: 57

Met Ser Val Thr Leu Thr Phe Asp Ala Ala Arg Arg Lys Thr Tyr Arg
1               5                   10                  15

Glu Ser Gly Tyr Trp Gly Asp Ala Ser Leu Gly Asp Tyr Trp Arg Gln
            20                  25                  30

Thr Ala Arg Ala Val Pro Asp Lys Ile Ala Val Val Asp Asn His Gly
        35                  40                  45

Ala Ser Trp Thr Tyr Ala Ala Leu Asp Tyr Ala Ala Ser Arg Leu Ala
    50                  55                  60

Asn Trp Leu Leu Ser Gln Gly Ile Gln Pro Gly Asp Arg Val Ala Phe
65                  70                  75                  80

Gln Leu Pro Gly Trp Cys Glu Phe Thr Leu Ile Tyr Leu Ala Cys Leu
                85                  90                  95

Lys Thr Gly Ala Val Ser Val Pro Leu Leu Pro Ala Trp Arg Glu Ala
            100                 105                 110

Glu Leu Val Trp Val Leu Asn Lys Cys Gln Ala Lys Ile Phe Phe Ala
        115                 120                 125

Pro Thr Val Phe Lys Gln Asn Arg Pro Val Asp Leu Ile Leu Pro Leu
    130                 135                 140

Gln Asn Gln Leu Arg His Leu Thr His Ile Val Gly Val Asp Lys Leu
145                 150                 155                 160

Ala Pro Ala Thr Thr Ala Leu Ala Leu Ser Gln Ile Ile Asp Arg Ser
                165                 170                 175

Glu Pro Leu Gln Ser Asp Ile Asn Ile His Gly Asp Glu Leu Ala Ala
            180                 185                 190

Val Leu Phe Thr Ser Gly Thr Glu Gly Met Pro Lys Gly Val Met Leu
        195                 200                 205

Thr His Asn Asn Ile Leu Ala Ser Glu Arg Ala Tyr Cys Ala Arg Leu
    210                 215                 220

Asn Leu Thr Trp Gln Asp Val Phe Leu Met Pro Ala Pro Leu Gly His
225                 230                 235                 240

Ala Thr Gly Phe Leu His Gly Val Thr Ala Pro Phe Leu Ile Gly Ala
                245                 250                 255

Arg Ser Val Leu Leu Asp Ile Phe Thr Pro Glu Ala Cys Leu Thr Leu
            260                 265                 270

Leu Ala Gln Gln Arg Cys Thr Cys Met Ser Gly Ala Thr Pro Phe Ile
        275                 280                 285

Tyr Asp Leu Leu Cys Ala Ile Glu Gln Gln Pro Ala Asp Leu Ser Ser
    290                 295                 300

Leu Arg Phe Phe Leu Cys Gly Gly Thr Thr Ile Pro Lys Lys Val Ala
305                 310                 315                 320

Arg Asp Cys Gln Gln Arg Gly Ile Lys Leu Leu Ser Ile Tyr Gly Ser
                325                 330                 335

Thr Glu Ser Ser Pro His Ser Met Val Asn Leu Gly Asp Ser Thr Ser
            340                 345                 350

Arg Met Met Asn Thr Asp Gly Tyr Ala Ala Thr Gly Val Glu Ile Lys
        355                 360                 365

Ile Val Asp Glu Asp Arg Asn Thr Leu Pro Ala Gly His Glu Gly Glu
    370                 375                 380

Glu Ala Ser Arg Gly Pro Asn Val Phe Met Gly Tyr Leu Asp Glu Pro

```
385                 390                 395                 400
Glu Leu Thr Ala Arg Ala Leu Asp Asn Glu Gly Trp Tyr Tyr Ser Gly
                405                 410                 415

Asp Leu Cys Arg Met Asp Glu Asp Gly Tyr Ile Lys Ile Thr Gly Arg
                420                 425                 430

Lys Lys Asp Ile Ile Arg Gly Glu Asn Ile Ser Ser Arg Glu
                435                 440                 445

Val Glu Asp Ile Leu Leu Gln His Pro Arg Ile His Asp Ala Cys Val
    450                 455                 460

Val Ala Met Pro Asp Glu Arg Leu Gly Glu Arg Ser Cys Ala Tyr Val
465                 470                 475                 480

Val Leu Lys Pro Pro His Leu Ser Leu Thr Leu Glu Glu Val Ile Ala
                485                 490                 495

Phe Phe Ser Arg Lys Arg Val Ala Lys Tyr Lys Tyr Pro Glu Arg Ile
                500                 505                 510

Val Ile Val Glu Lys Leu Pro Arg Thr Ala Ser Gly Lys Val Gln Lys
                515                 520                 525

Phe Leu Leu Arg Gln Asp Ile Ile Glu Arg Leu Arg Gln Glu His Thr
    530                 535                 540

Ala Val
545

<210> SEQ ID NO 58
<211> LENGTH: 515
<212> TYPE: PRT
<213> ORGANISM: Thermobifida fusca

<400> SEQUENCE: 58

Met Leu Asn Leu Ser Val Leu Leu Glu Asp Gly Ala Arg Asn Arg Pro
1               5                   10                  15

Glu Arg Asp Ala Ile Val Phe Gly Asp Met Arg Leu Asn Tyr Ala Leu
                20                  25                  30

Val Asn Met Ile Ala Asn Gln Val Ala Asn Leu Leu Val Ser Arg Gly
            35                  40                  45

Ile Arg Pro Gly Asp Lys Val Ala Leu Ala Cys Pro Asn Val Pro Tyr
    50                  55                  60

Phe Pro Phe Val Tyr Phe Gly Ala Leu Lys Ala Gly Ala Val Val Val
65                  70                  75                  80

Pro Leu Asn Val Leu Leu Thr Pro Arg Glu Ile Glu Tyr His Leu Arg
                85                  90                  95

Asp Ser Gly Ala Lys Ala Leu Phe Ala Phe Thr Gly Thr Pro Glu Leu
                100                 105                 110

Pro Leu Gly Glu Arg Ala Trp Gln Ala Phe Gln Glu Val Ala Glu Cys
            115                 120                 125

Glu Leu Tyr Ile Asp Leu Pro Ala Ala Gly Ala Thr Thr Ser Ala
130                 135                 140

Ile Pro Gly Ala Glu Thr Phe Trp Ala Ala Leu Asn Gly Gln Pro Gly
145                 150                 155                 160

Glu Phe Glu Ser Val Arg Thr Glu Gly Asp Asp Val Ala Val Ile Ile
                165                 170                 175

Tyr Thr Ser Gly Thr Thr Gly Gln Pro Lys Gly Ala Gln Leu Thr His
            180                 185                 190

Thr Asn Leu Leu Phe Asn Ala Val Ala Ser Ser Ala Leu Phe Asp Gln
    195                 200                 205
```

```
Ala Pro Asp Ser His Asp Val Phe Leu Thr Val Leu Pro Leu Phe His
    210             215                 220
Ile Phe Gly Gln Thr Thr Met Met Asn Ala Ala Leu Tyr Arg His Gly
225             230                 235                 240
Thr Met Val Leu Met Pro Arg Phe Asp Gly Asp Glu Ala Leu Ser Leu
                245                 250                 255
Met Glu Lys Glu Lys Val Thr Ile Phe Ala Gly Val Pro Thr Met Tyr
            260                 265                 270
Trp Gly Leu Leu Asn Ala Gln Gly Asp His Asp Ile Lys Gln Ile Ser
        275                 280                 285
Gln Thr Leu His Thr Ala Val Ser Gly Gly Ala Ser Leu Pro Ala Glu
    290                 295                 300
Val Ala Arg Lys Val Lys Glu Lys Phe Gly Ile Glu Ile Leu Glu Gly
305             310                 315                 320
Tyr Gly Leu Ser Glu Thr Ser Pro Val Val Ser Phe Asn Asn Pro Lys
                325                 330                 335
Arg Lys Ala Lys Pro Gly Ser Ile Gly Leu Pro Ile Trp Gly Val Glu
            340                 345                 350
Met Lys Leu Val Asp Glu Asn Phe Asn Thr Ile Glu Gly Glu Gly Pro
        355                 360                 365
Gly Glu Ile Ala Val Arg Gly His Cys Val Met Lys Gly Tyr His Asn
    370                 375                 380
Arg Pro Glu Ala Asn Ala Gln Val Met Arg Asp Gly Trp Phe Arg Thr
385             390                 395                 400
Gly Asp Ile Ala Arg Arg Asp Glu Glu Gly Phe Tyr Phe Ile Ile Asp
                405                 410                 415
Arg Ser Lys Asp Met Ile Ile Arg Gly Gly Tyr Asn Val Tyr Pro Arg
            420                 425                 430
Glu Ile Glu Glu Val Leu Met Thr His Pro Gln Val Ser Leu Ala Ala
        435                 440                 445
Val Val Gly Val Pro His Asp Thr His Gly Glu Glu Ile Lys Ala Phe
    450                 455                 460
Val Ile Pro Ala Glu Gly Ala Thr Leu Thr Glu Asp Glu Leu Ile Ala
465             470                 475                 480
Trp Ala Lys Glu Arg Leu Ala Ala Tyr Lys Tyr Pro Arg Ile Val Glu
                485                 490                 495
Phe Arg Thr Glu Leu Pro Met Thr Ala Thr Gly Lys Ile Leu Lys Arg
            500                 505                 510
Glu Leu Arg
        515
```

US 9,512,447 B2

MODIFIED NATIVE BETA-KETOACYL-ACP SYNTHASES AND ENGINEERED MICROORGANISMS

The present application is a national stage application filed under 35 USC §371, and claims priority to PCT/US2013/072973, filed Dec. 4, 2013, which claims priority to U.S. Prov. Appln. Ser. No. 61/737,232, filed Dec. 14, 2012, each of which is hereby incorporated by reference in its entirety for all purposes.

REFERENCE TO A "SEQUENCE LISTING," A TABLE, OR A COMPUTER PROGRAM LISTING APPENDIX SUBMITTED AS AN ASCII FILE

The official copy of the Sequence Listing is submitted as an ASCII formatted text file via EFS-Web, with a file name of "CX5-111WO1_ST25_substitute.txt", a creation date Sep. 16, 2015, and a size of 467 kilobytes. The Sequence Listing filed via EFS-Web is part of the specification and is incorporated in its entirety by reference herein.

FIELD OF THE INVENTION

The present disclosure relates to recombinant microorganisms and particularly to recombinant bacterial microorganisms exhibiting production of C12 to C14 fatty alcohol compositions.

BACKGROUND

Crude petroleum has traditionally been used as a primary source for raw materials for producing numerous specialty chemicals. Particular specialty chemicals that can be produced from the petrochemical raw materials include fatty alcohols. Fatty alcohols have many industrial and commercial uses. For example, fatty alcohols act as surfactants which are useful in personal care and household products, such as detergents. Fatty alcohols are also used in waxes, lubricating oils, cosmetics and solvents. However, obtaining fatty alcohols from crude petroleum requires a significant amount of energy and involves the use of a non-renewable energy source.

Further, even those fatty alcohols that are obtained from renewable sources, such as from plant or animal derived fatty acids, generally are prepared using a hydrogenation step. Hydrogenation is a costly process step but is utilized to eliminate the double bonds of unsaturated fatty acids. A number of prior art references disclose genetically engineered microorganisms that produce products including fatty acid derivatives such as fatty acid esters and fatty alcohols (See e.g., WO2007/136762, WO2008/119082, WO2010/075483, WO2011/008535, WO2011/019858, U.S. Pat. Nos. 6,143,538, and 8,110,670, and U.S. Pat. Appln. Publ. Nos. 2012/0115195 and 2012/0142979. However, a need still exists in the field for improved fatty alcohol production from bioengineered microorganisms that is efficient and cost effective and further that is tailored for use in particular industrial applications.

Regulation of fatty acid metabolism to achieve higher yields of fatty acids and/or to maximize yields of fatty acids with specific carbon chain lengths would also be desirable for producing downstream products including but not limited to fatty alcohols, which additionally may be used as components of or precursors to compounds used as soaps, polymer additives, surfactants, and the like.

SUMMARY

The biological production of fatty alcohols in engineered microbial organisms according to the instant invention requires the activity of a fatty alcohol forming reductase (FAR) and the modification of a native gene having β-ketoacyl-ACP synthase activity. The FAR catalyzes the reduction of fatty acid acyl-ACP substrates and/or fatty acid acyl-CoA substrates to produce fatty alcohols. Fatty acids which are used as FAR substrates may be synthesized by different enzyme complexes depending on the host organism. Certain organisms synthesize fatty acids by a fatty acid synthesis I ("FAS-I") scheme, where the enzymatic activities are present in a large multifunctional protein. Other organisms synthesize fatty acids by a fatty acid synthesis II ("FAS-II") scheme, where each biosynthetic step is catalyzed by a mono-functional protein. FAS-I is typical of yeast and animal cells. FAS-II is typically found in bacteria. Reference is made to FIG. 1 which shows the reaction schemes for the production of fatty alcohols by the activity of FAR which converts fatty acid substrates produced during fatty acid biosynthesis ("fab") in an *E. coli* FAS-II system.

In general, during biosynthesis of fatty acids the fatty acid chain is extended by the addition of two carbons at each elongation step. The elongation reaction step is carried out by β-ketoacyl-ACP synthases (KAS). KAS catalyzes the reaction of acyl-CoA or acyl-ACP with malonyl-CoA or malonyl-ACP [Chen Y., et al., 2011. Prot. Sci. 20: 1659-1667] to produce fatty acids with varying chain lengths. *E. coli* has 3 KAS enzymes: KASI (EC 2.3.1.41) coded by the fabB gene which catalyzes the reaction of acyl-ACP with malonyl-ACP to form 3-oxoacyl-ACP, KASII (EC 2.3.1.79) coded by the fabF gene which catalyzes the final elongation to C18:0, and KASIII (EC 2.3.1.180) coded by the fabH gene which catalyzes the initial condensation of malonyl-ACP with acetyl-CoA.

Generally, the FabB enzyme is the only enzyme capable of elongating the cis-3-decenoyl-ACP to form unsaturated C16:1 and C18:1 fatty acids. By modifying the native gene (e.g., by providing a variant FabB enzyme, which in some embodiments replaces the native fabB gene in a host cell) a higher percent of C12 to C14 fatty acids and fatty alcohols are produced as compared to an engineered host cell comprising the native gene encoding FabB or FabF.

In one aspect, the invention relates to a method of altering the carbon chain length of acyl-derived products produced from a bacterial microorganism, which comprise modifying a native bacterial gene having β-ketoacyl-ACP synthase activity. In certain embodiments the native bacterial gene is a native β-ketoacyl-ACP synthase I (FabB) (EC 2.3.1.41) and in certain embodiments the native bacterial gene having β-ketoacyl-ACP synthase activity is a native β-ketoacyl-ACP synthase II (FabF) (EC 2.3.1.179).

In another aspect, the invention relates to variant β-ketoacyl-ACP synthase I (FabB) (EC 2.3.1.41) polypeptides wherein the variant comprising at least about 85% amino acid sequence identity to SEQ ID NO:2 or a functional fragment thereof and comprising an amino acid substitution at one or more of the following positions 30, 34, 38, 40, 42, 43, 45, 51, 53, 61, 62, 63, 64, 65, 66, 95, 96, 97, 106, 107, 108, 110, 111, 112, 113, 114, 115, 116, 117, 124, 127, 128, 130, 131, 132, 133, 134, 135, 136, 137, 138, 139, 140, 149, 151, 161, 162, 164, 165, 191, 196, 197, 200, 201, 204, 205, 206, 209, 210, 212, 216, 217, 224, 225, 226, 229, 231, 267, 268, 270, 271, 272, 273, 275, 282, 285, 298, 300, 302, 303, 304, 305, 308, 311, 314, 315, 333, 335, 336, 360, 361, 367, 390, 391, 392, or 396 when optimally aligned with SEQ ID NO:2. In another aspect, the invention relates to variant β-ketoacyl-ACP synthase I (FabB) (EC 2.3.1.41) polypeptides wherein the variant comprising at least 85% amino acid sequence identity to SEQ ID NO:2 or a functional fragment thereof and comprising an amino acid substitution at one or more of the following positions 30, 34, 38, 40, 42, 43, 45, 51, 53, 61, 62, 63, 64, 65, 66, 95, 96, 97, 106, 107, 108, 110, 111, 112, 113, 114, 115, 116, 117, 124, 127, 128, 130, 131, 132, 133, 134, 135, 136, 137, 138, 139, 140, 149, 151, 161, 162, 164, 165, 191, 196, 197, 200, 201, 204, 205, 206, 209, 210, 212, 216, 217, 224, 225, 226, 229, 231, 267, 268, 270, 271, 272, 273, 275, 282, 285, 298, 300, 302, 303, 304, 305, 308, 311, 314, 315, 333, 335, 336, 360, 361, 367, 390, 391, 392, or 396 when optimally aligned with SEQ ID NO:2. In another aspect, the invention relates to variant β-ketoacyl-ACP synthase I (FabB) (EC 2.3.1.41) polypeptides wherein the variant comprising at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% amino acid sequence identity to SEQ ID NO:2 or a functional fragment thereof and comprising an amino acid substitution at one or more of the following positions 30, 34, 38, 40, 42, 43, 45, 51, 53, 61, 62, 63, 64, 65, 66, 95, 96, 97, 106, 107, 108, 110, 111, 112, 113, 114, 115, 116, 117, 124, 127, 128, 130, 131, 132, 133, 134, 135, 136, 137, 138, 139, 140, 149, 151, 161, 162, 164, 165, 191, 196, 197, 200, 201, 204, 205, 206, 209, 210, 212, 216, 217, 224, 225, 226, 229, 231, 267, 268, 270, 271, 272, 273, 275, 282, 285, 298, 300, 302, 303, 304, 305, 308, 311, 314, 315, 333, 335, 336, 360, 361, 367, 390, 391, 392, or 396 when optimally aligned with SEQ ID NO:2. In another aspect, the invention relates to variant β-ketoacyl-ACP synthase I (FabB) (EC 2.3.1.41) polypeptides wherein the variant comprising at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% amino acid sequence identity to SEQ ID NO:2 or a functional fragment thereof and comprising an amino acid substitution at one or more of the following positions 30, 34, 38, 40, 42, 43, 45, 51, 53, 61, 62, 63, 64, 65, 66, 95, 96, 97, 106, 107, 108, 110, 111, 112, 113, 114, 115, 116, 117, 124, 127, 128, 130, 131, 132, 133, 134, 135, 136, 137, 138, 139, 140, 149, 151, 161, 162, 164, 165, 191, 196, 197, 200, 201, 204, 205, 206, 209, 210, 212, 216, 217, 224, 225, 226, 229, 231, 267, 268, 270, 271, 272, 273, 275, 282, 285, 298, 300, 302, 303, 304, 305, 308, 311, 314, 315, 333, 335, 336, 360, 361, 367, 390, 391, 392, or 396 when optimally aligned with SEQ ID NO:2.

In certain embodiments, the invention relates to a polynucleotide encoding a variant as described above. The polynucleotide may be a codon optimized polynucleotide sequence. In some embodiments of this aspect, the invention relates to an engineered host cell which incorporates a polynucleotide encoding a FabB variant. In other embodiments, the engineered host cell having a polynucleotide encoding a variant FabB further comprises a heterologous polynucleotide encoding a fatty alcohol reductase (FAR) enzyme (e.g., a FAR having at least about 80% amino acid sequence identity to SEQ ID NO:4 or SEQ ID NO:6 and optionally comprises one or more heterologous polynucleotides encoding FabI, FabZ, FabH or FabD and/or a heterologous polynucleotide encoding a thioesterase. In other embodiments, the engineered host cell having a polynucleotide encoding a variant FabB further comprises a heterologous polynucleotide encoding a fatty alcohol reductase (FAR) enzyme (e.g., a FAR having at least 80% amino acid sequence identity to SEQ ID NO:4 or SEQ ID NO:6 and optionally comprises one or more heterologous polynucleotides encoding FabI, FabZ, FabH or FabD and/or a heterologous polynucleotide encoding a thioesterase. In additional embodiments, the engineered microorganism is capable of producing fatty alcohol compositions comprising at least about 25% (e.g., at least about 30%, 35%, 40%, 45%, or 50%) of C12 to C14 fatty alcohols. In additional embodiments, the engineered microorganism is capable of producing fatty alcohol compositions comprising at least 25% (e.g., at least 30%, 35%, 40%, 45%, or 50%) of C12 to C14 fatty alcohols.

In further aspects, the invention relates to a recombinant cell culture comprising engineered bacterial cells, said engineered bacterial cells comprising (a) a modified native gene having β-ketoacyl-ACP synthase activity and (b) one or more heterologous polynucleotides encoding a fatty alcohol reductase (e.g., EC1.1.1.*) and/or a thioesterase (EC3.1.2.- or EC 3.1.1.5). In some embodiments, the modification of the native gene results in the production of a protein having a substitution of one or more amino acid residues as compared to the protein produced by the expression of the native gene. In some embodiments, the engineered bacterial cells comprise a polynucleotide encoding a heterologous fatty alcohol reductase comprising at least 80%, sequence identity to SEQ ID NOS:4 or 6. In further embodiments the engineered cells produce a fatty alcohol composition selected from a) at least 60% C12 to C16 fatty alcohols relative to the total fatty alcohols produced by the engineered microbial cells; b) at least 25% C12 to C14 fatty alcohols relative to the total fatty alcohols produced by the engineered microbial cells; c) at least 10% C12 fatty alcohols relative to the total fatty alcohols produced by the engineered microbial cells; d) at least 20% C14 fatty alcohols relative to the total fatty alcohols produced by the engineered microbial cells; and/or e) less than 5% C18 fatty alcohols relative to the total fatty alcohols produced by the engineered cells. In other embodiments of this aspect, the produced fatty alcohols are secreted from the engineered microbial cells and are found in the culture medium.

In yet another aspect, the invention relates to methods of producing fatty alcohol compositions comprising culturing an engineered cell of the invention with a carbon substrate under suitable culture conditions to allow expression of a variant FabB and a heterologous FAR and further allowing production of fatty alcohols, wherein the produced fatty alcohol composition comprises at least 20% C12 and C14 fatty alcohols. In some embodiments of this method the fatty alcohol composition is recovered from the engineered cells and/or from the culture medium. In certain embodiments at least 1.0 g/L of fatty alcohols are produced. In certain embodiments a) at least 80% of the produced fatty alcohols have a carbon chain length of C10 to C16; b) at least 60% of the produced fatty alcohols have a carbon chain length of C12 to C16; and/or c) at least 30% of the produced fatty alcohols have a carbon chain length of C12 to C14. In certain embodiments, the carbon substrate is a fermentable sugar obtained from cellulosic feedstock. In certain embodiments the cellulosic feedstock is derived from wheat, wheat straw, sorghum, rice, barley, corn grain, corn cobs, corn stover, sugar cane straw, sugar cane bagasse, switchgrass or a combination thereof.

In yet additional aspects the invention relates to the use of the fatty alcohol compositions produced according to the methods outlined in the disclosure wherein the fatty alcohols composition is used in a cleaning composition, such as a component of a detergent composition or a hard surface cleaning composition and in a personal care compositions.

Other feature and advantages of the invention will be apparent from the following detailed description and from the claims.

BRIEF DESCRIPTION OF THE DRAWINGS

FIG. 1 schematically depicts a pathway for the production of fatty alcohols and fatty acids by an embodiment of the invention.

DESCRIPTION OF THE INVENTION

The technical and scientific terms used in the descriptions herein will have the meanings commonly understood by one of ordinary skill in the art, unless specifically defined otherwise. Accordingly, the following terms are intended to have the following meanings.

Also, as used herein, the singular "a", "an," and "the" include the plural references, unless the context clearly indicates otherwise. Further, the term "or" is used in the present application to mean the disjunctive "or" and the conjunctive "and".

Amino acids are designated using the three-letter symbols or one-letter symbols recommended by the IUPAC-IUB Biochemical Nomenclature Commission. Unless otherwise indicated, nucleic acids are written left to right in 5' to 3' orientation; amino acid sequences are written left to right in amino to carboxy orientation, respectively.

"EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

As used herein, the term "comprising" and its cognates are used in their inclusive sense (i.e., equivalent to the term "including" and its corresponding cognates).

The term "fatty alcohol" as used herein refers to an alcohol having the formula R—OH, where the R group is at least 4, 5, 6, 7, 8, 9, 10, 11, 12, 13, 14, 15, 16, 17, 18, 19, 20 or more carbons in length. R can be saturated or unsaturated. Further saturated or unsaturated fatty alcohols can be described as "Ca:b-OH", wherein "a" is an integer that represents the total number of carbon atoms in the fatty alcohol and "b" is an integer that refers to the number of double bonds in the carbon chain. In some embodiments the R group of the fatty alcohol is a straight chain and in other embodiments the R group of the fatty alcohol is branched.

In some embodiments, a fatty alcohol produced according to the methods disclosed herein is a C8-C20 saturated or unsaturated fatty alcohol (i.e., a C8, C9, C10, C11, C12, C13, C14, C15, C16, C17, C18, C19, or C20 fatty alcohol). In some embodiments, multiple fatty alcohols are produced with varying saturation levels. For example, in some embodiments, C10, C12, C14, and/or C16 fatty alcohols are produced. It is understood that a reference to a "Cx fatty alcohol" (e.g., C12) includes both saturated and unsaturated fatty alcohols having "x" carbon atoms unless indicated otherwise. In some embodiments, the fatty alcohol is any alcohol made from a fatty acid.

Fatty alcohol derivatives as used herein means compounds such as but not limited to fatty alcohols, fatty acid esters (e.g. acetyl, methyl or ethyl esters and waxes) and fatty acids. Fatty alcohol derivatives includes compounds derived from the fatty acid biosynthetic pathway as well as compounds derived from the fatty alcohols produced by the engineered microbial cells encompassed by the invention. In one example, the carbon chain length of any fatty alcohol derivative compound may be the same as the carbon chain length of the fatty alcohol from which is was derived.

The term "carbon chain length" as used herein means the number of carbon atoms in a carbon chain of a fatty alcohol, fatty alcohol substrate (e.g., a fatty acid) or fatty alcohol derivative. For example, the term "C12 fatty alcohol" refers to a fatty alcohol molecule having 12 carbons.

The term a "fatty alcohol composition" as used herein, means a composition which encompasses at least one fatty alcohol and which is produced from an engineered microbial organism according to the methods of the invention. The fatty alcohol compositions of the invention may include one or more fatty alcohols. For example a fatty alcohol composition may include only C12 fatty alcohols or a fatty alcohol composition may include a combination of C12, C14 and C16 fatty alcohols and these fatty alcohols may be saturated or unsaturated fatty alcohols and further may be straight chains or branched.

The term "fatty acid" as used herein means a compound having the formula $RCO_2H$, wherein R is at least two carbons in length and generally between 4 and 22 carbons in length. Fatty acids may be saturated or unsaturated and further "R" can be straight or branched.

The term "acyl-ACP" as used herein means a compound having the formula RCO-S-ACP, wherein "R" is at least three carbons in length and may be a straight chain or branched chain and further saturated or unsaturated. The abbreviation "ACP" refers to the acyl carrier protein that comprises a 4-phosphopantethiene moiety which can form a thioester linkage with the growing fatty acid chain during the biosynthesis of fatty acids.

The term "acyl-derived product" refers to any product of the fatty acid biosynthetic pathway obtained by the action of one or more enzymes which use acyl-ACPs as a substrate. (For example, the following enzymes use acyl-ACPs as substrates to produce fatty acids, fatty alcohols and/or fatty aldehydes: (1) fatty acid reductases (FARs); (2) ACP-thioesterases and (3) acyl-ACP reductases (AARs).

The terms "fatty acyl-CoA reductase", "fatty acyl reductase", and "fatty acyl acyl-ACP reductase" (EC 1.1.1.*) (collectively and individually referred to herein as FAR) are used interchangeably to refer to an enzyme that catalyzes the reduction of a fatty acyl-CoA, a fatty acyl-ACP, or other fatty acyl thioester. FAR enzymes can be divided into two general groups that differ with respect to the end-product synthesized. In one group the product that is formed by the action of the enzyme is an aldehyde. In the second group the product that is formed by the action of the enzyme is an alcohol. (Reference is made to Rowland et al., Plant Sci. 193-194 (2012) 28-38).

The term "acyl-CoA" refers to an acyl thioester formed between the carbonyl carbon of an alkyl chain and the sulfhydryl group of the 4'-phosphopantetthionyl moiety of co-enzyme A (CoA) which has the formula R—C(O)—S—CoA, wherein R is an alkyl group having at least 4 carbon atoms and preferably between 10 and 14 carbon atoms. R may be straight or branched and saturated or unsaturated. CoA refers to coenzyme A, the naturally occurring thiol compound having CAS number 85-61-0.

The phrase "fatty acid biosynthetic ("Fab") enzymes" as used herein means a complex of enzymes involved in a number of reactions to produce saturated and unsaturated fatty acids. The process is primed by the enzymatic conversion of malonyl-CoA into malonyl-ACP and continues by successive addition of 2 carbons derived from malonyl-ACP residues, providing ACP intermediates (i.e., acyl-ACPs). There are at least 8 enzymes involved fatty acid initiation and elongation biosynthesis including FabA, FabB, FabD, FabF, FabG, FabH, FabI, and FabZ, collectively and individually referred to herein as "fatty acid biosynthetic" enzymes. Furthermore, the ACP protein plays a key role in fatty acid biosynthesis by anchoring the nascent acyl chain and making the acyl chain accessible to other enzymes (See, FIG. 1).

The term "FabD" refers to a malonyl-CoA-ACP transferase (EC 2.3.1.39).

The term "FabF" refers to a β-ketoacyl-ACP synthase II (3-oxoacyl-ACP synthetase (EC 2.3.1.179) which catalyzes the conversion of palmitoleate to cis-vaccenate.

The term "FabG" refers to a 3-ketoacyl-ACP-reducatse (3-oxoacyl ACP reductase) (EC 1.1.1.100) which catalyzes the NADPH dependent reduction of beta-ketoacyl-ACP substrates to beta-hydroxyacyl-ACP products, the first reductive step in the elongation cycle of fatty acid biosynthesis.

The term "FabI" refers to a trans-2-enoyl-ACP reductase (EC 1.3.1.9 and 1.3.1.10) that catalyzes the reaction of a trans-2,3-dehydroacyl-[ACP]+NAD(P)H+H$^+$ to an acyl-ACP+NAD(P)$^+$.

The term "FabZ" refers to a beta-hydroxyacyl-ACP dehydratase (EC 4.2.1.59 to 4.2.61) that catalyzes the reaction of a (3R)-3-hydroxyacyl-ACP to a transΔ$^2$-enoylacylACP+ H$_2$O.

The term "FabB" refers to a beta-ketoacyl-ACP synthase I (EC 2.3.1.41) that catalyzes the chemical reaction of an acyl-ACP to a 3-oxoacyl-ACP.

The term "FabH" refers to 3-oxoacyl-(acyl-carrier protein) synthase III activity and is used interchangeably with "KASIII" and "β-ketoacyl-ACP synthase III." FabH catalyzes the initial condensation reaction in the fatty acid biosynthetic pathway using an acyl-CoA as a primer and is categorized as EC 2.3.1.180. The FabH enzymes have a His-Asn-Cys catalytic triad at their active site.

The term "FadD" refers to an "acyl-CoA synthetase ("ACS") (EC 6.2.1 (acid-thiol ligases)). In some embodiments, the ACS is classified as EC 6.2.1.3. These ACSs are also known as long chain fatty acid-CoA ligases. An ACS catalyzes the reaction of free fatty acids (both saturated and unsaturated fatty acids) into metabolically active CoA esters (e.g., acyl-CoA) during fatty acid degradation. In some embodiments the FadD may be classified as EC 2.3.1.86 (fatty acyl CoA synthase).

The term "FadR" protein as used herein, refers to a multifunctional dual regulator that exerts negative control over the fatty acid degradative regulon and activates expression of fabA and fabF. The FadR regulator is encoded by a fadR gene. A "regulon" comprises a set of genes under control of a single regulatory protein.

The term "FadE" enzyme as used herein means an acyl-CoA dehydrogenase enzyme (EC 1.3.99.-). A FadE gene is also known as yafH.

Throughout the specification a reference may be made using an abbreviated gene name or an enzyme name. For example "fabB" refers to a gene encoding a β ketoacyl ACP synthase I, KAS-I or as sometimes referred to herein a FabB enzyme.

The term "thioesterase or thioester hydrolase (TE)" enzyme used herein means an enzyme having thioesterase activity. TEs are identified as members of EC 3.1.2.1 to EC 3.1.2.27 and also EC3.1.1.5 and EC 3.1.2.- and these enzyme which hydrolyze the thioester bond between a carbonyl group and a sulfur atom are classified based on enzyme function and substrate identity. In addition, TEs are classified based on the ThYme database (Thioester-active enzyme). In this classification system, TEs have been classified based on amino acid sequence similarity. Under the ThYme system, TEs are further divided into 24 different families (TE1-TE24). Reference is made to D. C. Cantu et al., (2010) Protein Science, 19:1281-1295 and D. C. Cantu et al., (2011) Nucleic Acid Research 39:doi10:1093/nar/gkq1072. TEs have the ability to catalyze a thioester cleavage reaction hydrolyzing a thioester into an acid and a thiol. TEs useful in the invention may be obtained from any suitable sources, including but not limited to plant, bacterial, algal, and fungal sources.

The term "analogous sequence" or "homologous sequence" as used herein means a sequence wherein the function of the gene is essentially the same as a reference gene. For example, a reference gene may be a fabB gene from E. coli. In some embodiments, the analogous sequence will have at least about 60%, for example, at least about 65%, 70%, 75%, 80%, 85%, 88%, 90%, 91%, 92%, 93%, 94%, 95%, 96%, 97%, 98%, 99% sequence identity with the reference sequence.

The term "wild-type" or "native" as used herein refers to the form found in nature. For example a naturally occurring or wild-type polypeptide or polynucleotide sequence is a sequence present in an organism that can be isolated from a source in nature and which has not been intentionally modified by human manipulation. When used in reference to a microorganism, the term means a naturally occurring (not genetically modified or engineered) microorganism.

The term "substrate" as used herein refers to a substance or compound that is converted or suitable for conversion into another compound (e.g., a product) by the action of at least one enzyme. The term includes not only a single compound but also combinations comprising more than one compound.

The term "conversion" as used herein refers to the enzymatic transformation of a substrate to at least one corresponding product. "Percent conversion" refers to the percent of the substrate that is converted to the product(s) within a specified period of time and under specified conditions.

Nucleic acid sequences may be "introduced" into a cell by protoplast fusion, transfection, transduction, transformation, electroporation or any other suitable method known in the art. A nucleic acid sequence introduced into a prokaryotic cell may be integrated into a chromosome or may be maintained as an episome.

The terms "transformed" and "stably transformed" as used herein refer to a cell that has a non-native (i.e., heterologous) polynucleotide sequence integrated into its genome or as an episomal plasmid that is maintained for multiple (e.g., at least two) generations.

The term "gene" as used herein refers to a polynucleotide (e.g., a DNA segment), that encodes a polypeptide and includes regions preceding and following the coding regions as well as intervening sequences (introns) between individual coding segments (exons).

The terms "endogenous" when used in reference to a gene refers to a gene that is found in a parental strain of a cell (e.g., a bacterial cell). As used herein in making comparisons between endogenous nucleic acid sequences, "homologous genes" (or "homologue" genes) refers to genes from different, but usually related species, which correspond to each other and are identical or very similar to each other. The term encompasses genes that are separated by speciation (i.e., the development of new species) (e.g., orthologous genes), as well as genes that have been separated by genetic duplication (e.g., paralogous genes).

The term "heterologous" polynucleotide as used herein means any polynucleotide that is introduced into a host cell by laboratory techniques, and includes polynucleotides that are removed from a host cell, subjected to laboratory manipulation, and then reintroduced into a host cell.

In some embodiments, when "heterologous" is used with reference to a nucleic acid or polypeptide, the term refers to a sequence that is not normally expressed and secreted by an organism (e.g., a "wild-type" organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector).

As used herein, a "heterologous enzyme" is used in reference to an enzyme that is encoded by a heterologous gene. However, it is also contemplated herein that a heterologous gene can encode an endogenous or homologous enzyme. As used herein, the term "heterologous gene" refers to a gene that occurs in a form not found in a parental strain of the host cell. Thus, in some embodiments, a heterologous gene is a gene that is derived from a species that is different from the species of the host cell expressing the gene. In some embodiments, a heterologous gene is a modified version of a gene that is endogenous to the host cell (e.g., an endogenous gene subjected to manipulation and then introduced or transformed into the host cell). For example, in some embodiments, a heterologous gene has an endogenous coding sequence, but has modifications in the promoter sequence. Similarly, in other embodiments, a heterologous gene encodes the same amino acid sequence as an endogenous gene, but has modifications in codon usage and/or to noncoding regions (e.g., introns), and/or combinations thereof. In some embodiments, the heterologous gene is a gene that has been modified to overexpress a gene product of interest.

The term "expression" as used herein includes any step involved in the production of a polypeptide (e.g., encoded enzyme) including, but not limited to, transcription, post-transcriptional modification, translation, post-translational modification, and secretion.

The term "overexpression" as used herein refers to any state in which a gene is caused to be expressed at an elevated rate or level as compared to the endogenous (native) expression rate or level for that gene. In some embodiments, "overexpression" includes an elevated translation rate or level of the gene compared to the endogenous translation rate or level for that gene. In some embodiments, overexpression includes an elevated transcription rate or level of the gene compared to the endogenous transcription rate or level for that gene. It is intended that the term encompass overexpression of endogenous, as well as heterologous proteins.

The term "recombinant" as used herein includes reference to a cell or vector, that has been modified by the introduction of a heterologous nucleic acid sequence or that the cell is derived from a cell so modified. Thus, for example, recombinant cells express genes that are not found in identical form within the native (i.e., non-recombinant) form of the cell or express native genes that are otherwise abnormally expressed, under-expressed or not expressed at all as a result of deliberate human intervention. "Recombinant," "engineered," and "non-naturally occurring," when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (i.e., non-recombinant) form of the cell or express native genes that are otherwise expressed at a different level.

The term "plasmid" as used herein refers to a circular double-stranded (ds) DNA construct used as a cloning vector, and which forms an extrachromosomal self-replicating genetic element in some eukaryotes or prokaryotes, or integrates into the host chromosome.

The term "operably linked" as used herein refers to a configuration in which a control sequence is appropriately placed (i.e., in a functional relationship) at a position relative to a polynucleotide of interest such that the control sequence directs or regulates the expression of the polynucleotide and/or polypeptide of interest. Thus, a nucleic acid is "operably linked" to another nucleic acid sequence when it is placed into a functional relationship with another nucleic acid sequence.

The term "control sequence" as used herein includes all components, that are necessary and/or advantageous for the expression of a polynucleotide of the present disclosure. Each control sequence may be native or foreign to the polynucleotide of interest. Such control sequences include, but are not limited to, leaders, polyadenylation sequences, propeptide sequences, promoters, signal peptide sequences, and transcription terminators.

"Host cell" as used herein refers to a living cell or microorganism that is capable of reproducing its genetic material and along with it recombinant genetic material that has been introduced into it (e.g., via heterologous transformation).

The terms "engineered host cell" or "recombinant host cell" used interchangeably herein refer to a cell whose genetic material has been altered using genetic engineering techniques. An engineered host cell also refers to a derivative of or the progeny of a cell whose genetic material has been altered using genetic engineering techniques. An example of a genetic modification as a result of genetic engineering techniques includes a modification to the genomic DNA. Another example of a genetic modification as a result of genetic engineering techniques includes introduction of a stable heterologous nucleic acid into the cell.

The phrase "a corresponding cell grown under essentially the same culture conditions" as used herein means a reference host cell (either engineered or native) which is grown under essentially the same culture conditions, including but not limited to pH, temperature, time, and culture media as compared to an engineered cell encompassed by the invention and to which the reference cell is being compared to.

The term "carbon source" as used herein refers to a substrate that is suitable for use as a source of carbon for cell growth. Carbon sources may include but are not limited to carbohydrates, such as monosaccharides, disaccharides, oligosaccharides; alcohols; aldehydes; amino acids; organic acids; and ketones.

Nucleic acids "hybridize" when they associate, typically in solution. There are numerous texts and other reference materials that provide details regarding hybridization methods for nucleic acids (See e.g., Tijssen, *Laboratory Techniques in Biochemistry and Molecular Biology-Hybridization with Nucleic Acid Probes*," Part 1, Chapter 2, Elsevier, New York, [1993], incorporated herein by reference). For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. ("low" stringency), at least at 55° C. ("medium" or "moderate" stringency), at least at 60° C. ("medium-high" stringency), at least at 65° C. ("high" stringency), and at least at 70° C. ("very high" stringency). In some embodiments, the stringency conditions include those that: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. In other embodiments, the stringency conditions include overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors to accomplish the desired stringency.

The phrase "naturally-occurring enzyme" as used herein refers to an enzyme having the unmodified amino acid sequence identical to that found in nature (i.e., "wild-type"). Naturally-occurring enzymes include native enzymes (i.e., those enzymes naturally expressed or found in the particular microorganism).

The term "variant" as used herein refers to a polypeptide sequence or polynucleotide sequence encoding a polypeptide, said sequence comprising one or more modifications relative to a corresponding native enzyme (or other specified reference sequence) or the native polynucleotide (or other specified reference sequence) such as substitutions, insertions, deletions, and/or truncations of one or more specific amino acid residues or of one or more specific nucleotides or codons in the polypeptide or polynucleotide. In some embodiments, reference to a variant at an amino acid residue refers to a substitution of the amino acid residue for another amino acid residue. Mutagenesis and directed evolution methods are well known in the art for creating variants (See e.g., U.S. Pat. Nos. 7,783,428, 6,429,175, 6,376,246, 6,586,182, 6,117,679; and Ling, et al., 1999, "Approaches to DNA mutagenesis; an overview," *Anal. Biochem.*, 254(2):157-78; Smith, 1985, "In vitro mutagenesis," *Ann. Rev. Genet.*, 19:423-462; Carter, 1986. "Site-directed mutagenesis," *Biochem. J.*, 237:1-7; Minshull, et al., 1999. "Protein evolution by molecular breeding," *Current Opinion in Chemical Biology*, 3:284-290;

The terms "isolated" or "recovered" as used herein refer to a material that is removed from its original environment (e.g., the natural environment, if it is naturally occurring). For example, the material is said to be "isolated" when it is present in a particular composition in a higher or lower concentration than exists in a naturally-occurring or wild-type organism or in combination with components not normally present upon expression from a naturally-occurring or wild-type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still considered to be isolated, in that such vector or composition is not part of its natural environment. In some embodiments, the term isolated refers to fatty alcohol compounds of varying chain lengths which are isolated or recovered from an engineered cell according to the invention.

As used herein, the term "biologically active fragment," or "functional fragment" refers to a polypeptide that has an amino-terminal and/or carboxy-terminal deletion(s) and/or internal deletion(s), but where the remaining amino acid sequence is identical to the corresponding positions in the sequence to which it is being compared (e.g., a full-length FabB or FAR of the present invention) and that retains substantially all of the activity of the full-length polypeptide. For example, a biologically active fragment can comprise about 60%, about 65%, about 70%, about 75%, about 80%, about 85%, about 90%, about 91%, about 92%, about 93%, about 94%, about 95%, about 96%, about 97%, about 98%, or about 99% of a full-length FabB or FAR polypeptide. In some embodiments, biologically active fragments comprise 60%, 65%, 70%, 75%, 80%, 85%, 90%, 91%, 92%, 93%, 94%, 95%, 96%, 97%, 98%, or 99% of a full-length FabB or FAR polypeptide.

The term "attenuated" or "attenuation" used interchangeably herein, as applied to a gene refers to any genetic modification that decreases or eliminates the expression of the gene and/or the functional activity of the corresponding gene product (mRNA and/or protein). The term encompasses complete or partial inactivation, suppression, deletion, interruption, blockage, promoter alterations, antisense RNA, dsRNA, or down-regulation of a gene. This can be accomplished, for example, by gene "knockout," inactivation, mutation (e.g., insertion, deletion, point, or frameshift mutations that disrupt the expression or activity of the gene product), or by use of inhibitory RNAs (e.g., sense, antisense, or RNAi technology).

The term "deletion" in reference to a gene means the elimination or knockout of all or part of a gene's coding sequence. For example, a deletion may encompass (at least about 50%, at least about 55%, at least about 60%, at least about 65%, at least about 70% at least about 80%, at least about 85% 90%, at least about 95%, at least about 96%, at least about 97%, at least about 98%, or at least about 99%) or all (100%) of the coding sequence of a gene.

With respect to "homologs," reference to particular gene names is for illustration and not limitation. It is understood that gene names vary from organism to organism and reference to a gene name is not intended to be limiting, but is intended to encompass homologs and polymorphic variants with equivalent activity. In certain embodiments, the invention includes a polynucleotide or polypeptide sequence with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% identity with the named gene or gene product.

The terms "peptide," "polypeptide," and "protein" are used interchangeably herein to refer to a polymer of amino acid residues. In various aspects of the invention, the availability of a polypeptide sequence of a specific enzyme provides a description of all polynucleotides capable of encoding the polypeptide of known sequence because of the known correspondence of particular codons and the amino acids they encode. In certain embodiments, the degeneracy of the genetic code is used to produce a large number of polynucleotides that encode a polypeptide described herein.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (See e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Optimal alignment of sequences for comparison and determination of sequence identity can be determined by a sequence comparison algorithm or by visual inspection (see, generally, Ausubel et al., infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters.

An algorithm that may be used to determine whether a variant FabB has sequence identity to SEQ ID NO:2 is the BLAST algorithm, which is described in Altschul et al., 1990, J. Mol. Biol. 215:403-410, which is incorporated herein by reference. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1997. Nucleic Acids Res., 25:3389-3402). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a word size (W) of 3, an expectation (E) of 10, and the BLOSUM62 scoring matrix (see Henikoff & Henikoff, 1989, Proc. Natl. Acad. Sci. USA 89:10915).

Numerous other algorithms are available that function similarly to BLAST in providing percent identity for two sequences. Optimal alignment of sequences for comparison can be conducted (e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms [GAP, BESTFIT, FASTA, and TFASTA in the GCG Wisconsin Software Package], or by visual inspection [See generally, Current Protocols in Molecular Biology, F. M. Ausubel et al., eds., Current Protocols, a joint venture between Greene Publishing Associates, Inc. and John Wiley & Sons, Inc., (1995 Supplement)]). Additionally, determination of sequence alignment and percent sequence identity can employ the BESTFIT or GAP programs in the GCG Wisconsin Software package (Accelrys, Madison Wis.), using default parameters provided.

Multiple sequences can be aligned with each other by visual inspection or using a sequence comparison algorithm, such as PSI-BLAST (Altschul, et al., 1997, supra) or "T-Coffee" (Notredame et al., 2000, J. Mol. Bio. 302:205-17). T-Coffee alignments may be carried out using default parameters (T-Coffee Technical Documentation, Version 8.01, July 2009, WorldWideWeb .tcoffee.org), or Protein Align. In Protein Align, alignments are computed by optimizing a function based on residue similarity scores (obtained from applying an amino acid substitution matrix to pairs of aligned residues) and gap penalties. Penalties are imposed for introducing any extending gaps in one sequence with respect to another. The final optimized function value is referred to as the alignment score. When aligning multiple sequences, Protein Align optimizes the "sum of pairs" score, i.e., the sum of all the separate pairwise alignment scores.

As used herein, the terms "numbered with reference to" or "corresponding to," when used in the context of the numbering of a given polypeptide or polynucleotide sequence, refers to the numbering of the residues of a specified reference sequence when the given amino acid or polynucleotide sequence is compared to the reference sequence. The following nomenclature may be used to describe substitutions in a test sequence relative to a reference sequence polypeptide or nucleic acid sequence: "R-#-V," where # refers to the position in the reference sequence. R refers to the amino acid (or base) at that position in the reference sequence, and V refers to the amino acid (or base) at that position in the test sequence. In some embodiments, an amino acid (or base) may be called "X," by which is meant any amino acid (or base).

"Reference sequence" refers to a defined sequence to which another sequence is compared. A reference sequence is not limited to wild-type sequences, and can include engineered or altered sequences. For example, a reference sequence can be a previously engineered or altered amino acid sequence. A reference sequence also may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity.

As used herein, the term "reference enzyme" refers to an enzyme to which another enzyme of the present invention (e.g., a "test" enzyme, such as wild-type enzyme) is compared in order to determine the presence of an improved property in the other enzyme being evaluated. In some embodiments, a reference enzyme is a wild-type enzyme. In some embodiments, the reference enzyme is an enzyme to which a test enzyme of the present invention is compared in order to determine the presence of an improved property in the test enzyme being evaluated, including but not limited to improved thermoactivity, improved thermostability, and/or improved stability. In some embodiments, a reference enzyme is a wild-type enzyme.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, the term "culturing" refers to growing a population of microbial cells under suitable conditions using any suitable medium (e.g., liquid, solid, or semi-solid media). In particular embodiments, culturing refers to the fermentative bioconversion of a carbon source (e.g., sugar) to an end product (e.g., fatty alcohols).

The term "extracellular environment" means the aqueous solution surrounding a cell membrane, excluding the intracellular space. For example, a secreted enzyme or a compound is found in the extracellular environment. In some embodiments, the extracellular environment comprises the culture medium used to grow the cell.

"Solution" as used herein refers to any medium, phase, or mixture of phases, in which the recombinant host cells and/or products (e.g. fatty alcohols) of the present disclosure are active. It is intended to include purely liquid phase solutions (e.g., aqueous, or aqueous mixtures with co-solvents, including emulsions and separated liquid phases), as well as slurries and other forms of solutions having mixed liquid-solid phases.

The term "contacting" refers to combining an enzyme and a substrate under conditions in which the enzyme can act on the substrate. Those skilled in the art will recognize that mixing a solution containing an enzyme with a substrate will effect "contacting." Similarly, in the context of culturing microorganisms, culturing microorganisms in a media containing a substrate (e.g., a fermentable sugar) will effect "contacting" the microorganism with the substrate.

"Sugar" as used herein refers to carbohydrate compounds and compositions made up of monosaccharides, disaccharides, trisaccharides, and short chain oligosaccharides (e.g., 6carbon and 5-carbon compounds such as but not limited to glucose, arabinose, fructose, galactose, ribose, mannose, xylose, lactose, sucrose maltose and the like).

The term "fermentable sugars" refers to sugars that a microorganism can utilize for growth or which can be used in the production of end-products such as but not limited to hydrocarbons, amino acids, ethanol and other chemical compounds.

The terms "cleaning compositions" and "cleaning formulations" refer to compositions that find use in the removal of undesired compounds from items to be cleaning, such as fabric, dishes, contact lenses, other solid substrates, hair (shampoos), skin (soaps and creams), teeth (mouthwashes, toothpastes, etc.), etc. The terms further refer to any composition that is suited for cleaning, bleaching, disinfecting and/or sterilizing any object and/or surface. It is intended that the terms include, but are not limited to detergent compositions (e.g., laundry and fine fabric detergents), hard surface cleaning formulations (e.g., for glass, wood, ceramics and metal countertops, windows, etc.), oven cleaners, carpet cleaners, fabric fresheners, fabric softeners, hand and machine dish detergents, dish rinse aids, and textile and laundry pre-spotters. In addition, the terms encompass cleaning compositions for use in household and institutional use, including but not limited to liquid cleaning and disinfecting agents, such as anti-bacterial handsoaps and wipes, cleaning bars, mouthwashes, denture cleaners, car shampoos, bathroom cleaners, hair shampoos and conditioners/rinses for humans and other animals, shower gels, foam baths, etc. Indeed, it is not intended that the term be limited to any particular cleaning composition. The terms encompass any materials/compounds selected for the particular type of cleaning compositions desired and the form of the product (e.g., liquid, gel, granule, or spray), as long as the composition is compatible with the fatty alcohol(s) of the present invention. The specific selection of cleaning composition materials are readily made by considering the surface, item or fabric to be cleaned, and the desired form of the composition for the cleaning conditions during use.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered enzyme, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Different from" or "differs from" with respect to a designated reference sequence refers to difference of a given amino acid or polynucleotide sequence when aligned to the reference sequence. Generally, the differences can be determined when the two sequences are optimally aligned. Differences include insertions, deletions, or substitutions of amino acid residues in comparison to the reference sequence. Typically, the reference sequence is a naturally occurring sequence from which the sequence with the differences is derived. The present disclosure provides engineered pathways of enzymes, wherein the enzymes are encoded by one or more recombinant polynucleotides having one or more nucleotide sequence differences relative to a reference polynucleotide sequence, which is typically the corresponding naturally occurring polynucleotide from which the recombinant polynucleotide is derived. Further, the nucleotide differences may encode one or more amino acid residue differences in the enzymes, where the encoded amino acid differences, which can include either/or both conservative and non-conservative amino acid substitutions.

"Derived from" as used herein in the context of engineered enzymes, identifies the originating enzyme, and/or the gene encoding such enzyme, upon which the engineering was based.

"Amino acid residue" or "amino acid" or "residue" as used herein refers to the specific monomer at a sequence position of a polypeptide.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid (e.g., alanine, valine, leucine, and isoleucine); an amino acid with hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basic side chain (e.g., lysine and arginine); an amino acid with an acidic side chain is substituted with another amino acid with an acidic side chain (e.g., aspartic acid or glutamic acid); and a hydrophobic or hydrophilic amino acid is replaced with another hydrophobic or hydrophilic amino acid, respectively.

"Non-conservative substitution" refers to substitution of an amino acid in a polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" when used with reference to a polypeptide refers to modification of the polypeptide by removal of one or more amino acids from a reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, up to 20% of the total number of amino acids, and up to 30% of the total number of amino acids making up the polypeptide while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous.

"Insertion" when used with reference to a polypeptide refers to modification of the polypeptide by addition of one or more amino acids to the reference polypeptide. In some embodiments, the improved engineered enzymes comprise insertions of one or more amino acids relative to the corresponding naturally occurring polypeptide as well as insertions of one or more amino acids to other improved polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Improved property" as used herein refers to a functional characteristic of an enzyme or host cell that is improved relative to the same functional characteristic of a reference enzyme or reference host cell. Improved properties of the engineered enzymes or host cells comprising engineered pathways disclosed herein can include but are not limited to: increased activity (including increased rate conversion of substrate to product, or increased percentage conversion in a period of time), altered substrate specificity, and/or preference, increased expression, as well as increased secretion.

"Codon optimized" refers to changes in the codons of the polynucleotide encoding a protein to those preferentially used in a particular organism such that the encoded protein is efficiently expressed in the organism of interest. In some embodiments, the polynucleotides encoding the enzymes used in the engineered pathways of the present disclosure may be codon optimized for optimal production from the host organism selected for expression.

DETAILED DESCRIPTION OF THE INVENTION

The recombinant host cells, engineered pathways, and specific recombinant polynucleotides and encoded enzymes that make up the pathways and carry out the substrate-to-product conversions are described in greater detail below. Additionally, the following sections describe methods for using the recombinant host cells for the production of fatty alcohols and particularly fatty alcohol compositions comprising at least 25% C12 and C14C fatty alcohols.

FabB Variant Enzymes

In one embodiment, the invention is directed to fatty alcohol compositions comprising predominantly C12 to C14 fatty alcohols produced from engineered microbial cells.

To obtain the above objective, in certain embodiments a polynucleotide sequence encoding a variant FabB enzyme has been introduced into an engineered cell (e.g., a bacterial cell). FabB is one of the critical fatty acid biosynthetic genes involved in the collection of reactions responsible for fatty acid elongation. The fatty acids may then be used as intermediates in the production of fatty alcohols, aldehydes, esters, and the like. In one embodiment a variant FabB according to the invention when introduced and expressed by a host cell may increase the saturation level of the produced fatty acid intermediates as compared to a corresponding host cell.

In certain embodiments, the polynucleotide sequence encoding a variant FabB enzyme will comprise a nucleic acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 1. In some embodiments, the variant FabB is encoded by a nucleic acid sequence that can selectively hybridize to SEQ ID NO: 1 under moderately stringent, stringent or highly stringent conditions, as described hereinabove.

In some embodiments, the variant FabB comprises an amino acid sequence that is a least about 80%, about 85%, about 86%, about 87%, about 88%, about 89%, about 90%, about 91%, about 92%, about 93%, about 94%, about 95%, about 96%, about 97%, about 98%, or 99% identical to the amino acid sequence set forth in SEQ ID NO:2. In some embodiments, the FabB is a functional fragment of a sequence having at least about 90% sequence identity to SEQ ID NO:2. In some embodiments, the functional fragment is about 90%, about 91%, about 92%, about 93%, about 94%, about 95%, about 96%, about 97%, about 98%, or about 99% the length of the sequence of SEQ ID NO:2.

In some embodiments, the variant FabB comprises at least 85% (also at least 88%, 90%, 91%, 92%, 93%, 94%, 95%, 96%, 97%, 98% and 99%) amino acid sequence identity to SEQ ID NO:2 and an amino acid substitution at one or more positions associated with the binding pocket and/or the surface of a FabB protein of SEQ ID NO:2. The structure of the acyl-binding pocket and the active site of KAS enzymes is discussed in Olsen et al. 2001 Structure 9: 233-234.

In some embodiments, the variant FabB comprises at least 85% (also at least 88%, 90%, 91%, 92%, 93%, 94%, 95%, 96%, 97%, 98% and 99%) amino acid sequence identity to SEQ ID NO:2 and an amino acid substitution at one or more of the following positions 30, 34, 38, 40, 42, 43, 45, 51, 53, 61, 62, 63, 64, 65, 66, 95, 96, 97, 106, 107, 108, 110, 111, 112, 113, 114, 115, 116, 117, 124, 127, 128, 130, 131, 132, 133, 134, 135, 136, 137, 138, 139, 140, 149, 151, 161, 162, 164, 165, 191, 196, 197, 200, 201, 204, 205, 206, 209, 210, 212, 216, 217, 224, 225, 226, 229, 231, 267, 268, 270, 271, 272, 273, 275, 282, 285, 298, 300, 302, 303, 304, 305, 308, 311, 314, 315, 333, 335, 336, 360, 361, 367, 390, 391, 392, or 396 when optimally aligned with SEQ ID NO:2.

In some embodiments, the variant FabB comprises at least 85% (also at least 88%, 90%, 91%, 92%, 93%, 94%, 95%, 96%, 97%, 98% and 99%) amino acid sequence identity to SEQ ID NO:2 and an amino acid substitution at one or more of the following positions R30, T34, E38, K40, S42, G43, R45, N51, K53, D61, R62, K63, V64, V65, R66, N95, N96, P97, G106, G107, G108, P110, R111, F112, Q113, V114, F115, G116, A117, R124, K127, A128, G130, P131, Y132, V133, V134, T135, K136, A137, M138, A139, S140, P149, K151, S161, A162, A164, T165, E191, E196, M197, E200, F201, M204, G205, A206, T209, K210, N212, E216, K217, A224, H225, R226, F229, I231, A267, D268, V270, A271, P272, S273, E275, K282, M285, H298, T300, T302, P303, V304, G305, K308, A311, R314, E315, H333, L335, G336, N360, I361, Q367, F390, G391, F392, or N396 when optimally aligned with SEQ ID NO:2.

In some embodiments, the variant FabB comprises at least 85% (also at least 88%, 90%, 91%, 92%, 93%, 94%, 95%, 96%, 97%, 98% and 99%) amino acid sequence identity to SEQ ID NO:2 and an amino acid substitution at one or more of the following positions K40, S42, R45, G106, G107, G108, P110, Q113, A117, V133, V134, A137, M138, M197, E200, F201, A206, E216, K217, I231, T300, T302, P303, G305, L335, or Q367 when optimally aligned with SEQ ID NO:2.

In some embodiments, the variant FabB comprises at least 85% (also at least 88%, 90%, 91%, 92%, 93%, 94%, 95%, 96%, 97%, 98% and 99%) amino acid sequence identity to SEQ ID NO:2 and an amino acid substitution at one or more of the following positions 40, 42, 45, 206, 231, 216, 217, 303, 335 or 367 when optimally aligned with SEQ ID NO:2. In some embodiments, the variant FabB will comprise at least 85% (also at least 90%, 91%, 92%, 93%, 94%, 95%, 96%, 97%, 98% and 99%) amino acid sequence identity to SEQ ID NO:2 and an amino acid substitution at one or more of the following positions K40, S42, R45, A206, E216, K217, I231, P303, L335, or Q367 when optimally aligned with the polypeptide of SEQ ID NO:2.

In other embodiments, the variant FabB will comprises one or more of the following substitutions K40G/R/A/S, S42E/L, R45G, A206G, I231F/C, E216W, K217V, P303C/V, L335M, or Q367V.

In some embodiments, a FabB variant will include more than 1 substitution such as 2, 3, 4, 5, 6, 7, 8 or more substitutions when aligned with a FabB polypeptide having at least 85% (also at least 90%, 91%, 92%, 93%, 94%, 95%, 96%, 97%, 98% and 99%) sequence identity to SEQ ID NO:2. In some embodiments, the FabB variant will be a functional fragment having at least 85% (also at least 90%, 91%, 92%, 93%, 94%, 95%, 96%, 97%, 98% and 99%) sequence identity to SEQ ID NO:2 and comprising a substitution of one or more of the following positions R30, T34, E38, K40, S42, G43, R45, N51, K53, D61, R62, K63, V64, V65, R66, N95, N96, P97, G106, G107, G108, P110, R111, F112, Q113, V114, F115, G116, A117, R124, K127, A128, G130, P131, Y132, V133, V134, T135, K136, A137, M138, A139, S140, P149, K151, S161, A162, A164, T165, E191, E196, M197, E200, F201, M204, G205, A206, T209, K210, N212, E216, K217, A224, H225, R226, F229, I231, A267, D268, V270, A271, P272, S273, E275, K282, M285, H298, T300, T302, P303, V304, G305, K308, A311, R314, E315, H333, L335, G336, N360, I361, Q367, F390, G391, F392, or N396 when optimally aligned with SEQ ID NO:2. In other embodiments, the FabB variant will be a functional fragment having at least 85% (also at least 90%, 91%, 92%, 93%, 94%, 95%, 96%, 97%, 98% and 99%) sequence identity to SEQ ID NO:2 and comprising a substitution of one or more of the following positions 40, 42, 45, 206, 231, 216, 217, 303, 335 or 367 when optimally aligned with SEQ ID NO:2. In some embodiments the functional fragment of a FabB variant is about 90%, (such as 91%, 92%, 93%, 94%, 95%, 96%, 97%, 98% or even 99%) the length of the sequence of SEQ ID NO:2. In some embodiments, the FabB variant may be truncated at the amino and/or carboxy end of the polypeptide.

FabB sequences homologous to SEQ ID NO:2 can be identified by any of a variety of methods known in the art. For example, a sequence alignment can be conducted against a database, for example against the NCBI database, and sequences with the lowest HMM E-value can be selected. One could then test whether or not these identified sequences have FabB activity and reference is made to Edwards et al., 1997, FEBS let. 402: 62-66.

In another aspect, the present invention provides polynucleotides encoding the variant FabB enzymes as described above. The polynucleotide can be a DNA or RNA and can be single-stranded or double-stranded. The polynucleotides may be prepared wholly or partially via synthetic means. In various aspects of the invention, the availability of a polypeptide sequence of a specific variant FabB enzyme provides a description of all polynucleotides capable of encoding the polypeptide of the known sequence because of the known correspondence of particular codons and the amino acids they encode. In certain embodiments, the degeneracy of the genetic code is used to produce a large number of polynucleotides that encode the variant FabB polypeptides described herein. In some embodiments, the polynucleotides encoding the desired enzyme are codon-optimized. In particular embodiments, the polynucleotides that encode the FabB enzymes described herein are codon-optimized for expression in a bacterial host cell. Indeed, it is intended that the polynucleotides of the present invention be produced using any suitable methods and components as known in the art.

DNA Constructs and Vectors

In some embodiments, the variant FabB polynucleotide is introduce into a host cell on a DNA construct or vector. In another aspect, the present invention provides polynucleotides encoding the variant FabB enzymes as described above. The polynucleotide can be a DNA or RNA and can be single-stranded or double-stranded. The polynucleotide can be isolated from a naturally occurring microorganism, or prepared wholly or partially via synthetic means. Indeed, it is intended that the polynucleotides of the present invention be produced using any suitable methods and components as known in the art.

In various aspects of the invention, the availability of a polypeptide sequence of a specific variant FabB enzyme provides a description of all polynucleotides capable of encoding the polypeptide of the known sequence because of the known correspondence of particular codons and the amino acids they encode. In certain embodiments, the degeneracy of the genetic code is used to produce a large number of polynucleotides that encode the variant FabB polypeptides described herein. In some embodiments, the polynucleotides encoding the desired enzyme are codon-optimized. In particular embodiments, the polynucleotides that encode the FabB enzymes described herein are codon-optimized for expression in a bacterial host cell.

In certain embodiments, the present disclosure provides a vector or DNA construct comprising a polynucleotide encoding a variant FabB enzyme as described above, wherein the variant FabB is produced in a host cell. In some embodiments, the polynucleotide is a codon-optimized polynucleotide, such as a polynucleotide having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or even about 100% sequence identity to SEQ ID NO: 1.

Any suitable DNA construct and vector finds use in the invention (See e.g., WO 2011/008535 which is here in incorporated by reference). In some embodiments, the polynucleotide encodes for a variant FabB enzyme and the polynucleotide sequence will have at least about 90%, at least about 91%, at least about 92%, at least 93%, at least about 94%, at least about 95%, at least about 96%, at least about 97%, at least about 98%, at least about 99%, or even about 100%) sequence identity to SEQ ID NO: 1.

In some embodiments, polynucleotides encoding a variant FabB as described herein for expression in the recombinant host cells are operably linked to a promoter, and optionally, to other control sequences. Suitable promoters include, but are not limited to constitutive promoters, regulated promoters, and inducible promoters. Appropriate promoter sequences can be obtained from genes encoding extracellular or intracellular polypeptides which are either endogenous or heterologous to the host cell. Methods for the isolation, identification and manipulation of promoters of varying strengths are available in or readily adapted from the art (See e.g., Nevoigt et al. (2006) Appl. Environ. Microbiol. 72:5266-5273, the disclosure of which is herein incorporated by reference in its entirety). In certain embodiments, the DNA constructs, vectors and polynucleotides are suitable for expression of a variant FabB in bacteria. For bacterial host cells, suitable promoters for directing transcription of the nucleic acid constructs of the present disclosure, include, but are not limited to the promoters obtained or derived the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus megaterium* promoters, and prokaryotic beta-lactamase gene (Villa-Kamaroff et al., *Proc. Natl Acad. Sci. USA* 75: 3727-3731 (1978)), as well as the tac promoter (DeBoer et al., *Proc. Natl Acad. Sci. USA* 80: 21-25 (1993)). Additional promoters include trp promoter, phage lambda PL, T7 promoter, promoters found at PromEC (at website margalit.huji.ac.il/promec/index.html) and the like. Particularly useful promoters include the Trc promoter (Brosius J. et al., (1985) J. Biol. Chem. 260: 3539-3541). In certain embodiments, the promoter that is used in a vector or DNA construct is the native fabB promoter. In some embodiments, when the variant fabB is chromosomally integrated in a host cell, expression is regulated by the native fabB promoter. Additional promoters suitable for use in the present disclosure are described in Terpe H., 2006, Appl. Microbiol. Biotechnol. 72:211-222 and in Sambrook et al (2001) *Molecular Cloning: A Laboratory Manual*, $3^{rd}$ ed., Cold Spring Harbor Laboratory Press, New York.

In various embodiments, an expression vector optionally contains a ribosome binding site (RBS) for translation initiation, and a transcription terminator, such as the transcriptional terminators $T_1$ and $T_2$ derived from the rrnB operon from *E. coli* (See e.g., Orosz et al., (1991) Eur. J.

Biochem. 201: 653-659). The vector also optionally includes appropriate sequences for amplifying expression (e.g., translational enhancers).

In various embodiments, the polynucleotides useful for expressing the heterologous enzymes in recombinant host cells are operably linked to other control sequences, including but not limited to, a transcription terminator sequence, a signal sequence that when translated directs the expressed polypeptide into the secretory pathway of the recombinant host cell, and/or a polyadenylation sequence (eukaryotes). The choice of appropriate control sequences for use in the polynucleotide constructs of the present disclosure is within the skill in the art and in various embodiments is dependent on the recombinant host cell used and the desired method of recovering the fatty alcohol compositions produced. Indeed, it is not intended that the present invention be limited to any particular control sequence(s).

A recombinant expression vector according to the invention can be any suitable vector (e.g., a plasmid or a virus), which can be manipulated by recombinant DNA techniques to facilitate expression of at least one heterologous enzyme in the recombinant host cell. In certain preferred embodiments, the expression vector is integrated into the chromosome of the host cell and comprises one or more heterologous genes operably linked to one or more control sequences useful for production of a variant FabB enzyme. In other embodiments, the expression vector is an extra chromosomal replicative DNA molecule (e.g., a linear or closed circular plasmid), that is found either in low copy number (e.g., from about 1 to about 10 copies per genome equivalent) or in high copy number (e.g., more than about 10 copies per genome equivalent). In various embodiments, the expression vector includes a selectable marker, such as a gene that confers antibiotic resistance (e.g., ampicillin, kanamycin, chloramphenicol or tetracycline resistance) to the recombinant host organism that comprises the vector.

Expression vectors that, in certain embodiments, are useful for expressing enzymes as disclosed herein are commercially available (e.g., from Sigma-Aldrich Chemicals, St. Louis Mo. and Stratagene, LaJolla Calif.). In some embodiments, examples of suitable expression vectors are plasmids which are derived from pBR322 (Gibco BRL), pUC (Gibco BRL), pREP4, pCEP4 (Invitrogen) or pPoly (Lathe et al., 1987, *Gene* 57:193-201).

In certain embodiments, the present disclosure provides a plasmid for expression of heterologous genes in *E. coli* (e.g. the introduction of a FAR polynucleotide). Expression vector pCK110900, which comprises a P15A origin of replication "ori" (P15A ori), lac a CAP binding site, a lac promoter, a T7 ribosomal binding site (T7g10 RBS) and a chloramphenicol resistance gene (camR) is an exemplary vector that finds use in the present invention. This expression vector is depicted in FIG. 3 of U.S. Patent Publication No. 2006/0195947, which is incorporated herein by reference in its entirety. Other suitable plasmid vectors include, but are not limited to derivatives of pCL1920 and pCL1921 (Lerner and Inouye, 1990; NAR 18:4631). These vectors contain the pSC101 ori and confer resistance to spectinomycin (GenBank:AB236930). In some embodiments, the vector is an expression vector derived from pCL1920 including the Trc promoter and the lacIq gene from *E. coli*.

Modification of Native β-Ketoacyl-ACP Synthase Genes

In one embodiment, a native β-ketoacyl-ACP synthase is modified at the native locus on the genome. In some embodiments the native β-ketoacyl-ACP synthase is a β-ketoacyl-ACP synthase I coded for by a fabB gene and in some embodiments, the native β-ketoacyl-ACP synthase is a β-ketoacyl-ACP synthase II coded for by a fabF gene. In some embodiments, the general term "native gene modification" is used to broadly encompass the various types of alterations that result in modification of a native β-ketoacyl-ACP synthase. One of skill in the art is well aware of many methods that may be used to modify a native β-ketoacyl-ACP synthase. For example one or more of the following non-limiting methods may be used to accomplish native gene modification: 1) complete replacement of the native fabB gene by a variant fabB polynucleotide encoding a variant Fab enzyme as described herein above; 2) replacement of the native fabB gene by a fab gene from a microorganism other than the host microorganism (e.g. by a β-ketoacyl-ACP synthase (fabF or fabB) from *Lactococcus lactis* or a β-ketoacyl-ACP synthase from *plasmodium falciparum*) followed by modification of the gene; 3) partial replacement of the native fabB gene (e.g., replacement of at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and at least 99%) of the native fabB gene, 4) mutations (such as substitutions) of at least 1, 2, 3, 4, 5, 6, 7, 8, 9, 10, 15, 20, 25, 30, 35, 40, 45, 50 or more amino acid residues coded for by a nucleic acid in the native fabB gene, wherein the mutations are at the native FabB chromosomal locus, 5) introduction of a homologous or heterologous fabB gene which is then optionally optimized; and 6) hybrid gene replacement, wherein part of the native gene is truncated and replaced with a polynucleotide sequence introduced into the host cell comprising a substitution in the coding region of the fabB gene. The truncation may be at the 5' or 3' end of the coding sequence. Methods of gene targeting and replacement are known. Most commonly this method is accomplished by homologous recombination of similar nucleic acids and reference is made to C. M. Hamilton et al., J. Bacteriol. (1989) 171:4617-4622; N. R. De Lay et al., J. Bacteriol. (2006) 188:287-296; Y -G Kim et al., BioTechniques (2000) 28:198-204; and A. J. Link et al., J. Bacteriol. (1997) 179:6228-6237.

In certain embodiments, the skilled person could use a *Lactocococcus lactis* fabF to functionally replace the native fabF and/or fabB in *E. coli* (See, Morgan-Kiss and Cronan (2008) Arch. Microbiol. 190:427-437).

In some embodiments, the native gene modification encompasses the entire coding region of the native fabB gene. In some embodiments, the native FabB gene will have a nucleic acid sequence that is at least 85% (at least 88%, 90%, 91%, 92%, 93%, 94%, 95%, 96%, 97%, 98%, 99% and even 100%) identical to the polynucleotide sequence of SEQ ID NO: 1. In some preferred embodiments, the native gene modification of a native fabB gene is replacement with a polynucleotide encoding a variant FabB or with a mutation made at the gene level (such as, but not limited to, one or more point mutations) and this modification is stable over many generations.

Transformation of Host Cells

Methods, reagents and tools for transforming host cells described herein, such as bacteria, yeast (including oleaginous yeast) and filamentous fungi are known in the art. General methods, reagents and tools for transforming (e.g., bacteria) can be found, for example, in Sambrook et al (2001) *Molecular Cloning: A Laboratory, Manual*, 3$^{rd}$ ed., Cold Spring Harbor Laboratory Press, New York. Methods, reagents and tools for transforming yeast are described in "Guide to Yeast Genetics and Molecular Biology," C. Guthrie and G. Fink, Eds., *Methods in Enzymology* 350 (Academic Press, San Diego, 2002). Methods, reagents and tools for transforming *Y. lipolytica* are found in "*Yarrowia lipolytica*," C. Madzak, J. M. Nicaud and C. Gaillardin in "Production of Recombinant Proteins Novel Microbial and Eucaryotic Expression Systems," G. Gellissen, Ed. 2005. Methods for engineering cyanobacteria may be found in T. Thiel (1994), Genetic analysis of cyanobacteria, in D. Bryant (ed.) The Molecular Biology of Cyanobacteria, Kluwer Academic Publishers 581-611. In some embodiments, introduction of the DNA construct or vector of the present invention into a host cell is accomplished by calcium phosphate transfection, DEAE-dextran mediated transfection, electroporation, or other common techniques (See Davis et al., 1986, *Basic Methods in Molecular Biology*, which is incorporated herein by reference). In one embodiment, a preferred method used to transform *E. coli* strains is electroporation and reference is made to Dower et al., 1988) NAR 16: 6127-6145. Indeed, any suitable method for transforming host cells finds use in the present invention. It is not intended that the present invention be limited to any particular method for introducing nucleic acids such as constructs into host cells.

The present invention also provides a method for producing an engineered cell, comprising: (a) providing a DNA construct comprising a polynucleotide sequence encoding a variant FabB enzyme operably linked to a promoter and (b) transforming a host cell with the DNA construct, wherein the polynucleotide sequence encoding the variant FabB replaces the endogenous fabB gene. In some embodiments, the host cell is a bacterial cell and in other embodiments, the host cell is *E. coli*. In some embodiments, the host cell already comprises a polynucleotide sequence encoding a heterologous FAR enzyme as described herein (i.e., the host cell comprises the FAR sequence prior to transformation). In some embodiments the variant FabB polynucleotide and the heterologous FAR polynucleotide will be co-transformed on the same or different construct or plasmid.

Host Cells

In some embodiments, the host cell is a prokaryotic cell. Suitable prokaryotic cells include Gram-positive, Gram negative and Gram-variable bacterial cells. In certain embodiments, host cells include, but are not limited to, species of a genus selected from the group of *Acetobacter, Acinetobacter, Agrobacterium, Arthrobacter, Bacillus, Clostridium, Cornebacterium, Desulfovibrio, Escherichia, Erwinia, Geobacillus, Klebsiella, Lactobacillus, Mycobacterium, Pantoea, Rhodococcus, Rhodobacter, Streptomyces, Vibrio*, and *Zymomonas*.

In certain embodiments, the recombinant host cell is an industrial bacterial strain. Numerous bacterial industrial strains are known and suitable for use in the methods disclosed herein. In some embodiments, the bacterial host cell is a species of the genus *Bacillus* (e.g., *B. thuringiensis, B. anthracis, B. megaterium, B. subtilis, B. lentus, B. circulans, B. pumilus, B. lautus, B. coagulans, B. brevis, B. firmus, B. alkalophilus, B. licheniformis, B. clausii, B. stearothermophilus, B. halodurans, B. subtilis, B. pumilus*, or *B. amyloliquefaciens*). In some embodiments, the bacterial host cell is a species of the genus *Erwinia* (e.g., *E. uredovora, E. carotovora, E. ananas, E. herbicola, E. punctata*, or *E. terreus*). In other embodiments the bacterial host cell is a species of the genus *Pantoea* (e.g., *P. citrea* or *P. agglomerans*). In still other embodiments, the bacterial host cell is a species of the genus *Streptomyces* (e.g., *S. ambofaciens, S. achromogenes, S. avermitilis, S. coelicolor, S. aureofaciens, S. aureus, S. fungicidicus, S. griseus*, or *S. lividans*). In further embodiments, the bacterial host cell is a species of the genus *Zymomonas* (e.g., *Z. mobils* or *Z. lipolytica*). In further embodiments, the bacterial host cell is a species of the genus *Rhodococcus* (e.g. *R. opacus*).

In some embodiments, the bacterial host cell is a species of the genus *Escherichia* (e.g., *E. coli*). In various embodiments, the engineered *E. coli* bacterial strains useful in the processes described herein are derived from strain W3110, strain MG1655, strain B766 (*E. coli* W) and strain BW25113. In some further embodiments, the W3110 strain finds use in the present invention; the genome of this strain has been fully sequenced and annotated (See e.g., Hayashi et al., (2005) Mol. Syst. Biol. 2:2006.0007). For industrial applications, phage-resistant strains are particularly useful. In this sense, deletion of the fhuA gene (also known as tonA) confers resistance to phages T1, T5 and phi80 (Link et al., 1997, J. Bact. 179: 6228-8237). Another useful strain is *E. coli* W (Archer et al., 2011, BMC Genomics, 12:9.doi: 10.1186/1471-2164-12-9). Also reference is made to Elben et al. (2005) J. of Food Protection 68(2):282-291. In some embodiments, the engineered host cell according to the invention will be a bacterial strain already including the deletion of one or more non-essential genes. For example Baba et al., 2006, in Molecular Systems Biology doi: 10.1038/msb4100050 describes the deletion of various chromosomal genes in *E. coli*. In certain embodiments, the host cell is a cell that has already been engineered to include one or more heterologous genes such as for example a gene encoding a FAR, a gene encoding a Fab enzyme, or a gene encoding a thioesterase.

Other examples of useful *E. coli* strains include, but are not limited to, *E. coli* strains found in the *E. coli* Stock Center from Yale University (at website cgsc.biology.yale.edu/index.php); the Keio Collection, available from the National BioResource Project at NBRP *E. coli*, Microbial Genetics Laboratory, National Institute of Genetics 1111 Yata, Mishima, Shizuoka, 411-8540 Japan (www at shigen.nig.ac.jp/ecoli/strain/top/top.jsp); or strains deposited at the American Type Culture Collection (ATCC).

The disclosed invention further contemplates the use of other organism such as photosynthetic organisms including but not limited to algae (e.g., cyanobacteria (blue green algae) and photosynthetic bacteria. Non-limiting examples include strains of *Synechococcus, Synechocystis, Rhodobacter, Rhodococcus, Chlamydomonas, Chlorella, Prototheca, Cyanobacterium, Ralstonia, Alcaligenes, Rhodopseudomonas*, and *Saccharophagus degradans*. Additional heterotrophic species which may be used as host strains that are transformed with genes encoding enzymes involved in the synthesis of fatty alcohols include yeast cells such as but not limited to *Saccharomyces* (e.g., *S. cerevisiae*), *Yarrowia* (e.g., *Y. lipolytica*), *Candida* (e.g., *C. tropicalis*) and *Schizosaccharomyces* (e.g., *S. pombe*).

Fatty Alcohol Forming Acyl-CoA Reductases (FARs)

In some embodiments, the engineered cells encompassed by the invention are modified to express a polynucleotide encoding a heterologous FAR. Polynucleotides encoding FAR enzymes are known in the art (See e.g., WO2011/008535; WO2011/019858; U.S. Ser. No. 13/171,138, US2010/02036; U.S. Pat. Nos. 7,332,311; 6,143,538 and Metz et al., 2000, Plant Physiol. 122:635-644).

In some embodiments the acyl-CoA is reduced to a fatty alcohol in a two-step process. A NAD(P)H dependent acyl-CoA reductase converts an acyl-CoA to a fatty aldehyde and then the fatty aldehyde is reduced to a fatty alcohol by a NAD(P)H dependent alcohol dehydrogenase. Enzymes involved in this two-step conversion include for example the enzymes AcrI and YqhD. (See, Reiser and Somerville, J.

Bacteriol. (1997) 179:2969; Ishige et al., Appl. Environ. Microbiol. (2000) 66:3481; Hofrander et al. (2011) FEBS Letters 585:3538-3543 and Kalscheuer et al., 2006, Appl. Environ. Microbiol. 72:1373). IN some embodiments, these enzyme use acyl-CoAs as substrates.

In some embodiments, the FARs useful in the present invention catalyze the direct reduction of acyl-CoA and/or acyl-ACP substrates to fatty alcohols wherein free fatty aldehydes are essentially not released as an intermediate. Essentially these FARs reduce acyl chains to fatty alcohols by one enzymatic step. Depending on the substrate chain length it is possible to have trace amounts of aldehydes produced and released. In some embodiments of the direct reduction process, FAR converts at least acyl-ACP substrates to a fatty alcohol end-product without the subsequent action of an alcohol dehydrogenase.

In some embodiments, the FAR is a prokaryotic enzyme. In some embodiments the FAR is derived from a species of Marinobacter including, but not limited to, M. algicola, M. alkaliphilus, M. aquaeolei, M. arcticus, M. bryozoorum, M. daepoensis, M. excellens, M. flavimaris, M. guadonensis, M. hydrocarbonoclasticus, M. koreenis, M. lipolyticus, M. litoralis, M. lutaoensis, M. maritimus, M. sediminum, M. squalenivirans, and M. vinifirmus, and equivalent and synonymous species thereof.

In certain embodiments, an engineered host cell will comprise a) a modified native fabB polynucleotide sequence encoding a FabB which comprises at least 85% (also at least 88%, 90%, 91%, 92%, 93%, 94%, 95%, 96%, 97%, 98% and 99%) amino acid sequence identity to SEQ ID NO:2 and an amino acid substitution at one or more of the following positions 30, 34, 38, 40, 42, 43, 45, 51, 53, 61, 62, 63, 64, 65, 66, 95, 96, 97, 106, 107, 108, 110, 111, 112, 113, 114, 115, 116, 117, 124, 127, 128, 130, 131, 132, 133, 134, 135, 136, 137, 138, 139, 140, 149, 151, 161, 162, 164, 165, 191, 196, 197, 200, 201, 204, 205, 206, 209, 210, 212, 216, 217, 224, 225, 226, 229, 231, 267, 268, 270, 271, 272, 273, 275, 282, 285, 298, 300, 302, 303, 304, 305, 308, 311, 314, 315, 333, 335, 336, 360, 361, 367, 390, 391, 392, or 396 when optimally aligned with SEQ ID NO:2 and b) a heterologous FAR as herein described. In certain embodiments, the engineered host cell (e.g., a bacterial cell) will comprises a) a fabB polynucleotide sequence encoding a variant FabB which comprises at least 85% (also at least 88%, 90%, 91%, 92%, 93%, 94%, 95%, 96%, 97%, 98% and 99%) amino acid sequence identity to SEQ ID NO:2 and an amino acid substitution at one or more of the following positions R30, T34, E38, K40, S42, G43, R45, N51, K53, D61, R62, K63, V64, V65, R66, N95, N96, P97, G106, G107, G108, P110, R111, F112, Q113, V114, F115, G116, A117, R124, K127, A128, G130, P131, Y132, V133, V134, T135, K136, A137, M138, A139, S140, P149, K151, S161, A162, A164, T165, E191, E196, M197, E200, F201, M204, G205, A206, T209, K210, N212, E216, K217, A224, H225, R226, F229, I231, A267, D268, V270, A271, P272, S273, E275, K282, M285, H298, T300, T302, P303, V304, G305, K308, A311, R314, E315, H333, L335, G336, N360, I361, Q367, F390, G391, F392, or N396 when optimally aligned with SEQ ID NO:2 and b) a heterologous FAR.

In certain embodiments, the heterologous FAR is derived from M. algicola strain DG893 and has an amino acid sequence that is at least about 70% identical, at least about 75%, at least about 80% identical, at least about 85% identical, at least about 90% identical, at least about 93% identical at least about 95% identical, at least about 97% identical, at least about 98% identical and/or at least about 99% identical to SEQ ID NO:4 and/or a functional fragment thereof. In certain embodiments, the FAR is a variant of the wild-type FAR of SEQ ID NO:2 for example a FAR having at least 85%, (at least 90%, 91%, 92%, 93%, 94%, 95%, 96%, 97%, 98% 99% and even 100% sequence identity to SEQ ID NO:6 or SEQ ID NO:10. In some embodiments, the FAR variants will have at least 1, at least 2, at least 3, at least 4, at least 5, at least 6, at least 7, at least 8, at least 9, at least 10, at least 12, at least 14, at least 16, at least 18, at least 20 at least 25 or more amino acid alterations (e.g., substitutions, deletions and/or insertions) relative to SEQ ID NO:4, SEQ ID NO:6 or SEQ ID NO: 10.

In certain embodiments, the FAR is derived from Marinobacter aquaeolei. In certain embodiments the FAR derived from M. aquaeolei has an amino acid sequence that is at least about 70% identical, at least about 75%, at least about 80% identical, at least about 85% identical, at least about 90% identical, at least about 93% identical, at least about 95% identical, at least about 97% identical, at least about 98% identical and/or at least about 99% identical to SEQ ID NO:5 as disclosed in WO 2012/006114 and/or a functional fragment thereof. In another specific embodiment, the FAR enzyme has an amino acid sequence that is identical to SEQ ID NO:5. In certain embodiments, the FAR is a variant of the wild-type FAR of SEQ ID NO:5 that has at least 1, at least 2, at least 3, at least 4, at least 5, at least 6, at least 7, at least 8, at least 9, at least 10, at least 12, at least 14, at least 16, at least 18, at least 20, or more amino acid alterations (e.g., substitutions, deletions and/or insertions) relative to SEQ ID NO:5. In certain embodiments, the FAR is encoded by a polynucleotide sequence having at least 85% (at least 90%, 91%, 92%, 93%, 94%, 95%, 96%, 97%, 98%, 99% sequence identity to SEQ ID NO:4 as disclosed in WO 2012/006114. In other embodiments, the FAR derived from M. aquaeolei has an amino acid sequence that is at least about 70% identical, at least about 75%, at least about 80% identical, at least about 85% identical, at least about 90% identical, at least about 93% identical, at least about 95% identical, at least about 97% identical, at least about 98% identical, at least about 99% identical and even 100% identical to SEQ ID NO:1 as disclosed in us 2012/0184006 and/or a functional fragment thereof such as amino acids 1 to 364 or amino acids 365 to 591 of SEQ ID NO: 1). In certain embodiments, the FAR is a variant of the wild-type FAR of SEQ ID NO:2 that has at least 1, at least 2, at least 3, at least 4, at least 5, at least 6, at least 7, at least 8, at least 9, at least 10, at least 12, at least 14, at least 16, at least 18, at least 20, or more amino acid alterations (e.g., substitutions, deletions and/or insertions) relative to SEQ ID NO:2.

In certain embodiments, the FAR is obtained from a marine bacterium selected from the group of Meptuniibacter caesariensis strain MED92, Reinekea sp. strain MED297, Marinomonas sp. strain MED121, unnamed Gammaproteobacteria strain HTCC2207, and Marinobacter sp. strain ELB17, as well as equivalents and synonymous species thereof. In certain embodiments, the FAR is obtained from the genus Oceanobacter. In some embodiments, the FAR is obtained from the Oceanobacter species strain RED65 (e.g. NCBI accession number ZP_01305629) and has an amino acid sequence that is at least about 70% identical, at least about 75% identical, at least about 80% identical, at least about 85% identical, at least about 90% identical, at least about 93% identical, at least about 95% identical, at least about 97% identical, at least about 98% identical and/or at least about 99% identical to SEQ ID NOs:6 and/or 8 as disclosed in WO 2011/008535.

In various embodiments, the FAR has the sequence or is encoded by a polynucleotide selected from the group of FAR_Hch (*Hahella chejuensis* KCTC 2396, GenBank YP_436183) (SEQ ID NO:29); FAR_Mac (from marine *Actinobacterium* strain PHSC20C1) (SEQ ID NO:30); FAR_JVC (JCVI_ORF_1096697648832, GenBank Accession No. EDD40059.1) (SEQ ID NO:31); FAR_Fer (JCVI_S-CAF_1101670217388) (SEQ ID NO:32); FAR_Key (JCVI_SCAF_1097205236585) (SEQ ID NO:33); FAR_Gal (JCVI_SCAF_1101670289386) (SEQ ID NO:34); *Vitis vinifera* FAR (GenBank Accession No. CAO22305.1 [SEQ ID NO:35] or CAO67776.1 [SEQ ID NO:36]); *Desulfatibacillum alkenivorans* FAR (GenBank Accession No. NZ_ABII01000018.1); *Stigmatella aurantiaca* FAR (NZ_AAMD01000005.1) (SEQ ID NO:37); *Phytophthora ramorum* FAR (GenBank Accession No.: AAQX01001105.1) (SEQ ID NO:38); *Simmondsia chinensis* acyl CoA reductase (GenBank Accession no. AAD38039.1) (SEQ ID NO:39); *Bombyx mori* fatty-acyl reductase (GenBank Accession No. BAC79425.1) (SEQ ID NO:40); GenBank Accession No. DQ446732.1 (SEQ ID NO:41) or NM_115529.1 (SEQ ID NO:42); and *Ostrinia scapulalis* (GenBank Accession No. EU817405.1) (SEQ ID NO:43).

In certain embodiments, the FAR polypeptide encompassed by the invention is coded for by a polynucleotide sequence that has been codon optimized. In particular embodiments, the polynucleotides that encode the FAR enzymes described herein are codon-optimized for expression in a host bacterial cell. Indeed, it is intended that the polynucleotides of the present invention be produced using any suitable methods and components as known in the art.

In some embodiments, a FAR enzyme is encoded by a polynucleotide sequence that has at least about 70%, at least about 75%, at least about 80%, at least about 85%, at least about 90%, at least about 93%, at least about 95%, at least about 96%, at least about 97%, or at least about 99% sequence identity to SEQ ID NO:3 SEQ ID NO:5 and/or SEQ ID NO:9 and further hybridizes with SEQ ID NO:3, SEQ ID NO:5 and/or SEQ ID NO:9 under medium, medium-high, high or very high stringency conditions.

Further Gene Manipulations

According to one embodiment of the invention, an engineered cell may further include a heterologous thioesterase ("TE"). The thioesterase may be one that preferentially uses C12, C14 or C16 ACPs. Depending on the TE used a homogenous population of fatty alcohols may be produced. For example, if the TE is one that predominantly uses C12 ACPs then the fatty alcohol composition produced by an engineered microbial cell according to the invention will predominantly comprise fatty alcohols having a carbon chain length of C12.

Some nonlimiting examples of heterologous TEs that may be used include the "class I" and "class II" acyl-ACP TE fat genes (e.g. fatA or fatB genes and reference is made to A. Jones et al., 1995, Plant Cell 7:359-371). Plant thioesterases are also described in U.S. Pat. Nos. 5,455,167 and 5,667, 997). In particular, FatB are preferred TEs (e.g. plant acyl-ACP TEs) useful in the invention. In some embodiments, the TE may be a bacterial acyl-ACP TE. FatB may be obtained for example from *Umbellularia california* having Accession number Q41635; and AAA34215; *Ulmus Americana* having Accession number AAB71731, *Cuphea hookeriana* Accession numbers Q39513; AAC49269; AAC49269; and AAC72881; *Cinnamonum camphorum* having Accession number Q39473; AAC49151 and acyl-ACP thioesterases from *Cuphea palustris* (AAC49179; and U.S. Pat. No. 5,955,329). Other TEs include without limitation CnFatB (*Cocos nucifera*, e.g. JF338903; JF338904 and JF338905); ccFAT (*Cinnamomum camphora*); pdFat (*Parabacteroides distasonis*, ATCC 8503); gsFat (*Geobacillus* sp. Y412MC10); pvFAT (*Paenibacillus vortex* V453); pm FAT (*Parabacteroides merdae* ATCC 43184); cvFatB (*Cuphea viscosissima*, JF338906; JF338907; and JF338908); eoFat (*Elaeis oleifera*) AAD42220 (*Elaeis guineensis*) and mlFat (*Madhuca longofolia* var. *latifolia*).

It is known that different acyl-ACP TE have different degrees of chain length specificity. In some preferred embodiments, the TE useful in the invention is a TE having a preference for cleaving chain lengths of any one of C12, C14 and/or C16 fatty acids from ACP. In some embodiments, having a preference for cleaving chain lengths of any one of C12, C14 and/or C16 fatty acids from ACP means that the thioester hydrolysis will produce fatty acids having at least 85%, (such as at least 88%, 90%, 93%, 95%, 96%, 97%, or more) of any one of C12, C14 and/or C16 carbon chain lengths.

In one embodiment, the invention comprises an engineered bacterial cell wherein the carbon chain length of acyl-derived products (e.g., fatty acids and/or fatty alcohols) produced from the bacterial cell have been altered. In certain embodiments, the engineered cell comprises a modified native bacterial gene having β-ketoacyl-ACP synthase activity (e.g., a native β-ketoacyl-ACP synthase I (FabB) (EC 2.3.1.41) or a native β-ketoacyl-ACP synthase II (FabF) (EC 2.3.1.179)) and a heterologous TE. In some embodiments the TE is encoded by a gene comprising the polynucleotide sequence having at least 70%, (at least 75%, 80%, 85%, 90%, 93%, 95%, 97%, 99%, and even 100%) sequence identity to the polynucleotide sequence of SEQ ID NO:7. In some embodiments, the TE enzyme will comprise at least 70%, (at least 75%, 80%, 85%, 90%, 93%, 95%, 97%, 99%, and even 100%) sequence identity to the polypeptide sequence of SEQ ID NO:8. In some embodiments the gene encoding the TE enzyme is derived from *Umbelluria californica* (California Bay) and in other embodiments the gene encoding the TE enzyme is derived from *Cinnamomum camphorum*. In some embodiments, the TE is an *E. coli* TE, a variant thereof or a naturally occurring equivalent thereof that has been introduced into the engineered cell. More specifically the TE may be a TesA that is obtained from *E. coli*, or an analogous sequence (See, WO 2010/075483).

In some embodiments, the TE enzyme will be a functional fragment of a native TE, such as a TE having deletions at the N-terminal amino acid positions. In certain embodiments, the functional fragment will comprise at least 95% of the reference enzyme. In certain embodiments, the functional fragment will include a deletion of at least 1, 2, 3, 4, 5, 6, 7, 8, 9, 10 or more amino acid residues. In some embodiments, the TE is a variant enzyme having at least 1, at least 5, at least 10, at least 15 or more amino acid modifications, such as substitutions. Non-limiting examples include the TE FatB genes from *Umbelluria californica* (California Bay), *Cinnamomum camphora*, or from various *Cuphea* species such as those disclosed in WO 2011/008565 and reference is made to SEQ ID NOs. 21, 48, 52, 56, 60, 64, 66, 70, 72, 76, 80, 82, 86, 90, 92, 94, 96 and 100 described therein.

Further acyl-ACP TEs that are useful according to the invention are described in the following references: U.S. Pat. Nos. 5,344,771, 5,512,482; 6,150,512; 5,723,761; 5,910,631 and WO2010/075483.

Various assays are known which can be used to test for TE activity in a recombinant microorganism transformed with a vector comprising a polynucleotide encoding a TE according to the invention (See, Voelker and Davies, 1994, J. Bacteriol. 176:7320).

In certain embodiments of the invention the engineered bacterial cell comprises a) a modified native bacterial gene having β-ketoacyl-ACP synthase activity (e.g., a native β-ketoacyl-ACP synthase I (FabB) (EC 2.3.1.41) or a native β-ketoacyl-ACP synthase II (FabF) (EC 2.3.1.179) wherein the native β-ketoacyl-ACP synthase has at least 85% (at least 88%, at least 90%, at least 92%, at least 94%, at least 95%, at least 96%, at least 97%, at least 98%, at least 99%) amino acid sequence identity to SEQ ID NO:2 and comprises an amino acid substitution at one or more of the following positions 30, 34, 38, 40, 42, 43, 45, 51, 53, 61, 62, 63, 64, 65, 66, 95, 96, 97, 106, 107, 108, 110, 111, 112, 113, 114, 115, 116, 117, 124, 127, 128, 130, 131, 132, 133, 134, 135, 136, 137, 138, 139, 140, 149, 151, 161, 162, 164, 165, 191, 196, 197, 200, 201, 204, 205, 206, 209, 210, 212, 216, 217, 224, 225, 226, 229, 231, 267, 268, 270, 271, 272, 273, 275, 282, 285, 298, 300, 302, 303, 304, 305, 308, 311, 314, 315, 333, 335, 336, 360, 361, 367, 390, 391, 392, or 396 when optimally aligned with SEQ ID NO:2 and b) a heterologous polynucleotide sequence encoding a thioesterase. In some embodiments, the TE is encoded by a gene comprising the polynucleotide sequence having at least 70%, (at least 75%, 80%, 85%, 90%, 93%, 95%, 97%, 99%, and even 100%) sequence identity to the polynucleotide sequence of SEQ ID NO:7. In some embodiments, the TE enzyme will comprise at least 70%, (at least 75%, 80%, 85%, 90%, 93%, 95%, 97%, 99%, and even 100%) sequence identity to the polypeptide sequence of SEQ ID NO:8. In some embodiments the gene encoding the TE enzyme is derived from *Umbelluria californica* (California Bay) and in other embodiments the gene encoding the TE enzyme is derived from *Cinnamomum camphorum*.

In certain embodiments, the engineered bacterial cell comprises a) a modified native bacterial gene having β-ketoacyl-ACP synthase activity (e.g., a native β-ketoacyl-ACP synthase I (FabB) (EC 2.3.1.41) or a native β-ketoacyl-ACP synthase II (FabF) (EC 2.3.1.179) wherein the native β-ketoacyl-ACP synthase has at least 85% (at least 88%, at least 90%, at least 92%, at least 94%, at least 95%, at least 96%, at least 97%, at least 98%, at least 99%) amino acid sequence identity to SEQ ID NO:2 and comprises an amino acid substitution at one or more of the following positions K40, S42, R45, G106, G107, G108, P110, Q113, A117, V133, V134, A137, M138, M197, E200, F201, A206, E216, K217, I231, T300, T302, P303, G305, L335, or Q367 when optimally aligned with SEQ ID NO:2.

In some embodiments, the TE is encoded by a gene comprising the polynucleotide sequence having at least 70%, (at least 75%, 80%, 85%, 90%, 93%, 95%, 97%, 99%, and even 100%) sequence identity to the polynucleotide sequence of SEQ ID NO:7. In some embodiments, the TE enzyme will comprise at least 70%, (at least 75%, 80%, 85%, 90%, 93%, 95%, 97%, 99%, and even 100%) sequence identity to the polypeptide sequence of SEQ ID NO:8. In some embodiments the gene encoding the TE enzyme is derived from *Umbelluria californica* (California Bay) and in other embodiments the gene encoding the TE enzyme is derived from *Cinnamomum camphorum*.

According to an embodiment of the invention, the engineered bacterial cell comprises, in addition to the modified native bacterial gene having β-ketoacyl-ACP synthase activity (e.g., a native β-ketoacyl-ACP synthase 1 (FabB) (EC 2.3.1.41) or a native β-ketoacyl-ACP synthase II (FabF) (EC 2.3.1.179) and a heterologous polynucleotide encoding a TE, a heterologous polynucleotide encoding a FadD. In some embodiments, the fadD includes the *E. coli* fadD (Black et al., 1992. J. Biol. Chem. 267: 25513-25520). In some embodiments, the fadD gene will comprise at least 70%, (at least 75%, 80%, 85%, 90%, 93%, 95%, 97%, 99%, and even 100%) sequence identity to the polynucleotide coding sequence illustrated in FIG. 4 of Black, supra. In some embodiments, the FadD will comprise at least 70%, (at least 75%, 80%, 85%, 90%, 93%, 95%, 97%, 99%, and even 100%) sequence identity to the polypeptide sequence illustrated in FIG. 4 of Black, supra. In some embodiments, the fadD genes include without limitation, fadD from *Acinetobacter* sp. NCBI ID YP_045024 (SEQ ID NO:44); fadD from *Haemophilus influenza* NCBI ID NP_438551 (SEQ ID NO:45); fadD from *Pseudomonas aeruginosa* NCBI ID NP_251989 (SEQ ID NO:46) and NP_251990 (SEQ ID NO:47); BH3101 from *Bacillus halodurans* NP_243969 (SEQ ID NO:48); yhfL from *Bacillus subtilis* NP_388908 (SEQ ID NO:49); and fadD from *Rhizobium etli* CFN NCBI ID_533919; fadD from *Marinobacter algicola* ZP_01892995 (SEQ ID NO:50); fadD from *Marinobacter aquaeolei* YP_958864 (SEQ ID NO:51); fadD from *Mycobacterium tuberculosis* NP_215722 (SEQ ID NO:52); fadD15 from *Mycobacterium tuberculosis* NP_216703 (SEQ ID NO:53); fadD19 from *Mycobacterium tuberculosis* YP_177983 (SEQ ID NO:54); fadD from *Rhodopseudomonas palustris* YP_00993712; fadD from *Pseudomonas fluorscens* PfO-1 YP_350081 (SEQ ID NO:55); fadD from *Pseudomonas putida* ACC77300; fadK from *E. coli* strain W ZP_07590374 (SEQ ID NO:56); putative fadK from *Salmonella typhimurium* LT2 NP_460316 (SEQ ID NO:57); and putative fadK from *Thermomonospora fusca* YP_290214 (SEQ ID NO:58).

In other embodiments, enzymes and genes involved in β-oxidation particularly in bacterial cells (e.g., *E. coli*) such as acyl-CoA synthase (EC 6.2.1.-) and acyl-CoA dehydrogenase (FadE) (EC 1.3.99.3) may be overexpressed or attenuated. In certain embodiments fab genes other than fabB may be manipulated. Non-limiting examples include fabF (EC2.3.1.179); fabG (EC 1.1.1.100); fabA (EC4.2.1.60), fabH (EC2.3.1.180), and/or fabI (EC 1.3.19).

Culturing and Fermentation

Any suitable means for culturing the recombinant host cells finds use in the present invention. Indeed, any suitable fermentation protocol finds use in the production of the fatty alcohols provided herein. In some embodiments, fermentation of the engineered cells as described hereinabove comprises fermenting said cells which comprise a) a polynucleotide encoding a variant FabB comprising at least 85% (also at least 88%, 90%, 91%, 92%, 93%, 94%, 95%, 96%, 97%, 98% and 99%) amino acid sequence identity to SEQ ID NO:2 and an amino acid substitution at one or more of the following positions 30, 34, 38, 40, 42, 43, 45, 51, 53, 61, 62, 63, 64, 65, 66, 95, 96, 97, 106, 107, 108, 110, 111, 112, 113, 114, 115, 116, 117, 124, 127, 128, 130, 131, 132, 133, 134, 135, 136, 137, 138, 139, 140, 149, 151, 161, 162, 164, 165, 191, 196, 197, 200, 201, 204, 205, 206, 209, 210, 212, 216, 217, 224, 225, 226, 229, 231, 267, 268, 270, 271, 272, 273, 275, 282, 285, 298, 300, 302, 303, 304, 305, 308, 311, 314, 315, 333, 335, 336, 360, 361, 367, 390, 391, 392, or 396 when optimally aligned with SEQ ID NO:2; b) a heterologous polynucleotide encoding a FAR enzyme; c) optionally one or more heterologous polynucleotides encoding a fab enzyme such as FabA, FabI, FabF, and/or FabH and d) optionally a polynucleotide encoding a heterologous thioesterase under suitable conditions and for a time sufficient for production of fatty alcohols, as desired. Conditions for the culture and production of cells, including bacterial and yeast cells, are readily available and well-known in the art. Cell culture media in general are set forth in Atlas and Parks (eds.) *The Handbook of Microbiological Media* (1993) CRC Press, Boca Raton, Fla. which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue* and supplement (1997) also from Sigma-Aldrich, Inc (St Louis, Mo.) ("Sigma-PCCS"), all of which are incorporated herein by reference. Also reference is made to the Manual of Industrial Microbiology and Biotechnology. A. Demain and J. Davies Eds. ASM Press. 1999.

In some embodiments, the recombinant cells encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. Indeed, it is intended that any suitable fermentation temperature will be used in the present invention.

In some other embodiments, the fermentation is carried out for a period of time within the range of from about 8 hours to 240 hours, from about 8 hours to about 168 hours, from about 16 hours to about 144 hours, from about 16 hours to about 120 hours, or from about 24 hours to about 72 hours. Indeed, it is intended that any suitable fermentation time will find use in the present invention.

In some other embodiments, the fermentation will be carried out at a pH in the range of about 4 to about 8, in the range of about 4.5 to about 7.5, in the range of about 5 to about 7, or in the range of about 5.5 to about 6.5. Indeed, it is intended that any suitable pH range will find use in the present invention.

Carbon sources useful in the aqueous fermentation medium (e.g., broth) in which the recombinant microorganisms are grown are those that can be assimilated by the recombinant host strain. Such carbon sources are available in many forms and include renewable carbon sources, including but not limited to cellulosic and starch feedstock substrates obtained therefrom. Such examples include for example fermentable sugars such as monosaccharides, disaccharides, and short chain oligosaccharides (e.g., glucose, fructose, xylose, galactose, arabinose, maltose, mannose, arabinose, and sucrose, as well as numerous other sugars; it is not intended that the present invention be limited to any particular fermentable sugar). Other carbon sources include, but are not limited to saturated and unsaturated fatty acids, glycerol, lactose, succinate, acetate and mixtures thereof.

In some embodiments, the assimilable carbon source is from cellulosic and/or starch feedstock derived from but not limited to, wood, wood pulp, paper pulp, grain (e.g., corn grain), corn stover, corn fiber, rice, paper and pulp processing waste, woody or herbaceous plants and residue, fruit or vegetable pulp, distillers grain, grasses, rice hulls, wheat straw, cotton, hemp, flax, sisal, corn cobs, sugar cane bagasse, sugar beets, sorghum, barely, barely straw, switch grass, wood chips, municipal solid wastes, aquatic crops, and mixtures thereof.

In some embodiments, the cellulosic feedstock useful as an assimilable carbon source has been derived from a biomass substrate that has been pretreated. The term "biomass" is broadly used herein to encompasses any living or dead biological material that contains a polysaccharide substrate, including but not limited to cellulose, starch, other forms of long-chain carbohydrate polymers, and mixtures of such sources. Examples of biomass include, but are not limited to, wood, wood pulp, paper pulp, corn fiber, corn grain, corn cobs, sugar cane, sugar beet, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, switchgrass, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to cultivated crops (e.g., grasses, including C4 grasses, such as switch grass, cord grass, rye grass, *miscanthus*, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in some alternative embodiments the biomass comprises a mixture of fibers that originate from different biomasses. In some embodiments, the biomass may also comprise transgenic plants that express ligninase and/or cellulase enzymes (See e.g., US 2008/0104724 A1).

In some embodiments, the biomass substrate is "pretreated," using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis. In some embodiments, the substrate is slurried prior to pretreatment. The following references described various means of pretreatment. Steam explosion performing acid pretreatment of biomass substrates is described in U.S. Pat. No. 4,461,648. Continuous pretreatment using a slurry is described U.S. Pat. No. 7,754,457. Methods of alkali pretreatment is such as Ammonia Freeze Explosion, Ammonia Fiber Explosion or Ammonia Fiber Expansion ("AFEX") are described in U.S. Pat. Nos. 5,171,592; 5,037,663; 4,600,590; 6,106,888; 4,356,196; 5,939,544; 6,176,176; 5,037,663 and 5,171,592. Alternative methods to AFEX utilizing a dilute ammonia pretreatments are described in WO2009/045651 and US 2007/0031953. Chemical pretreatments with organic solvents are disclosed in U.S. Pat. No. 4,556,430. Other pretreatments methods are disclosed in U.S. Pat. No. 7,465,791, and Weil et al. (1997) Appl. Biochem. Biotechnol., 68(1-2): 21-40 [1997].

Production of Fatty Alcohols

In various embodiments, fatty alcohols produced by the methods of the invention are further recovered or isolated. Recovery or isolation of the produced fatty alcohols refers to substantially separating the fatty alcohols from other components of the culture medium or fermentation process. Recovery or isolation may be accomplished by solvent extraction of the aqueous nutrient medium with a suitable water immiscible solvent. Extraction may occur simultaneously with fatty alcohol production and in some embodiments, extraction is continuous. Phase separation followed by solvent removal provides the fatty alcohol which may then be further purified and fractionated using methods and equipment known in the art. In some other aspects of the invention, the fatty alcohols in the extracellulase environment coalesce to form a water immiscible phase that can be directly separated from the aqueous nutrient medium either during the fermentation process or after its completion.

In certain embodiments of the invention, at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, of the fatty alcohols produced by the methods described herein are secreted into the extracellular environment by the recombinant host cells.

In certain embodiments, fatty alcohols are isolated by separating the host cells from the aqueous nutrient medium, for example by centrifugation, resuspension and extraction of the fatty alcohols from the recombinant host cells using an organic solvent or solvent mixture. Suitable protocols for recovering fatty alcohols from recombinant host cells and/or culture medium are known to the skilled artisan. In some embodiments, fatty alcohols may be recovered by first lysing the cells to release the fatty alcohols and then extracting the fatty alcohol from the lysate using conventional means. Reference is also made to Yeast Protocols Handbook, (2009) Clontech Laboratories, Inc. A Takara Bio Company, Mt. View Calif. 94043; PNAS 2003 Vol. 100, 16:9156-9161; and Doan et al., (2009) J. Plant Physiol. 166: 787-796 which discloses methods to isolate and measure fatty alcohols produced in *E. coli* using FARs from *Arabidopsis*. Indeed, it is intended that any suitable method will find use in the present invention and it is not intended that the present invention be limited to any particular method(s) for separating host cells from the culture or nutrient medium.

In various embodiments, the compositions produced by the methods and microorganisms described herein comprise both saturated and unsaturated fatty alcohols. In certain embodiments, the unsaturated fatty alcohols are mono-unsaturated fatty alcohols. In some embodiments, the fatty alcohol compositions comprise both saturated and unsaturated fatty alcohols, and the amount of unsaturated fatty alcohols compared to saturated fatty alcohols in the total fatty alcohol composition is less than about 40%, less than about 35%, less than about 30%, less than about 20%, less than about 15%, less than about 10%, less than about 5%, or less than about 1% of the fatty alcohols present in the composition.

In some embodiments, the percentage of saturated fatty alcohols in the fatty alcohol compositions produced by the engineered bacterial cells encompassed by the invention is greater than about 50%, greater than about 55%, greater than about 60%, greater than about 65%, greater than about 70%, greater than about 75%, greater than about 80%, greater than about 85%, greater than about 90%, greater than about 95%, or greater than about 97%.

In some embodiments, the fatty alcohol compositions produced by the methods and engineered microorganisms described herein comprise one or more fatty alcohols selected from 1-decanol (C10:0), 1-dodecanol (C12:0), 1-tetradecanol (C14:0), 1-hexadecanol (C16:0), and 1-octadecanol (C18:0).

In some typical embodiments, C10 to C16 fatty alcohols comprise at least about 90%, at least about 95%, at least about 96%, at least about 97%, at least about 98%, or at least about 99% by weight of the total fatty alcohols produced by the recombinant host cells. In some embodiments, C12 to C16 fatty alcohols comprise at least about 60%, at least about 65%, at least about 70%, at least about 75%, at least about 80%, at least about 85%, at least about 90%, at least about 92%, at least about 93%, at least about 94%, at least about 95%, at least about 96%, at least about 97%, or at least about 98% by weight of the total fatty alcohols produced by the recombinant host cells.

In certain embodiments, C14 to C16 fatty alcohols comprise at least about 60%, at least about 65%, at least about 70%, at least about 75%, at least about 80%, at least about 85%, at leas, about 90%, at least about 92%, at least about 95%, at least about 97%, or at least about 99% by weight of the total produced fatty alcohols.

In certain embodiments, C12 to C14 fatty alcohols comprise at least about 50%, at least 55%, at least 60%, at least about 65%, at least about 70%, at least about 75%, at least about 80%, at least about 85%, at least about 90%, at least about 92%, at least about 95%, at least about 97%, or at least about 99% by weight of the total produced fatty alcohols.

In some embodiments, C12:0 to C16:0 fatty alcohols comprise at least about 75%, at least about 80% at least about 85%, at least about 90%, at least about 92%, at least about 93%, at least about 94%, at least about 95%, or at least about 98% by weight of the total produced fatty alcohols. In certain embodiments, C14:0 to C16:0 fatty alcohols comprise at least about 70%, at least about 75%, at least about 80%, at least about 85%, at least about 90%, at least about 92%, at least about 95%, at least about 97%, or at least about 99% by weight of the total produced fatty alcohols.

In certain embodiments, C12:0 to C14:0 fatty alcohols comprise at least about 60%, at least about 65%, at least about 70%, at least about 75%, at least about 80%, at least about 85%, at least about 90%, at least about 92%, at least about 95%, at least about 97%, or at least about 99% by weight of the total produced fatty alcohols.

In certain embodiments, the C12 carbon chain length fatty alcohols produced by a recombinant bacterial microorganism according to the invention is increased by at least 10% (such as at least 15%, at least 20%, at least 25%, at least 30%, at least 35%, at least 40% or more) as compared to the production of C12 carbon chain fatty alcohols produced by a corresponding bacterial microorganism comprising a native bacterial gene when grown under essentially the same conditions.

The proportions of saturated and unsaturated fatty alcohols produced by the strains may be calculated after quantifying all the fatty alcohol species using any suitable method known in the art (e.g., GC-FID as described in US 2011/0000125SA1). The saturated fraction represents the sum of all C12:0-OH; C14:0-OH; C16:0-OH and C18:0-OH. While the unsaturated fraction is composed of the sum of C12:1-OH; C14:1-OH; C16:1-OH and C18:1-OH.

In some embodiments, the fatty alcohol compositions produced by the recombinant cells comprise a % of saturated fatty alcohols that is greater than about 55%; greater than about 60%; greater than about 65%; greater than about 70%; greater than about 75%; greater than about 80%; greater than about 85%; greater than about 90%; greater than about 95%; or greater than about 97%. In some additional embodiments, the fatty alcohol compositions further comprise at least about 85%, at least about 88%, at least about 90%, at least about 91%, at least about 92%, at least about 93%, at least about 94%, at least about 95%, at least about 96%, at least about 97%, or at least about 98% C12 to C16 fatty alcohols. In some additional embodiments, the fatty alcohol compositions further comprise at least about 85%, at least about 88%, at least about 90%, at least about 91%, at least about 92%, at least about 93%, at least about 94%, at least about 95%, at least about 96%, at least about 97%, or at least about 98% C12 to C14 fatty alcohols.

In certain embodiments, the amount of fatty alcohols produced by the recombinant bacterial cells according to the methods described herein comprise saturated and/or unsaturated C10 to C16 alcohols in a range of about 10 mg/L to about 150 g/L of aqueous nutrient medium, such as in a range of about 10 mg/L to about 125 g/L, about 10 mg/L to about 100 g/L, about 10 mg/L to about 75 g/L, about 10 mg/L to about 50 g/L, about 10 mg/L to about 25 g/L, about 10 mg/L to about 5 g/L or in a range of about 10 mg/L to about 2 g/L of medium, using routine modification of culturing conditions. In some embodiments, the amount of fatty alcohols produced by the methods described herein is at least about 0.5 g/L, at least about 1 g/L, at least about 1.5 g/L, at least about 2.0 g/L, at least about 2.5 g/L, at least about 3 g/L, at least about 3.5 g/L, at least about 4 g/L, at least about 4.5 g/L, at least about 5 g/L, or at least about 10 g/L of medium. In various embodiments, the amount of fatty alcohols produced by the methods described herein is at least about 20 g/L, at least about 30 g/L, at least about 40 g/L, or at least about 50 g/L of medium.

In some embodiments, a recombinant bacteria (e.g., $E.$ $coli$) encompassed by the invention produces C12 to C16 fatty alcohols in an amount of at least about 1.0 g/L, at least about 5.0 g/L, at least about 10 g/L, at least about 15 g/L, at least about 20 g/L, at least about 25 g/L, or at least about 30 g/L of medium. One method to extract and quantify fatty alcohols is provided in US Patent Application 2011/0000125. However, it is not intended that the present invention be limited to any particular method(s) for extracting and/or quantifying the fatty alcohols produced using the present invention, as any suitable methods find use.

In some embodiments, the amount of fatty alcohols produced by the methods described herein are in at least about 100 mg/g, at least 500 mg/g, at least 1 g/g, at least 2 g/g, at least 5 g/g/ at least 6 g/g, at least 7 g/g, at least 8 g/g/ at least 9 g/g/ at least 10 g/g/ at least 12 g/g at least 15 g/g of dry cell weight. In some embodiments the amount of fatty alcohols produced by the methods described herein are in the range of about 100 mg/g to about 15 g/g of dry cell weight and also in the range of about 100 mg/g to about 10 g/g of dry cell weight. In other embodiments, the amount of fatty alcohols produced by the methods described herein is in the range of about 1 g/g to about 12 g/g; about 1 g/g to about 10 g/g; about 1 g/g to about 5 g/g of dry cell weight, and about 5 g/g to about 10 g/g of dry cell weight.

In certain embodiments, the amount of fatty alcohols produced by the methods described herein is in the range of about 10% to about 20% of dry cell weight, about 20% to about 30% of dry cell weight, about 30% to about 40% of dry cell weight, about 40% to about 50% of dry cell weight, about 50% to about 60% of dry cell weight, about 60% to about 70% of dry cell weight, or about 70% to about 80% of dry cell weight.

In some embodiments, the fatty alcohol compositions produced by the engineered cells and methods described herein may also comprise fatty acid-derived compounds. Fatty acid derivative compounds include compounds such as but not limited to esters (e.g. acetyl, methyl or ethyl esters and waxes) and fatty acids.

Uses of the Biosynthetically Produced Fatty Alcohols

In yet another aspect, the present invention relates to the use of the engineered organisms as described herein for the production of various compositions comprising the produced fatty alcohols, including but not limited to, fuel compositions (e.g., biodiesels and petrodiesels), cleaning compositions including detergent compositions (e.g., laundry detergents in liquid gel, spray, and powder form, hard surface cleaners, dishwashing detergents, and the like); industrial compositions (e.g., lubricants, solvents, and industrial cleaners); and personal care compositions (e.g., soaps, cosmetics, shampoos, gels, etc.).

In some embodiments, the fatty alcohol compositions described herein, and compounds derived there from, can be used as components of detergent compositions. Detergent compositions comprising fatty alcohols and fatty alcohol derivatives produced by the methods of the present invention include compositions used in cleaning applications, including, but not limited to, laundry detergents, hand-washing agents, dishwashing detergents, rinse-aid detergents, household detergents, and household cleaners, in liquid, gel, granular, powder, or tablet form. In some embodiments, the fatty alcohols produced by the methods described above and fatty alcohol derivatives are used directly in detergent compositions. In some embodiments, the fatty alcohols and fatty alcohol derivatives are reacted with a sulfonic acid group to produce sulfate derivatives that can be used as components of detergent compositions. In some embodiments, the fatty alcohols and fatty alcohol derivatives are reacted with an ethylene oxide to produce ethoxylated derivatives that can be used as components of detergent alcohols. Detergent compositions that can be generated using the fatty alcohols and fatty alcohol derivatives produced by the methods of the present invention include, but are not limited to, hair shampoos, rinses, and conditioners for humans and other animals, carpet shampoos, hard surface cleaners, light-duty household cleaners, light-duty household detergents, heavy-duty household cleaners, and heavy-duty household detergents. Detergent compositions generally include, in addition to fatty alcohols and derivative thereof, one or more builders (e.g., sodium carbonate, complexation agents, soap, and zeolites), enzymes (e.g., proteases, lipases, cellulases, and/or amylases); carboxymethyl cellulose, optical brighteners, fabric softeners, colourants and perfumes (e.g., cyclohexyl salicylate). Indeed, it is not intended that the present invention be limited to any particular detergent, detergent formulation, nor detergent use.

In some embodiments, sulfate derivatives and/or ethoxylated derivatives (e.g., C12-15) derived from fatty alcohols are used in products such as hair shampoos, carpet shampoos, light-duty household cleaners, and light-duty household detergents. In some embodiments, sulfate derivatives and/or ethoxylated derivatives (e.g., C16-C18) derived from fatty alcohols are used in products such as hair shampoos and conditioners. In some embodiments, sulfate derivatives and/or ethoxylated derivatives (e.g., C16-18) derived from fatty alcohols are used in products such as heavy-duty household cleaners and heavy-duty household detergents. Indeed, it is not intended that the present invention be limited to any particular detergent, detergent formulation, nor detergent use.

In some embodiments, fatty alcohol compositions as described herein, and compounds derived there from, are used as components in personal care compositions. In some embodiments, the fatty alcohols produced by the methods described above are used directly in personal care compositions. Personal care compositions containing fatty alcohols or fatty alcohol derivatives produced by the methods of the present invention include compositions used for application to the body (e.g., for application to the skin, hair, nails, or oral cavity) for the purposes of grooming, cleaning, beautifying, or caring for the body, including but not limited to lotions, balms, creams, gels, serums, cleansers, toners, masks, sunscreens, soaps, shampoos, conditioners, body washes, styling aids, and cosmetic compositions (e.g., makeup in liquid, cream, solid, anhydrous, or pencil form).

In some embodiments, the fatty alcohols or fatty alcohol derivatives can be reacted with a sulfonic acid group to produce sulfate derivatives that can be used as components of said compositions. In some embodiments, the fatty alcohols and fatty alcohol derivatives are reacted with an ethylene oxide to produce ethoxylated derivatives that can be used as components of said compositions. In some embodiments, sulfate derivatives (e.g., C12 to 14) derived from the fatty alcohol compositions produced by the methods described herein are used in products such as toothpastes. Indeed, it is not intended that the present invention be limited to any particular formulation, nor use.

In some embodiments, fatty alcohol compositions (e.g., C12) produced by the methods described herein are used in products such as lubricating oils, pharmaceuticals, and as an emollient in cosmetics. In some embodiments, fatty alcohol compositions (e.g., C14) produced by the methods described herein are used in products such as cosmetics (e.g., cold creams) for its emollient properties. In some embodiments, fatty alcohol compositions (e.g., C16) produced by the methods described herein are used in products such as cosmetics (e.g., skin creams and lotions) as an emollient, emulsifier, or thickening agent. In some embodiments, fatty alcohol compositions (e.g., C18) produced by the methods described herein are used in products such as lubricants, resins, perfumes, and cosmetics (e.g., as an emollient, emulsifier, or thickening agent). Indeed, it is not intended that the present invention be limited to any particular formulation, nor use.

In some embodiments, fatty alcohol compositions (e.g., C12) produced by the methods described herein are used in products such as lubricating oils, pharmaceuticals, and as an emollient in cosmetics. In some embodiments, fatty alcohol compositions (e.g., C14) produced by the methods described herein are used in products such as cosmetics (e.g., cold creams) for its emollient properties. In some embodiments, fatty alcohol compositions (e.g., C16) produced by the methods described herein are used in products such as cosmetics (e.g., skin creams and lotions) as an emollient, emulsifier, or thickening agent. In some embodiments, fatty alcohol compositions produced by the methods described herein are used in products such as lubricants, resins, perfumes, and cosmetics, e.g., as an emollient, emulsifier, or thickening agent. In some embodiments, sulfate derivatives (e.g., C12 to C14) derived from the fatty alcohol compositions produced by the methods described herein are used in products such as toothpastes.

In some instances, fatty alcohols (especially cetyl alcohol, stearyl alcohol and myristyl alcohol) may be used as food additives (e.g., adjuvants and production aids).

In some embodiments, fatty alcohols produced according to the methods described herein can be reduced to yield alkanes and/or alkenes having the same carbon chain length as the fatty alcohol starting materials. Without being bound by any particular theory, the hydroxyl group of an alcohol is a poor leaving group, and therefore, in principle a chemical moiety that binds to the oxygen atom of the hydroxyl group to make it a better leaving group can be used to reduce the fatty alcohols described herein.

Any suitable method known in the art can be used to reduce the fatty alcohols. In some embodiments, reduction of fatty alcohols is carried out chemically, for example, by a Barton deoxygenation (or Barton-McCombie deoxygenation), a two-step reaction in which the alcohol is first converted to a methyl xanthate or thioimidazoyl carbamate, and the xanthate or thioimidazoyl carbamate is reduced with a tin hydride or trialkylsilane reagent under radical conditions to produce the alkane and/or alkene. See Li et al., 2007, *Modern Organic Synthesis in the Laboratory*, p. 81-83. In another embodiment, alkanes are produced by hydrogenation of fatty alcohols.

The alkanes can be isolated from the reaction mixture (which may contain unreduced fatty alcohols) to yield a composition comprising substantially all alkanes Alternatively, the alkanes and un-reduced fatty alcohols can be isolated from the reaction mixture to yield a composition comprising alkanes and fatty alcohols. In some embodiments, the fatty alcohol compositions comprise at least about 10%, at least about 20%, at least about 30%, at least about 40%, at least about 50%, at least about 60%, at least about 70%, at least about 80%, at least about 85%, at least about 90%, at least about 92%, at least about 95%, at least about 96%, at least about 97%, at least about 98%, or at least about 99% alkanes by weight of the composition after reduction. In some embodiments, the alkane is octane, decane, dodecane, tetradecane, hexadecane, octadecane, icosane, docosane, tetracosane, or mixtures thereof.

In other embodiments, fatty alcohols are reacted with a carboxylic acid to form acid esters. Esterification reactions of fatty alcohols are well-known in the art. In certain embodiments, the transesterification reaction is carried out in the presence of a strong catalyst (e.g., a strong alkaline such as sodium hydroxide). In other embodiments, the esterification reaction is carried out enzymatically, using an enzyme that catalyzes the conversion of fatty alcohols to acid esters, such as lipoprotein lipase (See e.g., Tsujita et al., 1999, "Fatty Acid Alcohol Ester-Synthesizing Activity of Lipoprotein Lipase" *J. Biochem.* 126:1074-1079).

EXAMPLES

The present invention is described in further detail in the following Examples, which are not in any way intended to limit the scope of the invention as claimed. In the experimental disclosure below, the following abbreviations apply: M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) (hour(s)); U (units); LB (Luria-Bertani); MW (molecular weight); rpm (rotations per minute); ° C. (degrees Centigrade); wt % (weight percent); Δ (deletion); DNA (deoxyribonucleic acid); PCR (polymerase chain reaction); _F (forward primer); _R (reverse primer); (RNA (ribonucleic acid); gDNA (genomic DNA); cDNA (complementary DNA); PCR (polymerase chain reaction); rbs (ribosome binding sequence); Sigma (Sigma Aldrich, St. Louis, Mo.); Qiagen (Qiagen, Inc., Valencia, Calif.); Invitrogen (Invitrogen, Corp., Carlsbad, Calif.); and Promega (Promega, Corp., Madison, Wis.).

The following sequences find use in the present invention.
Native *E. coli* fabB DNA Sequence:

(SEQ ID NO: 1)
ATGAAACGTGCAGTGATTACTGGCCTGGGCATTGTTTCCAGCATCGGTAA

TAACCAGCAGGAAGTCCTGGCATCTCTGCGTGAAGGACGTTCAGGGATCA

CTTTCTCTCAGGAGCTGAAGGATTCCGGCATGCGTAGCCACGTCTGGGC

AACGTAAAACTGGATACCACTGGCCTCATTGACCGCAAAGTTGTGCGCTT

TATGAGCGACGCATCCATTTATGCATTCCTTTCTATGGAGCAGGCAATCG

CTGATGCGGGCCTCTCTCCGGAAGCTTACCAGAATAACCCGCGCGTTGGC

CTGATTGCAGGTTCCGGCGGCGGCTCCCCGCGTTTCCAGGTGTTCGGCGC

TGACGCAATGCGCGGCCCGCGCGGCCTGAAAGCGGTTGGCCCGTATGTGG

TCACCAAAGCGATGGCATCCGGCGTTTCTGCCTGCCTCGCCACCCCGTTT

AAAATTCATGGCGTTAACTACTCCATCAGCTCCGCGTGTGCGACTTCCGC

ACACTGTATCGGTAACGCAGTAGAGCAGATCCAACTGGGCAAACAGGACA

TCGTGTTTGCTGGCGGCGGCGAAGAGCTGTGCTGGGAAATGGCTTGCGAA

TTCGACGCAATGGGTGCGCTGTCTACTAAATACAACGACACCCCGGAAAA

AGCCTCCCGTACTTACGACGCTCACCGTGACGGTTTCGTTATCGCTGGCG

GCGGCGGTATGGTAGTGGTTGAAGAGCTGGAACACGCGCTGGCGCGTGGT

GCTCACATCTATGCTGAAATCGTTGGCTACGGCGCAACCTCTGATGGTGC

AGACATGGTTGCTCCGTCTGGCGAAGGCGCAGTACGCTGCATGAAGATGG

CGATGCATGGCGTTGATACCCCAATCGATTACCTGAACTCCCACGGTACT

TCGACTCCGGTTGCGACGTGAAAGAGCTGGCAGCTATCCGTGAAGTGTT

CGGCGATAAGAGCCCGGCGATTTCTGCAACCAAAGCCATGACCGGTCACT

CTCTGGGCGCTGCTGGCGTACAGGAAGCTATCTACTCTCTGCTGATGCTG

GAACACGGCTTTATCGCCCCGAGCATCAACATTGAAGAGCTGGACGAGCA

GGCTGCGGGTCTGAACATCGTGACCGAAACGACCGATCGCGAACTGACCA

CCGTTATGTCTAACAGCTTCGGCTTCGGCGGCACCAACGCCACGCTGGTA

ATGCGCAAGCTGAAAGATTAA

Native *E. coli* FabB Amino Acid Sequence:

(SEQ ID NO: 2)
MKRAVITGLGYVSSIGNNQQEVLASLREGRSGITFSQELKDSGMRSHVWG

NVKLDTTGLIDRKVVRFMSDASIYAFLSMEQAIADAGLSPEAYQNNPRVG

LIAGSGGGSPRFQVFGADAMRGPRGLKAVGPYVVTKAMASGVSACLATPF

KIHGVNYSISSACATSAHCIGNAVEQIQLGKQDIVFAGGGEELCWEMACE

FDAMGALSTKYNDTPEKASRTYDAHRDGFVIAGGGGMVVVEELEHALARG

AHIYAEIVGYGATSDGADMVAPSGEGAVRCMKMAMHGVDTPIDYLNSHGT

STPVGDVKELAAIREVFGDKSPAISATKAMTGHSLGAAGVQEAIYSLLML

EHGFIAPSINIEELDEQAAGLNIVTETTDRELTTVMSNSFGFGGTNATLV

MRKLKD

Polynucleotide Sequence of a Codon Optimized FAR from *Marinobacter algicola* DG893:

(SEQ ID NO: 3)
ATGGCTACTCAACAACAACAGAACGGTGCATCTGCATCCGGCGTCTTGGA

ACAACTTCGTGGAAAGCACGTTCTTATCACAGGTACTACCGGATTTTTGG

GCAAAGTGGTTCTGGAAAAGTTGATTCGTACTGTTTCCGGATATTGGAGG

TATTCATCTGCTGATTCGTGGCAATAAACGTCATCCAGCCGCTCGTGAAC

GTTTCCTGAACGAAATTGCGTCCTCCTCCGTCTTCGAACGTTTGCGTCAC

GATGATAATGAAGCCTTCGAGACCTTCTTGGAAGAACGTGTTCACTGTAT

TACCGGTGAGGTTACTGAATCCCGTTTTGGTTTGACACCTGAACGTTTTC

GTGCTTTGGCCGGTCAGGTTGACGCTTTTATTAACAGCGCTGCAAGCGTG

AACTTTCGTGAGGAATTGGATAAAGCCCTGAAAATCAACACCTTGTGTCT

TGAAAATGTTGCTGCTCTTGCAGAATTGAACTCCGCTATGGCGGTCATTC

AGGTTTCCACTTGTTACGTTAACGGTAAAAACTCCGGTCAAATTACCGAA

TCCGTCATTAAACCTGCTGGCGAATCCATTCCCCGTTCCACTGACGGTTA

CTACGAGATCGAAGAATTGGTCCATCTGTTGCAAGACAAGATTTCCGATG

TTAAAGCTCGTTACTCCGGCAAAGTTCTGGAGAAAAAATTGGTTGATTTG

GGTATTCGTGAGGCCAATAATTACGGATGGTCCGACACCTACACATTCAC

CAAATGGTTGGGTGAACAACTGCTGATGAAGGCCTTGTCTGGTCGTTCTT

TGACTATTGTGCGTCCCTCTATTATTGAGTCCGCTTTGGAAGAACCTTCC

CCTGGTTGGATCGAAGGCGTTAAAGTTGCCGATGCCATTATCTTGGCTTA

TGCCCGTGAAAAAGTTAGCCTGTTCCCTGGAAAACGTTCCGGCATTATTG

ATGTTATTCCTGTCGATTTGGTTGCGAACTCCATCATCTTGTCTCTGGCT

GAGGCGTTGTCTGGTTCTGGTCAACGTCGTATTTATCAATGTTGCAGCGG

TGGTTCTAATCCAATCTCCCTGGGTAAGTTCATTGATTATTTGATGGCCG

AGGCTAAGACCAACTATGCTGCCTACGATCAACTGTTTTATCGTCGTCCT

ACTAAACCTTTCGTCGCCGTGAACCGTAAATTGTTTGACGTTGTTGTTGG

TGGTATGCGTGTTCCTCTTTCTATTGCCGGTAAAGCTATGCGTTTGGCTG

```
GTCAAAATCGTGAGTTGAAAGTGCTTAAGAACCTTGATACGACCCGTTCC

CTTGCAACCATTTTTGGCTTCTATACTGCTCCCGACTATATCTTCCGTAA

CGATAGCTTGATGGCCCTGGCTTCTCGTATGGGTGAATTGGATCGTGTTC

TTTTCCGAGTTGATGCTCGTCAAATTGATTGGCAGTTGTACTTGTGTAAA

ATTCATTTGGGTGGTCTGAACCGTTACGCTTTGAAGGAACGTAAACTGTA

TTCTTTGCGTGCTGCTGATACTCGTAAAAAAGCTGCCTAA
```

FAR Polypeptide Sequence Encoded by the Polynucleotide of SEQ ID NO: 3:

```
                                          (SEQ ID NO: 4)
MATQQQQNGASASGVLEQLRGKHVLITGTTGFLGKVVLEKLIRTVPDIGG

IHLLIRGNKRHPAARERFLNEIASSSVFERLRHDDNEAFETFLEERVHCI

TGEVTESRFGLTPERFRALAGQVDAFINSAASVNFREELDKALKINTLCL

ENVAALAELNSAMAVIQVSTCYVNGKNSGQITESVIKPAGESIPRSTDGY

YEIEELVHLLQDKISDVKARYSGKVLEKKLVDLGIREANNYGWSDTYTFT

KWLGEQLLMKALSGRSLTIVRPSIIESALEEPSPGWIEGVKVADAIILAY

AREKVSLFPGKRSGIIDVIPVDLVANSIILSLAEALSGSGQRRIYQCCSG

GSNPISLGKFIDYLMAEAKTNYAAYDQLFYRRPTKPFVAVNRKLFDVVVG

GMRVPLSIAGKAMRLAGQNRELKVLKNLDTTRSLATIFGFYTAPDYIFRN

DSLMALASRMGELDRVLFPVDARQIDWQLYLCKIHLGGLNRYALKERKLY

SLRAADTRKKAA
```

Polynucleotide Sequence Encoding a Variant FAR (V1):

```
                                          (SEQ ID NO: 5)
ATGGCGACTCAACAACAGAACAACGGTGCATCTGCATCCGGCGTCTTGGA

AATTCTTCGTGGAAAGCACGTTCTTATCACAGGTACTACCGGATTTTTGG

GCAAAGTGGTTCTGGAAAAGTTGATTCGTACTGTTCCGGATATTGGAGGT

ATTCATCTGCTGATTCGTGGCAATAAACGTCATCCAGCCGCTCGCGAACG

TTTCCTGAACGAAATTGCGTCCTCCTCCGTCTTCGAACGTTTGCGTCACG

ATGATAATGAAGCCTTCGAGACCTTCTTGGAAGAACGTGTTCACTGTATT

ACCGGTGAGATTACTGAATCCCGTTTTGGTTTGACACCTGAGCGTTTTCG

TGCTTTGGCCGGTCAGGTTGACGCTTTTATTCATAGCGCTGCAAGCGTGA

ACTTTCGTGAGCAATTGGATAAAGCCCTGAAAATCAACACCTTGTGTCTT

GAAAATGTTGCTGCACTTGCAGAATTGAACTCCGCTATGGCGGTCATTCA

GGTTTCCACTTGTTACGTTAACGGTAAAACCTCCGGTCAAATTACCGAAT

CCGTCATTAAATCGGCTGGCGAATCCATTCCCCGTTCCACTGACGGTTAC

TACGAGATCGAAGAATTGGTCCATCTGTTGCAAGACAAGATTTCCGATGT

TAAAGCTCGTTACTCCGGCCGTGTTATGGGGAAAAAATTGGTTGATTTGG

GTATTCGTGAGGCCAATAATTACGGATGGTCCGACACCTACACATTCACC

AAATGGTTGGGTGAACAACTGCTGATGAAGGCCTTGTCTGGTCGTTCTTT

GACTATTGTGCGTCCCTCTATTATTGAGTCCGCTTTGGAAGAACCTTCCC

CTGGTTGGATCGAAGGCGTTAAAGTTGCCGATGCCATTATCTTGGCTTAT

GCCCGTGAAAAAGTTAGCCTGTTCCCTGGAAAACGTTCCGGCATTATTGA
```

```
TTTTATTCCFGTCGATTTGGTTGCGAACTCCATCATCTTGTCTCTGGCTG

AGGCGTTGTCTGGTTCTGGTCAACGTCGTATTTATCAATGTTGCAGCGGT

GGTTCTAATCCAATCTCCCTGGGTAAGTTCTTTGATTATTTGAACGCCGA

GGCTAAGACCAACTATGCTGCCTACGATCAACTGTTTTATCGTCGTCCTA

CTAAACCTTTCGTCGCCGTGAACCGTAAATTGTTTGACGTTGTTGTTGGT

GTCATGCGTGTTGTCCTTTCTATTGCCCGCAAAGCTATGCGTTTGGCTGG

TGTAAATCGTGAGTTGAAAGTGCTTAAGAACCTTGATACGACCCGTAAAC

TTGCAACCATTTTTGGCTTCTATACTGCTCCCGACTATATCTTCCGTAAC

GATAGCTTGATGGCCCTGGCTCAGCGTATGGGTGAATTGGATCGTGTTCT

TTTCCCAGTTGATGCTCGTCAAATTGATTGGCAGTTGTACTTGTGTAAAA

TTCATTFGCGTGGTCTGAACCGTTACGCTTTGAAGGGCCGTAAACTGT.A

TTCTTCGCGTGCTGCTGATACTGACGATGAAACCCGCCTAA
```

Variant FAR (V1) Polypeptide Sequence Encoded by the Polynucleotide Sequence of SEQ ID NO: 5

```
                                          (SEQ ID NO: 6)
MATQQQNNGASASGVLEILRGKHVLITGTTGFLGKVVLEKLIRTVPDIGG

IHLLIRGNKRHPAARERFLNEIASSSVFERLRHDDNEAFETFLEERVHCI

TGEITESRFGLTPERFRALAGQVDAFIHSAASVNFREQLDKALKINTLCL

ENVAALAELNSAMAVIQVSTCYVNGKTSGQITESVIKSAGESIPRSTDGY

YEIEELVHLLQDKISDVKARYSGRVMGKKLVDLGIREANNYGWSDTYTFT

KWLGEQLLMKALSGRSLTIVRPSIIESALEEPSPGWIEGVKVADAIILAY

AREKVSLFPGKRSGIIDFIPVDLVANSIILSLAEALSGSGQRRIYQCCSG

GSNPISLGKFFDYLNAEAKTNYAAYDQLFYRRPTKPFVAVNRKLFDVVVG

VMRVVLSIARKAMRLAGVNRELKVLKNLDTTRKLATIFGFYTAPDYIFRN

DSLMALAQRMGELDRVLFPVDARQIDWQLYLCKIHLRGLNRYALKGRKLY

SSRAADTDDETA*
```

Polynucleotide Sequence Encoding a Thioesterase Amino Acid Sequence of SEQ ID NO: 8:

```
                                          (SEQ ID NO: 7)
ATGACCTTAGAGTGGAAACCAAAACCGAAATTACCTCAGCTTCTTGACGA

CCACTTCGGCCTGCATGGTTTAGTATTCCGCAGAACGTTTGCCATAAGAA

GCTACGAAGTAGGACCAGATCGTTCTACCTCTATACTTGCTGTGATGAAT

CATATGCAGGAAGCCACGTTAAATCACGCAAAGAGCGTCGGGATCCTTGG

GGACGGATTCGGCACCACATTGGAAATGAGTAAGCGGGACCTGATGTGGG

TTGTTCGTCGTACCCACGTAGCGGTCGAACGGTATCCAACATGGGCGAT

ACTGTTGAAGTGGAGTGCTGGATTGGCGCTTCCGGAAACAACGGAATGCG

CAGAGATTTTCTGGTGCGGGACTGTAAAACTGGGGAAATCTTAACGCGCT

GTACCTCCCTGTCCGTTCTGATGAACACGCGTACCCGGAGATTAAGTACG

ATTCCGGACGAAGTCCGTGGTGAAATCGGTCCCGCTTTTATTGACAACGT

GGCGGTAAAAGACGACGAGATCAAAAAGTTGCAGAAATTGAACGATTCCA

CAGCAGATTACATACAGGGCGGTCTTACGCCCCGTTGGAACGACTTGGAT
```

```
GTGAATCAGCACGTAAATAACCTTAAATATGTGGCGTGGGTGTTCGAGAC

CGTTCCCGACTCTATTTTTGAAAGTCACCACATTTCCAGCTTTACGCTGG

AGTACAGACGCGAGTGTACGCGCGATTCCGTTTTACGTTCCCTCACCACG

GTGTCTGGCGGATCTTCCGAAGCTGGGTTAGTGTGTGATCACTTGCTGCA

ACTTGAAGGCGGAAGTGAAGTTCTTCGGGCCCGCACGGAATGGCGTCCCA

AACTGACCGATTCCTTCCGCGGAATATCAGTAATTCCGGCCGAGCCGCGG

GTATAA
```

Polypeptide Sequence Encoded by the Thioesterase Polynucleotide Sequence of SEQ ID NO: 7:

```
                                           (SEQ ID NO: 8)
MTLEWKPKFKLPQLLDDHFGLHGLVFRRTFAIRSYEVGPDRSTSILAVMN

HMQEATLNHAKSVGILGDGFGTTLEMSKRDLMWVVRRTHVAVERYPTWGD

TVEVECWIGASGNNGMRRDFLVRDCKTGEILTRCTSLSVLMNTRTRRLST

IPDEVRGEIGPAFIDNVAVKDDEIKKLQKLNDSTADYIQGGLTPRWNDLD

VNQHVNNLKYVAWVFETVPDSIFESHHISSFTLEYRRECTRDSVLRSLTT

VSGGSSEAGLVCDHLLQLEGGSEVLRARTEWRPKLTDSFRGISVIPAEPR

V
```

Polynucleotide Sequence Encoding a Variant FAR (V2):

```
                                           (SEQ ID NO: 9)
atggcgactcaacaacagcagaacggtgcatctgcatccggcgtcttgga acaacttcgtggaaagcacgttcttatcacaggtactaccggatttttgg gcaaagtggttctggaaaagttgattcgtactgttccggatattggaggt attcatctgctgattcgtggcaataaacgtcatccagccgctcgtgaacg tttcctgaacgaaattgcgtcctcctccgtcttcgaacgtttgcgtcacg atgataatgaagccttcgagaccttcttggaagaacgtgttcactgtatt accggtgaggttactgaatcccgttttggtttgacacctgagcgttttcg tgctttggccggtcaggttgacgcttttattaacagcgctgcaagcgtga gttttcgtgagcaattggataaagccctgaaaatcaacaccttgtgtctt gaaaatgttgctgctcttgcagaattgaactccgctatggcggtcattca ggtttccacttgttacgttaacggtaaaaactccggtcaaattaccgaat ccgtcattaaatcggctggcgaatccattccccgtttccactgacggtta ctacgagatcgaagaattggtccatctgttgcaagacaagatttccgatg ttaaagctcgttactccggcaaagttctggagaaaaaattggttgatttg ggtattcgtgaggccaataattacggatggtccgacacctacacattcac caaatggttgggtgaacaactgctgatgaaggccttgtctggtcgacttt gactattgtgcgtccctctattattgagtccgcttggaagaaccttcccc tggttggatcgaaggcgttaaagttgccgatgccattatcttggcttatg cccgtgaaaaagttagcctgttccctggaaaacgttccggcattattgat gttattcctgtcgatttggttgcgaactccatcatcttgtctctggctga ggcgttgtctggttctggtcaacgtcgtatttatcaatgttgcagcggtg gttctaatccaatctccctgggtaagttcattgattatttgatggccgag
```

```
gctaagaccaactatgctgcctacgatcaactgtttttatcgtcgtcctac taaacctttcgtcgccgtgaaccgtaaattgtttgacgttgttgttggtg gtatgcgtgttgtcctttctattgccggtaaagctatgcgtttggctggt gtaaatcgtgagttgaaagtgcttaagaaccttgatacgacccgtaaact tgcaaccattttttggcttctatactgctcccgactatatcttccgtaacg atagcttgatggccctggctcagcgtatgggtgaattggatcgtgttctt ttcccagttgatgctcgtcaaattgatlggcagttgtacttgtgtaaaat tcatttgggtggtctgaaccgttacgctttgaaggaacgtaaactgtatt cttcgcgtgctgctgatactgacgataaaaccgcctaa
```

FAR V2 Polypeptide Sequence Encoded by the Polynucleotide of SEQ ID NO:9:

```
                                          (SEQ ID NO: 10)
MATQQQQNGASASGVLEQLRGKHVLITGTTGFLGKVVLEKLIRTVPDIGG

IHLLIRGNKRHPAARERFLNEIASSSVFERLRHDDNEAFETFLEERVHCI

TGEVTESRFGLTPERFRALAGQVDAFINSAASVSFREQLDKALKINTLCL

ENVAALAELNSAMAVIQVSTCYVNGKNSGQITESVIKSAGESIPRSTDGY

YEIEELVHLLQDKISDVKARYSGKVLEKKLVDLGIREANNYGWSDTYTFT

KWLGEQLLMKALSGRSLTIVRPSIIESALEEPSPGWIEGVKVADAIILAY

AREKVSLFPGKRSGIIDVIPVDLVANSIILSLAEALSGSGQRRIYQCCSG

GSNPISLGKFIDYLMAEAKTNYAAYDQLFYRRPTKPFVAVNRKLFDVVVG

GMRVVLSIAGKAMRLAGVNRELKVLKNLDTTRKLATIFGFYTAPDYIFRN

DSLMALAQRMGELDRVLFPVDARQIDWQLYLCKIHLGGLNRYALKERKLY

SSRAADTDDKTA
```

PLS8379:

```
                                          (SEQ ID NO: 11)
GGCATCCGCTTACAGACAAGCTGTGACCGTCTCCGGGAGCTGCATGTGTC

AGAGGTTTTCACCGTCATCACCGAAACGCGCGAGGCAGCAGATCAATTCG

CGCGCGAAGGCGAAGCGGCATGCATTTACGTTGACACCATCGAATGGTGC

AAAACCTTTCGCGGTATGGCATGATAGCGCCCGGAAGAGAGTCAATTCAG

GGTGGTGAATGTGAAACCAGTAACGTTATACGATGTCGCAGAGTATGCCG

GTGTCTCTTATCAGACCGTTTCCCGCGTGGTGAACCAGGCCAGCCACGTT

TCTGCGAAAACGCGGGAAAAAGTGGAAGCGGCGATGGCGGAGCTGAATTA

CATTCCCAACCGCGTGGCACAACAACTGGCGGGCAAACAGTCGTTGCTGA

TTGGCGTTGCCACCTCCAGTCTGGCCCTGCACGCGCCGTCGCAAATTGTC

GCGGCGATTAAATCTCGCGCCGATCAACTGGGTGCCAGCGTGGTGGTGTC

GATGGTAGAACGAAGCGGCGTCGAAGCCTGTAAAGCGGCGGTGCACAATC

TTCTCGCGCAACGCGTCAGTGGGCTGATCATTAACTATCCGCTGGATGAC

CAGGATGCCATTGCTGTGGAAGCTGCCTGCACTAATGTTCCGGCGTTATT

TCTTGATGTCTCTGACCAGACACCCATCAACAGTATTATTTTCTCCCATG

AAGACGGTACGCGACTGGGCGTGGAGCATCTGGTCGCATTGGGTCACCAG

CAAATCGCGCTGTTAGCGGGCCCATTAAGTTCTGTCTCGGCGCGTCTGCG
```

-continued

TCTGGCTGGCTGGCATAAATATCTCACTCGCAATCAAATTCAGCCGATAG
CGGAACGGGAAGGCGACTGGAGTGCCATGTCCGGTTTTCAACAAACCATG
CAAATGCTGAATGAGGGCATCGTTCCCACTGCGATGCTGGTTGCCAACGA
TCAGATGGCGCTGGGCGCAATGCGCGCCATTACCGAGTCCGGGCTGCGCG
TTGGTGCGGATATCTCGGTAGTGGGATACGACGATACCGAAGACAGCTCA
TGTTATATCCCGCCGTTAACCACCATCAAACAGGATTTTCGCCTGCTGGG
GCAAACCAGCGTGGACCGCTTGCTGCAACTCTCTCAGGGCCAGGCGGTGA
AGGGCAATCAGCTGTTGCCCGTCTCACTGGTGAAAAGAAAAACCACCCTG
GCGCCCAATACGCAAACCGCCTCTCCCCGCGCGTTGGCCGATTCATTAAT
GCAGCTGGCACGACAGGTTTCCCGACTGGAAAGCGGGCAGTGAGCGCAAC
GCAATTAATGTAAGTTAGCGCGAATTGATCTGGTTTGACAGCTTATCATC
GACTGCACGGTGCACCAATGCTTCTGGCGTCAGGCAGCCATCGGAAGCTG
TGGTATGGCTGTGCAGGTCGTAAATCACTGCATAATTCGTGTCGCTCAAG
GCGCACTCCCGTTCTGGATAATGTTTTTTGCGCCGACATCATAACGGTTC
TGGCAAATATTCTGAAATGAGCTGTTGACAATTAATCATCCGGCTCGTAT
AATGTGTGGAATTGTGAGCGGATAACAATTTCACACAGGAAACAGCGCCG
CTGAGAAAAAGCGAAGCGGCACTGCTCTTTAACAATTTATCAGACAATCT
GTGTGGGCACTCGACCGGAATTATCGATTAACTTTATTATTAAAAATTAA
AGAGGTATATATTAATGTATCGATTAAATAAGGAGGAATAAACCATGGAT
CCGAGCTCGAGATCTGCAGCTGGTACCATATGGGAATTCGAAGCTTTCTA
GAACAAAAACTCATCTCAGAAGAGGATCTGAATAGCGCCGTCGACCATCA
TCATCATCATCATTGAGTTTAAACGGTCTCCAGCTTGGCTGTTTTGGCGG
ATGAGAGAAGATTTTCAGCCTGATACAGATTAAATCAGAACGCAGAAGCG
GTCTGATAAAACAGAATTTGCCTGGCGGCAGTAGCGCGGTGGTCCCACCT
GACCCCATGCCGAACTCAGAAGTGAAACGCCGTAGCGCCGATGGTAGTGT
GGGGTCTCCCCATGCGAGAGTAGGGAACTGCCAGGCATCAAATAAAACGA
AAGGCTCAGTCGAAAGACTGGGCCTTTCGTTTTATCTGTTGTTTGTCGGT
GAACGCTCTCCTGAGCGCCTGATGCGGTATTTTCTCCTTACGCATCTGT
GCGGTATTTCACACCGCATATGGTGCACTCTCAGTACAATCTGCTCTGAT
GCCGCATAGTTAAGCCAGCCCCGACACCCGCCAACACCCGCTGACGAGCT
TAGTAAAGCCCTCGCTAGATTTTAATGCGGATGTTGCGATTACTTCGCCA
ACTATTGCGATAACAAGAAAAAGCCAGCCTTTCATGATATATCTCCCAAT
TTGTGTAGGGCTTATTATGCACGCTTAAAAATAATAAAAGCAGACTTGAC
CTGATAGTTTGGCTGTGAGCAATTATGTGCTTAGTGCATCTAACGCTTGA
GTTAAGCCGCGCCGCGAAGCGGCGTCGGCTTGAACGAATTGTTAGACATT
ATTTGCCGACTACCTTGGTGATCTCGCCTTTCACGTAGTGGACAAATTCT
TCCAACTGATCTGCGCGCGAGGCCAAGCGATCTTCTTCTTGTCCAAGATA
AGCCTGTCTAGCTTCAAGTATGACGGGCTGATACTGGGCCGGCAGGCGCT
CCATTGCCCAGTCGGCAGCGACATCCTTCGGCGCGATTTTGCCGGTTACT
GCGCTGTACCAAATGCGGGACAACGTAAGCACTACATTTCGCTCATCGCC
AGCCCAGTCGGGCGGCGAGTTCCATAGCGTTAAGGTTTCATTTAGCGCCT

-continued

CAAATAGATCCTGTTCAGGAACCGGATCAAAGAGTTCCTCCGCCGCTGGA
CCTACCAAGGCAACGCTATGTTCTCTTGCTTTTGTCAGCAAGATAGCCAG
ATCAATGTCGATCGTGGCTGGCTCGAAGATACCTGCAAGAATGTCATTGC
GCTGCCATTCTCCAAATTGCAGTTCGCGCTTAGCTGGATAACGCCACGGA
ATGATGTCGTCGTGCACAACAATGGTGACTTCTACAGCGCGGAGAATCTC
GCTCTCTCCAGGGGAAGCCGAAGTTTCCAAAAGGTCGTTGATCAAAGCTC
GCCGCGTTGTTTCATCAAGCCTTACGGTCACCGTAACCAGCAAATCAATA
TCACTGTGTGGCTTCAGGCCGCCATCCACTGCGGAGCCGTACAAATGTAC
GGCCAGCAACGTCGGTTCGAGATGGCGCTCGATGACGCCAACTACCTCTG
ATAGTTGAGTCGATACTTCGGCGATCACCGCTTCCCTCATGATGTTTAAC
TTTGTTTTAGGGCGACTGCCCTGCTGCGTAACATCGTTGCTGCTCCATAA
CATCAAACATCGACCCACGGCGTAACGCGCTTGCTGCTTGGATGCCCGAG
GCATAGACTGTACCCCAAAAAAACAGTCATAACAAGCCATGAAAACCGCC
ACTGCGCCGTTACCACCGCTGCGTTCGGTCAAGGTTCTGGACCAGTTGCG
TGAGCGCATACGCTACTTGCATTACAGCTTACGAACCGAACAGGCTTATG
TCCACTGGGTTCGTGCCTTCATCCGTTTCCACGGTGTGCGTCACCCGGCA
ACCTTGGGCAGCAGCGAAGTCGAGGCATTTCTGTCCTGGCTGGCGAACGA
GCGCAAGGTTTCGGTCTCCACGCATCGTCAGGCATTGGCGGCCTTGCTGT
TCTTCTACGGCAAGGTGCTGTGCACGGATCTGCCCTGGCTTCAGGAGATC
GGAAGACCTCGGCCGTCGCGGCGCTTGCCGGTGGTGCTGACCCCGGATGA
AGTGGTTCGCATCCTCGGTTTTCTGGAAGGCGAGCATCGTTTGTTCGCCC
AGCTTCTGTATGGAACGGGCATGCGGATCAGTGAGGGTTTGCAACTGCGG
GTCAAGGATCTGGATTTCGATCACGGCACGATCATCGTGCGGGAGGGCAA
GGGCTCCAAGGATCGGGCCTTGATGTTACCCGAGAGCTTGGCACCCAGCC
TGCGCGAGCAGGGGAATTAATTCCCACGGGTTTTGCTGCCCGCAAACGGG
CTGTTCTGGTGTTGCTAGTTTGTTATCAGAATCGCAGATCCGGCTTCAGC
CGGTTTGCCGGCTGAAAGCGCTATTTCTTCCAGAATTGCCATGATTTTTT
CCCCACGGGAGGCGTCACTGGCTCCCGTGTTGTCGGCAGCTTTGATTCGA
TAAGCAGCATCGCCTGTTTCAGGCTGTCTATGTGTGACTGTTGAGCTGTA
ACAAGTTGTCTCAGGTGTTCAATTTCATGTTCTAGTTGCTTTGTTTTACT
GGTTTCACCTGTTCTATTAGGTGTTACATGCTGTTCATCTGTTACATTGT
CGATCTGTTCATGGTGAACAGCTTTGAATGCACCAAAAACTCGTAAAAGC
TCTGATGTATCTATCTTTTTTACACCGTTTTCATCTGTGCATATGGACAG
TTTTCCCTTTGATATGTAACGGTGAACAGTTGTTCTACTTTTGTTTGTTA
GTCTTGATGCTTCACTGATAGATACAAGAGCCATAAGAACCTCAGATCCT
TCCGTATTTAGCCAGTATGTTCTCTAGTGTGGTTCGTTGTTTTTGCGTGA
GCCATGAGAACGAACCATTGAGATCATACTTACTTTGCATGTCACTCAAA
AATTTTGCCTCAAAACTGGTGAGCTGAATTTTTGCAGTTAAAGCATCGTG
TAGTGTTTTTCTTAGTCCGTTATGTAGGTAGGAATCTGATGTAATGGTTG
TTGGTATTTTGTCACCATTCATTTTTATCTGGTTGTTCTCAAGTTCGGTT
ACGAGATCCATTTGTCTATCTAGTTCAACTTGGAAAATCAACGTATCAGT

-continued
CGGGCGGCCTCGCTTATCAACCACCAATTTCATATTGCTGTAAGTGTTTA

AATCTTTACTTATTGGTTTCAAAACCCATTGGTTAAGCCTTTTAAACTCA

TGGTAGTTATTTTCAAGCATTAACATGAACTTAAATTCATCAAGGCTAAT

CTCTATATTTGCCTTGTGAGTTTTCTTTTGTGTTAGTTCTTTTAATAACG

ACTCATAAATCCTCATAGAGTATTTGTTTTCAAAAGACTTAACATGTTCC

AGATTATATTTTATGAATTTTTTTAACTGGAAAAGATAAGGCAATATCTC

TTCACTAAAAACTAATTCTAATTTTTCGCTTGAGAACTTGGCATAGTTTG

TCCACTGGAAAATCTCAAAGCCTTTAACCAAAGGATTCCTGATTTCCACA

GTTCTCGTCATCAGCTCTCTGGTTGCTTTAGCTAATACACCATAAGCATT

TTCCCTACTGATGTTCATCATCTGAGCGTATTGGTTATAAGTGAACGATA

CCGTCCGTTCTTTCCTTGTAGGGTTTTCAATCGTGGGGTTGAGTAGTGCC

ACACAGCATAAAATTAGCTTGGTTTCATGCTCCGTTAAGTCATAGCGACT

AATCGCTAGTTCATTTGCTTTGAAAACAACTAATTCAGACATACATCTCA

ATTGGTCTAGGTGATTTTAATCACTATACCAATTGAGATGGGCTAGTCAA

TGATAATTACTAGTCCTTTTCCTTTGAGTTGTGGGTATCTGTAAATTCTG

CTAGACCTTTGCTGGAAAACTTGTAAATTCTGCTAGACCCTCTGTAAATT

CCGCTAGACCTTTGTGTGTTTTTTTGTTTATATTCAAGTGGTTATAATT

TATAGAATAAAGAAAGAATAAAAAAAGATAAAAAGAATAGATCCCAGCCC

TGTGTATAACTCACTACTTTAGTCAGTTCCGCAGTATTACAAAAGGATGT

CGCAAACGCTGTTTGCTCCTCTACAAAACAGACCTTAAAACCCTAAAGGC

TTAAG

Example 1

Construction of pSIM-CDX

The chloramphenicol resistance marker in the lambda-RED expression plasmid pSIM5 (Gene. 2006 September 379:109-15) was replaced with an ampicillin resistance marker to make plasmid pSIM-CDX as described below. First, the ampicillin resistance marker from pUC19 (Invitrogen, Carlsbad, Calif.) was PCR amplified with the following oligos:
BLA-Promoter-pSIM5-Mega_F:

(SEQ ID NO: 12)
5'-GGCAAGGTGTTCTGGTCGGCGCATAGCTGAGATAAATGCTTCAA

TAATATTGAAAAAGGAAGAG-3'

BLA-Promoter-pSIM5-Mega_R:

(SEQ ID NO: 13)
5'-AGGCAAAGAAAACCCGGCGCTGAGGCCGGGTTACCAATGCTTAA

TCAGTGAGGCACCTA-3'

The PCR reaction was carried out using the enzyme Herculase DNA polymerase (Agilent Technologies, Inc., Santa Clara, Calif.) with an initial denaturation step at 94° C. for 2 min, followed by 25 cycles of the steps: 94° C. for 30 sec; 56° C. for 30 sec and 72° C. for 2 min. The denaturation step was followed by a final elongation step at 72° C. for 3 min. The resulting PCR product was cleaned with ExoSAP-IT (Affymetrix, Santa Clara, Calif.) and the remaining template was digested with DpnI (Promega, Madison, Wis.).

Five microliters of cleaned PCR product was added to 40 ng of plasmid pSIM5. The mixture was PCR amplified using the enzyme Phusion DNA polymerase (New England BioLabs, Ipswich, Mass.) with an initial denaturation step at 98° C. for 30 sec. followed by 40 cycles of the steps: 98° C. for 10 sec; 72 for 3 min. The denaturation step was followed by a final elongation step at 72° C. for 5 min. After the PCR reaction, the product was digested with DpnI (Promega, Madison, Wis.). This reaction was transformed into E. coli DH10B electrocompetent cells (Invitrogen, Carlsbad, Calif.) following the manufacturer's protocols. Cells were plated on LB agar plates containing 50 micrograms/ml of carbenicillin and incubated for 24 hours at 30° C. The obtained clones were verified.

Example 2

Construction of Plasmid PLS8379

A low copy vector carrying the Trc promoter was constructed. A DNA fragment containing the LACIQ gene, the Trc promoter, and the multiple cloning sites present in PtrCHIS2-B (Invitrogen, Carlsbad, Calif.) was PCR amplifies using the primers:

1920TrcM_F
(SEQ ID NO: 14)
5'-GACCTTAAAACCCTAAAGGCTTAAGGGCATCDCGCTTACAGACA
and

1920TrcM_R
(SEQ ID NO: 15)
5'-GGAGAAAATACCGCATCAGGCGCCTCAGGAGAGCGTTCACCGAC.

The PCR reaction was carried out using the enzyme Phusion (New England BioLabs, Ipswich, Mass.) with an initial denaturation step at 98° C. for 30 sec. followed by 25 cycles of the steps: 98° C. for 10 sec; 65° C. for 15 sec and 72° C. for 15 sec. This was followed by a final elongation step at 72° C. for 5 min. The primers used for the PCR reaction carry regions of homology to plasmid pCL1920, and therefore the PCR product described above can be used as a megaprimer to amplify a defined region of pCL1920 (Lerner and Inouye (1990) NAR 18: 4631) which contains the pSC101 origin of replication and confers resistance to spectinomycin (GenBank: AB236930). This PCR reaction was carried out using the Pfu Ultra enzyme (Agilent Technologies, Santa Clara, Calif.) with an initial denaturation step at 95° C. for 2 min, followed by 16 cycles of the steps: 95° C. for 30 sec; 55° C. for 30 sec and 68° C. for 7 min. This was followed by a final elongation step at 68° C. for 7 min. The outcome of the second PCR reaction was sequence-verified and the resulting plasmid was named pLS8379 (SEQ ID NO:11).

Example 3

Construction of Plasmid pCDX11

To obtain a tightly regulated gene expression vector, the $P_{TRC}$ promoter present in pLS8379 was replaced with a synthetic DNA fragment containing a $P_{TRC}$ variant where a symmetrical Lac operator [Sadler et al., 1983, PNAS, 80: 6785-6789] was introduced upstream of the −35 region of $P_{TRC}$. This promoter was synthesized as an EcoRV-NcoI DNA fragment (GeneScript, Piscataway, N.J.) (SEQ ID NO:

16 and used to replace the EcoRV-NcoI region from pLS8379 previously cut with the same restriction enzymes. A ligation reaction containing the two DNA fragments was incubated overnight at 16° C. and then transformed into *E. coli* Top10 electrocompetent cells (Invitrogen, Carlsbad, Calif.) following the manufacturer's protocols. Cells were plated on LB agar plates containing 100 micrograms/ml of spectinomycin. Plates were then incubated overnight at 37° C. Obtained clones were sequence verified.

EcoRV-NcoI Fragment (SEQ ID NO: 16)

(SEQ ID NO: 16)
GATATCTCGGTAGTGGGATACGACGATACCGAAGACAGCTCATGTTATAT

CCCGCCGTTAACCACCATCAAACAGGATTTTCGCCTGCTGGGGCAAACCA

GCGTGGACCGCTTGCTGCAACTCTCTCAGGGCCAGGCGGTGAAGGGCAAT

CAGCTGTTGCCCGTCTCACTGGTGAAAAGAAAAACCACCCTGGCGCCCAA

TACGCAAACCGCCTCTCCCCGCGCGTTGGCCGATTCATTAATGCAGCTGG

CACGACAGGTTTCCCGACTGGAAAGCGGGCAGTAATAATTTAAATTGGTT

TGACAGCTTATCATCGACTGCACGGTGCACCAATGCTTCTGGCGTCAGGC

AGCCATCGGAAGCTGTGGTATGGCTGTGCAGGTCGTAAATCACTGCATAA

TTCGTGTCGCTCAAGGCGCACTCCCGTTCTGGATAATGTTTTTTGCGCCG

ACATAATTGTGAGCGCTCACAATTTCTGAAATGAGCTGTTGACAATTAAT

CATCCGGCTCGTATAATGTGTGGAATTGTGAGCGGATAACAATTTCACAC

AGGAAACAGCGCCGCTGAGAAAAAGCGAAGCGGCACTGCTCTTTAACAAT

TTATCAGACAATCTGTGTGGGCACTCGACCGGAATTATCGATTAACTTTA

TTATTAAAAATTAAAGGAGGAATAAACCATGG

Example 4

Construction of Plasmid pCDX11-V2-kanR-Term

The plasmid PCDX11-V2-KanR-Term was assembled in several steps as described below. The plasmid pCDX11-V2 comprising FAR-V2 polynucleotide of SEQ ID NO:9 encoding the FAR-V2 enzyme having the amino acid sequence of SEQ ID NO: 10 was constructed as described below. A DNA fragment containing the FAR V2 gene was PCR amplified using the following primers.

```
NcoI_F
                                        (SEQ ID NO: 17)
5' TAAACCATGGCGACTCAACAACAGAACA
and SalI_R
                                        (SEQ ID NO: 18)
5' CTATGTCGACTTAGGCGGTTTCATCGTCAGTATC.
```

The restriction enzyme sites for NcoI and SalI were incorporated into NcoI_F and SalI_R respectively, allowing ligation into pCDX11 (See, Example 3) digested with NcoI and SalI. Ligation reactions were incubated overnight at 16° C. and then transformed into *E. coli* TOP10 chemically competent cells (Invitrogen, Carlsbad, Calif.) using standard techniques. Cells were plated on LB agar plates containing 100 ug/ml of spectinomycin and incubated overnight at 37° C. Obtained clones were sequence verified. The cycling conditions and reactions were applied according to the manufacturers' instructions, unless otherwise specified.

(b) The plasmid pCDX1 I-V2-kanR-Term was constructed as described below. A dsDNA kanamycin resistance cassette was PCR amplified from plasmid pKD13 (Proc Natl Acad Sci USA. 2000 Jun. 6; 97(12):6640-5.) using the following primers:

```
OH-Bsu36I-KanR_F:
                                        (SEQ ID NO: 19)
5'-GTCGGTGAACGCTCTCCTGAGGATTCCGGGGATCCGTCGACC-3'

Bsu36I-KanR-term_R:
                                        (SEQ ID NO: 20)
5'-AACCTCAGGCGAAAAAACCCCGCCGAAGCGGGGT

TTTTTGCGTGTAGGCTGGAGCTGCTT-3'.
```

The reverse primer encoded a transcriptional termination sequence in addition to having homology to the kanamycin resistance cassette. The PCR reaction was carried out using the enzyme Phusion DNA polymerase (New England Biolabs, Ipswich, Mass.) with an initial denaturation step at 98° C. for 30 sec, followed by 30 cycles of the steps: 98° C. for 5 sec; 63° C. for 20 sec and 72° C. for 30 sec. The denaturation step was followed by a final elongation step at 72° C. for 5 min. After the PCR reaction, the PCR product was purified through a PCR purification column and eluted with water.

The PCR amplified kanamycin resistance cassette and the vector pCDX11-V2 were digested with the restriction enzyme Bsu361 (Fermentas, Glen Burnie, Md.) and the resulting products were ligated using Quick T4 DNA Ligase (New England BioLabs, Ipswich, Mass.) following manufacturer recommendations. The reaction was transformed into *E. coli* Top10 electrocompetent cells (Invitrogen, Carlsbad, Calif.) following the manufacturer's protocols. Cells were plated on LB agar plates containing 100 micrograms/ml of spectinomycin and were incubated overnight at 37° C. The obtained clones were sequence verified.

Example 5

Construction of pCDX11-V1

The plasmid pCDX11-V1 comprising the FAR-V1 polynucleotide of SEQ ID NO:5 encoding the FAR-V1 enzyme having the amino acid sequence of SEQ ID NO:6 was constructed as described below.

A DNA fragment containing the FAR-V1 gene was PCR amplified using the primers:

```
NcoI_F
                                        (SEQ ID NO: 17)
5' TAAACCATGGCGACTCAACAACAGAACA
and SalI_R
                                        (SEQ ID NO: 18)
5' CTATGTCGACTTAGGCGGTTTCATCGTCAGTATC.
```

The restriction enzyme sites for NcoI and SalI were incorporated into NcoI_F and SalI_R respectively, allowing ligation into pCDX11 digested with NcoI and SalI. Ligation reactions were incubated overnight at 16° C. and then transformed into *E. coli* TOP10 chemically competent cells (Invitrogen, Carlsbad, Calif.) using standard techniques. Cells were plated on LB agar plates containing 100 ug/ml of spectinomycin and incubated overnight at 37° C. Obtained clones were sequence verified. The cycling conditions and reactions were applied according to the manufacturers' instructions.

Example 6

Generation of FabB Variants

A library of fabB variants differing from the wild-type sequence of SEQ ID NO:2 by one amino acid was generated using synthetic oligonucleotides, employing methods described in patent application US2009057507. All possible amino acid substitutions were made at the following 96 positions within the fabB protein of SEQ ID NO:2: R30, T34, E38, K40, S42, G43, R45, N51, K53, D61, R62, K63, V64, V65, R66, N95, N96, P97, G106, G107, G108, P110, R111, F112, Q113, V114, F115, G116, A117, R124, K127, A128, G130, P131, Y132, V133, V134, T135, K136, A137, M138, A139, S140, P149, K151, S161, A162, A164, T165, E191, E196, M197, E200, F201, M204, G205, A206, T209, K210, N212, E216, K217, A224, H225, R226, F229, I1231, A267, D268, V270, A271, P272, S273, E275, K282, M285, H298, T300, T302, P303, V304, G305, K308, A311, R314, E315, H333, L335, G336, N360, I361, Q367, F390, G391, F392, and N396.

Example 7

Replacement of Native fabB

The native fabB gene in *E. coli* W3110K was replaced with a cassette encoding a library of fabB variants in several steps as described below:
(a) A dsDNA cassette encoding a kanamycin resistance gene, the fabB library of variants, and a chloramphenicol resistance gene was assembled. First, the kanamycin resistance cassette was PCR amplified from the plasmid pCDX11-V2-kanR-Term (See, Example 4) using the following primers:
Ultra_homolFabB5'KanFwd:

(SEQ ID NO: 21)
5'-CGTCAAAATCTCGGGAAACAGGTGTACCCTCAGCATTAAATTCGAG

GTTGGCAGGTTGTATGGAGTAGTGTTTCACGTAAGTTACTCGTCTTACA

GGCGGTGGCTCGATCTTAGCGATGTGTGTAAGGCTGCGCAAATTTATTC

CGGGGATCCGTCGACC-3'

KanR-fabB_R:

(SEQ ID NO: 22)
5'-GTACACTTGTACGCCGAACAAGTCCGATCAGCCATTTAATAGAGCC

GCATCAGGCGCCTC-3'.

The forward primer contained 140 base pairs with homology to the upstream region of the fabB gene in *E. coli* W3110K (SEQ ID NO: 1) and the resulting cassette contained a constitutive promoter, kanamycin resistance gene, and a transcriptional terminator. The PCR reaction was carried out using the enzyme Herculase II fusion DNA polymerase (Agilent Technologies, Inc., Santa Clara, Calif.) with an initial denaturation step at 95° C. for 2 min., followed by 30 cycles of the steps: 95° C. for 20 sec; 63° C. for 20 sec and 72° C. for 2 min. The denaturation step was followed by a final elongation step at 72° C. for 3 min. After the PCR reaction, the PCR product was purified through a PCR purification column and eluted with water.

Second, a chloramphenical marker was PCR amplified from pKD32 (Proc Natl Acad Sci USA. 2000 Jun. 6: 97(12):6640-5.) as described above with the following primers:
ChlorR-fabB_F:

(SEQ ID NO: 23)
5'-TGGTTCCCTTTTTCACATCATTGACAATCGCCGATTCCGGGGATC

CGTCGACC-3'

Ultra_homolFabB3'CamRev: 5'-

(SEQ ID NO: 24)
5'-ATTACTCCAGAATGCAGCGCAAGGCGAGGAGTATCCCCGTCTCATCT

CTCTGGTTTCAGGGTTACGGTGCGTTGGCAGGATTTAACGCGTACGTCTT

TTCAGAAGGAAATCGACAAAGCGGGAAGTTTGCCTGGAACTGGTGTAGGC

TGGAGCTGCTTCG-3'.

The reverse chloramphenicol primer contained 140 base pairs with homology to the downstream region of the fabB gene in *E. coli* W3110K (SEQ ID NO:1) and the resulting cassette contained a constitutive promoter for expressing the chloramphenicol resistance gene.
Third, the fabB library of variants (from Example 6) was PCR amplified as described above with the following primers:

FabB_F1
(SEQ ID NO: 25)
5'-GGCTGATCGGACTTGTTCGGCGTACAAG
and

FabB_R1
(SEQ ID NO: 26)
5'-CGGCGATTGTCAATGATGTGAAAAAGG.

Finally, the two antibiotic resistance markers and the fabB library of variants were assembled using the technique of gene splicing by overlap extension PCR (SOE) (Warrens et al., Gene 1997, 186(1):29-35). One microliter of each of the two antibiotic resistance cassettes and the fabB library were mixed and the assembled product was amplified with the following primers:

Rescue_Fwd2:
(SEQ ID NO: 27)
5'-CGTCAAAATCTCGGGAAACAGGTG-3'
and

Rescue_Rev1:
(SEQ ID NO: 28)
5'-ATTACTCCAGAATGCAGCGCAAGG-3'.

The SOE amplification reaction was carried out using the enzyme PfuUltra II Fusion DNA polymerase (Agilent Technologies. Inc., Santa Clara, Calif.) with an initial denaturation step at 95° C. for 2 min, followed by 30 cycles of the steps: 95° C. for 20 sec; 52° C. for 20 sec and 72° C. for 4 min. The denaturation step was followed by a final elongation step at 72° C. for 4 min. After the PCR reaction, the PCR product was purified through a PCR purification column and eluted with water. The product contained DNA bands of several sizes including the desired band of ~3.9 kb.
Next, the genomic fabB in *E. coli* W3110K was replaced with the kanR-term-fabB library-chlorR cassette using the known technique of lambda RED-mediated homologous recombination as described below.

Strain W3110K was transformed with plasmid pSIM-CDX. Cells grown to log-phase at 32° C. were induced at 42° C. for 15 minutes and electrocompetent cells were prepared as described by Datta, Costantino, and Court (2006) Gene 379: 109-115. Competent cells were transformed with 500 ng of the fabB library cassette from above. Cells were recovered at 37° C. for four hours, plated on LB agar plates containing 20 micrograms/ml of kanamycin and 15 micrograms/ml of chloramphenicol, and incubated overnight at 37° C. Several colonies were PCR verified to have the genomic fabB gene replaced with the double antibiotic resistance cassette encoding unique fabB variants.

Example 8

Transforming pCDX11-V1 into the *E. coli* fabB Variant Library

The plasmid pCDX11-V1 was transformed into the *E. coli* fabB variant library as described below.

First, the colonies from the kanamycin/chloramphenicol selection plates described in Example 7 were pooled, grown in LB media to an $OD_{600}$ of ~0.6, and concentrated 100-fold by centrifugation. The cells were washed three times with ice-cold sterile water, and then washed once with ice-cold 10% glycerol. The plasmid pCDX11-V1 was transformed into the pooled cells using standard molecular biology methods (Dower et al., 1988 NAR 16:6127-6145). The cells were recovered at 37° C. for an hour and plated on LB agar plates containing 100 micrograms/ml of spectinomycin. The plates were incubated overnight at 37° C.

Example 9

Production and Isolation of Fatty Alcohols

Recombinant *E. coli* host strains comprising a plasmid including heterologous genes as specified above were grown in M9 medium (Sambrook et al., (2001) *Molecular Cloning: A Laboratory Manual.* 3$^{rd}$ ed., Cold Spring Harbor Laboratory Press, New York) supplemented with 1% glucose, 2 g/l yeast extract and the specified antibiotic selection, for approximately 16-18 hours (overnight) at 30° C., 200 rpm. A 5% inoculum was used to initiate fresh M9 media, 5% glucose and 2 g/l yeast extract containing the spectinomycin at 100 micrograms ml$^{-1}$ when pCDX11 vector is used. The culture was incubated in a shaker for 2.5 hours at 30° C. and at 250 rpm to an $OD_{600}$ of about 0.6 to about 0.8. The expression of the heterologous FAR was then induced with isopropyl-β-D-thiogalactoside (IPTG) (1 mM final concentration). Incubation was continued for about 48 hours under the same conditions. Fatty acid species including fatty alcohols were extracted using 1 mL of methyl isobutyl ketone (MIBK) into 500 µl of cell culture, sealed tightly and shaken for ≥2.5 h. The extract was centrifuged and analyzed directly by GC-FID. A 1 µL sample was analyzed by GC-FID with the split ratio 1:10 using the following conditions: GC-6890N from Agilent Technologies equipped with FID detector and HP-5 column (length 30 m, I.D. 0.32 mm, film 0.25 µm). GC method: start at 100° C., increase the temperature with a rate of 25° C./min to 246° C. and hold for 1.96 min. Total run time was 7.8 min. Under the above GC conditions, the approximate retention times (min) of produced fatty alcohols and acids were as follows: 1.81, C10:0-OH; 2.41, C12:1-OH; 2.45, C12:0-OH; 3.17, C14:1-OH; 3.22, C14:0-OH; 5.40, C14:0-OOH; 3.95, C16:1-OH; 4.02, C16:0-OH; 4.20, C16:0-OOMe (internal standard); 6.16, C16:1-OOH; 6.29, C16:0-OOH; 4.89, C18:1-OH; 5.00, C18:0-OH; and 7.3, C18:0- and C18:1-OOH. Identification of individual fatty alcohols was determined by comparison to commercial standards (Sigma Chemical Company, 6050 Spruce St. Louis, Mo. 63103).

TABLE 1

| Variant No.[1] | Total C12 FIOP[2] | % 12:0-OH FIOP[3] | Total C14 FIOP[2] | Total Titer FIOP |
|---|---|---|---|---|
| P303C | 1.26 | 1.39 | 0.89 | 0.95 |
| P303V | 1.19 | 1.20 | 0.94 | 1.00 |
| S42E | 1.22 | 1.15 | 1.06 | 1.05 |
| A206G | 1.43 | 1.17 | 1.18 | 1.22 |
| R45G | 1.38 | 1.05 | 1.39 | 1.33 |
| L335M | 1.26 | 1.11 | 1.14 | 1.13 |
| K217V | 1.11 | 1.08 | 1.02 | 1.02 |
| S42L | 1.27 | 1.17 | 1.09 | 1.07 |
| E216W | 1.04 | 1.07 | 0.92 | 0.99 |
| Q367V | 1.03 | 1.04 | 0.98 | 1.00 |
| K40G | 1.04 | 1.04 | 1.00 | 1.01 |
| K40S/P303R | 1.13 | 1.15 | 0.95 | 0.99 |
| K40A | 0.98 | 0.96 | 1.02 | 1.01 |
| K40R | 1.13 | 1.08 | 1.04 | 1.04 |
| I231F | 1.52 | 1.27 | 1.14 | 1.22 |
| I231C | 1.15 | 1.23 | — | 0.93 |

1. The amino acid residue substitution modification is relative to the wild-type amino acid residue in the corresponding position of the FabB of SEQ ID NO: 2. The FIOP values are averaged from multiple selections of 1 to 10 from primary screens.
2. Total C12 FIOP or total C14 FIOP is the total amount of C12 or C14 fatty alcohols, respectively, produced (saturated and unsaturated) and measured by fold improvement over the parent control (FIOP) wherein parent = 1.0.
3. % C12:0-OH is the % of saturated C12 fatty alcohols measured by fold improvement over the total % C12 of the parent control.

Each publication, patent, patent application, or other document cited in this application is hereby incorporated by reference in its entirety for all purposes to the same extent as if each were individually indicated to be incorporated by reference for all purposes in the specification directly adjacent the citation.

While various specific embodiments have been illustrated and described, it will be appreciated that various changes can be made without departing from the spirit and scope of the invention(s).

What is claimed is:

1. A variant β-ketoacyl-ACP synthase (FabB) having at least 85% amino acid sequence identity to SEQ ID NO: 2, wherein said variant FabB comprises an amino acid substitution at I231, wherein the position is numbered with reference to SEQ ID NO:2.

2. The variant FabB polypeptide of claim 1, wherein said variant polypeptide further comprises at least one amino acid substitution at one or more of the following positions R30, T34, E38, K40, S42, G43, R45, N51, K53, D61, R62, K63, V64, V65, R66, N95, N96, P97, G106, G107, G108, P110, R111, F112, Q113, V114, F115, G116, A117, R124, K127, A128, G130, P131, Y132, V133, V134, T135, K136, A137, M138, A139, S140, P149, K151, S161, A162, A164, T165, E191, E196, M197, E200, F201, M204, G205, A206, T209, K210, N212, E216, K217, A224, H225, R226, F229, A267, D268, V270, A271, P272, S273, E275, K282, M285, H298, T300, T302, P303, V304, G305, K308, A311, R314, E315, H333, L335, G336, N360, I361, Q367, F390, G391, F392, and/or N396, wherein the positions are numbered with reference to SEQ ID NO:2.

3. A recombinant polynucleotide encoding the variant FabB of claim 1.

4. The polynucleotide of claim 3, wherein the polynucleotide is codon optimized for a host cell.

5. A DNA construct comprising the polynucleotide of claim 3.

6. A host cell comprising the DNA construct of claim 5.

7. The host cell of claim 6, wherein the DNA construct comprising a polynucleotide encoding the variant FabB is chromosomally integrated into the host cell.

8. The host cell of claim 6, wherein the host cell is a bacterial cell.

9. The host cell of claim 6, further comprising a heterologous polynucleotide encoding a fatty alcohol reductase (FAR) enzyme, wherein said FAR has at least 80% amino acid sequence identity to SEQ ID NO:6.

10. The host cell of claim 9, wherein the FAR comprises SEQ ID NO:4 or SEQ ID NO:6.

11. The host cell of claim 9 comprising a variant FAR having at least 80% sequence identity to SEQ ID NO:6 and having a substitution at one or more positions corresponding to residues N134, E138, P188, P405, Q418 and/or A511, wherein the positions are numbered with reference to SEQ ID NO:4.

12. The host cell of claim 11, further comprising a variant FAR having a substitution at one or more positions selected from the group consisting of Q7, Q18, R65, V104, N128, E138, N177, K224, L226, E227, M365, G401, G410, S433, S458, G487, L502, R508, and K509, wherein the positions are numbered with reference to SEQ ID NO:4.

13. An engineered microorganism comprising at least one polynucleotide sequence encoding at least one variant FabB of claim 1.

14. The engineered microorganism of claim 13, further comprising a heterologous polynucleotide encoding a fatty alcohol reductase (FAR), said FAR comprising an amino acid sequence having at least 80% sequence identity to SEQ ID NO:6.

15. The engineered microorganism of claim 13, wherein the endogenous polynucleotide encoding a FabB having at least 85% sequence identity to SEQ ID NO:2 is replaced with a polynucleotide encoding the variant FabB.

16. The engineered microorganism of claim 13, further comprising one or more heterologous polynucleotides encoding FabI, FabZ, FabH, FabD, and/or FabG.

17. The engineered microorganism of claim 13, further comprising a heterologous polynucleotide encoding a thioesterase.

18. The engineered microorganism of claim 13, wherein when said microorganism is cultured in the presence of a carbon source and is capable of producing fatty alcohols, fatty acids and/or fatty aldehydes.

19. The engineered microorganism of claim 18, wherein said microorganism is capable of producing a fatty alcohol composition comprising at least 25% of C12 to C14 fatty alcohols.

20. The engineered microorganism of claim 19, wherein said microorganism is capable of producing a fatty alcohol composition comprising at least 20% C12 fatty alcohols.

21. The engineered microorganism of claim 13, wherein said microorganism is a bacteria or yeast.

22. A recombinant cell culture comprising engineered bacterial cells, said engineered bacterial cells comprising (a) a modified native gene encoding variant FabB having an amino acid sequence 85% identical to SEQ ID NO: 2 wherein the amino acid residue corresponding to I231 of SEQ ID BNO: 2 is substituted and (b) one or more heterologous polynucleotides encoding a fatty alcohol reductase and/or a thioesterase.

23. The recombinant cell culture of claim 22, wherein the engineered bacterial cells comprise a polynucleotide encoding a heterologous fatty alcohol reductase comprising at least 80% sequence identity to SEQ ID NO:6.

24. The recombinant cell culture of claim 23, wherein the engineered cells produce a fatty alcohol composition selected from:
a) at least 60% C12 to C16 fatty alcohols relative to the total fatty alcohols produced by the engineered microbial cells;
b) at least 25% C12 to C14 fatty alcohols relative to the total fatty alcohols produced by the engineered microbial cells;
c) at least 10% C12 fatty alcohols relative to the total fatty alcohols produced by the engineered microbial cells;
d) at least 20% C14 fatty alcohols relative to the total fatty alcohols produced by the engineered microbial cells; and
e) less than 5% C18 fatty alcohols relative to the total fatty alcohols produced by the engineered cells.

25. The recombinant cell culture of claim 24, wherein the fatty alcohols have been secreted from said engineered microbial cells and are present in the culture medium.

26. A method of producing a fatty alcohol composition comprising culturing the engineered cell of claim 9, with a carbon substrate under suitable culture conditions to allow expression of the variant FabB and heterologous FAR, and allowing production of fatty alcohols, wherein the fatty alcohol composition comprises at least 20% C12 and C14 fatty alcohols.

27. The method of claim 26, further comprising recovering the fatty alcohol composition.

28. The method of claim 26, wherein at least about 1.0 g/L of fatty alcohols are produced.

29. The method of claim 26, wherein at least about 80% of the produced fatty alcohols have a carbon chain length of C10 to C16.

30. The method of claim 26, wherein at least about 60% of the produced fatty alcohols have a carbon chain length of C12 to C16.

31. The method of claim 26, wherein at least about 30% of the produced fatty alcohols have a carbon chain length of C12 to C14.

* * * * *